(12) United States Patent
Suematsu et al.

(10) Patent No.: US 7,790,372 B2
(45) Date of Patent: Sep. 7, 2010

(54) METHOD OF JUDGING RISK FOR ONSET OF DRUG-INDUCED GRANULOCYTOPENIA

(75) Inventors: Koji Suematsu, Tokushima (JP); Koichi Hasegawa, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 540 days.

(21) Appl. No.: 10/563,818

(22) PCT Filed: Jul. 28, 2004

(86) PCT No.: PCT/JP2004/010722

§ 371 (c)(1),
(2), (4) Date: Jan. 6, 2006

(87) PCT Pub. No.: WO2005/010183

PCT Pub. Date: Feb. 3, 2005

(65) Prior Publication Data

US 2007/0264631 A1    Nov. 15, 2007

(30) Foreign Application Priority Data

Jul. 29, 2003    (JP)    .............................. 2003-281937

(51) Int. Cl.
*C12Q 1/68*    (2006.01)
*C12P 19/34*    (2006.01)
*C07H 21/02*    (2006.01)
*C07H 21/04*    (2006.01)

(52) U.S. Cl. .......................... 435/6; 435/91.2; 536/23.1; 536/24.3

(58) Field of Classification Search ........................ None
See application file for complete search history.

(56) References Cited

OTHER PUBLICATIONS

GenBank Accession No. AF073310, *Homo sapiens* insulin receptor substrate-2 (IRS2) mRNA, complete (Mar. 25, 1999).*
Berliner, N. et al., Hematology, vol. 2004, pp. 63-79 (2004).*
Sugiyama, E. et al., J. Clin. Oncol., vol. 25, pp. 32-42 (2007).*
Hahn, K.K. et al., Am. J. Health. Syst. Pharm., vol. 63, pp. 2211-2217 (2006).*
GenBank Accession No. AL162497 (Jun. 2001).*
GenBank Accession No. XM_007095 (Apr. 2003).*
BLAST sequence alignment of GenBank Accession Nos. AL162497 and XM_007095 (Jun. 2008).*
GenBank Accession No. AL162497, revision history (printed Mar. 4, 2009).*
GenBank Accession No. XM_007095, revision history (printed Mar. 4, 2009).*
Brookes Anthony J., The essence of SNPs, Gene, vol. 234, pp. 177 to 186, 1999.
Martin Eden R. et al., SNPing Away at Complex Diseases: Analysis of Single-Nucleotide Polymorphisms around APOE in Alzheimer Disease, Am. J. Hum. Genet., vol. 67, pp. 383 to 394, 2000.
Murakami Yasufumi et al., "Bioinformatics no Jissai", Kodansha ltd., pp. 210 to 211, 2003.
Schacher Daniel H. et al., Developmental Expression of Insulin Receptor Substrate-2 During Dimethylsulfoxide-Induced Differentiation of Human HL-60 Cells, The Journal of Immunology, vol. 164, pp. 113 to 120.
Dolores Bernal, et al.; "Insulin Receptor Substrate-2 Amino Acid Polymorphisms Are Not Associated With Random Type 2 Diabetes Among Causasians"; Jun. 1998; Diabetes, vol. 47, pp. 976-979.
K. Iwamoto, et al.; "Identification of a single nucleotide polymorphism showing no insulin-mediated suppression of the promoter activity in the human insulin receptor substrate 2 gene"; Aug. 2002; Diabetologia, vol. 45, pp. 1182-1195.
Xavier Jeunemaitre, et al.; "Haplotypes of Angiotensinogen in Essential Hypertension"; Mar. 1997; Am. J. Hum. Genet. 60; pp. 1448-1460.
Michele Cargill, et al.; "Characterization of single-nucleotide polymorphisms in coding regions of human genes"; Jul. 1999; vol. 22; Nature Genetics; pp. 231-238.
William E. Evans; "Pharmacogenomics: Translating Functional Genomics into Rational Therapeutics"; Science; Oct. 15, 1999; vol. 286; pp. 487-491.
J. Claiborne Stephens, et al.; "Dating the Origin of the CCR5- 3 Al S-Resistance Allele by the Coalescence of Haplotypes"; May 1998; Am. J.Hum. Genet. 62; pp. 1507-1515.
S. A. Tishkoff, et al. The Accuracy of Statistica Methods for Estimation of Haplotype Frequencies: An Example from the CD4 Locus; Jun. 2000; Am.J. Hum. Genet. 67; pp. 518-522.

* cited by examiner

*Primary Examiner*—Teresa E Strzelecka
(74) *Attorney, Agent, or Firm*—Oblon, Spivak, McClelland, Maier & Neustadt, L.L.P.

(57) ABSTRACT

Means for determining the presence of the risk of drug-induced granulocytopenia in a human is provided.

A method for assessing the risk of drug-induced granulocytopenia, including detecting a polymorphism of the human insulin receptor substrate-2 gene of a subject, and determining the presence of the risk of drug-induced granulocytopenia of the subject by use of the genetic polymorphism as an index.

11 Claims, 1 Drawing Sheet

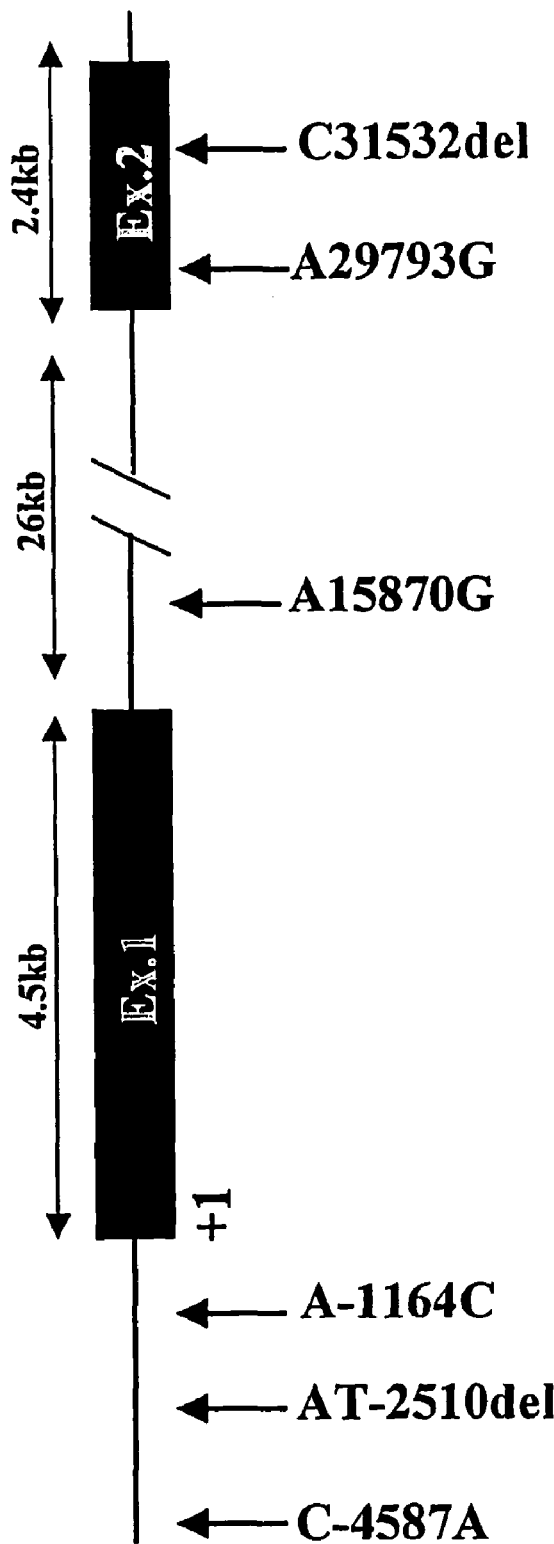
[Fig. 1]

SEQUENCE LISTING

```
<160> NUMBER OF SEQ ID NOS: 19

<210> SEQ ID NO 1
<211> LENGTH: 22
<212> TYPE: DNA
<213> ORGANISM: Artificial Sequence
<220> FEATURE:
<223> OTHER INFORMATION: Synthetic DNA

<400> SEQUENCE: 1
accactgtat ttgtgacaac tc                                            22

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
aaatatggat cagtctcttt cc                                            22

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
atgttcattt tatgagggag g                                             21

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
aactgccaat ccagagctgc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
tctcaccaca ccgcttcaag                                               20
```

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
ccacattttc ttcaagcacc                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
gagcttgctg ggatctgaac                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
atgtgactcg gcgttacgca                                               20

<210> SEQ ID NO 9
<211> LENGTH: 18
<212> TYPE: DNA
<213> ORGANISM: Artificial Sequence
<220> FEATURE:
<223> OTHER INFORMATION: Synthetic DNA

<400> SEQUENCE: 9
ccttgcagtg gaagcatg                                                 18

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
ctatcccgat tcctagatgt c                                             21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
gactcatctg tgactaactc c                                             21

<210> SEQ ID NO 12
<211> LENGTH: 19
<212> TYPE: DNA
<213> ORGANISM: Artificial Sequence
<220> FEATURE:

```
<223> OTHER INFORMATION: Synthetic DNA

<400> SEQUENCE: 12
cctagatgtc agcttgccc                                                    19

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
tctggaactc cagagattgc                                                   20

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
tgctgagcgt cttcttttaa tggta                                             25

<210> SEQ ID NO 15
<211> LENGTH: 22
<212> TYPE: DNA
<213> ORGANISM: Artificial Sequence
<220> FEATURE:
<223> OTHER INFORMATION: Synthetic DNA

<400> SEQUENCE: 15
gaggcttttt tagaggaaga cc                                                22

<210> SEQ ID NO 16
<211> LENGTH: 21
<212> TYPE: DNA
<213> ORGANISM: Artificial Sequence
<220> FEATURE:
<223> OTHER INFORMATION: Synthetic DNA

<400> SEQUENCE: 16
catgtcatgg agggagcatt c                                                 21

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
gcaaaagtct tcctgcttcc                                                   20

<210> SEQ ID NO 18
<211> LENGTH: 143409
<212> TYPE: DNA
<213> ORGANISM: Homo sapiens
<220> FEATURE:
<221> NAME/KEY: misc_feature
<222> LOCATION: (1)..(143409)
<223> OTHER INFORMATION: AL162497 an antisense strand

<400> SEQUENCE: 18
gcaaatcaaa accactgtgc gatatcacct acacccttta ggatggctat taccagagac      60
```

-continued

```
aagtgataaa tgtttgcaga gtgtggagaa aagagaattc ttgtacactg ttggtaggaa    120
tgtagattgg aagagccatt ctggaaaaca aaatggagct tccttaaata aatgaaaaat    180
agaactacca taagacccag caaccctctt ctgggtatat atccaacaga gaggaaatgg    240
ctaccttata aaatatattgg cactcccatg tgcactgcag cattatttac agtagccaag   300
gtatggaaac cacctaagtg tccattgaca gacaaatgga tgaagaaatt cctcgatgag    360
attggagatt attattctaa gtgaagtaac tcaggaacag aaaaccaaac atcgtgtgtt    420
cccactgaca tacggaagct aagctatgag gatgcaaagg cataagaatg acacaacgga    480
ctttgaggac ttaggggaa ggctggagg aggatgaggg ataaaggact acaaatatgg      540
tgcagtgtat actgctcagg tgatgggtgc gccaaaatct cacaaatcac cacaaaagaa    600
cctactcatg taaccaaata tcacctgttc cccaatacct tatggaaaaa taaaataata    660
aactaaaata aataatgtca catatgtaca acagaatgtt atttggacct cataaagaat    720
gagatcatcc catatgccac aacatcgatg aggctagagg cattatgct aagtggaata    780
aaccagacac agtaagaaaa atattgcatg atctcactca tatgtggaat ctaaaaagaa    840
aaattcaaat ggagatagaa aataaagcag ggttctgggg agatgcaagt tggaggacac    900
aacgtagccc acatgcaaga tgaacacctc tagagatttc aggcacgaaa tgaggacact    960
aagggccctg accaccctgg agtaagagct gacactactg ccttcccctg cctcggggga  1020
tcatcaccag ccacccagtg ggtgaagagg aacagtaaga aagaagccat ggggcttccc  1080
gcaatagctc ggtgtggtag agtctatcta aatgcagaat actttgatgg aggttactgg  1140
ctgggtcact gccactgagt ctctatcagg agctgggaca gggtggctcc catgcctggt  1200
tccacagcca gagaccttgc tgagtgacat gcagatttga gggacatggc tcatcttcct  1260
gcctgctact ctctagggct cactgatgaa tttctagtga cagtgtgttc tagaagttag  1320
ctctaactat aaaacatttt ttcaggtctt ccactttctg aacaatctga tcctaaagcc  1380
actgtgtgta tccaaacaag ggggatatcc gcaccgatgg aagggaccac agaggaacat  1440
agtgagcaag gatgggattg ggggaggttt gcaagagccc gagctgggca ttggtagggg  1500
acggtggcgg tccacatggc tgggtcatgg tgtcagagcc ccagtgcaat gaggaccggg  1560
ctcctgcagg agtaggacca tgggactttc agcctgagta gggtagagag agtgtccaag  1620
caggggaagg gactgaatgg aagggtggca ggcacccaga aaaatgaatg gggtttaagg  1680
gggaagcagc tggagcaaag tgtgcctctg ggcagggcaa ggagggcttc ggtgtaggaa  1740
gggaggaaaa ggggctttca tgtgggcgga tggtccagac aggaatggca cagcattact  1800
gggcagggag gatgctggcc tgggatgcag gccagtgcct ggcctcagag atcatacaga  1860
atttggaatc ggactgtgca gggggaggtg gcaatgctga tagaaaatgg caggggtggc  1920
acagggtgtg aatgagagtc acaaatatac aaaggaagaa agtggggtgg actctgaggt  1980
gcttgagtga actgaagata ttagcaccaa ctcatggctt tccatataga cagagctaga  2040
gacaaacata gacataaaca tctgtgtgtg tgtgtgtgtg tgtgtgtgtg tgtgtgtgtc  2100
tatatgcata tgctgtccag ctctgtgcac tgaggtacac ccagatcatg gtatctaaag  2160
cccattctcc tcttgggatt cagctctttt tggagaacca gctgacccat gatccagagc  2220
aggcagggtc cacaatgact cagaaacatc ttgaggacct gctcagagaa tgacaacaca  2280
cgggccagtg ggaacagctt ccaaaacccca gcaaaggtga acagtaagat aagtaatgat  2340
aattccaggt tataatccaa taaataagat agaaaactac acatccatac tgacataaat  2400
```

-continued

```
acaacataaa tgaataaatt aaacgttgaa tgaagagcag agtatttaca cagttttaag    2460
ctagtcctcc atgtaatact aattaattac aaaggaagaa aggagtgaag aaaccacaga    2520
caccacctcc atcaggtcac cagtgtgaac atcgtcagta accgggcaaa ttgcagtcct    2580
gccgacctga gagcacggag tgaggcggtc ccagggtcgc tcctgggttc tcctgccaag    2640
gacgctaaac ctgaatctgc tcatgaggaa gcatcaggca gccccgtgct ggggaaatc     2700 ctgcaatgta actggcctag agccattaga gtgtcaaggc cacgaaagtc acagaaagac    2760
tgaggaactt ttccaggtga atggagccta ataaaacaca acagccaaat gcagcatgta    2820
gctctgagat ggttcctttt gtttttaagg atgtctgggg gcaaatatga acagggtctg    2880
agaattaggc attaggaata tatcaacgtt gattatctga ttctgttaac tctactgtgg    2940
ttgtgtagga gcatatttgt gttggtacaa aatacacact aaagtattcg tattcaggga   3000
tgacaagata tcatgcaggc aacttactct caaaggtcc agcaaaaaaa aaattatttc     3060
tgttgtcctt gcaactattt tgtaagtagt ttgtacttgt taggaaaaaa aaaattcaga    3120
cttcttataa ctaatatcct tatgtgtgaa gaaatgataa aaatttccaa tgaaaataaa    3180
ttcccaaaca cctgggcagc ctctgcaccc atttggtaaa ctcctggctt tcatgcgctg    3240
tagttttgac ctgcagtggt tcccaggtca catgagtctc tgctgtaatg agacaggtat    3300
gcctcacgat gtcagtgcat ggcatcatga tgaaaacccc cctaagtttg ccagtgtcct    3360
cagtaaagga cagtgagacc aacagatgat atccatcagc tgccaaccca ggagggctgg    3420
aaagattgcc tagccctacc agtgtgggtc aagtaatttt tgttcttgga atctagtcaa    3480
acgaacaccc aataggaaga gatcagagaa tcttaggacc caggataagg gcagcactaa    3540
aaataaccaa aggtatcatt tattctgtgt gataaacctc ccactcaccc catcgcgtgc    3600
catcatcgca atagtctggg gaagtgagta ccgttactat ctcatatggg ccatgagaaa    3660
ctgaaagctc agaaaggaac tccaacaaat ttacaagaaa aaaacaaaca accccatcaa    3720
caagtgggtg aaggatatga acagacactt ctcaaaagaa gacatttatg cagccaaaaa    3780
acacatgaaa aaatgctcat catcactggc catcagagaa atgcaaatca aaaccacaat    3840
gagataccat ctcacaccag ttagaatggt gatcattaaa aagtcaggaa acaacaggtg    3900
ctggagagga tgtggagaaa caggaacact tttacactgt tggtgggact gcaaactagt    3960
tcaaccattg tggaagtcag tgtggcgatt cctcagggat ctagaactag aaataccatt    4020
tgacccagcc atcccattac tgggtatata cccaaaggat tataaatcat actgctataa    4080
agacacatgc acacgtatgt ttactgcagc actattcaca atagcaaaga cttggaacca    4140
acccaaatgt ccaacaatga tagactggat taagaaaatg tggcacatat acaccatgga    4200
atactatgca gccataaaaa atgatgagtt catgtccttt gtagggacat ggatgaagct    4260
ggaaaccatc attctcagca aactatcaca aggacaaaaa accaaacacc gcatgttctc    4320
actcataggt gggaactgaa caatgagaac acatggacac aggaagggga acatcacaca    4380
ctggggcctg ttgtggggtg ggggtagggg ggagggtagc atttagagat atacctaatg    4440
ttaaatgacg acttaatggg tgcagcacac caacatggca catgtataca tatgtaacta    4500
acctgcacgt tgtgcacatg taccctaaaa cttaaagtat aaaaaaaaaa aaacttggct    4560
actgtcactc caccgtgtgt attcatctcc taagggagt gcttacattc aaaggggtg      4620 caattattct ctctctctcc ctcacagagt aggaacctga gacacagaaa tgatcagcgg    4680
gctgcctgag atcacatggc taatgaggga tgaattgaac attctcaaat tctcattcac    4740
caccaactcc tcatgtcctg tgctgcccca cctcccaggt gggacttgca ggtcttttaa    4800
```

```
gaacttgcat tcattgacac tattttgacg acagtaaact ggtagcaaaa ttaatgtgag   4860
cacattcaaa tacaatttat tttttaagca gcctgggaga gtggaaaaag cactcctggg   4920
ctcagcctcc atcacctgct agctgtgagc ttctgtacaa tctcttcact ttttccaatc   4980
cccccaatgt ccttccttag attgaaatcg actctttaga atcagcacat tcaaggaggt   5040
aaagtcacag cttgtcttgc agcccaaacc tcccatccaa taggcccatg caaagaacc    5100 cacaggctgg gagcttcgca tcaggcgtcc ttgttttttgt ttgagccttt tctttcaaat  5160
atatggataa tgaccacgtt tggggctaaa cataaagcat tctattcatt aggaccatgt   5220
cacggacttg tggcatgtgg gaaatattac catggctacg aggaggtgc gtgtggatgc    5280 tggcagcggg gagggagccc atgcctgcct ggttgctgct aaacaataag tcaatctgtg   5340
tttcactggg gtgttagtgt tctgttccct ctcacctcct ggagaccaag gatgtctccc   5400
tgacatcaag ctgagcagtg ggaagctgag atatgagaga agaaagggcc tccgggggac   5460
tgtgtgcagg tgatggccct ggagcttcca ttcaattatt ccaccagcat gcaccgagtg   5520
actgccatgt gcaaagcaag ccagcagtaa gctacattct atcaaggaga caatatggag   5580
aaactctgca aggagcttcc acacaccgga tgccctttca tcactcaaag acatagtttc   5640
catgccagtc ttagggcagt aagtgaaagg ctacaattag aacagacgaa tcccaaaacg   5700
cagagcctct gctgtgcgcg aaccatgagt cagcacctcc acggtgcact aagcgtgagc   5760
tggcacctcc acggtgcact aagcgtgagc tggcacctcc acggtgcact aaccgtgagc   5820
tggcacctcc acggtgcact aagcatgagc tggcacctcc acggtgcacc aaccgtgagc   5880
tggcacctcc acgagcact  aaccatgtgt aggctttgaa ctagtctgtt ctggaaccttt  5940 gctttgctca ggaggttttt tcctgttcct tccctgtgtc cagtcctctt gagagaggaa   6000
aaccaaacca tgctgccgct attccctttc ttgataacaa tctgaaatca ttctggccaa   6060
actgggatgg gcacagtgct tttccacatt gactttttt ctgcttccca tgtttaggct    6120
caaatttcta aaacggacca gagatgtaaa agggatattc aagtataaag tcctgtataa   6180
acgtaaggca taaatattat gatcctcatc acttttagga gagtgaggta gaatgatgat   6240
tttaaaaatt aggaacaaag ttacttcttt gatctcttta ttagccactt ctaataatcc   6300
ctgtcccact catcctaaaa cctccagccc cctccagtct cccatccagc cacacacaga   6360
attaccacaa tctaaatgcg ccctttgaat cagacaatac tcctattgct attaataata   6420
atatattggt tagtcaccat tataaagatt ttacaaaata catttatggc atcaccagcc   6480
aacacataac aggttacttt tattaagttg catttgttat ccctgatctt cacaggattc   6540
ttacaagaca ggtattaata tgcccacttt tatggttggg gaaggatgat tcacagttac   6600
ggaaacttgc tcatactcag gaggaagcta agccatcttt ctggcccact accattgttt   6660
gatttcacag tgctggacag ctggtgtcac cctcagaggc cataggtaac cacatccccca  6720 gatccttaac agccaggccc cccgccacca cataactttg ggaaacacgg aagcccggaa   6780
tgcagcccca tgggctctaa tccaggtcaa ctgggtggga caccccgccc cgcgtacag    6840 gcacccccac cccgcccctg ctacctctct aggtctgaaa gccccagcaa taagtctcat   6900 cggaccgag  ctgcgattat ttatgccttc ctttcatctt tgcttcggtc tcttggtcag   6960
ggtgatttct tcatcctttt tgtagaaggc ttcccttgc attagcagct ttgctatagt   7020
tctagaataa atgagcacag gaagaagacg ctgtcatacg ggaccgatcc gtgtccacat   7080
gaagtcatca gatcggtatg ggtgagtggc aggcaaatcc ggtgtgggga agcggcaaag   7140
```

```
cctgaggagc ctgcacttat caaagattaa acactttcag gttctttaaa ggacaaactc   7200
tgagttttcc cagcgtagta tttgagctat ttgagggtct gaaaagatat cacacaggtt   7260
accctgcgtt ttgacagcct ttccttactt taatccaagc ctgtggcaaa ctggttgtaa   7320
actattactg aagaaatggc tctatatttc tattctctct ctctttctcc ctctcttccc   7380
gtttgaaatg aaaacacagt tctttcatta gctcattaaa aaatttactc ctttgtgaat   7440
attttgaaat cacagagcag atatatattt tatatcaaag actccagtga aatattgatc   7500
acctgtgtgt ttcactccct aaattcacca taactgtgcc tacgtggctt gtttcaaata   7560
cacatcttac cctccagttt gaagtttaaa tcattgtggt aggcgttgta cagaggattg   7620
cttttttatt ttctgtgctt aagtgcaggg cagccaaaac aagaacataa ttatatcgtc   7680
agagtcgata agcgcatcaa gcctctatca gatcttgctg ggctcagcaa ctgcctcaca   7740
ggaagtgctg gggagctctt ccgccaccaa atccatttgg ctctatttag gaactaagta   7800
caggaaggta gttattgtac aagattagtt tcctgtaggc cataaattgg cagtagcaga   7860
aaaatacagg atgaatttat tagcgtgcaa ggtcagctag aaggaagaca aggctgagcg   7920
attgcgcttg ttttctttca tttagcccac ctcctggacc tcagggctga aaaagaccct   7980
ctaactactt aattacttct taatagtttt aagcaaattc aaaaggcctg cgcgttgcta   8040
agtgcctgag gtaagagctg cctgggctag gttaggaatg cctgtttgga ctagagtttc   8100
tgaaacctga ctaggcccct tataatctga ggctttgtga gttttctgcg tttttttttt   8160 tttttttcctg ccttatttgg tgttgattgg ccaagcattt actttgaagc tagaatttta   8220
tacttgggaa taaaggagta gcttctaata gtgaaaatat aaaatccatc aagtcaaaaa   8280
tattgtttcc aaccagaggt atgataatgt gataaacatc tctgtagata tttgctttaa   8340
agagaacaag gacagattgc atttaaaaaa atttttttta aagaatacca cttcaaaaac   8400
actcatttaa aggtagccca aaaggtggaa tgacctcctt acacagacat ttctaccttc   8460
aaggagaaaa cctcgctcag ttacctgagc ctctttacca tgttagacac atgtaattca   8520
cattttaatt atactcagca tctgcagtga gttatgggag acccctcctt ctccatccct   8580
gcttccactg ggcctgctca cgctgcctct cctcacagat accctggtgg agcatacagg   8640
gctggatgcc tgaaagtaga aaggcagagt cctctctgtt ccttcctaga agacaaccct   8700
gttttggaat atgctttcct gatttcttag taaactgcag cactttgatg ctgtaaaaag   8760
cctcatgatc agctagcacc agctcctgtc ctgccatttg caaacaaagg gcccagttaa   8820
ccttcactgg gtgaggccat cctcccctga gggcagcccc gaggggtgag aggagcctga   8880
gggaggaagg cccgttcaga gacagacagg gctgctgttc ccggaggtcc aagggatgtc   8940
actgcttctc tattgtggac atttgtccaa gctgtactgt cttgataaaa gagtttgaga   9000
gcatttcgaa agcgcaggtc ttaaaacaga tctccaggtg aatttcacag ccccccttccc  9060 cagagcacag acgcagagta ccccacacag tgttcaggtg cccagccttg ctctgggta    9120 gggtggggggc aggcattgca acgctccgac atttgctgaa cgactgggtc acagtagctt   9180
ggctgatttt ctgttcctgt cactccctgg agatgtgggt ctgaggtgag ctctggcacc   9240
aagcctacct ctctggcatt ggctagagcc tccgtgtcag gccagagtca acctctcgta   9300 accttttccaa agccaattat cacaacacag attcagaaat taagggagaa gttcaaagcc   9360
caaattgtgc cagaaggagc cttcgcaagg cagtctgagg ccaagcagtc gcaggcagtt   9420
tcttcattta ctcaccaggg aagctgaagc ccggcattcc tgaaacaaag atagcttttc   9480
ttttccttcc catgttgttc tgaagtaggt tttagccaat cccaaaaaat ctcaaatcaa   9540
```

```
caaattttta gccctaaata atgatgggcc caattacctg ctctctgcca agcatacgac    9600
aaaaaaaaaa aaaaaaaaaa aaaaaaaaaa aaaaaaaaaa aaacataaca caattcttca    9660
ctgaatctcc tggatttctt agtccaggca ccctcagaga catatgctta gatcctacgt    9720
ctgcttctat agaaaataca aggaacgta gctctggaaa ggagggagcg tgagattctg     9780
agccagaaat gttcctgata gactttgaaa atgatttgga agttcttgct gactatctcc    9840
ctgctatgaa gccgccccga gttagatgtg aagactaaag tggaagcctt cagcagcctg    9900
tcctcaccag cctgctcctc tgtcttccac tctaccctgg gctgcgaccc tgagcagagc    9960
agccagctgc agtgttactc cattgctgga gggctcctct gtgaacccac aggaaggtcc   10020
ctgcctcaca gtgggtgacg gtgcatcctc cacctgctga gtggtgtgac ctccacacct   10080
gctgggacgc atggtggctt gaacctcact gtctccactt tgcccagcag caatcttgcc   10140
tttctccccc cacctcaaga cacccaccac ctacctctgt ggcttcacag ggcagatgcc   10200
ctgttaagtt gtggtgcctg tccccagcac tgtttagggt ttttttttgtt ttttgtttgt  10260
ttgttttttgt tgttttttttt ttgacggagt ctcgctctgt cacccaggct ggagtgcaat  10320
gccaagatct tgctcactgc aacatccgcc tcctgggttc aagcgattca cctccctcag   10380
cctcctagta ggtgggacta caggtgccca ccaccaagcc cggctaattt ttgtatttttt  10440
agtagagacg gggtttcacc atgttggcca gactggtctc gaactcctgg cctcaagtga   10500
tccgcctacc tcggcctccc aaagtgctga gattacaggc gtgagccacc gctcccagca   10560
catgttatta aagtcatgga caccaccaag tgctcagctt cagaacagcc atgactgtaa   10620
ctgttagacc caggaatggg aagaggaaaa agagtcttca gggccaccaa gttcttttgc   10680
tgcaaatctt gaaaggttat cagaagcata aaattgatta tcttcaccca cacccagcaa   10740
ccacacacac gcactcctga cttagggaaa gttatatgct gtcgaagaac cagcggtagc   10800
aaaatgctttt cctcaccagt gagttcagaa aatcctgcat ttatctggcc caaagtccgc   10860
atctcagata aagtctgaac gtgataactg cagaccaaca gcagtcctat cccaaagctc   10920
agtcaaagcc actctcaagc cagagaacag acaggactca gacagggtca gaacacaaca   10980
gtgcaacatc actgaggaag taaacaagtc accaaagaaa caccagagaa attcgtggac   11040
aatattccag gcattaccat gttagggcta gcatgttaaa agacagcata ttgtattggt   11100
gtgtttttttt aaattcttac tgaaaagtta gaaaatgagg aaacaaaatg tggtatatat   11160
ctctttaatg gaatattatt tagtcataaa aaagaaatga agtgctagca cacactcaaa   11220
cgtgcatgaa cctttaaaca ttacgttaag tgaaagaagc cagacacaac atataacgta   11280
tgattccatt tatatgaaat atccagagta cccaagtcaa tcatgacagg aagtggacta   11340
gtagttgtaa gggactagga gtcaagagaa atggggtgtc atggctatgg ggcttctctt   11400
tgggatgata gaacattctg aaattagatg gtgaagatgg ttgccaactc tgtgaataca   11460
cgaacaacta ctgaactaca ctcctttaa aagttggtat catgatatgt gaattacatc    11520
tttatggtga taaataaat gagggcggt ggcagaaaga aacagaaatg aattccctta     11580
tccaatatgt cttcacattg gccttcatgt tgagccactt ttatgcagca atctgagaca   11640
aaggccacta ggacttggat gggtacccaa tgttacaatg aaaccttcaa gaggacctag   11700
tcaactcagt ttcctggcta gctgacatgt ccctctttga gttttagttt taatgaacct   11760
gctaattcca gtgaactaa ggcctctaga aagaactgcc aacttggtca agaccttagt    11820
agtctgaata acgttggcct ggaaaccatg cacgtttacc tattttgtaa caaacccca    11880
```

-continued

```
actcaatgaa atgtgtttgt ctttaactag tctcagggga tttacatttt gccatctata    11940
gggcagggtt tcctggccaa cttgagctgg atttgcaggc aagcagattt cccaacctag    12000
gtactctagc tttgtgttcc cttatgcact tttccaatga ccggatgatg gcaagccccc    12060
tggctcagat ccccaaattt ccacatcagt aaatgttgag aaagaaatta tatttcttaa    12120
ttgcttagaa accgaagaca tacagggaa atggcatcgt gtcctacact cgtggatctt     12180
gaagacatga aacagaccta ataaaataag aatataaaca gacaacagag atttcgtctc    12240
tcccaatcgt caggcatttc agtggatctg tgctccttgt gagccgctct acggtggtta    12300
agtcaaagaa aaaagcaca cttcccaggg cgacaacgga ctctctatta gaacctgtat     12360
agtttcctag ttttcccttg tttataccta gtttcccatt attatctaca aagatgtttg    12420
ccagttccag tccttaatga tccatgcata cattcctctc tgggttctga cctctctccc    12480
ttcagtctca cctctgcatc ctgcctaatt gtggcttatc cttcagcttt gccctgttga    12540
ttcttgatgc caattcctgg agaggctaat cctcaactct ctcatccctc aaagaaata    12600
aacaaatgaa ttccttccac attctgctga ccataatcac tgaaggatgt gcacagcgag    12660
ggctaattgc ttgctggctg gctggttgtt tggttggttg gttggtttgt ctctatctca    12720
gcaatctctg attaattcat cgttccctct tctaaattct aggacctgga aaaaatgcc    12780
tgccacatac gagaaattta acaactatat gctagatgaa tgcggttaa cagaactttg     12840
tggcttaaat ttgagacaca aaactatgtt gtaggctcta cggatcctta aatgtaagaa    12900
ctgggttttt tgtttatttg acttggtttt tgtcccaaca tctctaccca agctctatgc    12960
ttggtgtgcc caagcataga gctaggagac aggacacttg ggcttgaatc ctggctgcca   13020
caggtctttt gatgacctca gatagggat gcgtcctctc agatggacag tcagctacat     13080
agaagcagaa actgacaagg gactcaagga ggaagctcca acttgaattt cagcctaaag    13140
gacagtgcaa tgagtatctc ctggattccc agtttctggg accatgtgtg ctccccacac    13200
ttcttggaaa tcatctgttg atgaatctgg cttctccact ggagtatgag cccctgataa    13260
tgaaggctga gtcttgttta cctccaggcc tgcacatagt aggcacataa tgaacagctg    13320
cagacaagct gaacttcaaa catcatttga aggagagtaa agtctgagtc agatctttag    13380
tatcagttgt ttcctgttaa aaataacatc ttttatttga aaaactgttt caagattgtc    13440
tgccagggta aaagtcaagt caagttcctt gctgttccca gtgtaagaat aacatgagta    13500
aaattcacag tataacccgc tgggactctc agaaatctcc ttgttctttc cttaaggctc    13560
atgatgccat agtaaagact atgaacaacc aatcctgaa ttctattaca aaactaaaaa     13620
taaacagggc agtgctgtgt aattttttaa aggcactatg agtataccag ataaatagtc    13680
tttgttggca gtaggaataa aaacttccaa tactcctgca aagttataag caaaatttgt    13740
tagcttcatt ttttttattt tgcagagcaa ttctattatt attgaatagc atgtgatgtg    13800
gtttggctct gtgtccccac ctaaatctca tctctaattg taatccccct gtgtcaaggg    13860
gggacatac ctggtgggag gtgattggat cacagaggag gtttcccaca tgctgttctc     13920
atgatagtga gttctcatgg tttaaaagtg gcagttttcc ctgcacgctc tctctctcct    13980
gccgccatgt aagacttgcc ttgcttcctc ttcatcttcc accgtgattg taagtttcct    14040
gaggcctccc cagtcatgca gaactgtgag tcaattaagc cttctttctt tataaattac    14100
ccagtctcag gtagtatctt tcaagcagtg tgaacatggg caaatacatc acgccatgat    14160
gataattacc gttttttaagt gcttatgcct gttaagagct gttttactca tattacctca    14220
gtggaactct cccattcctc agtaaggtag ccactggtat cacctctatt tgacaggtga    14280
```

```
tgacacctgt acacagatct ggtaagtgtg aggattgaaa tttaactcag gctgtcttgt    14340
cctagcactc ccacctccac atgaacctct tagcactgcc acaataatca aagcacagct    14400
gtcagagatg gcaacccagg gcaagatgat ttttttattc tacattttgt atattgaacc    14460
tttagagcat taaacagtaa atgccagagc ccaacttata aggtctatga aaggtcaaa     14520 gtctcctttt acttcatcac cactggagaa aaacctaaac aataatagta accaaagtcc    14580
atgtcttctt ttagaagacc aaaattttga gttcctctat tatgagtctt tgatggagac    14640
ctgcttaatt ttctttctgg ggatttacaa caaatctatt ttttttaat tcttcattct     14700 ctgttttgt aatggtttta agggataatt actattttt taaaaaact taatgagtta      14760 cagaacagtg atctctactt aaaattttgg tacactgctt tcactggtaa cagtatgggt    14820
tcgtgctcca accccagctc tgccacttac agaacactgg ggacctgggc caagttattc    14880
aacttctctt tacctcagtg ttctctgtaa atgggaata acaatagaac ttctggtatt     14940
aggctgttat gaggattaaa aaaaattcat atttacaaat tgcttagaag agtgcctggc    15000
atataataag tggctctgaa ggtgtttgtt ggataaaaaa caacttttgt ggtaattttg    15060
ggctggagga aggacaaaca agcaaacgtg ctgagccgag aagactcagg ccgcacacct    15120
cccgttggtg gtgcacatta tagatcctgc cagaactgaa gagagaagct cacacaatag    15180
ggtgaaaagg ctgggcttga agtaaggttt tgctagggag aatcagatta gaactgcatt    15240
tcagaaaatc tgatctggca gggatggatt ggagaaacaa aaaactggag gtagaaaaga    15300
atagccagga gttagaggta caacccatct gtgaatcaag ggaacccaaa ggcagatggg    15360
gttggaatga gggtgaaaca gagagaaggg aatgggaggg ttgggggag gcactggggt     15420 aactctcagg ccgagaattg ggcagcaagg gctcaaggct tctgcaagaa acaggtaaaa    15480
ggggagctca tttgaaagca aggttgagtt caaatgcttt gaatagttta tgtcaaaggc    15540
aagggtgggg gttcaggtgg agatggatac cgtgcagttg aaaacatgga ctagggttca    15600
gcagtcagag ggattaaact ggggatgtgg aagtcgtttg cctagaatga aagttgacat    15660
cttagaatga atgcaattgg cttagattga ggaaagacta gatgagaaaa gagggttaag    15720
ggaaaagcct gagagaacaa catttagggg ttgggaagga gaaaaagaac cagtggaagc    15780
aagagagatg aagcaaaaga gcctcaggat ggagctttcc ggaaatggag agtttccact    15840
gggtcagact ctgcagaaac tgcagaggct aatagattaa gaaagccatc agactgggca    15900
gtaatgtggt tcctagtgac actcagcaag caacgtcagt cattcaagga gatggggtga    15960
gtagatgata agaaagtaga taaatccaag cttcccaaac tgcagaggat aggcctatgg    16020
ttcccaaact acagtggata gatctatggt tcccaaatta cagtacctag ttctcatagc    16080
tttttacggg cacgcttact cccacaccca tctcactggc catgatttaa tcagaagacc    16140
acaaataagt gtaagcaaga ctaggagatg cagcctttat cccagatgat gacgcactca    16200
gctaagcact gagaattctg cacctaggaa ggaaaacgga catctggtag acctcagctt    16260
cctctgcctc atgttgggac agattattta ttaagaaatc caaaagctag gcatggtggc    16320
tcacgcctgt aatcccaaca ctttgggagg ctgaggcggg cagatcattt gaagtcagga    16380
gttcaagacc agactggcca acatggcgaa acccgtttc tactaaaaac acacacagaa     16440
aattagctgg gtgtggtggc acatggctgt aatcccagct actcaggagg ctgaggcagg    16500
agaatcgctt gagcccagaa ggcagaggtt gaagtgagcc gagatcgcgc cactgtactc    16560
cagccctggc aacagaacaa ggctcaatct caaaaaaaaa aaaaaaaat tccaaccatc     16620
```

-continued

```
aatgggcagg aagggataag ggattggctg taaattgggg gatggcaaaa atcaaaagtt    16680
agtcttttgt tttcttttttg ctttttttatt gttttgtctt ttcctcataa tttgggatct   16740
gtctaaatat ataggtaaaa caacagagaa acacagcagg ggtgctactg agaaagattc    16800
ctaaagagat gggaaggaga aactccaatc caaattccat acatgcaagg ttattttttta   16860
agtcttgaga acagataaag taaaaagtgt tgctttgata gactagtcag aaatttaaag    16920
tttctataca tgcagaataa tatatcatat ttgtttcctg acccttctat aataaagtac    16980
cacaaactag aggcttaaat gacagaaatg tattgtctca cagttctaga ggctagaagt    17040
ctgagattca ggtgttggat ctgccagaca gcatggctca cacctgtaac tccagcactt   17100
tgggaggcca aggcaaacag atggcttgag cttaggagtt caagaccaac ctgggcaaca    17160
tagagagacc gtgtctctac aaaaaataca aaaattagcc aggaatgttg gggaacactt    17220
gtggtcccca ctactcagga ggctgaggtg aaggatccc ttgagcctgg gagccggagg    17280
ctgcagcgag acatgattgc accactgcac tccagcttgg gtgacagagc aagaccttgt    17340
ctcaaaaaaa aaaaaaaaaa gtcaccggat ccttccaagg gaaaatctgt tccccgtgct    17400
ctcccagtgt cttctggcct tggcctccct tggcttgtag gtggctgtcc tctctctgtg    17460
tgtcttcaca tcatcttctt ctacaggtgt ctctgtgtcc aaattttccc gttctataaa    17520
aacatcagta atattctact agaggcactc taatggcctc accttaacca tctgcaaaga    17580
ctcaacttct aagcgaggtc acactggtga gtgagcatgg agagttagga cttcagcatt    17640
ttgggggaca caattcaacc ccttaattta agaacagtta tgacaatgtt tctatttaaa    17700
aacaaattcc attgttatat aatttcctac ctaatgctat aaaatcccca atttcattca    17760
ttgaggttct ctataaaaat ttaaaatgta attaatactt ctgtacttct gtcaaacatt    17820
ttatatattt gctttggaaa gtttccttat ccatatacat ctgaacacaa attggcaacc    17880
aattttacta aagccaattt tacataagga cagagaaatt atgttaaaat tcaaggtcaa    17940
cattcaaatt ctgaatctta atcaagagta attatgaaag caaatgttat gtatcacatg    18000
gaaagctgta taggaatgta cggagcagct ttattcatca tcacccaatg gcccaatggt    18060
ggaatcagcc caggcatcct taacagctga ttggtgaaat aaaccatggt acctccctac    18120
tgaggactgc cgttcagaaa cgcaaaggaa ccaagtacta atacaacacg ttgaatgaat    18180
cttcagaaaa ttatgctgag tggaaaaatc taattctcaa agatgacata tgattctttt    18240
tttgtaacgt ttctgaaatg acaaagtttt agaaatggaa gacagattac ggtacccaga    18300
agttagggat gggggaagtg gggtgagagg gaagaggcta tggaattgtt cagtgtcttg    18360
actctggtag tgaatataaa aacttacaca ggagagaagt ggatagaact taacacacac    18420
agagacacac acatacacat gcacacacgt gtgcacacag gcacgtgtac acacatgcat    18480
gtgcacacat gtatacacat gcaggcacac actcgcaaat acacatgcat acacacacac    18540
acacacacac acactactgg cactactgag gaaatctgaa taaatcagt ggactgtgtc     18600
aacgcccata tcctggctgt aatagttcca ccatgttttt gcaaaatatc accatggggg    18660
caagtgggta cctcaagtct ctctgtatta tttcttgcaa ctgcaggtga atctacaatt    18720
atctaaatga aaataattat ctaaatgaaa agtcaattat ctaaatgact atttttgtaa    18780
tgaaaaatag tcatctcgag ccttggcttt atgtattatt aaacctattt attttgaaaa    18840
caatttttat acttttttaac tacagagctg tgatgaaatg caatacaaat attataaata    18900
ttatttttttt aacacatcaa ttagtcacca caaagacaaa aagcagagtt aaaaggaaaa    18960
gtcaaagagg aaatgctatt ctaggaaact aaaatagcaa aacaacatcc aggtagatta    19020
```

-continued

```
gagatgagaa agaagactaa agagaatcca ctcagataga tagatagatg atagatagat   19080
agatagatag acagacagac agattaaata ttaggtactc tggtccttga ttgaaaacta   19140
agattcaaag ccatttattg tgggttcata aatctcccct ttataataaa aactctacct   19200
cattattcaa ttgatttcat tatttctagc agacttataa aggctaaaga aaaaagtagc   19260
taatgttgaa aacccacaag ccttatttac aaattacatt ccaaatagaa attcttttcc   19320
atttatgcct ctgaacaatt atcatattaa atgcaaactt tgctcacctc tctctgtatc   19380
tgaattgtca cattgtctca atcaggttca gcctgaccac cctgcttaag attgcccttc   19440
gcgcatcacc catatctttg ttttcctgtg tgtacaatat ttatgatatt ctaccatact   19500
gcattatgta cttattatgt ctatagttta ttatctgtct tcttcttcca gaatataagt   19560
ttaataaggc agggattttt tttgaagggg cgggggaggc atacgttaat gtacctggaa   19620
catagtaggt gcataatcaa tatgtatttg ttgaatgaat gaattttagg cattctatgg   19680
tccaattttc agtgcaaact ttttaggtag agactaaaaa aggaaataaa actgtgtgta   19740
acttcttgtt gttgttgcca ttgttgcaca gacattgttt ttatggcata aacactcaga   19800
ctgaggcaag aacaaggag tcgaccttgc catccctaca ataaagttcc taagcaccta   19860
taatgggaaa aacagtgtga taaatgttga aaagtatttt aaaaaaccaa gacatggtca   19920
tgttcttggc agtttacagt ccagaaggaa tgccaaaaca catccacaaa taccaacccc   19980
accagctata aaatgatcaa taccataaga gagatatagg caaattctac caaaaaaaaa   20040
aaaaaaaaaa aaagagctga ctcctgagtg gagggcatct gggactggat ttgaggatgg   20100
aatagcactt cagtttatgg agataaggta ctttctggga gggaaccttg tggagaagct   20160
gaagcctcag cccatatggg gagctttgat tggcttagga agcagagatg ggacacgaaa   20220
ggggaagagg taataacggg tccagatgag aaggtccagg gactaaataa ggaatatcgt   20280
acatggtgaa gagccaagac ggtgtgcagt taactagaaa acacagaatt acacaatagt   20340
gctaattgta acctatgaac catagagcca aggttcagca atgggggcat gtgccattag   20400
ggcccagagc agtggtgctg gttgtcatgc tcagaagcaa ggcaagggtc tccaagctac   20460
cttctccaag cagaattgtc tccaggtgtt ttatcagctc ttcccctgcc ctcatcagac   20520
aaggacatca atgatggtct gtgtcgtgga gaccctacat acttcctgga tgtattgggg   20580
ttagatgtga tgggtattaa gggtggaaaa cagagttatg tattcacaac ggagttatgt   20640
attcacatga gatgtgtttg ctgtaactaa ctgcacttgg gttccatcgc agttcaccat   20700
ctctgtttat ttcccgatag agttcaaggc ttaggctcag tctgcaaagt agaatctacc   20760
tggctgttca gatgatgagt agctggggca aaaccttgtc ttctggatac tttaccaact   20820
ttccagccag cttctccacg aatcccaaca ttgcacacaa gtgaacatgt gtttccaaac   20880
acaaggatgg actgtgttga ctgcccatcc tctccagcca cctgtccctc atcctgcacc   20940
agggcatgct cttgtgaaac agcacaccaa ggtcagggg catggcagag ctgtgagcag   21000
gaccagtggg agcgccacat tccaggcaca gggcctaaac aatgacattg gccacttcgc   21060
ccacatcctc cttttggcta tgtgcgatgc aaaaacttaa acaagtttct gctttaaatt   21120
gtaaatgcaa caaataaaaa catttatact aggcttgtat tccagagtat tattttgtca   21180
tctttttgtc aacattttaa gtaaatttca gtaacacatt tttcctttt tataatcatg   21240
gctgattgcg tttttttgg gggggaggcg ggagacagag ttttgactct tgtcaccggg   21300
gctggagtgc aatggcacag ccttgattca ctgcaacctc cgcctcccgg gttcaagcaa   21360
```

```
ttctcctggc tcagcctccc tagtagctgg gatcataagc atgcaccacc acccccagct    21420
aattttatat ttttagtaga cacagcgttt caccacgtta gccaggctgg tcttgaacta    21480
ctgacctcag gtgatccacc cacctcggcc tcccaaagtg ctgagattac aggtgtgagc    21540
caccgtacct ggccctgatt gcttttata cataaaaaca gaaaatttt aaaattagat    21600 caacatacag aaagagcttt aatttggaaa gaatttccaa attgttctaa taactccttg    21660
tataacatga aaaccagatt tataccataa caacgtatgt atttgttcat tttggggatt    21720
ttggaaggaa aggggctttt tccataatcg tatgtcataa tcattgtcat cacccactga    21780
actaaacact taccatgcaa tagttatttc atgtcttcct catagatgtc cgggactgat    21840
gatttattca tcttattttc cagctgatgg aaatgaagtt tagagtggcc aaacactgcg    21900
attacatagc tgacaaacct caggtttatg attccaaatt ctatgctttt ccccaaacac    21960
tgcattcttt gcacatagcc agtgctggtg tgtacacaca catacacata agcacagagc    22020
ctgcgaagtt ctgaacacca agcggttcac tttagtgcct cctccttttc ttctacaagt    22080
tacaagctcc ccccaacgtt atttcaagca gagggtactt cagaactaaa acagtatctg    22140
acagtgcctg gctcaaacac ttccaattcc ttcctagagt aagtaggaaa gcacagaaaa    22200
ggataaaaac acaagcacag acaggtggac ctgtcgatcc acaaaccccc tgccagactc    22260
tgggagatgc tggtgacagg aaaggacagc agacctggac cgggaaacac aatccacagc    22320
cttgtgcaga ggctggaatg aagtgcgcag gcggcttgag ggaggagccc cacacaactc    22380
tccttaccta ggagctggct cacctgaccc actagagcac agcaactggt tttgtgaaag    22440
aaaaaaagaa aagaaaaaac agtgataaat aacataggtt caattgtttt gacagtaaaa    22500
ctcattccaa aatacagcag aggcgtgtgt cctccacgtc tcgccttccc cacagagtga    22560
gcccttcatc tctccaaggt cagtctgttt ttagcccaac gttgcttgaa cctgtcatct    22620
tccctccaat tgcaccatca ctgtcaatgc tcccaccatc acagtgctcc caccatcatt    22680
agccctccct tggcttccta gaaaggtcac cctgctttaa tcttgcacta ttttaatgag    22740
ttctgcactg aaatcaagag tgtcttcaca aataccaacc tgagtctcct ttcctcatgc    22800
tcccatactc atgaggggct ccaccaatgc caacacgtgc ctccttttccc catgctccca    22860 tactcacgag gtacaaagcc catgctcacc ttttttacct ccctccctcc agtccacacc    22920
tggccatctt gtcctccccg agcttggttc agctaaaatag tccctgaatg catcaagttt    22980
gttctcagcc cctcactcat gagctttctg ctccctttct ctgcctagaa tgttcccatt    23040
ccctcggtcc tccttcactg gacttactcc tttttcatcct ttcagatgta gctccaggaa    23100
aacctcccac cacccgtagg caaagtcaga gtgctttctc cactgcagtt ctgaagacat    23160
tccccacacc ccatcacaag cacagttgag ctgtgatcag gtgctcatgt ctcctctacg    23220
gtaaactcct ggtgatggct tcggtcattc cttcaaaagc ttttatgag ccctatccc    23280 acagccagca ctcccaacat acagcagtga agcacaggc tctgtgactt cgatgctcgc    23340
aaataggcaa ttgtataaat aaacaagata attgctgaga atgatggatg cttcacaact    23400
gtagcttttt cttttctatc ccccaagatc caacccatt tttgacattt aaaaaaaaat    23460
gctcaataaa tgtgttagat gaatataaaa tggcaagtac catcgtgatg acggtaataa    23520
agttttgagt gtagaaaatg agtgataaac agaaatacag agaggaggag aaggaggaga    23580
tgaaggatta aggagaaatt taacattgaa ggtttagaga aggttttttc ttgactttt    23640 aagacagtgg caaagggta gaaaacagag ggaagatgac agattcgttg atacattgat    23700
aggaaaaaaa gcagtattga gtgccttctt gaaaagcaaa aggaataact tctctgatat    23760
```

```
gagcttaaaa caggtatgtg aacaggtaga aatgagttgg tagaaaagta acctgaaagt  23820
tgagggggtt tgtcctgatg tatctgtttc ctttaaaaag tcaaaatcac agttgggtgt  23880
tcagtgtgga gggtggggaa gggataaggt aggagttggg ggaaaatgaa aatggtgaaa  23940
gtatgcaatg accgttgtag gcaatgggaa aggcagcttt ctagaagctg aaacaggaca  24000
cccctccccc cagcccctgc cagcagcatc aatgcagcca catccctggg tataaactct  24060
gtgacttccc atggaagagc tctacaagct gaggtgcaga gagggaacac tcgctaccaa  24120
gaaaaactca aagcctgaca ggtctttggg tcatgaaagc aaataaacca caacaggagt  24180
tcacgtcttc agaaaatgac ttgtgctggt gtctaatgat gcctgggct gtggggtggc  24240 aggtgcaagg tcagagccaa aaatataatg cagtttggaa gttttgctcc acaaagcgaa  24300
gaagagtcat tagtttcaac tccaccaagt caggcaaaca cagtatataa gatcatttga  24360
ccctgcttcc agaacgattt ggcctaaccc agcagcctgc agttctccga cttatctcca  24420
ctgtataaaa tatttcctaa tgttttatga cataactaat ctgctagcac tgggctttgc  24480
tcacacaccc aggatcaggt caatccacct gtgtaacagg gcccattcca ggacacacct  24540
gtcatcgccc caaatggtaa ccctcttagg caccccaaga ggaagtgagg gatgggacac  24600
atctaggtca gacctcagca gacatgatta aaaagagatg tgtagttgga cagacagctc  24660
gcacactttt gaaaatggca cgcaggagaa accaccttcc ccttggcttc ctcgcattag  24720
gtttcactgg atctgaataa atgttacgtg gctctctgtg gcccagcaaa tacaaaggct  24780
ggagcattgt ctgtgctggc ctcagtcacc gcctcccttg gaaaaaccaa gtgtgaggca  24840
gagacattgc tcctgtggga aaagcaactt ggcccacagt caagtctaag tttgtaattg  24900
gagcaggaag gggtgggtgt gttttcagca gaggcaggtc aactaggaa aaggtgatgt  24960 ttacttcggg gctggggaaa gcagatttgc tgcgtggaaa gagctgaaat agcagcaaat  25020
gccaccgtgc ccgtgcaagc agctccagcg aagaaagaca gctctatcgt gtttaggcga  25080 aagggggaaag ttaggcaacc gtttggaatt aaaaaaaata aaatccggag cccactaagc  25140
ctgtgtcaac gggcgaaaat gaagtgaagg gttgagaaaa tgaactgggt atggcagccc  25200
caagtccacc atgggacagc cacctaaggc tggacccggc ctctgtgcag gttagaaatg  25260
cgaaaactcc actcagaatc aagcttggag caagcctcac atgcccagca ggggagaggg  25320
tggaaggagg agtgggaggg agggagaaag gaaggaagag gctatgtgga ttttttaaaaa  25380 tccagatgct agtgtagaag ggatcattgt gctttctcca ttgatttact tatgcttctg  25440
gaatttgcca ttcactgcat aattgcaacc ggaatgttat ggtgctcttc attaaaaatc  25500
tcttggagca agttgagcct ttattggagg ctaaatataa atgttgttgg accaaaggta  25560
cagcggtaaa tctggacttt tgtgtgtaca gtgtaatgtt gtggctgaca ttttggggtg  25620
tgaccacgtg gtcaaaatga actgaagcac tgaaacatta tttgggacaa tcagatcaat  25680
ggaaagagct gctcttcatc ccacaggaga aaacaaagtc ggcttaagta aaacctactc  25740
ctccttattt tctgtagcac atttatgtgc ataaattgtc ctgaaataaa gaactcaaat  25800 catattttg attgtcccat aaagccagat gtctaaacaa gggttcttaa aattacttag  25860
ggaatgaaac atcagaaagt tacgaaacat gataaaatat caatgtttac ctctgttttt  25920
tgaactaggg ttatttagc gattaaaagt atggcaacat taaaatcacg caatacaaat  25980
tcacaactat gagcacagct gtccatgaaa atccagctgt caggctaact caggtagcta  26040
tttccaaggt actcggttga gagtttggta cttgttcact gttttctta tcaatttaag  26100
```

-continued

```
tgctttccag cagagaagca gtagaatttc caaagattta agaaaaagtt attggggaac   26160
tttttaaatt gaaaaaagcc tatccctttt ctcaaccttg tatgtgcacc tggaaacgat   26220
cattatctca ctttaatagt aaaaccccag gttcagcctc cagagtacac gttttccaca   26280
ggaatcaagt tggagaacca tcgtcctgtg atgttttttca cttcccatgc tctgtcttag   26340
actatattag aaatgtattt ttagaataca gattttctgc tacaagaatg aagccactct   26400
tatttttctc tttgctctga tttcaggatc tattttttata ttattctatg tacattttat   26460
aagacaccaa agatacccttt ttgaagaggt ataaataagt tgcttaaata caacacaaac   26520
aaaaaacaaa cactaattca ctctaaactc tggagtctag aaatttagca tttaaaactt   26580
ctatttagtc atttatgtaa tcattcattc agtgaataat taaagcaaac taattctact   26640
ccaaacattg gttcagtcct ggttattaag cacataccaa ggatgctgga catagtaact   26700
cacacctgta atttcagcat tttgtggggc tcaggtggaa ggatcactta agcccaggag   26760
ttcaagatca acctgagcag cacagtgaga cccaacaaaa aatttagaaa ttggagctgg   26820
gcacagtggc tcacgcctgt aatcccagca cttttgggaag ccgaggcggg ctgatcacct   26880
gaggtcagaa cttagagacc agcctggcct atgtggtgaa accctgtctc tactaaaaat   26940
acaaaaatca gccgggtatg gtggcatgca cctgtaatcc cagctactca ggaggctgag   27000
gcaggaaaat cgcttaaacc tgggaggtgc aatgagccaa gactgcacca ttgcactcca   27060
gcctgggcaa cgacagtgaa actccgtctc aaaaaaataa taataataaa ttaaccaggc   27120
attgtggtgc ccacctgcca acccaactac tcggaaggct gaggtgggag gaccacttaa   27180
gcccaagagg cggagtctgc agtgagccgt gatggcacca ctacactcca gcctggacaa   27240
ccagggcaag actctgactc aaaaagcaag aacaaaaaaa aaaacaggt gcctggtcac   27300 agagaatttta cattctggaa gggataaaca ggagataaac aatgcaatat gcatttaata   27360
aaataaaatg tcagatgcta gtgttattga aaactggcag gatcaagggg acagaaagaa   27420
aaattcttct tagagtggta agggatggcc ttgcagataa agtgacattt aaacgggaaa   27480
ccgaaagaaa aattcagggc aaagcacaca gctatctggg acaagagcat tccaggaagc   27540
aggaagaggg accagcaggt gcaccggctc tgggcagggt ttgctctta accctcctag   27600 aactaattgg tccacaaagc cttttgtacct tttacacatt taaatagcct ccaaatgact   27660
tcttttatga gataagcaca aagtcaaagt cctttggatt gaacatttct gtctttttcaa   27720 aattccaata tcacctctac cagaaactcc tgttggcttg atctcagatg caagtttcaa   27780
agcattctct ttatggtttc cactaattgt gctcttattt actttccctg caccaggac   27840 aaagaaagat gagctcctgt ggtgttggaa attcactgtg acttcgggca gaaggcctgc   27900
tttgagaacg tacctaattc ctgccaaagc tcatccctgt atttcctcaa aattgttggc   27960
gggtttctca tttgaccgag atttctttga aatcaacagc caggaaaaac aagtaaacaa   28020
gcaagggcag cctcccaggg tcacccacac ttggtgaaca gtagccagga tgggagcacg   28080
caggccgcgt tgtcctccgc aaaggcctgg gtttccatgg tgctaggtct gcaaagggca   28140
gtgttcaaaa tcaagccact gcgtggtgaa actagcaccg caaaacccca aatgctttgg   28200
gtgttggttt tacaaaggat ttacactatg tcgtgggcat agaggttcta cctgatcact   28260
ttttggaata actccaggat gctttccatc tctcactaca aatctcacat cacctctctc   28320
caggcctcag ctgctgtttc tcctaaaaat atggcagtgg gaggggatgg ctgagccctc   28380
tgaagtttta ctaatatcag ggcgcaaaca cttgcctcga aatgacttcc ttctcctgtg   28440
caataacaaa attaataaaa gctcggtggc cactaccaga tagtgacttt ttcatagaaa   28500
```

```
tgtagagaac atcaccataa tccttgtcca actgtgataa ctccaacatt tatattaagt    28560
taagtgattg aggtctgcag tctttgcttg ccatagtcaa ctgtacagca atatatttta    28620
tttcctaatc atgccccag aaaccctgt ctggaatatg ctattggaca gaggacataa     28680
tatgcaaata catcttatcc atcataaaac caaagctaag gctggaagca aaaggacat     28740 ttgtttgcaa ctcagctctt ctcttcagac tccccatttc ccagctcatg ttcctctgag    28800
tgcagcgtct gcatctcacc atcagaggga aaacctccac gcagcagtgt ctttaactgt    28860
ttgacttcat tgcttttcaa aattttttctt aaatcattga aaatatctta gaagtcacag   28920
taagaggtag aatgggcttc catagcatct aatgttttaa ttctttaaaa actatctgag    28980
gcgaatgtgg caaaatgcta agatacagca aagctgagag gtgaggactt gagtgttcct    29040
tagtctgtct tttcgcatgc atatatttaa caataaatac ccaatagtaa tagatatttta   29100 ctaatgaaat gcattagtga aaacatccct ggatgttgtg acttcaacta attgatagag    29160
ctaaatatat ctgcatactg ttttcatgta cagcatttgc aattcatgtt tagacttcct    29220
ccctcctctc cccagaagtt tccaaaaggc aggccacgta attgctttac attatggtat    29280 ctatttttttg ttaattgatg tcttcttgtg gcaggacctt tcttcccgct atcctgagac   29340
tcagcagctg cctgtgggca tgtaacccag tggaggccat cagctggtgt ggtccccagt    29400
ctcagtgagc aagggctgcc tgcagcctgg ggtccatggg ctaaggccct tagctgattg    29460
cacacagact caccagggct tagacacaaa ggagatggat gctgaatatt tcacctgagt    29520
gtcacctgct ttctgttttc ttttttgaact gccctagaaa tccctcctca agaaaattca   29580
tcaaacgaaa ccaaagcagg gtatttctgt cgtctcttct gcttagtact gtcctcttta    29640
caaattgtta gttgtctcaa cattacatat gagtctactt tagggctgtg aagtatatta    29700
ttcaacattg attttttcctt ccttcagcac tggcgaccct ggatcactgg ccactgttta   29760
aatcaccctg tgctggcttc ttctgagccc gttagcacca tgtggtagcc ccagtgccga    29820
tggcatccca gcctgcatcc aggtcagagg aggcgcatgc ttccgtcacg cacgggcaca    29880
ctcctccacg aagaacccca gttcaccggg gctgccctca tgcccataaaa acagaggcac   29940 tgccggccgg gcatggtggc tcacgcctgt aatcccagca ctttgggagg ctgaggcggg    30000
tggatcacca gccaggaggt cgggagatcg agaccatccc tggctaaaat gtgaaacccc    30060
gtctctacta aaaatacaaa aaattagccg ggcgtggtgg cacatgtctg tagtcccagc    30120
tactcaggag tctgaggcag aagaatggca tgaacccggg agacggagct tgcagtgagc    30180
cgagatcgtg acactgcact ccaacctggg tgacagagtg agactccatc tcaaaacaaa    30240
aacaaacaaa caaaaaatac gaaggcactg ccattaggac agagtcagag agagccacac    30300
acctgacatg tggcctctta agaggacaga gacgtgctct gctggaagaa ggaaaacgtt    30360
agaagaggtc agttgccttg cctggccaca tcagtccagt gtggactgat atatatctta    30420
tattccaatt tctttacttt tcaaacatgc ttttagccca gcacagaact gtgtgtctct    30480
ctttacggca gggagggaa agtgcaaaga tgagatcaaa atcaaacatt tcaagattgc    30540
gaggaagagt tggaaattgg tacttttcac ccttctcttc ccctaaagtc attctcacct    30600
ttccctcagc tcacaggcga aaggagggta cctgacaatc ccctcaaggg gaggttcagc    30660
agatacaaat gaggactgaa caaaatatta gaacagttca agaaaaggt gactgcaagt     30720 tggaaatcat aaacatcacg tgttcataca ttacatactc atgcaccaat atttgcttta    30780
aggataaagg cttttcttaa aaatggatca gggccgggca tggtggctca cgcctgtaat    30840
```

```
ctcagcactt agggaggcca agatgggtgg atcacctgag gtcaggagtt caagaccagc   30900
cttgccaaca tggtgagacc ccatctctac taaaaataca aaaattagcc gggtgtggtg   30960
gtgcatacct gtaatcccag ccacttggga agctgaggca ggagaattgc ttgaacccag   31020
gaggtggagg ttgcagtgag ccaagatcat gccactgcac tccagcctgg gcaacagaaa   31080
tggatcagtc gattagagtt cggcacttat tattattatt attatttggc atacataaca   31140
ctgaaagtgt ctattcctaa attctagttg agatgtcttt cagtaactta ggaagccatt   31200
gggaaacaat ctgaatgcaa acttttttcta gagttttttgt ttgccaattt ttcacaatca   31260
tcacatctag gtataactta acagagaaaa gtttgtgact cgactatact ctttccaaag   31320
ttttaacttt acaaaaaaca gcttgatttt cccctaatag ttctttatta tgtatgcatc   31380
ccatatatgt ttatatatgt tcaagtgtac aacaaaaatt cacaaaatac tataaaggat   31440
gtaccttgtg attttccatt ctagcccaag gaagttgagc cagttctatt ctttcaaatg   31500
cagaccacga cccattaaat tgatttaaca acctgcaaat agtcaggctc cccagcatga   31560
aaggcactgc ttcagtagct gtctgtaagc accaagcagt gagggcagag aggagaaccc   31620
ctgagcacct cccataccca ccgactgcat ctcagtgtaa tgtcccaata gctcaggaga   31680
aacatagcaa atgcttaaag tatcaacact actgaaatca atgatgtaat cttttgaactc   31740
acagttacac ttgtctttgt tttgtgaaag catacaaatg tcttgttctc catcaagaca   31800
ggaaaagagc acacagacag cttcagtgcc tgctcctccc tgtgctcaag gttcactcca   31860
ttcttccaat tttttttcctc taagttcaga ggctggcaaa ctgcagtcca tgggccaagt   31920
ctggccagtg cctgtttttg tcaaattgcg tcggaacaca gccacgctgg atttgtgtgt   31980
gtgttgtctg tggttgtttt caagctgcag cggcagagtt gtttgatcgg agaaggtctg   32040
ccacacaaag cccaagacat tcacgaactg gccgaaaaga tggctcaccc cccgcactaa   32100
gtcatctcct agctctgaga aaatggcgat cctctgagaa ctcagaagct cttttccccat   32160
attaaattat ttgctcacaa acttgtttac tgggataaga agaaggtggt attatttcca   32220
ttgccatttta tgcatcagag caaacaaatg atcaagtcag acttagagat aggacatatc   32280
ttacaggttt gaaatgaacc cttttccactg tcttagttta ctttgctttg tttaccacag   32340
taacagagga agaaaatttc agggccctgc aaccatgttc atatttttttc atctcatgtt   32400
tagttctaaa gatatatgta atatacgcat cacactttat actgtagtta tgtttatatt   32460
aaaatacttt aaattgctta ccttcaagta aaacttgtgg tcccagaaaa ctcagagctt   32520
caagaaacca gtgacattaa atagagccat atttcacctc aaagtgccat accgctgttt   32580
gaaaacatgg aagaagaaat ggacatcacc aggaattatg aggaccacct catgcccact   32640
gagggtgttt ggggacagca gctacctggg ctgggatgaa gggaatggtc ttgcctgggg   32700
tacagaaaat ttctgttaaa agataattca tacacgataa gtaagccaag caaaactggc   32760
ctgctttttat cccaacaaga gagtcattcc aaacacagtt agtgatgaaa cagtcctaca   32820
cacacacaca cacacacaca cacacacaca cacacaatca tttgttgatg aaagttctaa   32880
ataattgctc ttgtgactgt tgagttttca ttacatatat ttgggtgtgt gtgtgtgcgt   32940
gcacgtgtgt gcgcgtgtgt gatgggttga aatgcatcgc ccaaaaagct atgttcaagt   33000
cctaaccccct ggtacctgtg aaggtgactt tatctggaag tgggggggtct ttgcagaagc   33060
aatcaagtta agatgaaacc atactgaagt atggtgggtc cttcatccaa agtgactagt   33120
gtcctgataa gaagagggga agaaaaccaa gacaacacaa gagaatgtgg aagatgtgaa   33180
catggagcag agatcaggca atgtgtctga gagccaagca gtaccccgat ggccccagcc   33240
```

```
accaccagaa gctggagaga ggcaggggggc cgattccttc tcccagcctc caaaggaacc      33300
agccctgcag acctccagcc tcgagaacca tgaggaatac atgtctgtta ttttaagcca      33360
cacagtttgt ggtcatttgt gacagcagtc tggcgaaact tatacaccta tgcaagcttc      33420
aatcaattca tttgtatctt tatcacttaa taaacatcat actctacagg aaagttattc      33480
cagaaaactc caagttattc agctgaccct ggcacacagg cacccagccc ccgccttca       33540 tgtgaacgga aggagctgga tggagtaaac tattaacact ggttccaggt gcttctccaa      33600
cccgggggat aatacatatt ctcgcactta aaccttagat tctaaattaa acgtgacagg      33660
acagtgcctg tcaaaataaa ggaacacaac ttgacttatt ttaattcagt catcagaggg      33720
gaccatttgg aagtttgtgc ttaaaatcta aacagtgca acaggggaca aactgcacaa       33780
tgtaatattt ttgtttagta aatgcaaatg tcagttcata aaacatttta ctgaatctga      33840 aaaattttt taaaaataga aatgtataat tttaactgat ttctactcat tttaatatta       33900
aaagaaatat aaatatataa tatatataaa tataaattta tatataatat ataatatata     33960
atatatattt aatatataat atatattata tataatagtt atataataa tatagttata      34020 tataatatat atttcatata taatatataa tatatagtta tatataatat atatttcata     34080
tataatatat aatatatata tatcatatat aagttatgta taatatatat ttaatataca     34140
atatataata tatatattta atacataata tatagttata taatatatat atttaataca     34200
taatatatag ttatataata tatatttaat atatatgtta tatataacat atatttaata    34260
tataatatat agttatatat aacatatatt taatatataa tatatataaa tataaataaa     34320
tataaatata taaatataaa tatatattat ataaatataa atatatatta tataaatata    34380
tataatataa atataaatat atattatata atatatatta tataaatata aatatatatt    34440
atataatata tattatataa tataaatata tattatataa tatatattat ataaatataa     34500
atatatatta tataatatat attatatatt atataatata tattatataa atataaatat     34560
atattatata aatatatatt ataaatatat aaatatatat tataaataa tatattatat     34620 aaatataaat atatattata taaatataaa tatatattat ataaatataa atattataat     34680
aaaatattta ataaataata ttaaagaaag tcattactac tactgagtct tacatgatca     34740
ttactaaaag taattttgtt acgtgcagga gagaagtgtg gaaaatcatc tgtactgtat     34800
atcacatgtt ctgactacac cttagtggga gcagccacgc tgtgagcact ctctcttagt     34860
tattcaacta tgcaaacaca tagcaatcaa gttaagatga aatcttcact aggctttgag     34920
gttgcagaga tgacacaaac atgcaggcac agagtcctgt taagcaacct gtagtgtgtg     34980
cgaacgacca acatgtaagt gattattccg gctctggctc ccaaacctgg ctgggcctca     35040
gagtcaacta tgaatcttgt ttaaaaaata caagcatcca ctctcaaaaa tggtttcaca     35100
ggctcttatc aagtaaaaca tgcccttacc acatgactca acaattctgc tcctgggtat     35160
ttatcccaga taaatgaaaa tatgtcttca cacaaaaacc tgtacatgaa tgtttgttgc     35220
agctctgttc ataattgtcc caaactggaa acagctaaaa tgcccctcca aaagtgagtg     35280
aataatcagc tgtggctcct ccacacaatg gaatacaacc cagcaaggga caaacatgaa     35340
tcaacaactt agatggattt tacaggcatt acggtgagct aatgaagctg acctcaatag     35400
gtgagggccg tatgattgca ctggtatgac agcattggaa agatacatcg gcagtgatgc     35460
aggacagaat agtgggtgct ggcgtcagaa ttcaggaggg tgagcctata aagggatagc     35520
cccaaggagt tttgggggtg agggaattgt ttgtaacctg attgtggtag tgatcacgca     35580
```

-continued

```
aatctatata tgagtcaaaa ttgatagacc tatgcactaa aaagaaaaaa gtcaatttta   35640
ctgaatggct gaagggccca tgcagtagtg cataaagact caagaagcag gtggcagggc   35700
tgtacagagc tagaaagagg tttcaaatgc attctggagg caatagggaa actaaaaatt   35760
tttcctcatg agacagacat gattagatct gggttttagt aggatcattc tgttgacaga   35820
ttgaagatgg attggaggtg gttacatgga agagaaggaa gtcaattagt attccatggc   35880
aagaaagatc aattaagggc aacagataat gaattcagct ctgtacatag tgagttagag   35940
acactcacag ggcattgaag caaagatgtc catgggggtg gaagacagga gtctgaagct   36000
ccggaaagag ccccaagcta atagtaacag tatggtagtt gaatgcatgt gtacagatga   36060
agttgtcttg gatgaactgt atgtagggtc agggaggaaa aaagcagttt gggattagag   36120
tcaagggaa ctgcattatc tggaaaaaaa gaaaaaaaca tatagagaga aagaagaaac   36180
tgataatgtg tagtcacaga ggagtgcttc agaaactaaa ggaagaaaga agaaaggagt   36240
caacggtttc caccectagt gcatgagtct ggatgctatc gtctaactgc acagaataag   36300
caactgggct gtacacagaa tcacaaagcc acaggatttg gccaccaaaa gagatctatg   36360
tgatcgccca gtccaaaccc tcattcaata gctaaggaaa ctgaggccaa ggaagactag   36420
ctggtttgtt tgaggtaaca cagctaatgc acggtaaggc tatggcaggc atccaaactg   36480
ccagattgtt ggaataaaac aattgaattc ttcaacaagt cttccataag aaaatttaaa   36540
tttcaatcaa cacattatcc ccaccagttt cccttacatc cacttatgag agaaaaccat   36600
cttctatccc aacacagaaa agtaagaacc aggatgactg gattcatccc atttatctac   36660
ctgttgctta catcagtaga tgccaatcta cctgattaat ccatttactt tcctctttct   36720
gtccagtagg agaatacaaa cagattttga actacccata tagctcccca aatttggctc   36780
ctagataaat ttatcagata tttgtggtgg aaattctatt tttcctcagc cttgacttt   36840
ctgttttcta ttgcaaaata tttctcactt gctactcacc aggctatgga gagactgtga   36900
ggcacacagg atttcctaca aaggggcca cttcccaaa cttcctaatg gcttaacaac   36960
tagaacatat aacttttaa aaatcttaca cgtttcaaaa atgtacaatt aattcattgt   37020
aagaccaaca ttattctttc cagaagggtt aaatgtcaag catttcagct ccaaatttt   37080
ggctcatttg attcttctg agtaaatctc agttaataaa aaaatacac aatgcaaaca   37140
tgccaaaatt gctttctgat ttagagattc cttaagaatt ttattttgca tagtaaattt   37200
ggatggaaat ttgtctctaa aaatatagca agaagataaa ctagtctaga actaaagcta   37260
tagacattta aatgagtgtg atgctgtgaa aatctttctt ggataagaga aggagtgtga   37320
aaagcaaaca aagacggcag atcaataaca tgggaacgag agaaagatct ggcgagttct   37380
gaagtagcca ctggaatggg caagagggtt catgagcaaa cttgggtcct ggcggaagtg   37440
gtgtgttagc aggacattca tacgtgagta ggtgtcagag gcatagaaga gaagttcatt   37500
tcaggataag agaagaatgg gctgtgaaaa caaaaggtat atttttggaaa gctcagtgac   37560
acacagctca taaataagtg gaagatgagg caggacaggg tgcagacttg tgtcatgttg   37620
ccagaatttg ggtatgtctt taaatgcact gagagtgtct gaggttctag aggagcggta   37680
tgattctacc tcagcttctg gaaaggggtt ccagcaacag tgtctttgta aagagaccat   37740
cacaaaaaga tccaagtgaa ggaaatgggg gcccgaggca gtcatgtgag tgaggagagt   37800
aggaaaagaa ggcagagaga aggatttggg agatatttca gagggagaag caagaggacg   37860
tggtataggg gaagggtcag acaggtccgt gctagggatt gacgtcccgc gggagaggct   37920
gacgttccta cccggcagct gggacagctg cagttatcag cagctcaaat gtgaaataca   37980
```

```
ggagaaaagg cagcagggaa ggaaggccca tcagattagg gcacggtgag ttctgatgac   38040
tgcccagatg tccagagagc ctttggaaat tcaggccttg ccattcatag aatgacatca   38100
agatgtaggt ctatcactcg aaatcagcag gtttgaaatt atcagagtgt aggaggtttg   38160
tctagacatt tgctttaagg ctttggcagt ggaagaaaaa cccaaaatac actcaggagg   38220
agaatatggg gtagggagac attattttt aataactaat tacaatccct ggcaagagtt   38280
ttgctggtaa ttttacttcc tactgtggtt gctatccatg gatgtactat acatataaaa   38340
gagataatat caaataactt gtttctgtga catactaaaa aagaagtat gaaaaatatt    38400 ctacctcatc taaaattctg ataccttcat attttggaaa ggcacatacg tattaaagta   38460
tacaactgtc aacaatttgt aaatattcca caccaagtgg ctgctaggca aagccttacc   38520
ttgtgttgat atgacatctt ttatttcttg agtcctattg caaaaattta aaagatttct   38580
cgttatatct ttttcatgtc gctcacactt tccaataagt atgtgccaag cttttattct   38640
tcaaggtcaa caaaccctgg cttagccatc ataatcaatc aaactgcatt tttacaaatg   38700 taagttttcag ccatctgata aaatgagcaa ttctgcaatg ttttgtggtt ttttttatttc  38760 cgtttgaaaa caactcattt tagaggaact ctgttccctg tggttcttag tcatccttat   38820
cccagaaaag agtaattttt cagtgtccat tctcactaac tctggaatat attgtatgat   38880
tagctaactt tgaacctcaa atacttacat taaaagtgca gaaaccatga tggtttgaat   38940
agttttgttt tgtgatttag aattcaagta gagctggata ataactgaca acataaaatg   39000
tggaatccac aaagagtcag tatgattcaa agttcaccat tctaattcaa ataaaatttt   39060
aagaattaaa actgatgtcc agcccaatat agaagctcaa gcaaattcaa atggctgatg   39120
gaggagctgg cttggctcca attttttctat tcctcaagtt acttttgaga aaataatac    39180 atataaatga aaacataaca ttactggaaa agagaaaaat gaaaatagcc atggaataga   39240
aatgttgaaa gcttcttccc aagcaagcct agaaaaagct ctgagagcaa agtcaaggag   39300
gcaaagacct tgccatgagt caaacattag ggcgagagct ggaacggctc actacagctc   39360
ctaccaccaa tcccccaaaa tagagtcgaa aaatgacggt cggagaaatt gtttctccca   39420
aagacaaagc ccaaagacta gttttttaaag aaaattaatt tgtcggtgaa cttacagggc   39480 ctaaagaag cacagcagat cttcgccccg gcaaacccac aggggcgctg tggagttttct   39540 tcattttga gagaaacaca acctcttgga catccatcag cccctccatg aaacgtctgc    39600
tctagcaaag ccaccgatcc aaggctcaag agcgctactt tactttccac gaggccctgg   39660
ctggatgttc agcaggtgct ctgataaaaa gcaggccccg tatgaaaacc agcagggaac   39720
agaaaacgca gcagggctct ccaatctcat gccaaggtag gtgaggctgt gctgtcccca   39780
gcaggcgcgt gcagcgctgc taagtgatgg gaatttcaga gcaaaagaaa agatgggttg   39840 tttttttgttt tgttttgttt ttgttttgttt tttcttaaa ggtatatgta ttggttttc    39900 aaacagttac taagttgtta gggcatgcat aattatgtcg tttggctcta actacttata   39960
cacagaactg ttaagaagtt gctctggcct agggccactg taaaaaaatt actgaaacaa   40020
tgatagagac ttgaaccaag aaagcgagga agtctctgtg ctgtagttat cggctctcag   40080
gaaagaaaaa ccctcctggc ttggcagctg gcccaggagg ggcgtgggca ggaggaggtc   40140
cccaggctgc tggatagttc ttcctgctgt tggagcctca tccacagaca caggcctgta   40200
gttagccagg cagggaggag gctgagcagg aaacagatgt gcctggctgc aaaggaaacc   40260
cacaagcaat caacccccatc ttcattcata aaaaagaacc aaatcaagtg ccacccaata  40320
```

```
caggaggcaa ataccagggt ggaggataat gtgaacaaat aaaacagctc acctgagagg    40380
aaatagaagt aataataata ataaaaatcc aacttgatac tgagagatta gagaggaaat    40440
tgcacccata aaattagaat tagctacaat taggaggagg aggaggtagg gagggtaagg    40500
aacagggaat aagaagataa cagcacttac gaaaaaggaa gaggtatggt aaataaaatt    40560
taactgacaa aatgaaaatt aaatggaact gccaagctgg ctgtccagaa gaggggctgt    40620
tccaccatgg agaccaggca gctagagggt cgagccaaag aaacctccca gatctaaaag    40680
gaaaaataaa cagacgaatg aataaaaacc taaaagtctt gcaagatata ttcaggaggg    40740
tcaaactaat agagactttt acaaatagag aacaaaaata ttagaaagaa atactaggag    40800
aaatgattga agcctctttt ctggagctga agttccttat acagtgatcc actgagggct    40860
gtgtgtccac ccacaggtcc cctgataaaa cttatagacc ccaaaataaa agaaaaactc    40920
taaaagctcc cacaacacag aaggggacaa catgctgtgt aggaaccagt ggctgccatc    40980
agaagctaag aagacgcaca aaggttgtga aaaaggtccc gcagatcttg gccttaggtc    41040
acgcttcgag tagtgggagt tttggtgaca gatagcgttt cccttgctac aggtttattt    41100
attcaccttg tttcaaagag aataaaatat gcataattat aataccatgt gctgacgtgg    41160
agggacatcc atcacatgaa aaacaagttg caaacaaat ggataatagg atcctactga    41220
gcttaaatac acatacacag gcacaactag acaaataggc agatagatag ataataggta    41280
ggtaggtagg tagagagaga ggaatttaaa aatatctaga atacgtagca gacagctgag    41340
attggggagt agaggaggtg aagatgtttg cttttaatct tcaccacttg atactctcat    41400
tttttaacag agtataaatt tcttttgaaa ttaaaaaaat tatcgtactt ttagtggaat    41460
aaaagcagca tcaggcacat agtaggtaat taatcaatt ttgttaaatg aatgcgtgaa    41520
tgcaaaatat atgccttct accatcagaa gtatagctct attcaaactt tcttcagtat    41580
ctcctgtagc actgacaaat taagttttct gtctcttctt aagtcatatt tggtaatata    41640
ttttcctaga aattcattca tttcagctag atatcaaaat ggattatctc atggctgtgg    41700
actgcaacct cctttccata ttgcttgttt tacataagaa acacatacat attttctttt    41760
tgaaaccctg ttataaaagt actcgacaaa ttgtattagt cagttttcac actgctgata    41820
aagacatact ggagactggg caatttacgg aagaaagaga tttaatggac ttacagttcc    41880
acacggctgg ggaggcctca caatcatggc ggaagataaa gaggagcaag tcacacctcg    41940
gatggcagca ggcagagaga tcgatctggt gcaggagaac tcctctttat aaaaccatca    42000
gatcttgtga gacttactca ctatcacgag aacagcatgg gaaagacctg cccccatgat    42060
tcaattacct cccactgggt ccctcccaca acatgtggga attcaagatg agatttgggt    42120
ggggacacag ccaaaccata tcacaaatgg taactcaatg taattttttt aacagcacta    42180
tgagccgtgg gaatccaagg catgagacaa gaaggctgga cagcgttcct ggatcacaca    42240
gctgagtacc ggtgaagtca acccagtgtg cctcggctaa gggactgctc tcaccactat    42300
gcctctcccc agtgtcctga attctaatgc tgaatatttg tatgttctct gcttttctct    42360
tagccttcca aagatttgtc atcagtagta tttaatatca aagaataaag gtttgaatta    42420
ctatatttgt tatagttttt caggttctaa gtcattaatt tctactatat cttcgttttc    42480
ttactcatgt ttttgttggg ctttttaaa ttattttttg cttctgcagt aacatggata    42540
tttcatttgc aactttctta taaaaacctt gaaaacttac aaagttttct cctagcacaa    42600
tgtgggttac attccatata ttatggcatc ttctaaacaa tctctttatt cagttttaat    42660
tttctctatc attttctttg agttaacagc tcatggatta ttcagggagt attttttagtt    42720
```

```
tccacatggt tttagatttg gtgttaaact ttttattact taaattctat tgtttattgt    42780
caaaatatgg cttatgggaa tgctttgtat tgagcttttt tttgacacag aagctataat    42840
caatgtttaa ctatacgatg cacatttgaa gacattttct ttaaagaaat actgagtaaa    42900
taaaacatat taattattca gttctctgta aagtttatgt acataacata aaaagtagag    42960
atattgttaa gtagcctgtt aagactgtgc tttgccagtt tcttattgca tttataacaa    43020
cttttatgtc ttttgatgct gttatttggt ttttaaacat ctctggctac tacattctca    43080
taataaatta tactttagaa aattaatata aagtagccct cgctcattcc ttattttctc    43140
tcaagttcca ctttgtatga tattaatatt gcactttggg gttcatttta tttttgtct    43200
tacatttaag aatttactca tctattttct atgtcatttt gcttcgtaca catgtatgtg    43260
tatataaaat ttaatatgac aatatctttt gtaaaggaag tttgacccat ttatatttac    43320
tgtatattat catgagtgat cttcttgata agagttctga aacacacaca catattactt    43380
ttggcatcat tcactgctat taacacaggt atatgacatt ttaaaaaata aatcaccctg    43440
atctaactta aggcttcaaa tcgttcattt atacatttgc tccaggaata ttttgtaaag    43500
tctctattac atcatggaat tgtactagcc actgaaaacc ctttggtgaa aaagatacat    43560
atgagttgcc atcttgaagc ttaccttcta aaaatactaa cagcaggaca acaatgcaaa    43620
tctgtgtgct ttctatccaa gggcactgtt ctctctgctt tacttacttt attaaatttt    43680
cacaactaaa tgactttcta ccaatgagca aattgagaat cacagagttt taaaaacata    43740
cctattgtta tctactttgc atgtggtaga tccaagttgc taatgtatat ctgaacacag    43800
agccggtcac tatgaacatg ctacccacca acatgtgctc tctctctctt cgggctccaa    43860
gctttcata acgcttccag gttgccaaac cgtcaatccc agccactttg aagacccctc    43920
ctaatgcttc cctgccattc acaactacac cttgtggtga ctgaacagct gttctgtttc    43980
gcttcaggct gttttcctgg gaaccaccag ccattcctcg tgcccactgg gtcttactct    44040
cactggcccc atggaccccc tgaggttgtc agtgacttct gttgggttcc aggtacaggc    44100
accctttgcc acagagatga cctctggaat gttctcagcc tccttccatg ccctccatgt    44160
acctgtggga atgtcttgat gctttccatg ccacagtgac aaggacagca agctcagatc    44220
ctcactctac ctatttgagc tgtgcagtca ctagcactgt gagaagacca ccctgaagtg    44280
ccggagcagg ggcatcctac aaggccgtat tgtgcactg cccctctgcc cttgacaggc    44340
gaccctccat ctttctggat ttttgccatg cactcccacc ctcaccccac atcctgccca    44400
tcaaccttga ggagaaggcc ccacacttgg cgtggacagg acctggcact gtgctgcttt    44460
acactctgct ttgccttccc tgccccatgg tgtggcaccc gacaggccat ccctcttctc    44520
tttctgttcc accacacctt ccagacacaa aactctatga tcaattacac tttgcctagc    44580
tttgaatatg ccaaaaaggg agcttcccaa actgggaaat attttttcttt ctctacaaag    44640
cttggccttc gggcctcgtg tgtttctgtg aactcagata gcttcattag catgcagaac    44700
ctgcccatcc ttccccgtat gagtaaaccc gctgtctgca tcctggcagg tcaccctcct    44760
ccctgtaggg caggaggctg cccaggttgc gtaggagaag cccatatacc gggaaatgca    44820
aagcataaaa ttcatcagt gtatctcaaa actgtttgcc ctatttcgta acaactcgag    44880
aagtacatgg cacggtgaca tcaccaaaga gaatatttgc ctactttgaa actgaaaaaa    44940
aaagattcct gaaggagtaa tgctcgaggt gagttttgaa gaaccatagg aagcacctgg    45000
tggaagagga agttaattt ctttccgggc aaaatgaatg gtgtctgcaa atagccagag    45060
```

```
gccacaggag catctgtgtt taaacaactg aagaaagccc acagggctgc agaacgaga      45120 gagaacaaga ggcataagga gatgccagac agtgggcttt ggcagggcag ggaaggcttg      45180
cgtttgtcag gcgtggccat gtctccctgc tctaaaggga aggagaggaa aaatgggagg      45240
ggccggcagc ggatactgtt gcggcagctc tggcacagag cacataagat tacaaaatct      45300
gatgcctgct agggttggtt tcatgcccct ttcagctgac gcactcatga tccacaggct      45360
gaaggaggca agggttgtga gccccaggtg ccagctctgc ccaaggaccg aatcccggct      45420
cccttcctgc gttacccccac cttcttccaa gcggccccac cctcaactgt ggaatttaat      45480
tctcccagaa ggcctggcac ggtggcttac acctgtaatc ccagcacttg gggaggctga      45540
ggcgggcggg tcacgaggtc atgagattgc gaccgtccta gccaacatgg tgaaaccccg      45600
tctctactaa aaatccaaaa attagctagg tgtggtggcg cacgcctgta atcccagcta      45660
ctcaggaggc aggagaatca gttgaacccg ggagttggag gttacagtga gctgagatcg      45720
tgccactgca ctccagcctg ggtgacagag tgagactcca tctcaaaaaa aaaaaaaaaa      45780
attctcccag acatgctcag agccaaagca agcaaaatga gggtcctcca ctgagtgatt      45840
ctcctgcacc ctccttagct gtccaccaac actgcctcca gttgtcccaa gcctgaaatg      45900
cacttgagaa cacgtcctca aatccagtgg aaaagtctac attattttgg gagaacagag      45960
catcagacag agctcccaac cccaccgctt cctgtccttt gccttgagga cctccctcag      46020
ggtagggggg cctgtgggcc aggagtgggc agcccagccc cttcgatttc acaactgcct      46080
ggtttcctct ctggtggaaa tgcacaggtg gtgacaaaac tggatgaatt tcatcttctt      46140
tactcttgtt ttagagctgt gagttcgagt cagttacggt gtgtgactta ctaacccatg      46200
tttgcatctg tgtgcttctg atcttcacac acgctgagca cattagggc gccttcctgt      46260 ggaccgggcc ccacactggc aatggggcag gcgcacagtt cctccaaaga acctcacagc      46320
tgtgccttgt cctctgagaa aaggtgtcag ccagttccac tggacagccg gcactgtcag      46380
aaatcctacc ttagcagctg gaccaaggtc tcaccggaga agatgtgtca attcaatttc      46440
aaggtccttt tatacaattt aatcaaaggt catcattaga aaaaaaaatc atgattaaga      46500
aacgaataaa attcaagtca tactgttacc tctgttttaa acaaaacaat gtttctttac      46560
atataaattt ttatttcaaa acatttgatc ccaggaaagt cttttcacaat aagtgagttt      46620 ttagcagacc aggagagtca tcagtggata agagttctgg ggtgaaggtt ttcacaaagt      46680
gccctagatt gttgatgata tttttaatcat ctatccttgg aatacaatgg acataaaatc      46740
aagaagtgta ctgaaccttg aatgaaacag cagaatgaac tctgagtccc agaaaacacc      46800
taagaactaa gaatgcgttt ttaatgctca tgaaaaacaa atggcaatat agaatgtggg      46860
actaaagaat ggttacttga agccagaagt gggtgttctg caggtgaaac ccaagcgcgg      46920
cccctcccca aggctccttt ctgtgttgtg agtgccccac tccccaggga cagcactttg      46980 ttttcttttca gcttttctga catcatatga tgcaacctga tgcaaagcaa agcgataggc      47040
atcttgtcac aggagaaatt cacagagagg agggggcac gctgcagctg gtgcggaaat      47100
tctcaagaga ggcctgggag tggagctgag ccgttgcaga ggaaggtgga gaacctcttg      47160
agaagttcat ggacacatag cgtggttcag aagaaaagtc aggttccagt gattgaagaa      47220
aaaagcgaga cattattgca ggcaaggatc tccatgttgg gatacaaagg caatgctgat      47280
ttcaggatat ctgtgtacgt ctgtgtgtca tgggaaggga ggctgcagtt ggacacgaat      47340
agaacatctg ctcaggacga ggacacgtgg gatcacatcc tcagagcccc gtcgtcttca      47400
gagcccttct ctaggctgga ggcagtgagg acaggatggg agtgtctcct cccttccctg      47460
```

```
tttcccaggg agcatggcca gcttggtgac tgtcacagca ggtgagcagc aaactcccag    47520
gccagcaggg aggggcgact gtgagcagaa tgacagccac atggtaggtg tgtactttag    47580
agcaggggcc tctcctcgag gttacccagc tcatgcccc agcagatagc ttggtgggag    47640
tgctgtgcct gaccctccca taacctacgg agcccaggtg gggagagtca ctctccagat    47700
cttacataaa agatgtagca cctcacacac tgctgttaca gagcagataa taaatattca    47760
tgatatgcaa ttgaatagtt atttaaaatg tttatctatg gatgaatgaa tgaactgaac    47820
aaagagcaaa atatacagac aagtaaggtg tcacaaagct ggctctgagt aaccagcctg    47880
ttatcaaatt catttgtaca gtaataaaag aaaacatatc ccaccagcca tgtgccaggc    47940
actgacatgg gagcttcaca catatgaagg cgcagagcaa tcggcacaat cctctgcttc    48000
atggaagagg aaacaaaagc cccaagaggc tgggccggga gcctgaggcc cagcggggcc    48060
agcttcgggc cacctcactg tgtttcaagg cccgccgtcc atcactgcgg ctgtcacaat    48120
ccctgtcttt tcttggttgt catatttgct tctcacctca tcatgtctat tttccatgtg    48180
gttcaagctt ttaggttaca tggctaatag gttaacccaa ataaaccaca ttatggcttg    48240
tttattgctc tctgtacagc actactaaga cgggtgttaa acccaacttc ctcctcgtga    48300
aagaacacct aagcctggaa acttcccact tcgctgttca ttataaggtt cgaaaaacac    48360
aaactccatg acagtgcttc agaggtgctt tccagcagct ctaggcacaa ggagtactat    48420
catttgaggt tttcaggatt ttatgttaga tgaagcagag ttagtaaaat cattttaaat    48480
tttcttctaa agaactatca agattgtaag gacattcaaa aacaaatttt atgtacatag    48540
tactaataac atccacgtat ttccaaacat ctaaatactt gaaattgtat gtaatcagca    48600
agtatcatag tataccttta tcatgactga taaaaccttt ggaagctgag taagtaattt    48660
tcaaaaatta ttagttcctg aaagaccctg aaatctgttt cataaattgg aaatgaaatc    48720
tagctattaa ttcaagatcc tctagataaa tcatacccctg gcaccttga aagaatcaaa    48780 gattttcagt acttttttcc acatactcaa ggtataatat tataagacaa gaaaggagat    48840
agactgaggc ttccatttat ctactactca ttaatcattt attgagcatc tacactgggt    48900
cagatattat gttaggtatt gtggatacaa agatgaatga agcaaacttc ctgtccacaa    48960
ctcattgtaa ctagagagaa taattttagc aggggagaag tagaattgta agttgggaag    49020
gcagatttga acaacagtgt ggtaaatctc aaatattaga ctaaaggttt tatcctgtaa    49080
ttattggaga atagggaatt atttggaaaa taaaattaac ataaaagaaa taattaaaaa    49140
catactacca gcgccggaag tagctttaga gcaggggtcc gcgagctcca gggcatggac    49200
tggtaccagg tccatggcct gttaggaact ggctgcaccg cagaagatga gccacaagcc    49260
acggggagca ttaccaccta agctccgcct cctgtcagat cagcacttgc attagattca    49320
ggaacattgg agcacaaaca ctattgtgac ctgtgcatgc gagggatcta ggttgtgcac    49380
tccttatgag aatctaatgc ctgatgatct gtcactgtct cccatcatcc ccagatggga    49440
ctgtctagtt gcaggaaaac aagctcaggg ctcccactga ttctacatta cggtgacttg    49500
tataattatg tcattatata ttacgatata ataataataa aaataaagca cgcacttgaa    49560
tcatcccaaa accatctccc cacccccagt ggtctgtgga acagttgtct tccatgaaac    49620
cagtccctgg tgccaaaaag gttagggaca gaatatccag cctctactct catcccctct    49680
ggactggagc cactttatat ctagaaaggc gatttatttg ttttgttctc tgcagtgcct    49740
ggtagaaagt aatccactca atatatgttt aataaataaa tgaaagaaac aggaaagtat    49800
```

```
aaacccaagt aactgattta atgacttgcc tgaggtcacc ctgaagtggc caaaccccag    49860
gttccctgtt cagctatgac cagagcccat tcttcattca ttgttaaaca taaactagat    49920
gttttatcca cacagagata gctatctaga gatatgaact tccagaaagt tgaccgtatt    49980
ttttgtttac atgtggatat ctgatatctt gaaaatatac acatttagtc attaagttta    50040
aaattaaaat ataggcctaa aattttttgg agccatactt ccaataataa tattatatgg    50100
atgcacaagc tatattacat attaggaaaa acaataaagc cccaaaccta cagatttctc    50160
tctctcacac acacacacac acacacacac acacacacac acactgctca ccaagattgt    50220
tgattctcca gttttccaaa cactttgttt ctctactgta gctctaggtg aaacaagact    50280
gatcctgagt ttatagctgc tgaagctggg tgatgactcc atggcttctc attagaccat    50340
ggcctcttca tctgtatatt tttcaattgc ccattaaaaa atgttttaa attgagagcc    50400 aaaaagagt atccattaac aaataaatgt atcattcagt cggcttattt agcagcagtc    50460
agaagaaaac tccttctgaa ctgagcaggt caggcatcta tatagaattg tttcttggca    50520
gatggctgag ctgtccagga gtaccaaatg taggcacctg cccaaggtaa cttaggaggt    50580 tttccccctta gaagggagag agagagagga ggatggagaa cgtctctgca atcccttata    50640
tcttattgca taactttctg ctgaatggag agctgcctgc ttgtttcagg gagaatgtca    50700
tttttttata cccaaaactt aaaaaacaat attgttatgc agaaaagatt taaaaaattt    50760
ctagagttgt aagtgaaaac taaattacta ggaatcattc atcaaatttt accaactcta    50820
gattctgatt ttattttgt atgtgtgcca aaatagatgt ttacccatgg gtacagatca    50880
caaccaattt gcaagagcaa gtgggaagaa agctgactac tccttcacct ctgctgcact    50940
tcctaagttt gaccattgat atctgaagat agaagtcaca tgtgcatgtg tgaatataaa    51000
atataccttc ctcaattaaa tatacaagac aaagccactt taggaagcat attctcagat    51060
tgttggctgc agtctttgac caacccaaat aaagattaga tagttgtaac tgtaagagct    51120
gaagaaactg aaaactgagc atatttcctg aaattgtgag catagttaag tgtcttcact    51180
ttttcagaaa aactgaaatg ggatgaggag acaaaacccc tcataaccta aagctctgtt    51240
attttttttt tttctttttt ggagatgaag tctcattctg tcgcccaggc tggagtgcag    51300
tggcgcaatc ttggctctct gcaacttctg cctcccgggt tcaagcgatt ctcctgcctc    51360
agcctcccaa gtagctggga ttacaggcga gcgccaccac accagctaat ttttgtattt    51420
tcagtagaga ctgggtttca ccacgttgtc caggatggtc ttgatctcct gacatcgtga    51480
tctgcctgcc tcggcctccc gaagtgctgg gcttacaggc atgagccact gcaccgggcc    51540
ctgaactata tacatttcta tctgcacatc taatgtctag tatccgctga ccacagaata    51600
aactcaataa atgtttgctt tgaacatat aaatcattgt tgtttataact ctaattatat    51660 gagaataaat ggaagatact ggcataatct atatacatat ttacatatat aggtatatgt    51720
catctataca ttgttcatac agatttgagc agaaaacctt aatgagcgaa ccctgacaca    51780
tggttgcttc agctttaagt gtgtccaaat gtctaagaaa atatggaata gaatttgtaa    51840
tagggtttta agatcaatgc ataaaatatg tcactatgtt tatgaaagca tagaccgcct    51900
gagctgtaac aggtacagag ttctggaaat atgaattctt cctttcacac actattaaga    51960
tgtcctgcag gagtcgaatc gttttaatgt ttctgttctg gatgaaataa gccacattta    52020
cgcagctaca atctctagct aacacagatg agtaataagt tttaggccga aatgattgtg    52080
atgtgatgct ttcaagtgag gaagtgccgt ccagagtcac tggctctcag aattggaggg    52140
aaattcatgc agtggggaag ctcacagagg atctcgctaa agactgagtt aaatggcctg    52200
```

```
gaactcaact tacaagcagg ttaaaaaata acaaccttcc ttccttgtct agctccttta    52260
agtgaagtat tttctatctt ggaggcctct tttgaaatgc aatactcctg agagtggtca    52320
caccttaagt tatcagctaa cactttccga gggattagca gacagccggc agagaaaaag    52380
aaatgggatt taggcaaaat gcctgagggc tggaggggag acactgcctg agaaaggtt    52440 aactagtctg ttgatttgct gatagacaaa tttcacgtac tccagagcat ttggtctaca    52500
gtggagactc ccaaattctg gattctataa caccaccaaa aagcctacaa tttcccagat    52560
tatcttgcaa gcaacttaag tctgcatgga atacaaacaa aataaaccca ctattggcct    52620
ttgtataatt gaaattatt aactttactt agaacatatt caaattattt ctgaggattg    52680
tttatataca tgagatcaga cttttttaaat tataaatgca ttttaagaag gtaaaggaca    52740
cagtaaaaat atagcaagtc ttaataagcc tacacagtga aaactcatca gattcttcta    52800
gattgcaact aagatacact acaaaaaacc ccagatgggc caggcacggt ggctcacgcc    52860
tgtaatctca atactttggg aggccgagaa gggcagatca aaggtcggg agttcgagac    52920 cagcctggcc aacatggtga aaccctgtct ctactaaaag aaacatttct gttccgtatg    52980
aaataaacca cactcacaca gctacaatct ctagctaaca catacaaaaa ttagtcgggc    53040
atggtggcgg gcacctgtag tcccagctac tcaggaggct gaggcaggag aatctcttga    53100
acccgggaag cggaggttgc agtgagctga gatggcgcca ctgcactcca gcctgggcga    53160
tggtgtgaag ctccttctca aaaaaaaaaa aaaaaaaaa aacccagatg tgccctgcct    53220
taggattttt tgacttaaca atggcacaaa agcaacacac atccagtgga aactgtattt    53280
ccagagctga aataaccatt ccgtgtttca ttttcaagag gctgttcagt caattatatg    53340
agatattcaa ctcattatta taaaacaggc tttgtgtgag gtggttttgc ccaactgtag    53400
gctaatgtta agtattccga acacgtttac ggtaggctag gctaagctat gacgtttggt    53460
aggtgtattc aatgcatttt cgacttacat ttttagttta caatgggttt ataggaatgt    53520
gtattagtcc attctcatac tgctataaag aaatacctga gactggataa tttataaaca    53580
aaagaggttt aattgactca cagttccaca ggctctccag gaagcacggc tcaggaggcc    53640
tcaggaaact ttcaatcatg tgcgggcgaa ggggaagcag gcacatggct ggagcaggag    53700
gaagagagtg aagcgggagg tgccacacac ttttcaacaa ccagaactca ctgtcacaag    53760
aacagcaagg ggaagatcca cccccatgat ccaatagcct cccaccaggc ccctcttcca    53820
acagtgggga ttgcaataag attttggcag agagacagac ccaaaccata ccagatgtaa    53880
ctgtatcata agttgaggga cattggtata tagcttatat aatagaaaaa gagaatttct    53940
cttcagtttt aggaatcttt ttttttccca ggagcctatt tttaattgtt cttactactc    54000
tgggtatagt atgttacagt cttagagtat ttatgcttta tcttcaaatg tcagcttaca    54060
ctgatcaatt tagggcagaa gcctgttata gtccttttctt ggaaccacac cacatagaag    54120
aaataatttt ttttttaactt ttttttgttt tatgcttttc tgatactttt tcctacggac    54180
ttcctggagg caacaaagct aaacaagctc ttcaaagttt aatcgacctc ttcggatcta    54240
tgactgtatg ggtaggccct aatggactta aatattatca aaagttgctg agcacaggct    54300
ttgtaagtgc acatttcgtt aatattgcct ccacttctcc atttatgatc atggggaaca    54360
cacgcagcac agacagaagg tatctcccca ctccattttt ttcattgatt tgtatcttct    54420
tttgccatga aacttttcac tatcaccaat aacaaagagc cagacagaga tgaatttaca    54480
ttcattacct taccttatttt ttaaccttag gcaaccataa tcgtgagcaa gtgaagggtc    54540
```

```
aaagctatta gtattcctaa atgaatagta gatttatttt gaaagtgatc attaaggaga    54600
aatgtgctta ttccttagtg ctttaatttg gcaaacacat ttgagtttct cttgtgcccc    54660
aggtaccgtg ctaggctctg ggtgtcaaag gataaggaca aacacagctg ttgcctctca    54720
agatctagca taaggcaaca attagtaaac tgggtctaat ttgtgaaata gcagtatgtg    54780
aattctgttg aaaaatactg aactcatgcc caaaagactc ggtttatcat cccagcgttg    54840
acatttacta gttatgtgac cttgaacaag tcactgtgtc tccctcacct ctaggttttt    54900
ctcccaaaaa gtgtgacatt tgaccacaac tagatgattc tttctgttc caaagctgta    54960 tgattccctg gtcatagtca agcccatcga tggggaaaac tagaatagaa cttattggat    55020
gggtaccatg catgccatca tttaacgtcg ccttgtcctc tgggggccgt tatcccacag    55080
gactccatgg cttcctgcct ctctaccatc tcctctctct gtggaagcaa gggtcggctc    55140
acagtttgga atctcaattg ttgagaaagt gtaattgttt acaaggacag accaatgagt    55200
aaaaccagcc atattttcac acacacaaaa aggggcgata gatctcaact tctcattatg    55260
gataaaaatt tcaaaatatc aagtcaggtg aaggacatgt gcagcgagga ctggtgtgac    55320
ctcaggactc agcatttatt ttacctcatt agtgtaagaa tgtcacaaga ttgacaggaa    55380
cagcaattca atcaatcggc ttcaatcaag gctaccaaaa atgagagcca atctcttgcc    55440
attagatttt gggcttcaaa caattttagg aagaagttct attcgctagc tgtataaaca    55500
ctagaaattt attgcctgaa atctttgtat gaaagattat tccctgaagt ctttgtctga    55560
aagttttgcg tgtaagatta gcaaatcttt ttaaaaagca ataaatatca aacaataaga    55620
aaaaggaagt tgagaaactc aaagaccaca gtttaatctg gaatggatcc actggaaaag    55680
tatattgtta acatgagttc atctaaacgt acacgctaac ttgtagcaac tgagtttcaa    55740
agcccctccc tcattctgcc cccactggca aacaatttct aggtctgcta ggagaaaaag    55800
atcttcaatt gcctcagtga gaggatgggg gcagaaagga gcctcaaatc ttccatgtcc    55860
acataaaccc ttagtcatct gtcacatgtg aaatccctgc tgtcagccct gacccacatg    55920
gcaggagcca ggctcattct gaagcaacac ttgttgctgt tgcaaggagt gacctgttca    55980
tataaaagcc tacttcacag tgccaggcta acttttgttc agggacaaaa tcctctgttg    56040
ccagaaacaa caacagcatt tgctcctcag gtcaacgtaa tacctcacta atgagattac    56100
cttcttcatt ctaacagatt tttctgctat gtggagacca agaatatgag aatgcctact    56160
taatttaatg tcctctgaat attatactga tttgaaaaaa aaaatactgt tgtttcaatg    56220
ttgctgttga catttgaggc agagggacag tttacaatgg gacacgcagg actcacatcc    56280
agtgagtagg aaggactttt tcagcctggg ggaaaataag acaaagtgat ggttaaaggt    56340
gatggctcca gagtcacagg tgtgggtttg aaccctgggt ttctcatcta ctagctgtct    56400
ggtcttggat aagtttctta atctttaaat cttagtagtg ctggtaatat gaaggtttgg    56460
gtgagattta agtaagattc tgcactaaaa gcaattttca ccataccttg cacgtagcga    56520
aggcctacat ttccatatat atattattcc tatttgtatt acattaccat ggctgtcaca    56580
acaaagtacc ccagacttgg tggcttaaac aatagaaatt gattatctca cggttctgtg    56640
ggccagaagt ccaagatcca ggtggtggca gggctggctt cttctgacat ctgtgaggga    56700
ggctctgctc caggcctctc cctggctgta gacgcctatc ttctccctga gtctctccac    56760
atcgtcttta ctctatgctt gtgtctatgt gcaactttcc cctttcgcta aggacagcaa    56820
ccatagtgac cttgattacc tctctaaaga ccctgtcccc caaatataat catattgtgt    56880
gatgctggga gtttcaaatt tcatcacata aatttggagg agacacaatt caatccatac    56940
```

```
tgctgttgat ataggtaata ataacaacta ttattagtat catgtttaga gcagaggtca    57000
tccactccag aaaactgcat gtctttgaaa tgggaaattc tttcctagtg cctcgaacgt    57060
aataaatgac ttgaagtggg taagaagagg ctacaagaat gaatgagtga gtgagtgaac    57120 aataaaatg acttgaagtg ggtaagaggc tacaagaatg aatgagtgag tgagtgagtg    57180
aatgtaataa atgacttgaa gtgggtaaga ggctacaaga atgaatgagt gagtgagtga    57240
gtgaatgtaa taaatgactt gaagtgggta agaggctaca agaatgaatg agtgagtgag    57300
tgagtgaatg taataaatga cttgaagtgg gtaagaggct acaagaatga atgagtgagt    57360
gagtgagtga atgtaataaa tgacttgaag tgggtaagag gctacaagag tgaatgagtg    57420
aatgagtgag tgaatggtgg gcaggatatg aggagcctta aggatttacc tccagcaggg    57480
atggggcaag tgaccaatgg agctccaagc atctgcggga ggtaaacagc agatgtataa    57540
aaggagcctt ctcgagagcc tgcaggtcta agaccacagc gataggagga cagggcaaga    57600
acctctgttc cagaaggatt gggaccagga agaaagctgc agagaggcag gctcgtgctc    57660
acctgcagtc atgcccatct tgcccacctg ctgtctgcga ctaggccaac tcctaaacct    57720
ctctgaagct taagacctgc cacagtgggc tgtgccagag ttggagtgga gactcactga    57780
gatcatctag aagaggcacc tgcctcaaag ccttcaggta atacccacac ataaaccttg    57840 gggttttttcc tacctgcaat tctgtgttct ggccccttca cgatgaccca gccagcctag    57900
gcatcaagcc acggaaagtc ctagaggaag tgggacctgg ctgaagtggg tataagcatg    57960
tagagaccaa agctggcaga agatgaccccc ggctatccat ccccatattt tgggaacttc    58020
ctggaggaag ccatcctacg aggtgcccca gaggaaagga acctattttt aatgaggtta    58080
cattgtaact aaattgatag cagggaggga gaaacagaag cttctgaggg agtataggtg    58140
tggtggatat ttgataatac tctgaaatat ttttggtctt attttatttg cttttactac    58200
aagaaaagaa aatctgcttt atttagaaag ccatttagaa gtccttactg gctaataaat    58260
acataataag taaatattta ttatacttat tataatatat ataatactat ataatatata    58320
aatactatat aatatagtaa tatatattaa gtaaatattgt gacttcttag gaaagtcaca    58380
ttatacattt attagccaac ttaaactcaa aaatgagaaa taagaatgtc cttttataaa    58440
ataaacaaga cacacaaaaa aatctaactc caaatatcta attcaagctg ctgattgaaa    58500
gttggattgt aagtggcccg tgggcaactt ctacttccta ctacaaaata tgttgttttc    58560
cttgcaaaag agtacttgga aattcttcca ggcaacagca aattcagtaa gcagatgagg    58620
gactctgact gattaatata aatgagagtc tagaacagca gaactctgga aaatgagcaa    58680
gtaaagaagc cctgaaaaag aaaaagcaat aaagcttgcc tgttgattca ggaaaacagc    58740
ctccattgtt actgaaactt gattcacagt tgatggtgag ttatggaaag gcaaaagga    58800 caaaatcctt ttataaatat agttctgtag ggcatgggaa gcaatcaaat ggtgctgtga    58860
gactgaacac aaatcatgct tttttcaagg ataattattt tgaatcaaca acctaagtat    58920
ttccagtgca cttctgcaag acaaatattt tcttgggatg aaaaaataaa tatgttttgc    58980
aaagaaatcg agaccatatc caaaaggct gaaagggtg tgtgtataca catatatacg    59040
cctatataaa cacatcatat atggtctatg tacatacacc acgtgacacc atgtatcaca    59100
tacatgcaac ataccacaca caagctagta ataattattt gtaccaaatc tatttcttaa    59160
gactgtaata ctgtgttcac acagtcacca tttagagata tattatcaca gtgtcaatca    59220
ccaggactac agactattct tatagcttgc tgaagtttag ttttgtactt agaaatcaga    59280
```

-continued

```
gctgatctct catacacagc aggaattaaa tatttaacag ttctccatag aacttcataa   59340
aaaaagagta aaggagacag aaattactgc ttttgtagaa gaagaaaatt agtgctttgt   59400
gtaatattta cagggactgc tgatggagtc tcaaagcaag aattgttttt tagggtaaag   59460
aagtgaattg gcaatacctg cgttactgga cagtccttaa ctccttggtg gtattctgtt   59520
taggaccttt ggtgaagggt cagtcatggg attttgaagg gtgcattgat ctcatcagga   59580
aacattctgc tgccattgta acccttgccc actgtgattt tctctaaaag agtggagact   59640
ttttagaaca cggaatgact ccaacaaggg tcagactcta acaaccaaac aacaacaatc   59700
aacaactact tcacagttct cagagatcag ccctgccacg ggaaacgcac agtaaagcaa   59760
gagcagggtt gacattctct gtgaaatggc atcaggcatg actctggagc aatcttacag   59820
atggatagcc ttgatctcct tccaccagtt ggctaaagga ttgaattttt tactatctgt   59880
aggagatagt ctatgatctt gttccaaata tctgaataaa ctttaagaac cacagtgcaa   59940
tcacttggac acgatcccag atccatccgt ccattcatcc atccacccat ccatccatca   60000
ttcacgattg actcaatatc ctgctgggag ctgggaaaaa agagacatga agtatccctg   60060
cctctgagca gctttcagtg cagatggtat gccaggaca atatacaaga cagaatagag    60120
ttcattcaag tattctatgt tttgttattt agttttcaaa tatgaaccct ggatggaacc   60180
aggctttgtt cccccaagtt atcagctaaa gagaaagagc tcagccaagt gacaaggtgt   60240
tgccgcagtg ataactcaat tttgtggttt tcagaaatgc agaagaaaga aggttggaaa   60300
gaatgggctg gcactccccg aagagtgggg ctcaaagttc tggtctcagc agatctttga   60360
gggagacgta gggtctaggc cggcaaaacc agagagaagg ataggctttt agatgctcat   60420
cccacccaaa accatgaaat aatctcccct gtctcctgat tagtatttgt cagcctcatt   60480
tacccttaag atttgtgcaa atgaaaaacg ttaaatgcag ttcctggatc agtaattaaa   60540
cataattatt tcagtggaag agattttttgt tttcataatc tcctctttgt ctgcatagag   60600
ccagctcttg gttacatctg ccactgatag cctttgctct gtttacttta aagaataagc   60660
cactgtttga tttggtttct tgttttcaat atgtaaaccc tggtctcttg attccccatt   60720
ccaggaagga aaaaataaaa gaacaaggct ctttaaatat cagagccatg atgacttaac   60780
agatacacgc aggctcaata ttttatgtaa cagccactta ggaaaatgcg taagaatttc   60840
ccagctggca gccctgattt ggcaggtgta cctcaattga accaatcgct tttcatctgg   60900
ctgtcaattt gtttggtttt tctggctaca ttgcaccaga gtctgtgtgt attccaaaag   60960
gtcgttcacc tattccacgg ttcaaaggga tcattctgtt cacttaaagg gtcactgtaa   61020
tcatatattg aaacatagct aagtacgatg agctagaatt ttaggagggg taaaactaat   61080
aggaaaatcc aggagtataa accacaaaac acacataaaa aaagagataa aaacagaaaa   61140
cataattcct caattaaaaa aaaaaaggaa ccaaaaagaa aaaaaatcta taacaaacca   61200
cactgtagga gtctcactat acactaaaat taacaatcac agctggggta aatactttat   61260
ttatttttatt catattctgc actggcagca tattctagtt gcctgtttga tttcattaat   61320
ccaaagcaaa agagaagtag agatttatgt aaatttcatg ttatgctcag attgtaaggg   61380
agccactaat tgaacttcag gtcttcctta ttggaaggaa gacctgaaga tgaatggctt   61440
catgaaaataa tcgtaaatga ataattcccc cacatccgta agtcagccta cttctgtaaa   61500
cagaaaaaca aggtagtagt cccatagtct attttttaat ccagaaaaag tcattcttgc   61560
agcaagaata agggaaacta tgtcccaaaa ataccaggtt ttccagatat agggatcatg   61620
tttgaccaaa acaacccttg gcctaaaaat actgctatat tcaaataaga ggagttgctg   61680
```

```
ttatttaatt ttactatact atttatactt acatgggatt tttataatga tactactgtg   61740
gttttcacag atgtttggct tgtaaaaatg ctaaagatta caatctttag gtcaccaact   61800
acctgtattt atggaggcta caggacagag cacagaacag ccaggaagcc aaaacgcgct   61860
cgaattacct ccagcactta ctgccgcggg actcaaaccc gagtcctttc tgggactgct   61920
tttccttgaa cataaaaatg ggggtgatat caccttccac agggatctcc taactgtaca   61980
gagggcttag cacactgtct ggcactcaga ggccttgctg gatcgtgatc cgccccctcc   62040
agtcagcgac tgagacccct cactggttca agggcaaaca cagtgctgag agctgtgtgc   62100
ctggatcccg ccagcaggtg tgctggggta gggaatggaa gtcaggcatc ttgatctcca   62160
tatgtatcca ccgatggaca ccctgcctgc ctttcactgg gctcaccta aaatggtgaa    62220 caaagaaaac agctctcacc tctggagcca acacggaggg gtgggtatga gtgcagatgt   62280
ggtgggggtg ctggtggagg cttgctgccc atctggcttt tcctgttatt gacatgctca   62340
gatgaaagtg ggcctgttc acaaacatgg catccattcc tgggactcat cccgagcaga    62400
acctcaaata aaaaccagaa caaactacac taatttgctg aaccccaaat ggagccaaat   62460
tcaaagctct tacgaaacta caaacagaac cacagtttca aaaacaccag gaaaatagtc   62520
tcaacaagac attacctaca tgaaggatgt ctgaaatcta ttttagtgta aaaatgctat   62580
aagtttactc tcctactttc taaaattact gaattagtta ttaaaataac aacctaagta   62640
atctgactgt aaattgagcc atattttatt taccctaaga tctctcaatc aaatggagat   62700
ataacaaggg ttatcaattt ctactgcatc tattcctgta acatattaaa tctccatctc   62760
cttgagagaa gtacattgat ttttccacag gagaattttt ttctagctcc aagaacagct   62820
gagggctgca aaactgagca gatggccaca tggaagaatc tgcttggttg ataagatagt   62880
ttaaaagaaa aatcacctga ctgcacatcc caaatacctg tcaaagtagg tcatgaacac   62940
tgcttgattg gaacaaacca aaatatttaa tggatcgaat cttccagagt tcatgataac   63000
tgccccacca aaggtctggg cttaagcact gatgtttcct ttaattataa agcccagatt   63060
gtaaggcaaa cacagccctg ccagtgtgtt tgtaggtcca gtcagtgact gtgctgcgtc   63120
cacaatggtc tttatcattg tcacttgttt gacctgacta taactgagta aagcatcatc   63180
attacaaaat gcagcatgcg ggatagtaat cacctaaaga tatggttcaa gcacttcacc   63240
aacctctgaa cctgaatatg cctaatgaat tttgtaaacc ttacaaaaag tgaagccagg   63300
tgattatcag aaaaaagaca tgtgtcatac taaagaaaga gcatgttctg gacctgagaa   63360
aacagcagtg cagaagggaa tgtcttttct ccacagtgat atgtggccac agccttgaac   63420
agcaaatttg cagattaatg aagatagtaa aatagatcac atcctcctgc ctccaggtat   63480
aatattttat tcatataaga gctatgtgag ccttgattta tatgaacttt cattagtagg   63540
caaaattcaa tcataaggtt tcctcttttc acctctaggc gtcctttaaat tcaacacaca   63600 gtcaaatggt gattggcttc ccctctccct aggtaatacc ccaccccca gcctcccaaa    63660 aaagacagaa aaagaggaaa atgaaaaaca agcacgttag aaaggtggcc agacaaaacg   63720
gtttgcatca acaacataac ttctgatttg ttctcccgct gggacagtct aatgcagcct   63780
cattcagctg tgcattttca atattattca acagagccca ctcaggtcaa agtagagtct   63840
tttccttcac aagtacagag atacaacact aggtttacgg gagggctatt ttcaatcttc   63900
ttgagcggta atgtgtttcc attatggttc catctatttg tgatctataa tgctttccaa   63960
atagccccaa atttcaaaga agctctagtt ggttccaaat ggaaatgaga ttacatattt   64020
```

```
agtattattt tattctcaaa tgttagattt aattaggttg ggagcattca ttcatctgcc   64080
cattgtgttt gttgacttca ttaagggaca atcacagaat tgcagggaag tccacgtagg   64140 gcccccaaa ctgcgattgc ttttagcttt tataaaccat taaaatgtaa gtcaagcaca    64200
taaatatatc tgctatgaaa agaagtggta ttgctaagtt ccctgataga tgatgacagg   64260
acttctcaga attcgaaggc cagtgtttta atcttcaggt tctctcaggt cacgtgcttg   64320
ccaatgacat tggaccagga atctccagag gtgagaaagc cccggccaac cccaaatgca   64380
gctcttgctt ggtgaaagca gagatggggt gaggacaggg acacaggcag aaccctgccg   64440
cgctccagct gagctgctca cttgccactc cagagaaaa caggaggatc gacctttctc    64500
tatgcaacgt ctaaaattaa tttggtgctt aaaatcagag gtgggtcaag cagttgatta   64560
cctgaggttg cctttggact aacaaaggcg tctcttcagc atggtgaatt gctctgatgt   64620
ccctgggccc ggagcagtga tttgagaaaa tcacccatgg caaccattag gcaatgagtc   64680
tccattgact gccaaaatct cactgaatat tgaaggaaaa gagaatttat atgtaatcca   64740
attcagagca acaacaacaa caacatcaac aattcaatgt tccccagttc ttcatgggaa   64800
aacttcaatc caggtccaaa gagagctgca agaacagcgc agttcacaca gaaagtctgc   64860
attcacaggc tgggctgggg tcgcaactct gcgggcctcc ccaccctgcc acgctttgta   64920
ctgctgtgtg attttagcgg aggcatttag ctcacacagc cttagtttcc tcatctgtaa   64980
aattgaatag ctaccttcta ggctttggga gaatgcaatg gaaaagaat cttgcctagg    65040 gcatcatcag ctcagtaaat aatagttatt atcatgatga ttatcctcca ggtagctgtg   65100
atgtgtagaa gcccagaacc aagtagcaca ggagacagag gtagttaatt caaccctcct   65160
ccaatacaac tgagtgccct aattatccga atagaagctc cactgcagga aaactctgtt   65220
ttggagctca aggaaagacc tacaagggag aaccacagag ctgtaattat cagctgaaag   65280
aggaaggaag ttctaatctc acagagccct tggagacttg tgaacacccg aagcttggag   65340
aaggcttcaa cagggaacaa acggtgaaag ccacacaaaa atgaacttag cagcaggaag   65400
gagtactcca cgtgcccctg cacctctcac caaagggata cagatatgtg atgggtgttt   65460
ctgtaatata tgcctcattt tccaatggaa aacctccata tacacatgag tgcatggaga   65520
ggtcatagtc actggtcaag gagttagaga tgagtgggga aaagtgatag ggtgagcatc   65580
ctcaatctgg ccccacccta tctggcgcca gacacctaat gaaccacctt tactggggga   65640
gacagggtca aggatgaagc aatttcctct tcatatctag ctatcattta ttctacatag   65700
ttgatgcagg caatatgctg gctgtttgaa gcaggtgata tttctaatcc acacaatggc   65760
ctgaaaggta agtattatgg aatcacttat ctggataaat aaaacatgag gttcagagag   65820
attacgtaac tggcctagat caataggtgg gtaggcagac aggtaggcag gtagatagat   65880
atagagattg aaatatactt taaaaacact ctgtttgccc tacattcctt gctttagata   65940
ggattctgaa tgtggggcgg gcaggaaagc tgtcagtcac gaagggagcc tgcccaccac   66000
aaggcgagtc atgtgaccca ggccagagaa tcaggttacc ccacagggaa catcagtgat   66060
tggcccaggt gtaagcaggt agctcatgta gcaccagagt catattttg aagtttttat    66120 ggaagttgga aagatctctt ttggaaatta ccaactccag agaggatgtt agcctgggag   66180
tgccaggaac tttctgtgtc actggggaaa gcgagacttg attctccgga tatcattgac   66240
catctgggtc ctgtggtgcc tgacgctatg agttctcaaa gtggggcccc caaagcagca   66300
gcagcagcct catggccttg ctggaaatgc gaattctcaa cctcagctcc cagactcact   66360
gcattacaaa ctctggaaga tggagctgac tcagtgagat ctcctttccaa gctctctaga   66420
```

```
tgggcctgat gcttattttg aaaagcactg ttctaggtca atccagggaa ctgttaaact   66480
tcatgagcca atagataccc ctcttcttgc ctaaactttg attataataa aagaaaaata   66540
cagcaagata gttttgaggg ttttttaata aaaatttaca attatttttt aatcgcaagt   66600
aaacttaatt attttaccat taaaacctct tcaacacaga aattcctttg aggtttttag   66660
ttttgttctg tgtttgtttg tatgtgaggc aagacacccc tggatgcttg caaagaagag   66720
gcaatttgaa gtgaaacagg cagatgtaca atctgatccc ataagtgacc cactgcagaa   66780
cagacagctg gacatatgga catatgcagc tgcctgtcat ttatacacga gagttaaaca   66840
gttggcaaag agagtctggg ccacagagtg gtgagctggc tagaggtgcg gatctagcca   66900
ttggataaca ctgtacttaa aacacaaaac tctatccaag aagaggaaat gattgaatac   66960
gaagtatttg aaaaaagatt tgaaagactg aaaatgaaac acttccttac attcgctaag   67020
tgagctgaga aagaattgcc cagaagggtg atacggaggg ctagaaatg aagacgacag   67080 ggagtggaag gagagagccc acctacatgg cacccagctt tgcagaggct cctgaagaca   67140
caaggttgaa ggccctggac tcaaaaattt ccttgactct gccagcaag agggttagct   67200 gtttcagcag agggtagagc caagcgaaag ctggagagtg aataagaaat gctaggagca   67260
attgcgtcag gtggggcaac caggactgtg tttgccttcg gaccagggct gccgagtaca   67320
gatagcaggt ggtttatgtg aggcctggag caggggtcat tgcaggagac ggggttgctg   67380
tgtgcctata aatggagtga aaagtgagt gcaaagaaat ggaaaagtta ggagatgcag   67440
cataacctgt gaatcatgat ccctgacaaa gtggggaggc tcatgggtgc aggtgtaggt   67500
gtgtgtgtgt gtgtgtgtgt gtgtgagatc acatggctgt ggacagaggt gggctggaac   67560
ccctaacttc caggaaactc caggttcttt tcttcttcta cccataggtc tgcattgtgt   67620
ttttctaggg tcactcatct attcatccaa caaatattca acaagcacct gttacatacc   67680
agattattac atacatgtgg cagtgcacgt aactgtgaag ctgtgtacta cagctgcagg   67740
gcgaggactg gggctttagc tcccaccttg tgcaatgtgg gatcttctcc atcgtcatat   67800
caagccaccc cacgtgtatt taatgtaagt tggaacactg tgcttgctac aaaagtcagc   67860
ttcagaagaa gcccctccgt ggatcaccac ctccctacaa gctgcagtcc taatctccta   67920
tgtcaaaatc agggactgct gctgccccgg ggggtttaga gatgaagacc cagactctga   67980
ctgaggagtc tcccagtgaa aggaaggagg cagaagccca gtcaccagtg acgccaccca   68040
gctgagtgga ccgcgcagag ggaggcggac gcagggcact ccaacatgga cctgagaggc   68100
acacactgca atgcaaatcc tccacgatag tccacaggat gtactgggag aaactggaag   68160
gccacaggag aaacgtttgc tcacgaaaac acaggcattt catgtgcctg gagcacggga   68220
tgaagaattc cttagacttt gagtgccaag ctagtgcttg gactttcttc taaaggtcat   68280
gggtgagccc ttggggaatg tggagaccac tccggcctgc gatggagaag gaaattgtgc   68340
cagaagctgg gaagtcaaag ttaaccctcc aggctagatg taagtaacgc gtgggctgc   68400 acatacggct gtggcagagg aaatgggaca gagggattga ttttagtaca gaaatcctaa   68460
ttgggcttaa agtaggtatg ggaaaacccc tgaaagtgtg tgctgatctt ggtatgtgca   68520
gatattattt tcctcctggg gtaaacttta attctcaaag gagtctatga cccccaaaaa   68580
agtcatctcc ctacttgaaa gatgcttgag tgtctaatgg ccaggagcgg gtgttggtgg   68640
gataccaagc ggtgggagga acacagtatc gtcctcaagc ctctgacttc tcctagacag   68700
ggtagctaag aggacttttc agatatgttg cttttgaggt gtctgtgagg agagggaggc   68760
```

```
aggaaacgca ggcacacgca ctcacagtgg acgcgtcttt agaaagctgc acattctcta   68820
attgagttaa ttgttcacgc actgaatgga gctgttctg ctcaagctag ggaaagactt    68880
gtcagctgtt tcttcacttc catgaccttg gaaaatccgc tgtctccacc agacactgat   68940
ccttggcaca gccactattt gatacactta actctgctca ggattttaga tctcaaccca   69000
ggaaatgagc tacagtctca ccccaggcaa gtacagaaca ttttcctaac caggagagac   69060
gcctgtgtca cacattccaa aggtagccag cagctaagaa agccgcaaca aaggaaatca   69120
aacagctctc tctcccctaa acgctgcttt caggcaagtt ccaaacaaaa atggaggatg   69180
cactgcaaat taaaaacaaa agcctgccag tcaaaggcag tgttttaaa cacagaaaga    69240 gcaataccac tgcaggggggc agataaaaga gcttttgagc atctcagaag ctactcacac  69300
acaaaagcac ctctgtgcct tcaaacagga tctcctagaa gtttcccaag gtttcataac   69360
ccaaataccg ctggtagtga tgtggtttgg aaattaacct tgcttttctc cccactgctg   69420
ttttacatat taattaaagt gttttcctca gatcaggaac gcctgcaggc tggctaggtt   69480
ctgcagaagg tgcctcattt tcctgccgct tcccgccccg gccccacttg tgcatagttc   69540
aatgattaaa acttccccag gtcagctgta gacgcctccc ctcccttaac tgccatcgtg   69600
atatagaaca cacactttaa tgtggctttt aaaaagtaat cgcttcccca ccccccaaga   69660
aagataggtc gtgcagagct aatttcggga agccatttag aagaaattgt tgagaaggca   69720
ttgaagtatt tgggtccaac tctgcttacc tcattcatgg acctgtttct tttcttttt    69780 ttcttttcca gtgcttgaaa taggtgtgca aacaattcac atattataaa tacgttgact   69840
tgggccgggt gtggtggctc acgcctgtaa tcccagcact ttaggaggct gaggcaggag   69900
gattacttga ggtcaggagt tccagacaag cctggccaac attgcaaaac cctctctcta   69960
ctaaagtaca aaaattagcc gggcaaggtg gtccgtgcct gtaatctcag ctactcagga   70020
ggctgaggca ggagaatcgc ttaaacccag gagatggaag ttgcaatgag gcagatcac    70080 aacaacccac tccagcctgg gcgacagagc aagaccctgt ctcaaataaa taactaaaat   70140
gaaaataaat aaattgattt gttttcattc atatatttg gggatacaat ggagcttaaa    70200
gtttgaaaac caaaacggag ctggccacca aaggtgtgga tttggtcaac agggtgtgga   70260
ctccagcagc ccgtgtcact ctcagactcc atgtctcaat ttgaatgttt ccatgtcact   70320
taaaaagtag aatattcata gtgatgttga agatacaaaa gatataccag gattaatttt   70380
ctagtcaatt ttatgtgtct gtgacccaag acaataaaag ttaagtcatc gttagttcct   70440
tagttgctgg acactttagc ccaatatacc accttcaatt ttgaattatt atttggactg   70500
tgttcatgag attcttggag tatgttaaat caacacattt ctttgtaatt attgagaacc   70560
ttttgttccc tataaaatca agtgtacgat gatgtaaact ataaaacgca aattgtaggg   70620
acaattggta atctgcagtg aaaataaagt caaaatagca aagagcagat tattctcaaa   70680
tttatgtaac agagttctta catgtggaag tggatacaag tattagcaca ttcagttgat   70740
gtactgaaaa taaaatgaaa ctattttct acttactact tgcttgtgaa atccaaaggg    70800
gtgaataaga gccaggattc attgtcatga gtgtaggggt gccctgggaa ggaggcctcc   70860
atcccacgtg tcagtggcgt catcagaaat tccatgatcg tcggcttatt ctttgcacac   70920
gtgtctacag ggtccctccg cacaccgact tggtgtcctc caggatgcag aaacccaaa    70980 ttaaactagt ttaatgaata aggaaactaa gtggctctta ggaccataag ccctgcggtg   71040
acgcctgctt cagggctgga ggagctaagt gttctctggt tcaccaaagc ccccagttct   71100
ttccgtctgt cactcatagc ttcggcttcg tccccggctc actgccagtg gtaatcaggc   71160
```

```
tgcccaagaa cttctgaaat ccacagcccg gtgtttccaa acgaattatc agtagggttg   71220
gaatcccttc tccccagccc cagccccagc aaggccctcc aacgccactg cagttccctg   71280
gatagcagga agaggcctga gccggctctc ccggagctcc aggtgcagag tctccccaca   71340
tgggagtcag tgttctcaga gcagcatttg ttgacctgag ctaaccaagt tctctaactg   71400
aaagcctggc tgtgtaaagc cacagatgtc tggcattaga atagctcaag gacaggagaa   71460
aaaactgaca atcagtccag aacggcatcc caggacttct gctctgagga gaaaacagga   71520
ctaaacccca gctgaggtct atttccaact ccaagattct gcaatgttat ctctgtttaa   71580
aaagatatcc cacttttga tgacagtgtg tctggaattg gtgggttctt ggtctcactg   71640
acttcaagaa tgcagctgcg gaccctggcg gtgagtgtta cagctcttaa aggcggcatg   71700
tccggagttt gttccttcta ggtgggttcc tggtctctct ggctcaggag tgaagctgca   71760
gaccttagcg gtaagctgtt acagctctta agtcagcgcg tctggagtcg ttcgctcctc   71820
ccggtgggtt cgtggtctcg ctagcctcag gagtgcagct gcagaccttc gtggtgactg   71880
ctacagctca taaaagcagt gtggacccaa agactgagca gtagcaagat ttattgcaaa   71940
agacgaatga acaaagcttc cacacgacag acacaaaccc taacagattg ccaccgctag   72000
ctcggagagc ctgcttttct tcccttatct ggctccaccc acatcctgct gattggccca   72060
ttttacagag agctgattgg tctgttttac agagagctga ttggtctgtt ttgacagggt   72120
gctgattggt gcgtttacaa tcctgagcta gacacaaagg ttctccaagt ccccaccaga   72180
ttagctagac acagggtgct gattggtgca tttacaaacc ttgagctaga tacagagtgc   72240
tgattggtgt attcacaatc ccttagctag acataaatgt tctccaagtc cccaccagat   72300
cagctagaca cagagtgctg attggtgcat ttacaaacct tgagctagat acagagtgct   72360
gattggtgta tttacaatcc cttagctaga cataaagatt ctccaagtcc ccaccagact   72420
caagagccca gctggcttca ctcagtggat cccgcccggg ggctgcaggt ggagctgtct   72480
gccagtccca cgctgtgcgc ccgcactcct cagcccttgg gcggttgttg ggactgggcg   72540
ccgtggagca gggggcggcg ctcataggg aggctcgggc cgccaggagc ccacggcggg   72600
ggtgcggggg caggctcagg catggcgggc tgcaggtccc gagccctgcc ctgcggggag   72660
gcagctaagg cccggcgaga aatcgagcgc agcgccggtg ggccggcact gctggggac   72720 ctggcgcacc ctccgcagct gctggctcgg gtgctaagcc cctcactgcc cggccgctcc   72780
gagtgcgggg cccgccaagc ccacgcccac ccggaactct agctggcccg caagcgccgc   72840
tcccagccct ggttcccgcc cgtgcctctc cctccacacc tccccgcagg ctgagggagc   72900
cggctcctgc ctcagccatc ccaggagggg gctcccacag tgcagcggcg ggctgaagcg   72960
ctcctcaagc gcggccagaa tgggcgccga ggccgaggag gcaccgagag cgagcaaggc   73020
ctgtgagggc tgccagcatg ctgtcacctc tcgacagagt cacaaagcat ttactgaatg   73080
cctactgtat gccaggccct tttctcaagt ctgcttaacc aggagtgaag aaggctgaca   73140
ttaccgtcca tgtcacattc tggtaggaga gggatacaga gaacactaca agtaggtgaa   73200
ataggtagta ctttaaagaa tgagaacaac atggaaaagg aggctatgaa atactgagaa   73260
tatggctgga gttttcattt tagataagta aatagccaaa gaagccttga ctgaggaagc   73320
agccagccct gtaagaaagg agaccctgc catggtcctg agacaagggt ttgagtggtt   73380
tccgcaggag gcatttccag gaggggaagg agggaaacaa cgagggaaaa gtacaaggtg   73440
tgctcacccc tgaatgagtc cccggggcaa cccggatcca cctgtccagg ctcctctgag   73500
```

```
cacgtgggga gcacgtggag agggagtggg ggagtcgtgg gggagcgtgg gcagcgcttg    73560
ggggagccgt tggggacttg gggagagcgt ggagagccgt ggggagggcg tggcggagct    73620
gtcggggagc cgtgggggcg cgcgtggtca gcacttgggg agcgcattga gagccgtggg    73680
gagcactgag ggaggatgcg gtggccacgg ctgcgtggca cccccaggcc atggccagga    73740
gaccctcggg cggcgcaggt gccggaagca gcgccatccg tgctatggac gggtccccc    73800 aattggcagc ggtctcgggg gtgagccaga ggatgggtg actgagaggt ggccgatgtg    73860
gggatggtgg ttttcaaata gaggcgagat cggagcagga gctgggaacc aaaccagaag    73920
gttttcagga cgtggttaga ctttgaagcg gcctaaggct gtggcacatc tgacccactt    73980
tctcaccaac attgcggtgg cttcttagta aggaacgggc tgaaaggggt aagggaaagg    74040 gtggggcag ggcactggga aaccaccatt gccaacatcc aggccaggca ggggcggcag    74100
gggctgggcc agggcgcagg ggacccgact cttgctgcgg ccgctgggaa gagggaattg    74160
ccatagagcc agaacaggag gcgctggggc agggctctgc tgtggggcgg ggtgctcagt    74220
ttgggacagt gttgacactt ttggagatca tcagccatcc cagtaggtga ctccaggagg    74280
ccactggata tacagctctg ggaacaaaaa acggaatcat cagcctattt acaactctgg    74340
aatggatgag atggctgtga cgactggcag cagctgcgcc tgagccctca gcacctgcag    74400
ggtcccatgg gaggtgaggg ctgtaaggga gcaagcaact cctctccctg gagcaggcgg    74460
gcagggagaa cagaccgcca ctgtgctgct ctcaaaacca agtgcatggc cggtcgggt    74520 ggctcaggcc tgtaatccca gcactttggg aggctgaggc aggcaggtca cctgaggtca    74580
ggagttcaag accagcctgg ccaacatggt gaacccctg actaataaaa atacaaaaat    74640
taggtgtggt ggcacacacc tgtaatccca gctactcggg aggctgaggc aggagaatcg    74700
cttgaaccca agacgcagag gtttcagtga gccgaaattg tgccactgca ctccaacctg    74760
agccacagag tgagcttg tcttaaaaaa aaaaaaaaaa aagtgcaga gttgctttac    74820 atctttacat agaggagaat ggtgtaagac gcagctattt ggtcaaacct atgtgattga    74880
aacatttgca tagaaagaga gagagaaagg atgggagaag aaaatataaa ctaaataact    74940
ctcctttttc tttgctggct tgtgtgtttg catttatgaa caccaacatg aaattttgaa    75000
ccttaaatct agtataaaaa tatggaacag ccagcttcct agagtgaggg caccattctg    75060
tgtttgctgc cggtggacct agtgtgggtt ttggcgccaa tgtccttttc tgctaaaaca    75120
acttggcctc ttggaaggaa acttggactc tgttgccctg actcaaactg ttgtttcatt    75180
tcttatgatg tctcctcatg ttaaaaaaaa aaagaatgtg gacattatgg gtttaaacat    75240 aatttgaat gaatgaggaa attctggtag agggtttgtc ataatgcagt atcaattggt    75300
taggtcttct aaagaaacat gtagggttct cttaggaact ggttcattaa atctaaaagg    75360
caaaaaaatt aaaacacact tttgatatat ttgttggagt tacatataat catatctttc    75420
aagagcagat gtgccaaaat atacacaaca gagtgtagct gggtgacccg aactgaccac    75480
gaaagtcatt tatcaaaatt caaagttagt tccccacagg cctgaatttt cagacctaca    75540
cacaattcca caaacaaatg atggtaaagt cccaaacacc acattcttgg agggatccaa    75600
tgctattggc actgatgctt taatcagaaa gaggctcaaa cccactggag ttaagctctc    75660
tgaaagtctt tgctccttgg caaccacgag caaacctcta cagctgactt ttttagagta    75720
ttttttacat ttttaaaagg attatttctg aattataaaa ccaccgttac caccttattc    75780
ttgtaactct aacttattat tttgagtcaa tttataaaac ttgattcatg agagtcaaga    75840
ttcagggtag gccagacagt cactcattcc taccctcaaa gagcatacac tcaaatagag    75900
```

```
aatgaaacac gtgccccaag tcagaggtaa atattataag caaaagccaa agtgttctgg    75960
gtcaaacact tttgggggg tcagtgaggt cttcatgcag gggtaacagt ggagaaaggc    76020
cttcaaggat ggggaagatt ttcccaggca gagttaagaa caaagagaaa gcagtttgcc    76080
aggagacagg gaagcaagtg tgcagggagt gaatttgagg ccttcctaac tctgggtgtg    76140
acagcagagg ggacctgccc atgagctgtc cgagatgcag ccaaaggttt caccgcccac    76200
gtgataaggg gctagaacac tgaagtgtag aatttggact ttattcagta agaacgggga    76260
agtactgggg gtccctgagt agagaagtgg gatcctgcaa gctgagcatc acaatgattc    76320
gtcaggtgat gtctcagagt ttctctgaat ggcacataaa ccagagacag gaaggtgagt    76380
ccagccgttt ctgtggccca gcaagaagta acaagtaata agtaaagtgc tatcagtggg    76440
aatggcaagg gaggggcggt tacaagtcac atttcagaca ggagttgatt ggatgtgggg    76500
agggcccaag gatgtgggga gggagctgtc agaaataagt ggccctctaa attttagccc    76560
cagtgactta gagaaaatgg tcaagagatg gaattggttt tcagggaaga cactgatcca    76620
ttctggacat gttgaattta agatgccatt aggaaaacca aattaaggca ccttgcaggg    76680
aaattgcaca tgtaacatcc tggcttctgg gatttgagag gtggctgcaa agagagaaag    76740
gcagtaaggg atctccagag aaggagatca cacaggaagg aagtgaggga tgggaagtca    76800
ttgttgggaa gttgagggtc aaggacattt agagagcaga gggagaaaga aggggtggcc    76860
attgcactag ccaaagaaaa tgttcagcca ctcgccctgc agggaaggcg aggggcaggg    76920
tggctgcgca tagatgtgga attagccgga ctcagggtga agccatgatt ctgctagtgt    76980
ggtcttgtaa cctgggacat ctatctgagc gccctgtcag cgcttctctg cattgtaaat    77040
gggagttgtt gcaagggtga aataagacgt aaggtgtttg gtgcaaggtc ttgtgacaac    77100
tagcactaag gaatggtgcc tatgaccttt attaggcagg aaggagtcaa cagagtgagc    77160
tgctgctgca gggggttggg agctcttgca acggtggcat cgagaaggtt gtcaacacag    77220
ccctgtcaac ggctgagggt ggcagagtcc atattgcaaa ggagcacggc ataagtggcg    77280
aggcaagaag tagatggatg ttctattttt tcctttctct atctggacaa aggtctttt     77340
ccttccaagg tgtagctgga ttttctctct atagagcttc cctggggcgg ttccattttc    77400
tagtgtctcc atgagtcttt gttctttata tgaggtccca atgatgccat ccactcattt    77460
gctttctcac aggcatgttt tccaccagcc acccacgctg attagcttga gagtgactca    77520
aggcaggaac gatgcccttg tcgtagaaca gcctctgatc gagtgcttgc tgaacagctg    77580
gctagctctg agcatgaagc aaaatgcagg aagctgggt gtgtgaggag gagcagggac    77640
agcttaaaga agagaggagg gagaggaggg ggactcctgc ttggggcacc ccacctcctg    77700
gatatgagat cacttgtgtg gagcaggcct agtagcaggt aagtgggccg aaggggaggg    77760
agtgaaaaag tccatgtatt gagtcacctg aggtgtcatt taaagagaca ggaataacaa    77820
aacatcaatg ggacctaagt tgagattaga attaccgact tgacttgtag tgtcacctgc    77880
cacccagggt gaggaatgtc ccttaccaca aggtcacctg gggtctgaga tttgaaatct    77940
gtcagccttt ctgggctggt ctcttgcctc agtttatgct cacacagctg cctcaggatc    78000
agtgtggaca gaaaggtacg tgagactgtg caacggagat gggctgggag aatgaggaag    78060
agggagggga caggaggtgt ccatcacctg gacacgggac tgaacaacca cacaacctca    78120
tggcggacac cagcacacct tgaccttgc tcataagtct gtgagtcggg atggggggct    78180
ggcgacggct catcctgctg ggcttcctac gtgtctgaga caaccggatg gactggtgcc    78240
```

```
ggctccgtgt ggtctctctt catctcgcag atttgcctgg gcttgtttcc cagcagacag    78300
cttctgagga taggtttggg acgggcacct gccacttcct ccacattcca ttggccacag    78360
tgagttgcaa ggctggccag actcaggagt gcagagaaat accctctact tccagatgag    78420
aagagccaca aagtgacatc accgcaggct ggatgcaggg cagggcaaga cagcggaacg    78480
cgtgggctgt tttgacagtc agtctacccc aggatgctcc aggaagggga aaaggacaag    78540
ggaagagggg cgctgtggcc aagcagggga acttctgtgt tcaaaatctt ggagatggat    78600
cactttcagt tcccgataag gcttagtgta tggccctgag acttgccgtt tgatactata    78660
atctgtcata tacaatgtaa cttagtgaat tgggtaaagg atcttcaggg tttattttga    78720
atggttgtca tttattataa aattaattta ttttataata attttatcta attggctggg    78780
catggtggct caaacctgta atctcagcac tttgtgagag cagattgctt gaacccagga    78840
tcttgagacc agcatgagca acatagcaag acctcatctc tactaaaaaa aaaatccaaa    78900
aaattagcca ggcgtggtgc catgtgcctg tagtcccagc tacctgggag gctgaggtgg    78960
aaggatcgct tgagcccagg aggtcaaggc tgcaataagg tatgatcatg ccactgcact    79020
ccagcatggg caacagagca agaccctgtc tccaaataat aatttgatat caatttgtaa    79080
taatttattt taaaagaatt gtatgaagga cccatgcctt ggggcatagg ggcactgata    79140
gaaggtaggt gatcagtata gatatttgct gcattaatct atttcagtca cctgtgagat    79200
gattcaggta aaggaaagt gaggccccga gaggtcaaat gtttgctgag tcccacacag    79260
gtgaacacac ttttctcctg gatcctagtc taccccacct tcttttctcc ttttgaaaat    79320
taatgttttg taagtgatta aaaagaaaaa tgatcgggct gggcatggtg gttcatgcct    79380
gcaatcccag cactttggga ggctgaggcg ggcagatcaa aaggtcagga gtttgagatc    79440
agcctggcca acatagtgaa accccgtct ctactaaaaa tacgaaaatt agtagcgtgt    79500
ggtggcacac gcctgtaatc ccagctactg gggaggctga ggcaggagaa tcgcttgaac    79560
ccaggaggca gaggttgcag tgagccgaga ttgtgccact gcactccagc ctgggccaca    79620
gagtgagact ctgtctcaaa ataataataa agaaaggaaa agaaaatgat tgaagacaca    79680
gtgacattaa gtttcataat ttttatttaa tccaagtcta tccccaaaag gattatgcct    79740
actgtactat attatacggc atgaaataga tgatcctgta acataaggga tcagattcta    79800
tgccaacttc taacactgtg gcttaagaag tcagacccaa gaatgttgtt caattatttt    79860
atcattagcc taatttattt ccaccctgga ttttccatg ataactaatt ccacacttcc    79920
tctggatccc ctctttcagt ttcaggattc aggaatggct tcggggaaag agcccttatg    79980
tttttgcttt caatccactt gtgtttccct ttgtcaagag acaaatggga actgcacccc    80040
caaactgcat gatgttcttg gcagagaaaa tccccagacc acagaggagt ggtatctgca    80100
gaagatagaa cgagaggaag cagctcaaag acaaggttcc agaatgagct tgcaccatgg    80160
gatgcagcca gtgacagtg actgaccagg aaacacctgt gatggcaagc ggcagtgacg    80220
agcgagtcag aggtgaccgt gccggaattg aatgtgcgag cactgctgtt ataaaggaaa    80280
agaggaaagt gcaggcaagg acttttattc tcatgtgctg attataccaa ttcatataga    80340
tgacgtctgt gtgggcattc agatgggcat tttcagttca aatgattgtg tgaacatgaa    80400
tcgcctaatc aaaattagat ctttattttc tcctttccca gtcgtaccct cagcccaaca    80460
acatttaaag gtgaatggat gtgcaatatt ggcacgaatg gacgtgacac acagtaggcc    80520
tttgtgcacc ctggaaggga gggcagattc tgcttcaagt gtgctggaag acatgggagg    80580
gatctgaact ggctgacgct gcactgtagt agggagaatg gagtggaatg agggaagga    80640
```

```
tgccaggggg aggccactta ggaggctgct gtgtagccca agcaagaaag gatggcgact   80700
tttctatcag gggaagggat gagaggaggt tggactgaga ccgggatatg ctctgaggtc   80760
aaggcgacag agttgctgaa ggatggaatg tgggctgtga gatggaggag tcctggcgag   80820
tgctcggctg gttggcctga gtgtgtggac ggctggtggt gccgtttatc ggtgcagaga   80880
aggctggtgg gagggcacct taggggtggg ctggtgggg ctgttcagga aagaccacgc    80940
tttgatcatg ttggttttga ggcatgtgca ggctaggcat gtggagatgc agagtggatt   81000
tgagtgccat cggcatgcag atggactcag gccatgcgat cttgtgagat gccagcccag   81060
gtcttgttcg gaagaggcag agtatgtttg gctgcaatgg ctgagtgggg cttagattca   81120
gcaggaggag caggccatgg cagggtgaga ccttctgttt gagaagctag gcatgggca    81180
tccatggcac agccctggga gttgccgcgc aggcagcagt ggatgtgagg gtggaagtca   81240
aagttgagga tgtagatgag ggagctgaag tcatggggg atgagggcac ctggggaagg    81300
ggtgtcaagc aagagagcgg tgcacagatg agaactctga cctttatgag atgggagaca   81360
aacgtgcgga tgaaaggtgc ggtgtcacac aaactccagt cgagaggcaa taaatatctc   81420
acatctcagc tgcatcgtcc tttctaacca agcatggaaa ttctgtctgg caagccgtca   81480
ggtacatttg cagaaaagga gaaggaaagt cattgagggc cacactggag tgagacagga   81540
tcagcaggaa gggaaagaat caagaccatg atgtttacat gacttctggt tacttctccc   81600
caagctccag aaggcaaatc ttgcatggac ctctggcatg catgggtggc tgcagagagg   81660
cctagagaag aggcattcat ttggggtgag gctcctcctc tctttcaggg atttacagg    81720
gatccttcca gccagtgggt ctgtgctgga tcctccacca gacacccta gtcagggcgg    81780
aggccctcag cactccagcc tcagagccca gacagttctg gttcccagct cccttcctgc   81840
catgtctgtg agtccatcct cctgttccac ctcaggactt gtaaggcgta ttactgtgcc   81900
ccctgggtaa ggcagagttt gaggaagaac gaataaggtg agggccactg actttcagga   81960
tttagctcct cttctcaaca tgcatttcct gtctactgtc tgcttcacat cacccacccc   82020
tcactgtccg aaatgcgtgc cccagcccaa catcagcatc acccaggagc tggttagaaa   82080
tgaggctctc aatctccacc caacctcctg aatcagactc tgcattttaa cgagatcgcc   82140
agagagattt gtgtgcatgt tgacatttga aaagcattat taggcacagt ggctcacgtc   82200
tgtaatccga gcactttaag aggccatggt gggcaggatc gcttgaggcc aggagttcaa   82260
gaccagcctg ggcaacaaaa gaaacccat ctctacaaaa tattttttt tttgagatgg     82320
agtctcactc tgttgcccag gctggaatgc agtggcatga tctcagctca ctgcaacctc   82380
catctctcag gttcaagcga ttcttctgcc tcagcttccc aagtagctgg gattataagc   82440
gtgtgacacc acgcccagct aattttttgta tttttagtag agacggggtt tcaccatgtt   82500
ggccagtctg gtctcaaact cctgacttca tgatccaccc gcctcggcct cccaaagtgc   82560
tgggattaca ggcatgagcc accacgcccg gccaaaacat ttttaaacat tagccaggtg   82620
cggtgcatgc ctgtagtccc agcaactcag gaggctgagg tgagaaatc ccttgagtct    82680
ggcatttcga aactgtggtg agctctgata gcacctaatg catgccagcc tgagtgaaag   82740
agtgagaccc tgtcaagaaa gaagaggaa aggaagagag agaggaagga gaagggaag     82800
aggaaggaaa gaaggaaaag cagtatcata tattatttaa tgacacttca cccaaggttt   82860
tccaaataaa aacatccaaa gaaactagac aacaagcatc cttacctttc aataaaggac   82920
tcacttgaca attttaggta tgtgccaaag caccaaagca aattgttgat gttcagctta   82980
```

```
gtaactgaca tggcttcaat acctacccgg catggtgctt cgctcactct ttaaagacta    83040
cctttatgca cttttactat ttcactgcca cgctaaacat ctaagcgatc atatccttat    83100
gcctactgat tatgaagtcc atgacattca acaacatcaa cccttttgccc actgccccac   83160
ccgacttgaa ccaagttttc ccaagttcaa ttcctggggc ctttgatagt ttcatgcctt    83220
ctccacgtgc cagagacaga gaagagtgag ctctatcgtt tttggggggtc tactagtttt   83280
gcctttatta tttagacagc ttcaggtcag cttcttcctt gtataccagt cacaagtggg    83340
tttttatttt acaaagaaaa catagaagtt atcattttct agaaaaaggt acaataacta    83400
tttcaagaca tattttagat atacttacag gcacaccttg gagcagttca ataattaaaa    83460
atttcatctg tctgcctgac cgccaatgca aggaaacat aattaaaagt ttttttgttt     83520
cttctccaag ataatagttt ataaagtagc ttaatgaaac actgaaaatc cagaatggaa    83580
gaggacgtgt gaaatcccct ttccggtgtg aacttattct taaacaatca atgaaaagtg    83640
cccgtcagcc tttgcaagat gctaaccatc tggcccctgc atcctgtctg agtcacccga    83700
taaatagctg caggttgttt taagcacact gcgccctgca caagctgttt tgctctgcta    83760
ctcactgccc ttaggtgcag atatttacac ccggggttga gcatattttc agccacacct    83820
ggatgcctcg aggtaattag gaggaaactt ttagcggaaa ggaaacagca tacctttgag    83880
tagcccgatt gtgtatgcag gagaaaggtt aagtaggaag agaggggagt tctctcctga    83940
attgagtagc tttgcttcct attggaaaag tgtgcaaatg aaaggaagta gaaatgctaa    84000
aaagctctgt gactgcctcc tgctgtattc aattagcctt ccagaggatg ccagaaggaa    84060
ggctcaatta ccagagcggc tccaggactt aagagaaggc tggagggcaa accaaagggg    84120
ctgccatctt gcagacctgg tgtgagacca aggcggggca gctgtgtgat tggattatac    84180
acgggaacct tactttagtt tctattgcat ggccagagct atgcatgcca cctttgcat    84240
ggagtcttga aaagtcacct aattttaata aagcagaagg ggaaagcgat aagaagaggg    84300
agagtgcatc tctctgaaat gcctaagcat cggccttgcg ggaaccggcc tcatcgagga    84360
gcagggccac caccgttgga gcatcggagg agcatcggag gagccctagc tctggcctct   84420
tggctggacg tcactgtttc aggccgagca gataaaagca gaaggcattg accgtgagcc    84480
aagagctcag tgttttcaga aaatggactg gacgggagga aagagtgtga gtgtgctttg    84540
agagcaataa acaaactatt ggctgccggc cagggaggag tgtgctgaca tcttcaagcg    84600
gatcctcgaa agctccacag agcggctgag gaagcctcct tagggctgtg gatgggggtg    84660
ggggcaagg gctgccgtgg cgccatgcag cagtgggcat cgggcctcag ccacacccag    84720
cagggaggcc aacagcagaa tcccaggcaa acgcccctag ggttcgcccc tcatgcctcc    84780
actccctggc ctggctctct gaagggcagg gcggtggagg agaagcagag ccaggcggtg    84840
ccctccgcca gctctagctc aaaggctgct ggggctgacg ggtggagctt gtgtagacga    84900
agccccttac cctggaagtg aaggttatgg ggtttcctgg agggagggca ctgggcctcg    84960
ctcttaactg aggcttcccg tcccccgagg gagggtgatg aagggtgtcc agacacatcc    85020
acggggacaa aggaggttgg caaggctgac cgcaggagtt tctcctctaa tgcctttcaa    85080
atgaacaggt ctgtgtcgct gctccgggag cgcctgcgct cacataccccc gcggtgcaca   85140
gttaccaacc agatcctacc acgccactgc ggacatcgcg gtttccggga agtctctggc    85200
cttcgtatga aaagacagcc cgacaggttg aattctttaa aaccttatct ttggttattt    85260
taataggata tgcaatctc ctctcctcag catgtcgata aatgtttatt gcccttact      85320
gtgtgagagc aggggtcctg ccgccgcttg ttttatttt cttttagacg gcgtgaacat     85380
```

```
ttttagcacg tgtaaccaat gatggtaatt aagattataa taatgctgat gccaacattt   85440
atatcagtgg atacagaaaa tacacagcct gattatttt tattactcgt acccataaaa   85500
ttaaagatct taaacatggg atggagggtg catccgcatc aagattttgt tagcatgaga   85560
ccgaacccat tcagccacgg ccttcatcag aagccttttg agtgatgaga cagtgatgag   85620
atagctcgcg ttatcctgca gcacagagct gcgcctggtc acggcagggt gcaccggctc   85680
tcgggcttca gacaacagct tatcagtacc ttgcccgtgt gcaaggacag tactccttga   85740
tgccctgaaa cctccgctcc tactaactgt ccttggacac gtcggcatac agagaatcaa   85800
tcgtactctc agcagtggtt tctgcagcaa ctctgggtca tggaagaagc caagtgcatt   85860
gttgaaacag cagagcccag gcagtgcccc gatagaaacc aggtattgag tgcttgcacc   85920
cgttcctgtg caggcgggcg tcacgcacac cttctgctgg aagacacact gtctacgtga   85980
acgcccagcc tccctgtgcc ctgccttgtc ttgtggaata tgtcggcacc cccaaagaat   86040
acaccttcaa agccaaaggg gagtttctgt ctgtctgctt cacactgtcc ttcctcctct   86100
cccacccctt ctctgtgtga agaagtaaag caaagctctt aatgatcacc cttaaatggc   86160
aagactttga tagactgttt ctataatagg ttctcattga aacatgggag ttctaaatag   86220
agaactgtta aaaagtggaa tgagagatga gggaccgagt cgtggccctc cttcctggtc   86280
tccaccatgt caagtatgcc tccaccccgg ggcctttgca cctgctgcgc tgctcttcct   86340
tcaggtcccc acagtaggcc ctttgggaac tctgatcaag tgttgccttc tccgagaggc   86400
cgcctctgac catcccctgg aaaccagcct tctctccccc acgcctgggc tattcctccc   86460
ggttcttatc ttcatcttgt gtttcatatt tgttttactt gctgatcacc agaagaaggc   86520
cttataagtc caggcactca ggcttcctct ccactcgatc tccagtatcc agaagcatat   86580
cggatgagga ggagaatgca atagaaatta gtcgcagaaa tcaatcatgg agaaaggaaa   86640
tgttctcagt gaggtgtttc aaatatgcag cgtacaagac ttaagtggaa gactcactta   86700
taaagtagct gactcgccca gcagaggcac ccattttat actttcccct ttcacctttc   86760
ttgtggataa agccagtgtg atggctggag cttcaggagc cacgttggac tatgaggcac   86820
cttgaagaca gaaaggtgtg cactgaaaat gctaaagctg aatgacggtg ggaaggtggg   86880
tcctgggaag tgatggaaac cccgtgccag ccttggaatg cccacatctg tctagtttca   86940
tctgagagaa taaaacatta tatatgttcc agccattgtt gttttggctt ttctgctata   87000
tatagttaaa ggtttcctat acatatatca gagaaccatt gggattcaat tttagtcact   87060
tattataatt caacgaatgc actttacttc tctgagcaat gttatgcctt cataaagcca   87120
ataaaacagc gtaattgttg aagaaattgt gcaaatatag aatacaatca ttcaaggcaa   87180
cctagtctct tagcctgcga gtgttctaga tgtatacaag acaaatgcat tcattcaaat   87240
attcaacaaa tatttgttga gtacctacta ctatgtgtcg tgtattgtgt taggttcact   87300
aaaacacagt aggaaagagc tggaattgga ataaatgctt tgaattctga ctcactgctt   87360
attagttgtg accctgagca aggtgtttaa cctttctgag cttcagtttt cttaatagca   87420
cttagttctc agaggtgtgt gaatatggaa tgagaggtag ataaatgtct gaacagagtt   87480
gctcagcggt tacagtaaca cagttttgct agctaccatg tctgcaatgt gatccttttcc   87540 atcaaggagc cccctcgtgg gagaaacaca gataaacaga taatacagtg aaacttggaa   87600
ggtgccgtaa cagaagggta agcagagtgg tttgagaatc tggagaagtg ggtcactagc   87660
tctgtttagg tgagttgaaa tcaggttgca ttatagtcat tggaagcatt cactggatat   87720
```

```
ttccagtttt ccttctcctg acacatggta gagttgtctt gaagagtcag tacaagtctc   87780
tagatgaaga aagaggtttc aacactctag ggcaaatgaa atttttatgc aaagccgagt   87840
cataaaagga ttaaaatttg gtgataggat cagtgcaact gtgaccaacg ctgggttcat   87900
ggggtggtag aaggcagaag gtgagtctgg ttaggtagat agggttgtat atttagggca   87960
cctttgtgca aggtgaattt ccccagagta atttgaactt gaaaaccact catcaaaatc   88020
tcctgattca ataaataaga aggctggaga aatgtcacaa acttctttgg aaaggcgtat   88080
gggacctaag agtgatctac atagccaatt tgttgctcat ctataaagac aacaggcaaa   88140
ttacctctca aatatgagag agctcaggga acagagcata ttaaaaagtg tctggaaaga   88200
agttttgagt tgtttgtttt cagtaacaaa atccaagcaa ttaatagatg gttaaaaaat   88260
aagcatgttc aaagaacggg tggcatgaaa tggatcaatg taaatgaagg ataagtattt   88320
taaactcata ggaattacat tacagaaaaa atgtattttt ttaccttgaa aatgcagaaa   88380
ataatgtaac tgacaaatgt taaggtgggg aaaaaggaga aaggagaggt gaatggaaat   88440
gagatgatga atgtcctcag atttcaaagg aagaagtgaa gcaatgctgt atagcattta   88500
aatggtattt ttaaaaatgc ttctaacttg ttgcatacct ttcctcaagg gatcttttag   88560
gaaatagtaa ctcttggtag ataaacattt gttttttaggt tcagcaattc tttgtctttt   88620
cattttatgt tctcctcctt acttgagcta ggtgcacttt atgtgctcta ggaaggctta   88680
ggtgcagaca caggggagggg tggagcggga gggacagggc cttgaagatg tgtctgggga   88740
attaggcaga agccagttca tatagtgcct tatgtctcag gcctaccacg ttcaggaact   88800
ttgacttttc ctaaaagata atgggtgagt ggggaggaag gagaatttga attatacatg   88860
catttatttt ttttttcttt tttgagacag gatctagcta tattgtgcag tttggccccc   88920
aactcttggg ctcaagtgac cctcccaact tagcctccta agtagctggg actacaggtg   88980
ccagcaagag ggcccggcta tttgataaag atcactttgt cactttggct gtcctgtatt   89040
taaaaacctc tttaagcaac atgatttaga gctgctctat cagcatgatc ttatgatctt   89100
ataatcttat gaatctggac tattcaggat ggacctcata ctctgatcct tccttcaaat   89160
ttcagatctt tccttcagat tcctaaatac tactttggta aacactttac agactaaact   89220
aggcagaaaa aactatggtg attcttttg ctgattaaat ccatgctcag tagttctctt   89280
atcctcagag aagccaggat ctcaggcttc aggccatgcc ctgtgcaagt ccaggggagc   89340
tgttgacatg agcaacaaag ggggtggctg cctcctcagc tgtgcgatgc tgagcccctg   89400
ggggaagggg ctggtcgaga ttatgtggtc tatgtccccct ctcccatcac tacgaagaaa   89460
gacagctgca aagtcctatt ttttaaggcc tccaggcaat gaaatcaaca attatttcaa   89520
agttgatatt taataacct cgttattatc aaattatttt ttatgaaat cggacacatt   89580
tttctaattg tattctaccc ctttctctgg ttttatcatc ttttgaggag gtcagctgac   89640
taatctttat tttatctata gcccctaatg ttatcaatgc taatcaatca ccacgtagtt   89700
tcctcttttc cagtctaaat agtcctagct ctttgatgta ccttcaaatg tccaattttc   89760
caatccttta tatcttgatc ttttataaaa cagcttccca tgttcacaa aatttaataa   89820
caaaagcaaa gatacgtgaa gcctatagtg aagcaatgac gccatcctct ttttgaccat   89880
gctagattca taattttgtt ctactttttac cctattttaa atccccccctt tcaaaatcgc   89940
tgtagatgga gatcatacat tagagatata attgcatttg aaaaggatgg ccctttcatt   90000
ttctgctgtt atagcagaca ctgttagttg ctactgaagt gacagtactc cttttttcctg   90060
gtttccaatg cccagctttt gttcaactgt ctcttcatgg gatgtggaca cctcccagcc   90120
```

```
ctggagggtg catctctttt agtgtaaatc agccatctcc ttcctcataa tcaatggaac    90180
caggagcttg ggacccaatc ccagacaatg gaagtgaggc agaggcagct ggtggtgggg    90240
tggctctggg gtcatttgca tcattccaaa aagacacccc aggaagagac actgctttgc    90300
tggacattgt tatgagatga catgctgcct ggagctgccg caaccatctt agaaacacag    90360
ggggccaagc gtctgaaatg aaagcaaaga tcgggaggat ggctgagtag aaagatgaag    90420
agatccaggg cttctgtgca cgccacttag ctgcctaatt aaccagccct gggcttcctg    90480
ttgtgtgagt taacacatcc cttttgcaatt tagtgatttt cactgtgtgg tcccagacca    90540
gtatcagcat catctggaaa tttttagaaa tgcagatttt ggggccctac cccagacttg    90600
ctgagaagag tctaggagtg gagtccagca atctgttttt aacaagcccc tccagataat    90660
tctaagaagt cctgaagttt gagaactact gctctgagct tgctacagtc tgaatgtctg    90720
tgtcctccca ccactcctat attaaaattt gaatccccaa agtgctggta ttaggaggtg    90780
ggggtcttta ggaagtgatt cagtcatgag ggcagagctc tcatgaatag gattagtgcc    90840
cttatgaaag ggaccccaga gagctaggtc aaccccttctg tcacgggagg gcactgagac    90900
agtaccatct atgaagcagg cagcaggcct tcaccagaca ccacattata gcagcttgtt    90960
cttagacttc tcagcctcca gaattgtgag ggaaaaaaaa tactattgcc tataagctac    91020
ccagtctatg gcattttgtt atagcagctc agatcagcta agagccattg aattgaggtt    91080
tcaattactt gcagctaaat gcatgctaat taatacagct cctttattgt tttatgcatc    91140
ttttctagaa aaatctatca atcagtatgt tttctgtcaa tgtcatctga gaattaagtg    91200
tcataaccag aaagatctgg agagacagga gcacgttgta cagttcctga tatgtatttg    91260
acacacccag acaggctgga aaagagctgg ggtaggtttc ctgggtata agtaattttc    91320 gtaaaattt agaacttttt gagttccaag gtgaaaggag aggattttga aatgcagaaa    91380
aagaaaagtt cagaggcaca aactcagaca gagctcctgt cagaggaacc aagtgcctaa    91440
aataggacag agtctccaga tgcagcggaa aggctgtgag tcatctgacc gctcaggtag    91500
gaaagcggga ccagtgtgaa atgaaggagg cactaatgat aagaggacaa gaaaccacca    91560
aattgctatt tagggtcatt gggatctgca gagggaaaca aggctgaaga gacaagagga    91620
aagacacagc tgtgagggtc aaaatctaaa aggagtcct gaagggatgc ttaatgtttt    91680
caagctatca actgcagcat gctaggtcta tcatctgtgt atcattgcca aagcaagacc    91740
cataaacatc agatttcact tggttataga attcagagaa atactactgg ggcaatgaca    91800
gggaagagac actgcacatt ctcagtggag gaatcgtccc ctctgtcctt caactggtgc    91860
catccaaaag ttgctatgtc aagtaatgct agcttcactc aaatgctatt accccctggtc    91920 aactcacagt gatatgcact aatgagcaac ccatctaatc tgtgaagcaa tgcttaagga    91980
aggtttgagg aaggacgagc tgcagatcag ctcaaggatg ggactcaaat atcatgcacag    92040 taccatgagc taaggtgcct cttgcaagct gcctgtcgag gccatcagtg ggttagaacc    92100
aaattcttcc aaaattattg cagcctgcag tcttctcatc ttgtcatata acacttaaca    92160
ttctggaaaa ggccctgcat tggttttgag tggtatttcc agaatctgtg gacctttgaa    92220
acaactccat tttgctgtac tttctccaca atggctcttt cagataaatc acttgtccgt    92280
tcctgcctta gatgaggcct gtggaatgac tgcatcattt gcccttcat tgttgaaatg    92340 gttatcagat ttcaggtata tcaagacttg cagatcaggc ctcttactct gtgtgactaa    92400
caggctcccc cagaacaaac catccaggca caaacagggg atgcagcctg tggctatccc    92460
```

```
atcacaggtt tccacaccac agtgtgagtc catcttgctg acttaacaac cgtaatttaa   92520
aaatcacctt ccaaattgca ctgattttat ttgttcaaaa gataacacac acattattac   92580
atgactatca ttttagggca aagtggatgc acggacaaat gtttcaagca aggaggtaaa   92640
actctcctgg ataaaaattc acagcatcaa ttttctattt tctgcttcct gaattgcatt   92700
ttcctggatc tgatgatttt cttctttgta ttcttgatgt atgcatcggt atgtcttctt   92760
ctgtgtttgt gtcatggagg cagcattctt cttcttttt ttttttttt ttgagacgga   92820 gtttcgctct tgttgcccag gctggagtgc aatggcatta tcttggctca cggcaacctc   92880
tgcctcccgg gttcaagcca ttctcctgcc tcagcctccc gagtagctgg gattacaggc   92940
atgcgccacc acgcctggct aattttgtat ttttagtaga cgggggttt ctccatgttg   93000 gtcaggcttg tctcgaactc ctgacctcag gtgatctgcc tgcctcagcc tcccaaagtg   93060
ctgggattac aggtgtgagc caccacgccc ggccggagga agcattctta atgtatgcat   93120
tggtacatct tctgtgtgca tgtcatggag ggagcattct tgatgtacac gttggtgtat   93180
cttctgtgtg cacatcagga agggagcact aagcagaggt gcataagcag attctggact   93240
gcagagctgg ggagcggtcc tggttttacc actcatggac tgtgtgctct cacacaagtc   93300
tcttagcatt tttgtacctc gggctcctcc tctgtagaat gaggatgaca attcttacct   93360
cctaagattg tcatgagcta tcaagaagtt aatatttgtt atgtatttag aatggcatcc   93420
agcacgtcat aaggactctg ttttgtagag tacatcgaat gttctgtttt gttatataac   93480
acatttactt ttcataaatg ttgttatctg gcaggtattt tttggcttcc agaataaaag   93540
ttttaaaatt aaaaggggta tccaagtatt tttaggagcc tagtatttcc tcacttactc   93600
ccaaactcta aaagtagatt ggcttttatgt taaacagaga attcgtacag aaaaaatctt   93660
caggactgta ttcatttcat aaataatgta ctttattttta ttgcatatgg ctattaagga   93720
gggcatccat gatcaataca gactaaatac aatgcactat tctagtccag tttattctcg   93780
tctccagcag catcacattg acccctatat acagcgtgta cagtggaaga cagagcaaga   93840
taagttaagt ctcttgtcat atcacaatag caagaaatat atttaacatc ttgatatcca   93900
gaaacaatac gtacccaaaa agaaaacact gtttaataac tgttaaagtt tatatagcaa   93960
aaaatatttt aaatttaagg taagtcaggc aaaatgtaca aagacccaat atacattgtg   94020 aagtttagc aaacataaca tttatacatt ttggttccat tctgtaaact aaattaaaaa   94080
tgtaaatatt gcatatgcct ttttgtgaaa tgtacaggat agaggaaaat ttagcatatt   94140
atcatctgtg tattttgctt gttttaagct gcagtatgaa cacgaaccat ctgtatagtg   94200
tcatgactac tctacggata gagggcgagt taaatatgcg tcaatacact gctttcagca   94260
gggtccatat tcagtcccta tcgtacctgg ggggagttac aaagcaaata ccacccattg   94320
atgcctattc ccaaaactaa ataaaaactt caggattttt atacatctta ataaagtata   94380
tcatacactg aaattgacct tccagctaac attatatggc ctatgcactg ctgtgatgta   94440
taatttcaga aaagtaaaac cttaaaaatg ttcagggaga tcactttaca ttcaactttg   94500
tcttgcaata caatcctctg ttctaaagtt cagcacggaa gcaggaagac ttttgcattg   94560
ccattaaata tattttttaag acattgaatt ttttggtctt cctctaaaaa agcctcattt   94620
tattaatgca ttattctata gcgatagata tctattatat atttatatat attttttctaa   94680 aaacaaaaca aaacaaaacc aacaacttac atctccaatg aattagtgta acctctccat   94740
gactatcaga gaagataggc actgggaag ccccacggg aggagaggtc gacagccctc   94800
caatcaagtg tcgagggagc agaaaacggc agaacattct gccggtcaag ttcagcagtt   94860
```

```
ttaggtaaca tctgcgagaa ctgccacaca ctggtatttt cagaatactg aaaacataaa   94920
acaagggtag tcttgtccgg aattttttcg acaagtaaca tgtactgcga gattgctttt   94980 cttcttttc ttttttccatc aataacatag gggctggaat gcctctttt atcagtttct   95040 ttctttcctt tttttttttt cttttgttt ttttgttca gggcagcctc actggttgac    95100
ataataacat tttattaaag ataatacgtt ttttaaaaat caaatctgcc aaacccggac   95160
caccctggaa ttgctagcac gcctacaggg attttggtt acagaaaggc atgcccaaga   95220
ttcaggagag cagagacatc tgagcttgta aatagaataa aaggcgtttg caatgtgaag   95280
tacctacata aacatctaca tcgagaagat taaacaagtc tgttaaaggt aaaagagat    95340 attcatcccc ttcccaaagc ccttccctcc cacctcccac tacccaatac agttgatttt   95400
caaaagtagg ttgcttcagt tacatataat aattattatt tagtaatccg tcttcaaagt   95460
ccaatcccaa atttcacttc cattgagaaa tgtcagtccc acactgggct cggtgtggac   95520
gtaaacatcg caggtacctg cactggaatc caacaagcag ctgtctactt ggaccatttc   95580
aataaggccg aggaccgcgc tccagacaca cagcgcaggg gctactacag gaggtcctgt   95640 gggaccccg ccacggaaat ccggctttac cttgaactga ggtaggactg tggtcgtttt    95700
gagtgtaagc cagtaaatac cagattttac cacttccata ggtacgggtg cactctccta   95760
gcatgctgag ggttatatct gctttgccaa aaggaaaaga agaagaaatt aaaagacact   95820
ggccacaatt taagaaggcc aatgaaaaca tccaattttc ttgagaataa cttcttcagc   95880
taattttgtt aaaacaaaac aaaacaaaac gcaaacagca caatgatgaa tgccccatcc   95940
gggaacaagg gaaagaggca ggtgaccttg ccttgttggt gcctcatcta acagagtcca   96000
cagatgtttc caaacacagt cattgctcag atccaaaaga aaactgcaag cagcttcggg   96060
ctgaaacagt gctgagcgtc ttcttttaat gatactctct gacatgtgac atcctggtga   96120
taaagccaga cagatcttca ctctgaaaaa gaaaggaggg aagttagcag agaccctcag   96180
gagaacagag caatctctgg agttccagaa agggcccctc taacccacag ctaggacctg   96240
ggtcattttc ataaactgat gacctttgag aaagaaacat gtattcattc tgttttccag   96300
aggtgagttc agtgggaaaa ctctgagttt tcctggaagc agagctgtta ggttcatggt   96360
gagttgtcta gacagttagg ttcgtatttt caatttaaga aaaatattcg catgtgtttt   96420
tgtgaatcat tctgtcgaac aagatagaaa aagaagggcc agttcctagg ttgcactgcg   96480
tgtctgtgtg atggaatgac ccctgtaact ccttaggcct tgatgcttcc tgtgttgtgt    96540
gggatacaca gaatccactt gccttcctcc cagggctgca gagatgaaaa actatgacac   96600
acattacaat gctctgtaaa ctatgtttat tctacaaatg tgcattatgt tatgaaagtg   96660
gagtaactaa taactccaca cttctgccct cagaaaactt ccaaccggat catctacctc   96720
tttttgaacg tgcccagcaa tggaaggttc ctgcacggcc tcatgtgttg ttgcataacc   96780
ctcaacatta ggaaagggtt attttatcc actcaaactt tcatatgttc cagtttaagt   96840
aatttaccct ttcgctgtgc tcagagggga cagggactga ggacacgtgg ccagatctaa   96900
ttgcttcctc ccttccagga tgaaggatca aaattcttta acctttctca atttccagtg   96960
ttttaggcct atttttactt gatatattcc ttcttcaagg gacagaacaa attggaagat    97020
tttgaccttt cacagcgtgc tgttttcttc tttctaagct tcttggcttt ttaaccaaaa   97080
tgacatactg ttcattttca tcactcagca acatgagggt gagcaccgct ttgctctcaa   97140
acaggtacat ttccttcctt tgcagatgca tttataccaa ctgcatttct ggacactctt   97200
```

```
ctaaaatcct ttagaattct gatcctagcc tcttatcata ctccctgact tacttttttg    97260
tgaaccaaat tcttttctct ccatcttaag tttagaggac tgaactcaac aagacagaaa    97320
cttccagtgt gccctgaagc tgagagtgag tccctcaaaa ccacatctcc ttatgaactc    97380
gaggcactac atgctatagc cccccaaaaa ccccaaaagc tttacagaaa aaatacttgt    97440
caatatacaa agtggacatt ttaaaattcc ctacaacgcg acattctgag gctgttttat    97500
ctattttatt tattattatt attagtcttt tttaagatgg agtcttattc tgtcacccag    97560
gctggagtgc agtggcatga tcttggttca ctgcaacctt cacctcccag gtttgagcaa    97620
ttctcgtgtc tcagcctccc aagtagctgg gattacaggc acgtgccacc atgcctggct    97680 aattttttgta ttttttagtag agacggggtt tcaccatgct ggccaggcta gtcttgaact    97740
cctgacctca ggtgatccac ccacttaggc ctcccaaagt gctgggatta caggcgtggg    97800
ccactgcggc cggcctatct tgttattttt aaaaagcttt atgtccatta taaatttaat    97860
aagtaaacaa tgttctgcca atgaaccttta acagaattaa tttcttccta aggaaagatc    97920
tgtctttgag ttatctgatt cattattgtt gtgattttca atcccaggag acttcagtga    97980
gaatctaatt gtttgtatcc cctaaaaaaa aacaggcatt tgctaaaaca caccttgaga    98040
cttgtaattc accctaaaat gagcttgcat tttgtccctg agaccctgat tgggaagaa     98100 tcccatggcc accacaagca ggtaactgag actctgcaaa tccattgaca gaagaatttc    98160
taatcaattg cttattttat tttgacacta acaattagct aaatgtggct gaattatctc    98220
atgttaactc taagtctgtt attttgaaaa cagctaaact agtaagttct tcagtttctc    98280
aaacttaagc actttgtcat ataaatggcg ggtaaattat tgctgaaaaa aattactttc    98340
cattttcatt tgtgatttca tgaggccact gacattttca ttgtttttttt taggatgctg    98400 tatcgctgta atattcaact cttatcatta catctttgcg agctccaatt aagttgaaca    98460
tgtaatttta ttttttggaa gtagaataca gttatcaaaa cgttaatttc taagcattag    98520
cattatgcaa gaaagagct gataaatggc aaggaagtaa ttcatccatg catttattca    98580
tgcaatgacc tttcaacaat tttcttttttt taattctact ctggtgcaag gcctcactga    98640
taacttgggg gaagatggct gacaaaaaaa aaaaaaaaa gaaggaaagg ggaaaaggaa    98700
gggcaagcgg aagaggaaga ggaaggggaa gaggaagggg aaggaaagaa aaaaaaagaa    98760
ggagggagga aggggaaagg gaaggagaag ggaggaagga agggttatta caggaagatg    98820
aacctgttaa tggcacactc aaaggacaca agagagctga ggtgagggag accagaaaca    98880
ggatgaccac ccgctcagag ccaggcatgg gggtgtcagc tgtgcagcgt tcacacaca    98940 tctacatgca cacacgtgca ccagagcaag cacaacgtgc atgtgtctca cctagcctgt    99000
ctcctgttag gttaatacaa ccgctttcaa cggccgcctc ctttcacggt aaagcgagaa    99060
ctgtggtctg ggtgtgctca gcgggcacag gcctgtggtt ttgctcccca gtgccctgcc    99120
tctcacagac ctgcttgctt agacatcccc ccaccccagg aggctgaggc tgattccagg    99180 tgacccttg ggatgcttgg aagcgctcgc ggtgatttaa acagaattaa ccagcagaaa    99240
caatcctttg cggaggtgca aaagggcagc gaggaaaagg ctggagcaca cctcagattg    99300
gacccagatg actaggacct gccagccgca gcagagggat tgggatacaa cagagaccta    99360
agaagcatca gtactaagaa tttatggtgg aaaaaaggga tctgttttga aaccctaagt    99420
atcattttta ttcatttgtt agagaaagaa ggtctaagac agaagccatc tgcctgaact    99480
gatgtctcaa ataccttttt ccaattgagc tggtggtaga atctttgcca cacatactat    99540
taaaggcccc aggcataggg ctaaatgatt aacacgtgca agggctcagg agggctctct    99600
```

```
gtagttcaca cacagctttc agacaccaaa caccaagagc tggtgcccct ggttgaaacc    99660
accacggcaa cacgatacct accacccacc tgacagccac ccactcatca gtgacactcc    99720
cctaccccag gaagaagaaa gctggaaaac actccagaga ttcaaaccta ggaatgagag    99780 taaactttg cctttatatt catttacttt caaagtaact gaagttatcc ctcaccctga     99840
aaatcagcct ggttcatcct gaccagggga aaaaaacaca ccaacaattt tctaacacta    99900
atcatctgac atcctcaacc tttaaatatg atcaaacttc aggcttcctg aagatgagat    99960
tccagcaaaa atttatttgt tgtattatct gtgttcattt tagtagaagc aaagaattat   100020
taattttatg gctgttctac cctgaatatt cactaagaag gaagagattt tctgaattca   100080
tcagctgtaa tggcaaaacc aaaaagaaaa caataagact cacgtgttgc tcatgaacac   100140
aatgacagaa caccacacac cagttctgct gctacaggta atctatataa aaaatgtaaa   100200
cttactgata ctcattgaat ttgtcacatc gctcattaca cactgtacta ctctgtccct   100260
tagacgttgc tttgtgagga aatccatcca cagacgtatc cacgtagagt tatttgagca   100320
aataaaacca acaaacaaaa acactttag cagagatgag agttgttcca tgtgacatgt    100380
cgtgcagtgt atccactccg catctccttt ctgctgtcgc ttgtgacaga tgacattcat   100440
acgtgggata cagtcccctg tgccactcac cataatgccc tgcagatggg caataattcc   100500
tccccttttc tcctccactt acaagagcaa tcagaatgca aatgaaggag agagctgtca   100560
gtaaaagctc caccttcaaa ctgctcaact tgactccccc gaaagagaga aaggaggaaa   100620
gaaaacaaat cactagaaaa cattgtgatt aagacaagga ggaaagcttc cttgtaatat   100680
atggaacaat gtcccaacaa tgacatgtca cacggagctg gcaccatga ctgcaatcac    100740 attacagaaa actgaagtgg gcatcaagcc tagaacatgt tggaaataag gtcaatttgc   100800
tccagccaat aaaatcaggc agcattttcg gcacacagtc tgactcacca atccttttttc  100860 ttcataattt ctcctgacaa tttgggtttg gacatgtttg cctccaatgt tacatttcga   100920
tgttcaaaat ccaggatata cacctgggtc gtggcagctc tgcccaggga ggccccggtc   100980
ctctctgcag agggcttac ggccaccacg tagggcccca tggcacggct gtgggacatg    101040
gggcctcaca ggcctttggt gagcaacact ggaccaccca gaggccaaat tcatggagta   101100
ggtaaagatg ctttcacatt ttcagccata gctgaattag gagtgttaca atactgatg    101160 tacttgacaa aatgaaacga tacacttctt aaaattaaaa tttgtatttc tagtagcaaa   101220
tgtgattccg aaagcaagga aaccttccat gagctcaaac atatcgtaca ggtacatctc   101280
agtgcccagt ttcagccttt tatgttaaac acagaattac aagggaaaat tgacttttca   101340
gttgcaggag caattctgag aaaaataaac ccgataattt agtatctcca gactttacta   101400
aagcaagaca ctctaagaac atgaaaaaaa aaaaaggta aggttgggta tgataacaaa    101460
agccagagat tctaggaaaa acggttactt gaacttttct tttaaattgg aaaaaaaact   101520
aacttaaaag gaaatatgg aagaataagt tccccatgac aaacaggggc ataacttgc    101580 tttcctgctg ccctccttga gaaagactga aaacattctt ttctatgagc tcatcacttc   101640
cactgacaat taaaatcatt tcattttgaa tgcttgttag taaaaaaaat tccgaatatc   101700
aagttgcaac ttgatgttaa tgacacaata caaaatagga tgagcaatc tagttgtctc    101760 acaggctgga tttagtaaaa ggtatctccc cctttaactc ctgtttaatc ctgcacataa   101820
gacctggtct taatcatcca aaactaggaa aatcaggcct cctaaacttt tacctactgc   101880
acttccaatt ccctctacac attcaacttt ccctatacagg agcctgtata aattttacag  101940
```

-continued

```
tgcacggcta cagcagattg tgtaacacag aatgtacacg gttcttttct gagtgttatt 102000
gttaaaaacc ctgccatgtg catgaagtga gctattcgtc tatggcaaga attgcccact 102060
gcccctgcag cagccgccaa tgccatagga gaaacagtat cgatgattct tctgcacaaa 102120
cacctgagat acaaaaagtt ccaagaattg cgggtggacc ctttcttta aattatgaaa 102180
tgttagaccc ttttagtta aaacccagac caggaagcac gaacaacttg ctgaagcctc 102240
cctgccagtc tgtggaagaa cagggtcctc aacttctccc agaacactt cctctctgct 102300
cccctttggt gacaatgaga tgggtgggac agggcaggag cagagacacc tgcaactgtc 102360
acctggggcc ccagagtgtc aacttccaca gtgaaccact agctctttat aaaactctcc 102420
tcgaaggaca ttaaacagca tgctagcatg tcacaagatt cagtgaagcc tgtgagtcga 102480
tgagggtgtg ctccatggtt ggtcttcctt gccagctgat gcccaggccc tgccttctca 102540
cctccctgtc cccagcagcc agcagcctgc tggtcaggtc cttagtaaag cttataggta 102600
ttaaattgaa gcgaaaaccc catgtggttc atgccatttc tcacaggcag aaatgctcaa 102660
taaagttttc taaaagagaa caaagttttc taaaacagaa cgaagcttta ggactgcgtg 102720
agacccagaa gaaaagaaaa ccctttccag cccacttgga gagtgacgtt ccaagcagag 102780
gtcagtaaag taaggccaga tctggcttgc ctgtctctgc aaataaagtt ttatttgggc 102840
acagccgtgc tcacgcattt acatatggct gctttcacac cataagcaga gtggagcagc 102900
tgtgacagag actgcatggc aatgaaccta aactctttac tacctgacct ttcacagaat 102960
gtttgttaat ccttcaagga gcacatgaac atggcaacct ttactaagga agacaatgcg 103020
aagaaaaaca ggcaaatttg tcagaaaaac accatatatt tccatctgtg tgttatactg 103080
ggaaactaat tgatatccct ttgaaaatta tctgcaagct tacgtacttt agaaatgcaa 103140
tactatctac taaaaaccac actatcctgt tacagaccct actgaaaaag aggacacaca 103200
tcacaaaatc atttatgaag ccagcacact tttggaatga atttctctta gctaccgcta 103260
ttctatttga ttttttcatgc ataacacaaa agtgctcaat aaatctaatc attgctaaat 103320
acatcctaca ctagcattct tcctttaaca gaagtaaagg tttatatatg agatctacaa 103380
ctcattaagg gtccaaatct tttctctttc ttgggtcatt tgagaatgtg aatgtaagca 103440
ttatgcttct gccctaagag tatttgggcc aagtgatata aggtgcatta aaatcgcaaa 103500
tagccaatga acgacgtaat tctttcctca gacttaacac atgtttatac gtatggtttt 103560
cttactaatc taaaaaaatt ttatgtacac cataacaatg tttatattgt ttatatcaga 103620
aattataaaa cctaattata ttttgctgc caaattaaga gaatgtagaa taattattta 103680
ttcacaatat atccatctcc agatagcctg ttgttatata tcatttcaac tggacctttt 103740
ttctacttta aaagcttaaa taactgtagg taaatccccc ctcctcggtc tataacatct 103800
atgtgatata ggatttcagc tttgtctctc cagggacaaa tccatctatc taatttaaaa 103860
gcctcctaag aatcaccacg tagccttaa ctgagccatc tactagagtc aaggttgaag 103920
ggtcaaatcc tacttagtca ctgaagcgca ggctctcttt gcagagatca aagtgcccat 103980
tcttcctaat cggccatatc aaaaacatcc tgctcttccc tgggagccta ggaatgactc 104040
catgccccca tctctgtact ttaaactaca tgccattccc acgactctca ggatacaggt 104100
gtgaaaggcg ctgtcgccac accagagccg ggtcccagg gctagcatct aggaaccact 104160
tcttaccagc tgtgtaatct ctacagctat gtctctaagt ctgctccctc ttatgaagat 104220
gggggcacta cctctcccac cctgaattcc ccagtggagt cacagggaac ctgtcaaatg 104280
agatttcatg tataaaatat ataaataatt aataccaaaa atgcgtatgt tctttcattc 104340
```

```
ataaagaagc acatgctact agcacaactg gcattttgtg gttggcttcc ctttgctttg    104400
tgcaccttca aataatgtat acatgtaacc acatgctgtg ttctcaacta cagacttctt    104460
aagaccaggc agccctgtgc tgccagggaa agacaggctc ctcccaccct tatgttctgg    104520
ctaatttgtg gagagccaca gtggtgtctc ttagtgcatt tgtcatcaca gctcttcctc    104580
gttcaaaatt gtattcgtga atgataccac gaacaaccac aactgcaagc agcaaataaa    104640
caactgccga atgcacaaaa acaatggcaa attgctccta aaataaaatg aacaaacttg    104700
ttttaattgg acagaagtgg aacagaagta gaattgtttt tctgggggta actctaggcc    104760
atttaaagct gcaaagagtg cctttgccta gctgctttct tcatgtcctg aggacaggac    104820
aaaatgcccg ggaaggggcc tcacatgtct actactcagg cagctgccca cagagaacat    104880
gaatcccttg ccacgtcaca catgccaagc acacacaatg catcatcaac aggctgggct    104940
ccgcctggtc caggccactg ggggacagca cttcccttct ctctgctcta tacaaaaagg    105000
tgccctaaaa tgcaggccga catttaagtt cctctgccac aaatgacaga gatttacatc    105060
taactaaagc actatttatt gaaatttcag taatgcaaaa tggaaaacgc caagctacca    105120
actatataaa gttcatttac tggagaagca aataaaataa gacagcagca gctgatcacc    105180
agtccttgcc caaggatgtg gagacagagg aaatccacat ctttggctcc tcttccccaa    105240
caagcatgta gatatcccag cctcaaccac cctgactcca actccccacc aagcatgtag    105300
atatcccagc ctcatccacc ctgactccaa ctccccacca agcatgtaga tatcccagcc    105360
tcaaccaccc tgactccaac tccccaccaa gcatgtagat atcccagcct catccacctt    105420
ggatccaact ccccaccaag catgtagata tcccagcctc atcccacctg actccaactc    105480
cccaccaagc atgtagatat cccagcctcc tccaccttgg ctccaactcc ccaccaagca    105540
tgtagatatc ccagcctcat ccactttggc tcctcctccc caccaagcat gtagatatcc    105600
cagcctcaac caccctgact ccgactcccc accaagcatg tagatatccc agcctcatcc    105660
accctgactc caactcccca ccaagcatgt agatatccca gcctcatcca ccttggctcc    105720
aactccccac caagcatgta gatatcccag cctcatccac cttggctcct cctccccacc    105780
aagcatgtag atatcccagc ctcatccacc ctggctccga ctccccacca agcatgtaga    105840
tatcccagcc tcatccaccc tggctccgac tccccaccaa gcatgtagat atcccagcct    105900
catccaccct gactccaact ccccaccaag catgtagata tcccagcctc atccaccttg    105960
gctccgactc ccaccaagc atgtagatat cccagcctca ccaccctga ctccgactcc    106020 ccaccaagca tgtagatatc ccagcctcat ccaccctgac tccaactccc caccaaacat    106080
gtagatatcc cagcctcatc caccctggct ccgactcccc accaagcatg tagatatccc    106140
agcctcatcc accctgactc caactcccca ccaagcatgt agatatccca gcctcaacca    106200
ccctgactcc gactccccac caagcatgta gatatcccag cctcaaccac cctgactccg    106260
actccccacc aagcatgtag atatcccagc ctcatccacc ctggctccga ctccccacca    106320
agcatgtaga tatcccagcc tcatccaccc tgactccgac tccccaccaa gcatgtagat    106380
atcccagcct catccacctt ggctccaact ccccaccaag catgtagata tcccagcctc    106440
atccaccctg gctccgactc ccaccaagc atgtagatat cccagcctca tccaccctga    106500
ctccaactcc ccaccaaaca tgtagatatc cagcctcat ccaccctggc tccgactccc    106560
caccaagcat gtagatatcc cagcctcatc caccctgact ccaactcccc accaagcatg    106620
tagatatccc agcctcatcc accttggctc tgactcccct gcatgtgacc cactggcact    106680
```

```
gaaacagtgc acaagtcata ttcagttact gcacatgccc tttcagccaa aatgccaaag  106740
tgtctataaa gttactcaaa aacttaagtc taagcagagg aaacatacat tctttagcct  106800
cggtagaacc taaaatggca aagatcttgt agacattttc caatgctcat gggctgggag  106860
gagcctcaca caccagagga cccagatctg cgaaatgctt tggtcaggga catggaggga  106920
ggtttggatg agtgggcagc ctagaaacgt gggccccaac ttctcctgga gggtccagca  106980
gggtgccctg agtcaccagc agttggattc agagtgagga caggccccct gctcctgcct  107040
ctcaggccca gggacagagg ccagaggctg tgcaggtcag tgtgcaccct ggctcctgtc  107100
caggcgggcc acaccgggaa tgtggccaca aacacgtctt ctgccctccc ctcctgtcca  107160
gcaaggagaa ggaggtgtgg aaggagaaaa tacccagcaa cataaagatt ccatttccca  107220
aattgccaga agtttggaaa ggggagaact gatcaattaa tgataaagaa aacatttcct  107280
acacgaaaag gaagttggac tgtgtggtga ttgacacagt cacatttcct ggtttcccaa  107340
ggctgtgcct gagtccttga aggcctttaa gaatggattc aagagagatg taactttcta  107400
accaccttgt tagtaaccaa ggtgacaaaa ctgaggatca agcagatgcg tacagaatag  107460
acagtagttc tgtcctgtgt gttacagact taatgccttc tcttcccaga gagcatcacg  107520
cagtgatatt ccattctgga aaatcagctc gaccattttt cctttttttt tttttttttt  107580
ttttgagatg gagtctcgct ctgttgccca ggctggagcg cagtggtgca atctcggctc  107640
gctgcaacct ccgcttcacg ggttccagcg attctcctgc ctcagcctcc taagcagctg  107700
ggactacagg catgcgccac cacacctagc taatttttct atttttagta gatagggt   107760 ttcatcatat tggccaggat ggtctcaaac tcctgatctt gtaatccacc agccttggtc  107820
tcccaaagtg ctgggatcac aggcgtgagc caccgtgcct ggcccagtgt gaccatttaa  107880
acatttctag ttacatgatt ttgtaatatt caatatatat gaaatttcta gaaaataatt  107940
gttatttccc tcattttgct tagagaatga tggaccattt tacaaattct acttggaata  108000
actagcaaca cagttcaagc agataattca agaattaggt cctctttcac cattagtttt  108060
ctacatattt caggaaaact aagtcaaatg gagcctaaat tctgaagata gacctaaatg  108120
ctcaaccaca ttttaaaat tatgcaggct acaaataact gcacacagtt ggctggagcc  108180
catttattaa acatgcactt tcctcaccag caggctaaga ggacatcagg gcacccgtac  108240
acacctagcc ctcaccttcc ccaagctctt acgccctcag caaaacccat gcccttggct  108300 cttcctgtg aagccaggat ctctatgaaa caaatggaat aatacattgg aataatactt  108360
tttctgcaca tttttttctaa cttctataat tttcatttcc aaattagctg aagagtgaaa  108420
ttgatttgtt tgataagccg atggttagca ggtcctagtt aaccataatg cacggggcat  108480
cccgcctcaa ggcagagttc gaaataagcg gattcagctt ttagtctgtc agagggaaag  108540
accttgtctt ttttttttta aatgacggct gtgtgttacc agaagataca gaatcaggca  108600
ggagccaggc ttgccaggac cacatcctct ctctacagac tgggaaagtt tctccaacag  108660
caggagccag gctcaacggc ggggcaggca tatacatggc ctaccatctt caggcctcag  108720
attttccatt aaaaaacagg gataacaaca agatccaacc ctacgcatag gttattggga  108780
ttcaatacca tttttaaatg tcttatgaat tataaggtac gctacaaacg ttaagttttc  108840
agaataaggc atgtcattcc atgattacaa acttgtgctt ttgttttgca gtttatcctg  108900
taagcacgtc ccagtagttt ccccaacctc aatggtacct cagcgtcttc attccactag  108960
atcacttcta ggtctttca aatttatat acttttgagg aagaaattcg agttgacgta  109020
tactctacca agtaaccacc accacccagg gataccacca ccatgatgat ggaattgatg  109080
```

```
gctacagtat gaaagttttt aaaagctctg catattattg ttcccaagga ctctatctcc  109140
ctcacacact gtgacatgtg ggctaacatc agtagcacgg ctggccgggc tcaattcctc  109200
ctggtccctt actacctctt tctcttcact ttctcctttg agccttagct ctccatgcca  109260
gccacactgg cctccttcct gttctggaac ataccgggca acctgctgcc ccagagcctt  109320
tgcactgctg ttcatcccct ttgcctactt ggattcctcc cttaacatct gtaagaccgg  109380
cttcccctga ccttcaggtt gcttggctca aatttccttt ccccctctc ccttccctgc  109440
ttcattgcta gagcatttca ccacctgtag tgcttcatct cctaaatgca catccaaatt  109500
aagtttactt cctaggtttc aaaggcagac agctcactga agactcgccc actttctgtt  109560
attcttttta gcttgaaaaa ccaaatctgt ttctctctag cctattcttt catattgctc  109620
aaatggatga agtatttttg agatagtcta tatgcaacaa ttgtcatctt tgtaatgaaa  109680
acatgcagaa atttaacagt ttgaatacat ttaaaaatta aagggagatc tcaccatttt  109740
tgccatcgtc ctttctgccc ccaactttct acctttctca agcaacccat aagtaaagtt  109800
cctattttc tttttttctg aaaactgcaa aaggtggcaa aaggtgagaa tgggaggaga  109860
ctcatctgtg actaactccc ccatcagcct cacgggtggg tgacttggag ctccccaacc  109920
caatgggact tccttctttc gcctacactg gccaccacca tggagggcag ggaggccaag  109980
agcggcaagc agccctttga gccggtgggg gctgtggctg gcaggaaagg aggggctttt  110040
cctgaacagg ctagggatgc ctatagaaag aatgtgatca ataccettaa cgcagccttt  110100
ggggctgcct acaaaaagga gccaagaaac ctgacaatgg ggaagtttct ggaatactac  110160
catttacaac aaagactgag cacagaatga agtaccagga gagcttggag gcaaggccgc  110220
caagagctca gggcaagctg acatctagga atcgggatag cagcagaatc aaagctacta  110280
tttttcagag aagaaaactt acaaacacta cctcatctga tgcacccag gttcacgcag  110340
gggtgaaggg gtgaaacatc tgagtggtcc cagctgtgaa tgggaccagt actgtgaatg  110400
ttccagcaag gatatccact gtcgcagcag agacatcccg tgaaacatcc cattctctgt  110460
gctcagccaa gattgcctgc ggggtggaca cttatgaaaa ggatcagagg ggctgcccag  110520
aaaatggtgc ccggtgggat gctgccaagt tgactctgaa ggcacctagg gaacagaggc  110580
caggcttcac atttcttctg catctcccag gacatctact cttgtgctga cacacgctga  110640
actctcaata cattgattgg cttaaaatat caactgtgtt ctgcgttttg gaaatggctg  110700
aagacccagt gattctaaac agcccagcga acctggacag atcaagactc acacagatga  110760
atgtgtatca cccagacttg ttctaagaac ttcattaaat gctccctgct gggaaaactt  110820
ggacatttca ttgcagtgat tatttcatct cgaactagga acactgataa gctaagctgc  110880
aaataacagt aagacggcaa actgaaccaa ggtgtgtcct ttctactgga ccactgaaac  110940
tttcatctgt ccccaaacac caaaatgccc ttacatgtag aagctacaaa acctttagga  111000
gaaattctca tttaaaaaac ttgtcagaac aaataatctc aacaatgtct ttgcatcaat  111060
gaatgcaaat tcatggatgt ttatatctaa aagggttttg tgtagccttt gtatctagta  111120
ttttcatgca gttcaatatt aatatttaat ttttttctct tttgctttct cagccagcta  111180
aattaaagtt agttttctga aactgcaatt aaaataaatt tacaatcctg gatttataat  111240
actttaaaag agaaaaagag atttggtact tttgcaacta acacatttg ctaaagcata  111300
ctcaaatata ctttcagttg aactatacat ttagtagatg tctacttgac aacataagtt  111360
atttgtacaa gtctcagcac actcacctga tatatagaac tggaagaggg tatgggtagc  111420
```

-continued

```
ttatggattt gttttctgtt tcatttgcgt atgtaaaacg ttattttagg ttgcttttat 111480
gcaggaagac aataaaaagt gaatacctac tatcatacca gaataaaact gaagcaaagc 111540
actttagtaa tttattttt taaaatgcac caaaggtgtg gggtaagaaa ctgaccacaa 111600
gactctactt ttccaggaat ttctgctgtc tgggaagttc agaagccctg caatgtccac 111660
agtaaactag ggtcccagta cctccatttc tgacctcttc aaacagaaac agtctctgct 111720
caatacactc taatccacga cttgcttaat cctgcttatt gcgtggagtt tctaaaggat 111780
tatgtgcatg gttttaaat ttagtaaaga aattctggcc tatttccaaa acttttctcc 111840
ctgcttcaca attcccctta tttatccatc catctgggta tgggaagtcc cgaacaaaga 111900
aaggagggca gagaggctca cccggcatgc gctgggccca ggcagcgcag ggcagtcatg 111960
ggtgagggtg gccactgaga tgacgggatc gggggcggct tctgccgcag acccgggaat 112020
tcacgtggtc agatggtccc tgacttcagt ccctattttc ggtggttcat agcacggagc 112080
ggtgcaggta ggtgcacgct cttcccaggt cctctgcaga aggcaaaagt tcccagaggc 112140
acccaaacct tgctggggaa aaggcttctg gccgattcat gaagaccccc agaccacacg 112200
tctgcatcag ttttcctgac taaattggtg ggtgctcaac aaacccatca ctgcaacaca 112260
gggcgctccg aacgtggctt tcttcttaac ctggaagaag gtccgtaact ccattcgccc 112320
ggatagcaaa actgctttcc tgctttgctc atccagccag gtctccaatc tcacctgctg 112380
tttggtgggt cacggcgctc accgttgggg gtgctggcca ggaaggaggt actgtctctt 112440
gatgctgaga ggcctgacag cttgcacaaa gcaaacactg cactgcccac aagagttcca 112500
ggccacagat ttgcctatta cattttttt ttttttttt gagacggagt ctcgctctgt 112560
cggccaggcc ggactgcgga ctgcagtggc gcgatctcgg ctcactgcaa gctccgcttc 112620
ccgggttcac gccattctcc tgcctcagcc tcccgagtag ctgggactac aggcgcccgc 112680
caccgcaccc ggctaatttt ttgtattttt agtagacg gggtttcacc ttgttagcca 112740
ggatggtctc gatctcctga cctcatgatc cacccgcctc ggcctcccaa agtgctggga 112800
ttacaggcgt gagccaccgc gcccggccgc ctattacatt ttttaaagtg tgaatatctt 112860
aagaatttt atgtgtttgc taaagtgttt ctttctgctt ttgaaagtga ggttataccc 112920
acgtcattag aataatggca gcttctgtga aattaaattt gtatgaaaac tatttatctt 112980
catataaaaa tccagctaaa tgatttttt cctgagaatt aaaaaaaaag aaaaaaacaa 113040
gggctgttaa aaataaaaag gcactgacaa aatactcaat tccccagaag ataaccacct 113100
agcaacaact gattagttag ttattggtcc ttaggcaaat tctaaattga ttagttttca 113160
aataaactca ttaaatagggt taatgactca tttcttagaa aaatgttaat ggacttatcc 113220
ataatgggga atatatgata tttcacttat agaacaagca cctgtcttag agacacagag 113280
agcagtgacc gaatgcaccc gctgactcat cactgtgtca ccgcccaggc tgaacctgtt 113340
acacagagcc gccttcaatt ctgctagata atctaggcct ttcgatttca ctgggggtct 113400
tcatgaaaca ataactttgt ttccttttct ttgataaagt aaatacatga ccttaaatat 113460
ttgccaaatc ttctccccac tcagtagaca ccgtccacat agtcatgaac agccatattt 113520
ctctgattta taacgcgttt cttcattaag gaattctgca ttctctattt ctggctttca 113580
gggtttcttt tagtctatgg atgaagaaag ttactaaaat gttccaaagt aaaaagacta 113640
atatcatttc cacaaatact aagttgttct aaagagcata ggctgtatcc tgggagaaag 113700
ttattcatca agatacaaag aaccaactga gatgtgtcat tgtttgtatc acattctcct 113760
actctttctt gatgatatct acaaacaact ctaccactaa ttgaatcagt gaccttgact 113820
```

```
aagactccgg acctcacaca gcctctgttt tcacaacctt aaataactaa gttacattct 113880
atcaacggtt ctcaactctt ccttctcaga acacccttgt atatttttt cgtattgtca 113940
ccacctgagt tgcaagagtt ttaatgtatt tgatggtggc ggtggtgggg aggtatctta 114000
ccaagtatca tatacagttt gctttaccaa gaggtaatga aagacagcca gagcaatcta 114060
agttttccac tttgttgaca catctagagg tccaggaagc atgactggag tccccagaac 114120
agatccatca ccaacttgat ggtcaacttt aaaattcact agtaacatca cagccttgaa 114180
aatagtatca aatactaaac tctccaaacc ggaggatgta aaaactgatt caataaata 114240
gagcgctttc ctaccagtct tcctcctcaa tggtccccat tttcctttga attgataccc 114300
agtggaagaa aaaggggag atgattaact atcactccag caaaatatta acttaaatgt 114360
tgcttgaggc aagggtctag gataaaatcc taatgtaatt attgcatatg agcttcccaa 114420
gcagacaata tgacattaga gaactgggct agggatacca agatgttatg aggttgaacc 114480
cgacactcct tctcctttttg gctcagagat ctggagcaag tcatctggcc tctccacact 114540
gtaggttctt gattccaaag aatggggttc atggtggttc tgcctatgcc ataggatttt 114600
ttggaatatt ataccatatt gtatatagga aaatgtctta ccactataaa gggaagaaaa 114660
acacccttttg aattttacac aactcttttta accccaagag aagagtggca ggcagttatc 114720
cgtcaatatt gatcagaata atggtacatc gtcattgcat tcaacttcaa taagattctt 114780
tcaaaatctt cagttgccag ttgtctacca agttgtggga ttatctgtta cacttatact 114840
ttggaggcca aagattgact tatttaagtc catagaatgc atacagaaag cactgtatca 114900
tattcttaaa tattaaagat taagcattaa tactatgcaa aatctttctt tttttttttt 114960
ttttttttga gactgaattt cactcttttgt tgctcaggct ggagtacagt gtcgcgatct 115020
cagctcactg caacctctgc ctccctggtt caagtgattc tcctgcctca gcctcctgag 115080
tagctgggac tacaggtgca tgctaccatg gctggctaat ttttgtattt ttagtagaga 115140
tggggtttct ccatgttggc caggctggtc ttgaactcct gacctcagat gatccaccca 115200
cctcggcctc ccaaagcgct gggattacag gcatgagcca ccaagctcat ccaagaatga 115260
atcattctta acataaacat aaggattta aggtaacaaa atcacacagt ataataggat 115320
tgtaaagtaa caaaatcaca tagtataatg aactatatca taatatctgt ttttatgcat 115380
tgaaaacaat tgaaatttca taccacaccg taataactga ctcaagtatt tgtactaact 115440
gtatagggat aaagtagcag tagactatgc ttaagttata aagtttcaac atgaacaaag 115500
aacacatcat taatccttga atttcagtta tggagaaaaa tatcatatcc agcctcctgg 115560
agcatgactg gatgagatat tatggaaaca cacacacaca cacacacaca cacacacaca 115620
cacacacaca caccagcccc aaatatttgt tgctggaaaa cctgatactc tttaaaatga 115680
atattaaaag atccagcatt aggccgggcg cagtggctta tgcctgcaat cccagcactt 115740
tgagaggctg aggcgggaag atcacggggt caggagatcg agaccagcct ggctaacacg 115800
gtgaaatccc atctctacta aaaatacaaa aaattagcag gcatggtgg catgcacctc 115860
tagtcccagc tactcaggag gcggaggcag gagaatcgct tgaacccggg aggtggacgt 115920
tgcagtgagc cgagatcaca ccactgcact ccagactgag tgatagagtg agactccgtc 115980
tcaaaaaaaa aaaagaaaa aaacccagca tttacagggt gcaatgcgtg tgatcagtta 116040
tcttttaaaaa atatatcgtg ggtcaaaata tttgatcaaa tattccaaat ttcagtaaaa 116100
acacagtaag caaggaatat tttataaacc ttgtgtatat agatatcata tatgacataa 116160
```

```
gaaaactgga cagagttttcc aaggcttcac ctttacccat tcaagttttta cagtgtctttt   116220
ggacacataa aagtgactct atacaaactt agtattttcc tagtctaata gaaaattaat      116280
cagaaccacc aaattgacta ttttatcatt tgtaaacatg taacccataa gttttaatcc      116340
aatctatttc agaattctta tgtaatgaat tcacttaagt aataaagcta taacacacag      116400
aagcatcttg cattatttgc acctacagag caaaatgttg gtatacaaca tatactccaa      116460
ctctttctac actaaccttc acctatgcat tgtattttag cacccagtta atgtaagtct      116520
ctgtagctat cttgaaagaa attgaaatca gtagcaatca tcaaccccat catctcctcc      116580
atgccaaatg atgactttac tagttttctt cagaaaagtc tagcactgaa ctctgtgtac      116640
aataatctac ctgaaatgag tcagaataac cactgcagtc ttgaagaacc cactcaaact      116700
aaatatagaa agagtgtccc tatctaaact tggacagcat tcttttcaca aaaatcatga      116760
tctgacagtt aatgtgttta taaccaatac ttttggacat tcagaaaatt ttgttttcat      116820
ttgttcatta aaacgccaac attaaaacgt tttgttcatc ttgtatagaa atatacattc      116880
tgctgtcatc cgtactagag aaatgaaaca gagaatccac ctgcattaca gctgtccaaa      116940
tgcaggatgg ggggcggggg gcacagcact ttgcctcacc cagtgttttc ctcattctac      117000
ttggcaatgc agatgaaaga ataaagttac attttcccctt aagtttataa ggtgaaatgg     117060
gaacacttga ttctgtgcta ctcccccctag aaaaaaacca aaacaaacaa acaaaaaccc     117120
tttctacttg ccaaatctga taccaaaatt agctcttaga actacgtttc taagaaaat      117180
gcattagtgg gaattttaac agaaaaccca ttatactcat gctgttacta aaactttttcc     117240
aagttcttct cttcagaaaa aagagcctca ttttaaatac tcatacttct aaagaaaata     117300
aaatatcaat tctctactaa gattcctttt tgggtggtag aaaaacaaaa gaatcacgca     117360
ttttcctact atgtttgata agcacagtgc taccatcaaa actgcaggaa tgaccaccct     117420
cattaaatcg accccaaaga atgaaccccc agactaaaca atgagtagtc aaacaacctc     117480
agggttctgt ttttctttca atgcattcgg cattaagagg cgattttaa aatgtatatt     117540
ctaattatac attttcatct tgtcaacatc tcttaatata aaaaccagta ataaaaggta     117600
atcagaagtt cagtcttaac atagtttcag gattaccata ctgttttccc taattgttac     117660
tttactatgt aatttagaac accactttgt tacaatctgt tcataaatat ctatgaacag     117720
atcttaagtt acataaaggg ggaaaacaat ggctcttggg agcctggagc ggaactagca     117780
ataagcagta aagtaagca atttttaagg tgctggctcc attttcagac tatgctgtta      117840
ctgtttgttt caatttaaga gcacccattt acaaaagtgt cttttcctgta tacattcatg    117900
gtttcaaagc aataagtatc aacaactgga tttattagca tcttccttta gaagagctta     117960
aaacactctt gatgtttatg acctcattta ccttccagcg gccttgtgac acagaaaggg     118020
gaggattata attacccccca ttttacagac agggaaagtg agaaggcagg attaagtggc    118080
tctcccatag acacacaatg actcattaag atcagcaact agaaacctgg tttcctgatt     118140
cctggtttag tgttccacat actatgcttc cttctatgaa gtactatttt tgtaaaggtt     118200
tctctttcaa taaaggaaac agaacaagtc atgtgacttt cattcacgaa agccggtgtg     118260
tgttttcatt agcaccttag ttgtctgctc ctgcgaatag ggcagcagca gtgcacgcta     118320
ttgtcttatt atggcagag ccagccaact aaagcaaact agcacccgcc acagcaaaca      118380
gaaaacttgt gtggtttgtc aatcacctca ctggatttct gaatttagga aaattctctg     118440
ctttacgact tcaaaaggca aaacttttca acataaatcg tgattttatt gtcccttttgg    118500
aaacatatct cttatcattc tttcccctta agaaatgata atcctttat tcaacaaaat      118560
```

```
ttaaatatgg atactttcag tagtaattct gatctaatct gtcttataca tacatacata 118620
tatatacgcc aattttagaa taaaatccct aaaatcacta aaaggaata ctaaaacagc 118680
aaattttatg gcattcatca atctaccatc ctaacacaaa aacatataaa gttaatttta 118740
aaaatcagtt ttaaagcaca ggaaattcag tagcgtcttt ccaattccca aacaacaacg 118800
aaacctaaca aattggttag agttttccac atgcacacac accaaaaaca catgataagt 118860
aaccttaacc tgccctcaaa taagatgcat aattttgagt ttgctctgga ctaataaaaa 118920
cagatgtacc tgagatatac tttttaactg gctcttgcac tgaaagccca cccccattca 118980
cgattctatt gtaaacaagt gccagacatg gctggaacct tacctctctg ctatcactta 119040
tgcaaatacc aaacattacc cacataaccc caaaattatt ctgcatcagc atcactaacg 119100
aggtcttccc atgcagaaca ggaagagctc agggtggaaa cacaggccac ttctaagagc 119160
caggcagggc aggggccgc ccaggaagtg ctttctctat ttcatcttca aagaaatgct 119220
ttgcaagtcg gccttctaca aatcatttcc tcaaggaca ctgatctact gtgaactctg 119280
tatttatgag catcccaaac aaatttctag tgcatgtatg agttaaataa aagtgggtat 119340
ttatcccaag ttcctaaatg cttcctttct gtctcaacgg accacaactt tggtgctacg 119400
tggactaagg tgacactagc cttcctatt ctgctgttct ctgtgttcaa cttactttac 119460
tagaaaccca atggggcaga tatttctttt tttttaaatg tcgttgggca tggtggactg 119520
actgcagttg tctattttga tttaaaagat ccttttactt cttagaagag ggttcatcat 119580
gatacccaca caaacttcgg acaaacagca gccccagtga tctctcatct ttgttcagca 119640
gctacagaac acaggcttct gtctggactt cagaatcaag aatcctatgg gctgaaagga 119700
attttacgca ggtgggaaat cttaaacaaa agctcaatcc agtctctaaa taaacttatc 119760
tcttagagtt caacattttc actagcctga aaagggcatt atttcctatt tggaccccaa 119820
ttctgaatgt atcggcttca tcagaaacgc cttgcgtccc tccaggcctg gaggcacaaa 119880
ttccagctta tggcgcctgc tatggcagag cccactgctg gggcccage tccacccagt 119940
ccaggtttgt cccaccagct ccactgaaag caggaaaagg tgttatgttc ttggctgttt 120000
tctgattaga atcagattcg ggtaagatgt aatttacttt catgttcact ctggcatata 120060
cccatttgtg cagaccataa atatgtgtgt ttttccccac tcaattatac tgctgctgct 120120
gctgctgtgt ttataatggt ctgtgtctta aaggcagct aatccttcaa ctttctgaca 120180
cactagcaat agtgtataag taactccaac caaagtgacc ttcagctgag aatcactgtt 120240
cacaggatac attctggcga cttccaatga tttaattgga tgctgaagca ccacactcct 120300
gataattctc tgtgactctt catcttctag tatacggttt taataaagga aatagctttt 120360
ctctattaca ctagaataac agggagttca ccccacagct ataattttaa atcccatgga 120420
ccgacagtcc taagtatact ataaaacaga tgctggattt agatagcact aaactggtct 120480
atttaagaac aaaaggctgt gaatctccag cccaccttga tcctcatctc atgacccttg 120540
aagactgttt acaccttagg ctcacatcta atccagcatc caaattttac tatatgtttc 120600
actgttccca caaagcctct atcctgctag gaaccctaca aagaaaacag ctacaaaatt 120660
aaataaagtc tcccgaattg agcattcacc tttccctctc atctccccga ccccaaacac 120720
cattcaaagt ttagacagcc agaatgcacc accagctgca ttctgcatca gctctctctc 120780
ctcatggata tttgatcaga acgggaagaa caataccagg caccctccta tccaattgtt 120840
cttgagaaga cctgtgtttt ttgtcttttcc cttgttttct ccaaagcact gattgtaaat 120900
```

```
cctggctgca cattcaaatc acctggacaa ctctgaaaaa tgtccgtccc tgcctcctag   120960
ccatctcatg tttcacttca acgggtctgg ggtgaggccc aacaggtaat tttcaatcc    121020
tccccaggtg agtctcacct ggggcagggt cctcacaggg tggtcccccg ccagcagca    121080
tcggcattat gcggagactc actagaaatg cacagcctgg gccgcgcccc aaagctacag   121140
catcggaaac tgcggggtta acacaggcca gagatccatg tttcagcaaa gcctccaggt   121200
aactcccaca tatgctcaag ttgaacacca ctgcattagg ctgtgtgcag ccttaccgtt   121260
tcacccttc cgagaaaaac aatgcctctg atggaaaagc tcccacagtt tgtgtgtaaa    121320
acggaaatgg ttaactgtcg ctattagcag ccatcaaaat ggatgctcat ttcttaaatg   121380
actttcaggt ctgaaccttc aagctcacca agaatcaggc ggagcccagc tccaggaaca   121440
cagggaaagg tgaaagctgc ggctgagggc agcggtccgg acccgaggtc cttccagaag   121500
gacggaccca cgcagccgga tgaagacagt cgggtgcccc gcggcctcta gtgtggccgg   121560
tctgggagaa cttccactgt gttaagggac aggggggctgt gggacgcaca gaatgggtga   121620
atgggtgggg cctcaaaaaa tcagtctccc tcccacgcgg aaaacgtcac attcaactcc   121680
aagacgaatg ttcctggcaa gttctctgaa ggaagagaac agggcagccc gcagaaaaac   121740
aaaacaagga gccagtgcca ggctgtcggc ttctgggtca aggtccccaa aaagtgggag   121800
cagtgaaacc caagaggctc cctcagcgcc ccgcccctcc ttcccgccag acgccaaggc   121860
aaagggcctc ctcacctttc acgatggtgg cctccttcaa gtggtgggac aagaagtcaa   121920
tgctggcgta ggtgttggca gggggcaggg caccgggacc cggccccccg cacccgccgc   121980
cggtgctgcc gacgcccaca gcgctgatga gaccccgag gcttcgggtc cggccccagg    122040
agctcttgtc tcccggctga ggaagcggcg gcggcggcgg ctgcggctgg ggtggcagcc   122100
cgggctcctc cctcacgtcg atggcgatgt agttgagacc attctggaag ccggcagagg   122160
tctctctgcg catgggcgat ccaccgctcc caggacaacc gaccaagccc ccgggctgac   122220
ccggggtcca cggccggccc tgcggtgcca aaggggggcgc cggctgcaac tgtcgtgggg   122280
aggtgggcgg ctcgtcgccc cctccagggc cgacacccac gccgccctcg ctgcttttcc   122340
tgagagagac attttccacg gaggccgagt tgtggcgctt ggggttgtgg gcgaaggacg   122400
gggacacggg ggtgaccgtc gtggtggagg agaaggtctc ggaactgtgg cggcggcggc   122460
cccctgcgg gtctgcgcgg atgaccttgg cgccgcggtg ggggtccggg ggctggctgg    122520
cctgcaggaa ggcctcgact cccgacacct gctccatgag gctcagcctc ttcacgcccg   122580
acgtcgggct ggccacgcgg gcagcttctg gcttcggggg ggccgcgata ggttgcggcg   122640
gggtggcggc cacaccaaaa gccatctcgg tgtagtcacc attgtccccg gtgtccgagg   122700
acaacgatga ggcggcgccc gggccctggg cggtggcaac ggccgaggcg ggggcaggc    122760
ggtacagctc ccccggggcc ggcggcggtg gcggcggctg cagagacgac gacggggacg   122820
cggacggacg cggggcaac ggcggatacg ggaggaggc ctcgggggac aggaggccgt    122880
ccaaggagcc cacggggtgg ccgctcgggg cgccggctt aggagacttg ggggagctga    122940
agtcgaggtt catgtagtcg gagagcggag accgctgccg gctgtcgctg ctggtgcccg   123000
gggtgcctga gcccagcgac gaggccgggc tgctggcgga caagagcgag gaggacgagg   123060
ccgccgacgc cagcagggga ggcgcgggcg gcgacaggcg ggccccgggc tcgccaaagt   123120
cgatgttgat gtactcgccg gggctcttgg gctccggtgg cagtgggtac tcgtgcatgc   123180
tgggcaggct gggcagcccc tccagggaca ggcgcgtggg cctcaccgcc cggccgcgct   123240
ggcccaagaa gccctccggg cggccgccgc taggccgcac gggcgaaggc actacagggt   123300
```

```
gaggggctg cgtggggccg gccccgaagg cgctggccgc ctggctgggc cctggcgtgg   123360
cctgaggctc cagacgctcc tcctccagga tgcgccccac gggggagctc atgagcacgt   123420
actggtcgct gtccccgcca caggtgtagg gggccttgta ggagcgggc aaggagctgt    123480 agcagcagcc gggaacgccc ctgagcggct ccccgccggg gtgcagggct gcggagaaga   123540
agtcgggcgg ggtgcccgtg gtgaccgcgt cgctggggga cacgttgagg tagtcccgt    123600 tgggcagcag cttgccatct gcatgctcca tggacagctt ggaaccgcac cacatgcgca   123660
tgtacccact gtcctcgggg gagctctcgg cgggcgagct ggccttgtag ccgccccgc    123720 tcgccgggaa tgtcctgccc gccgcagagg tgggtgctgg ccccgcaggc cccgcagaag   123780
gcacggcggc ggcggcggcg gcggcggccc tgggctgcaa gatctgcttg ggggcggaca   123840
cgctggcggg gctcatgggc atgtagtcgt cgctcctgca gctgccgctc ccactgcccg   123900
cgagggccgc gccgggcgtc atgggcatgt agccgtcgtc tgcccccagg ttgctgctgg   123960
agctcctgtg ggagccgatc tcgatgtctc cgtagtcctc tgggtagggg tggtaggcca   124020
ccttgggaga ggacgcgggg caggacgggc agaggcggcc cgcgctgccc gagaaggtgg   124080
cccgcatcag ggtgtattca tccagcgagg cagaggaggg ctggggcacc ggccgctgcc   124140
gggctggcgt ggtcagggag taggtcctct tgcgcagccc tcggtccagg tcctgggccg   124200 cgtccccga dacccggcgg taggagcggc cacagtggct caggggcctg tccatggtca    124260
tgtacccgta gaactcaccg ccgccgccgc cgtctcgggc cggggcgtc tccgcgatgg     124320 actcgggcgt gttgcttcgg tggctgcaga aggcgcgcag gtcgcctggg ctggagccgt   124380
actcgtccag ggacatgaag ccggggtcgc tgggggagcc cgaggcggag gcgctgccgc   124440
tggagggccg ctggccgggg ccgtggtgca gcggatgcgg cagaggcggg tgcgggccgg   124500
gcggcggcgg gtaggagccc gagccgtggc cgctgctgga cgacagggag ccggggctgg   124560
tggcggcggg cggcgagtgc gccacgggca tggacatgga gcggctgtgt tgcagcgcgc   124620
cccctgccgg cagcagcgcc accttgctcc cgcggccgcc gcagccgccg ctcagggtgt   124680
gcgagcggct caggggcgcg cgcaccggcc cggggctcag ggggctccca gccaccgaca   124740
ccggcctggc gcccgcggcc gccgctcccg ccgccgcgcc gccgtcgccc tcgctggcgg   124800
tgcgcacccg gcacgagctg cacttggccg ccggcggggt ggcggccagg ctgtcggtgc   124860
gcgagcggcg caccaggccc gtctggctgg ggggcaggtt gaccaggtgg tggtggcggc   124920
gcgcgccggg gacgctgatg gggtgcgtgg ccgacgaccc cgacgattgg ctcttactgc   124980
gcggccggaa ctcgaagagc tccttgagcg ccttcatggc ctccaggatg gtctcgtgga   125040
tgttctgcgc caccaccgag tcgtccgcct gcatccacag ctcgccgggg cctgtgacgg   125100
ccgagcggcc cacctcgatg aagaagaagc tgtccgagtg gccgcagcgg cggatgttca   125160
tgagctgcag cgtcaccgac ggctgctcgc agttgagctt cacgaagccg atggcgcgcg   125220
cagacaggca cagacggtac accccgtca  ggttcttgct ctggcccaga cccttgggct   125280
tcaggttcac ctgccacacc tcacggtagg cggccgtggc gggagccacc agcccgtagc   125340
tgtcctcggc cccggcggcg ccggcagagc cgcccagggc gccgggcagg gaggcgctgc   125400
aggacgcggc gggcgcggcg gcgggggggcg cgtctccggc ggccgcgcgg ccctcgctga   125460
ccaggtcggt gagcgcgcgg taccagccct cctgctcctg ctcgttctcg gcggccacgg   125520
cgaagtactc gtccttggtg tagagggcga tcaggtactt gtgcttggcg tcggcgcgct   125580
tgttgatgtt caggcagcag tcgagagcga tcacccgttt cggcgcgcct gccttgctcc   125640
```

```
gccactttttt ctcgctctcg tagtactcga gccgcggcgg ttgcggcgcc gaccccccgc  125700
ccgccgtcgc ctcgtcgccg cccgcgccgg gtccgcgcag cacgaagaag cgcttgtggc  125760
catgcttctg cttgcgcagg tagccgcact tgcgcacgct gtggttgttg ttgttgttgt  125820
tgttgttgag gttggggccg tctccgctcg ccggcccggg cggcccgtgc cgcggcgggc  125880
tcgccatcgc gggcgcttca ggccgcgcgg cccgggcccg cgcccaggg gttggggcga  125940 ggggcggagg gggcgcgggc gggggcggct ccctcccacc cttgcgcccg gccgcccgcc  126000
cgatcacgcg tccctcgggc ccaggcggtg gggaaggtcc ggggaggccc gcggggccca  126060
gcaccgctcg gcgcgccgc gccctccgcg ctctggggct cctgaggatg cccggcgcgg  126120
gcggtggccg ccccctccc cggctgcctg cggccgctgc ctcctcgggc tctcgggcgg  126180
cgccggggga cgcgctcgct gggccgggag tcggggtccc cgagccgcgg ggccgagcct  126240
aaggcgcgcg cggccgcacc ggggctgctg ccgccgcgtc gcgctccggg aagccggggt  126300
gcgcccgggc gctcggggtc cgcgccgccg ccggggctgc tgctgctgct ggtgttgctg  126360
ctgctgctgc caacggcgac ccgggctcgt cgcggtcccc gccgcacagt gagtaacaca  126420
tcgcgcaccg agtgactgaa ctaagaagag caaaacaaca tgtgactcgg cgttacgcag  126480
gcacacacag cgcggccgcc ccgccccgct gcctcgcatt ggcgccgcgc ccccgacgg  126540 acggcgcgct cggccaatcg gcgcggcgct cgcggggcg ggccgcgcgc ccccgccccg  126600 ccccccttttc tccccggggcc gcgtttcccg ccgtcccctc ccctcccgc gaaggccccg  126660 gcccggccgg gcggggtggg gcggcccgg cctcattaat cagcggcttg ttgtggatgc  126720
cggcggagga gatgccaccc agggcgggaa aaggggcgcg gaagaggggc ggggcgggcc  126780
acggcgcgca gggcccttcc ctcccgcctc ggactcaatt aattgggctt gagcttccgc  126840
cggggagggg gcgccgggcg gggccgcggc tgggcggggc ggggatcgg gatcggcggc  126900 gggggctgcg gccttgcagt ggaagcatgg gcggcgagcc gggccgtgct ctcggggcgc  126960
ggggtcccca tttgggcga gggcggccgc tcccgcgctc ggggtgggcg cgcccatcc  127020 ccgtcccccg tttcccgtcc ccgtctcccg gccgcatctc cgtccccccg cagccgcgaa  127080
acgcggggag gttccagggc ccgcggccgc gggttcgcga gcaccgcgct ccagatcgag  127140
agcggcgcgc gcccttccgt ggaggacaga ggggcgcgga ggggcgcct gtgtcccacc  127200 cgctcgcggg cgctttacgg ggcgtcctct gcgccattca cttgtcagct tgtcgggaag  127260
ttgaaatcgc gtttgggagg taataggaga aagagatcgg ggacggcagg cggagaaagt  127320
gcggtttcca tagcgccggg gagagggcgg acccgcgagc cagcggtccc tgagccggga  127380
gaccgcgcgg gcgtctctcc agcccccgca ggagcgccgc cttccttccg caggggcgtc  127440 ctctccccc accgctgcag gagcaccccc ttccttcctc ggaagcgtcc tctcaccaca  127500
ccgcttcaag agcccccct tccttccaca ggggcgtcct ttcccctcc gaggcaggag  127560 cgccccttttt ccccccacag gagcgccctc cccaccccag gagcgccctg cgcccagcag  127620
acgggcaggt gggcgggcgt ccactacctg tgtgcgcggt gcgggcggtg actgccaagt  127680
tggagatgcc cttggagaac tgcttcgaat tcatgtatct actgggcttt tgtgactttc  127740
aaagcctata gcaaataagc accctgcaa ttacgtctcc tcaatgacca agtcagggtg  127800
aggtgagggc ttcctgagtt cagatcccag caagctcccg atcctgcgca acgaagaaaa  127860
ctcaacaaaa caggctttgg ctgtttattt tattttttttt ttaattgtgc cttcatgaaa  127920
taatttacag caataattta tcttataata ttggttattg tttttaagtc ccggatgttt  127980
acttttggat gtcctctata attcatagaa gtatcttaaa agtaataaaa tcttaatcta  128040
```

```
agagaaaata agtgtaattt ttgaaagagt gatatatatt ttaatatgtt tttgtaacat 128100
gtgacttgaa gattgtgttg gctaatttta tgtgccaaga gagccctgac tagtacaaag 128160
attatagcgt ttttatttt agcatgtata cagttaggat tattgatcag tagcctgaat 128220
ttgggaagaa taatcattgt ggcaaatatc acccagtgtg cctcaaaaag gtgtgtttaa 128280
agttgatctt ccattttaa atcatacctt aaaaaaaat acctcaagaa atgccatttt 128340
aagtctgtgc acctatgtgt gcatgtgtgc gtgtttgttt atataataga ttgtgtgatt 128400
gtgtgtgtat aggtatgtgt gtatgattgt gtgtgttggg ggcgccacct ttatgaacat 128460
tatgcttcgg cgttcttttt agatcttgtt acctttcttt acgttcacaa atgttgccta 128520
gcaatatgtc tagtcaggaa agatgaaggg attcttatct tggtgcttga agaaaatgtg 128580
gtgtagtttt attggctttg tgatcactta catcccactt ttatgaggat gtaaatgggc 128640
cacctctatg ttcctgtatg ttgccagcca tcagtagaca atgctaaagg aaccaccact 128700
tttaaacatc atgtgatggt ttcttctgag aaagtatatt ttgcaatctt tttcttttc 128760 atgttgactt ttattatgca gttgcatttt catatccgta ttgaacattt acttgctgtg 128820
cctgtcacac gctagcaggt gtcatctttt cctgtttgct tgtttcttgg ggccatccta 128880
gtgttaaagg ccagtgtttt taaggtgtca gcagctctgg attggcagtt agcacttttcc 128940 ccatgtactg cctcagttac cagactgggg acaaaagaga gaaggttaaa gaattatcac 129000
ctatgtccgt ggtattctgt catagagagt ataaatttcc tacagcaaac tggaaattaa 129060
ttgcaattct gcagttagaa cctccaaata caaatgtgga tgatcaatt tcaattctca 129120 ttgagagtca gcccatgaaa caaaccaaca gtaagaaact ctgtaattag aagtatccca 129180
gtcctcttcc tcaaccgagg aacttgtttt ctttcccct ttctattgcc agataagcta 129240
tttatttatt taaagcttgt tctacacctt gtgattttcc aactgttctt ccatacttt 129300 tcaacaaaag tcagctaata acatctgcca acatgctctg cacgcaggac tggctggggc 129360
tggcatggcc tcttgccagc aaacagcctg gttgaaattt ttctcatgg tccaagatct 129420 ttccttggaa gctttctttc ctttcacagc taataaaatg gccatatctt tcagcaggga 129480
gttttttctg tttgtttgtt ttttctattt ttaacagaat catatacaat aatgattatt 129540
ttattagaag tcttctgaaa taattacttt tcaagaaaga atcaattata taaagtgta 129600 gagatttaaa aatatgttac aggttcacaa tacaaatact agtagcacta ccaataatga 129660
acatcactaa ttattttctt tgtttcatat aggaaaggca agtatgggag gagaaaggtg 129720
aatagcattt tattgcttgt gaaattttct ttctttttt agttctttgc cctgtaggtg 129780
tttgacagta ttttgtattt aggtgagctc aatctaaaaa ctaagcagat taagtggaat 129840
gctatataac tagttagaat agctttaatt taaaaggtat tttaagaggg aaagattttt 129900
aacttcacag gttctgtca aaggatatat ttaatctta aaatgagtgg caccatttca 129960
ttatatttca ttttattaga taatgttgtt cagtagctca tttgagaaat tccattcctc 130020
tgatgaacga actgtggaca gacttttcct catctagggt ttataaggaa acttcttgca 130080
ctttaccagc aaatttattt gctaatgttt caactgaaat ttcacaagag ttttgtaaca 130140
tgctaactct gtgtatgggc aacagaatga cttacatgag agaatataac tgctgtttgg 130200
atcatttgct atgtatggca ttgcaaacat ttaaagtatc aggatttgtt aatggaattg 130260
atcagcccct tggaaattat aaaggctttc tacttgtgtg tttattattc ttgttaaaaa 130320
tatggatcag tctcttccct aaatgttcat tttatgaggg aggattttct aaaataaatg 130380
```

```
attatttaat gtgcatatat gatagaacaa actactataa cttttttaaa gtcttatcaa   130440
ttgaattaat actgtttaga aaaatatgtt gtagttacaa atgcagctaa tccagtattc   130500
tcaacatttt ttcattataa atataattat gttgaagaaa tacataaatg cccaattaaa   130560
aagtgactgc ggttaggagt tgaaaatatt tattaatatg cctctggatt ttgttctgtt   130620
tgaattttga gaatgtgttt ctagatttaa gaagcaacac aagctttttt tcccagaagg   130680
cttcctatta ttgaaatgga aattatacat taatgactgt ataacactag tagatatttt   130740
taaaatgcaa gagcatcttc ttagatcatt acttttcctt ggaatgcttg gccctgtaa   130800 tataatacac cggtattttg catgatgaaa ttgatgtcct gtgtgttgct tcatgttgct   130860
atcctagctg ccgattaaaa cgttttttttt ttttcatgcc agagcagaac aaaattgtct   130920
gcttctcaat ctgcacatca taagcagatg acattaaaaa tgtctgtaag atgacacagc   130980
tatattttct gggagagggc gggaggatgc tcagcgaggg tggcccggag tgtccttgta   131040
cagagtacag atgttatgaa gtggggaaga ccagcctgtg ttcattgatt cacctattga   131100
ttccaggagc aagctcaccc tgtttcatac actgctcagg aggtaaacag gaggaaggga   131160
gccagcctgg cttttttgcc acatgctctg ctgtttggta gaactgtatt atagtcagaa   131220
accttccgct tttctgcagt tgtttgcatg ctgtttccaa ggctagccct ctgagtctgt   131280
tttctagagt tgttttgaaa ttcaacctaa agataacaga ggaaatgtga ccctctcttg   131340
tgaatgctgc caccaactgg caatgtttct tcccaaggca gattcagggt tctggcatga   131400
gttgtcacaa atacagtggt ggttgctttg agagaaaggt gcttacaacc tgacataaat   131460
ttgctttgca tgaaacttta aggaaattaa tagaagtaag attaaacaaa gaaattttga   131520
tagtgagtga ctaagagcaa tatcagatga caaatgaggg aagagaacat taataagtgc   131580
aatactttat tttttatggt tgaattaagt atcaagcaaa tatgttcata ttttctaatg   131640
caatttatat cccaatttgc atagttactt atacagttta atagaaatgt atatcactgc   131700
ccacttaaga gtttagaata ctagccaaca aaataaaaac aagaatctaa attcagtatt   131760
attttagaat gtttacctaa tcaaaaataa gttataatca agatttgctt atctggcaag   131820
ccaagtgttt tttaattgta tttctcccct acattgacct ttaagtctca cattcttttt   131880
aggataagcc aaagtcatct tgaaagattg aaaagcaaat tggaaaaagt aagataggaa   131940
agaaaacata ctctgaaaat gacacataac aaaaatgtat tttaaaaaca taaataacaa   132000
atggcaataa gcatcgaatg tcactatctt tttgattgcg taaaattatt tgaacttaca   132060
tactcattac taatttggca attctaaatt tacaaattac accttccttc ttaactgctt   132120
tattctcaat ctttaggcat tgcaaataga agatattcaa gttagtcaaa gtgttcagag   132180
ctgttattca atagagtgaa gggatctgaa aacttatttg ctactgaaca tgtcgttgag   132240
gtacttttat ggatgaaaaa aagttgatat ataaaatatc aataatagta atagcttgtg   132300
agagtagttt gtcagtatac tcacaaagat catgaatttg acgcttacta gtatgaggga   132360
taaataaaaa acatttata atatgtagct accataaaga tacgattatg acacaactga   132420
gaattgagcg gtcttttaat tctccttttg agtaatcttt accaacctgt cctctgagcc   132480
tccgtgtata tgctatgttt aagaccaatg attagctatt tatacatgaa ttttccatttt  132540 ttccttgttc aaaacacttt tgtcacacaa ataatattaa ctaaactaaa gtgacttgag   132600
ggagtatgga ttaatgaggt tcacaagaaa ataaataaag caacaacttg tgaaatttag   132660
ggcagatgcc atttattgcc atttcccgct gactgttaag tagagatttc agttcagata   132720
aacacattct aagaattact actgaaagtg taaacatcag cctgcatttt agtacttgct   132780
```

```
ggttctttag taaaaatttc gaatgtcagc ccaaggttgt cttgctaaaa gagaaaaaaa   132840
ataggaatta tatattgaaa acatcttaaa attatatttt atactacaaa aatttccttt   132900
taggtagtaa aagtgagaat ttaaaaacat gattctcact gctactaaaa gcacacagaa   132960
aatgaaatac atattttga gacttgatac ttacctgttt tattttgata aacttgtacc   133020
tagttttaaa gtttcttcac actaaaagta caccacaatt tcaaaatggc acccttgtct   133080
ctcacaatat aaactttaaa ggaaattaat atctagatca tcattttgct ttgttgtttt   133140
aaatatcatc atgttttagt tacagaataa tacaaaagtg ggctcaccct ttatcgtgaa   133200
ggtgcattta tggcattttc aattcaaaat ataaaaatcc gcaaacattg ttactaaaaa   133260
tgtgctagat atttgttaag cctcaaacgt atactaagaa ttacccagaa cataggtctt   133320
tgccccatta gctttctgtc taagtaataa ggcactattt tcctcaacta tttctttcct   133380
caaatatttt tttcttgtgt cttttgttac aatattgcca cacataattt gaagataaaa   133440
attgccatat attataacca tcatctggct tttttaaaaa aactttctta gtgcttgatt   133500
ttaatgtcca atgctgcaat tttaccttct tcttactaat ggtgtagagt agagaaagtg   133560
acttttatct ctgagctgag gaagtttcta aatttcattt cacagaaatt agttttaatg   133620
agtcaaacag taattctatt tcttttattt ttaggttgct tcctttagaa ggtaccgttt   133680
tggactcttg acgctgcctg ggtccatagt gtgaggaccc atctgtgtag tagagaataa   133740
tactcaatag atgtagtgat gtagttatgc tgtgtggtgg taaattcatt ctaacccagt   133800
gaaatgttgg attcggtcaa atttatcaac gtttcttaag cacctacttt gtactagaca   133860
ctgatcctgt ggacatcaaa atgcaaaccg accacaacca ctcagctgtg tctgctggga   133920
aaggccctcc tctgtgcgtc tctcctgctc ccacgcctgt tagtgggtca gtgaaatacg   133980
caagaccctg gctttgcttt actcaagcct tttttaaggg ttgtgcttgc agcaaaccac   134040
actaagaggt gaggtcgcat tccagaacaa agtgcgggcc tgcttatttc ctgctacaaa   134100
aatggtggat tacccaagtc ctttgtgtca gccgaaacac agcccactgc aggcgtggca   134160
tccaacaggc cccgccctgt tgccccatgc tgcccgggaa gcaagaggaa tagaggcaag   134220
tcatgccact ttctgtgcca tgagtctctg accggaaagg cttacatcct ctgccagcat   134280
ccacctaacg gtgacgggct aacattactt tctaagggaa agggagtaaa atctcaaacc   134340
ctgacagtgt gcttaggaag ctcacaaatc agtgggaggt ggagaaccta catgaacata   134400
gccaaatcaa aaggtcagtt gtatttggta cagaactaaa tctagataca agggacaaag   134460
catattataa agctggcagt ttatttcatt ggaggataag agattattca gtaaatgggg   134520
ttggcagaac cagaaaatat acctgtagac acataaaaat tagatgcctg tgtcctttca   134580
ctaaaatgtc aggtgaagca aaaaattaaa tattaaaaca tgaaaccata aaccaagta    134640
gaaaagtaaa gaatattga taaacttgac tttctaaaat aggattctgt aggggaata    134700
cagtaaaaac aaaacaaaaa cagtaaaagc aaagttaaag tagaagctgg aaggaaattg   134760
cagccagtat catagatgaa gtgctaatga tgcttattta atactttaaa agagcgctgt   134820
aaaaaataag aaactaaaaa cattctaaaa attggtgaat gacctgaata caaatttcac   134880
aataatgaaa attaatgcaa gaaaggctta aatgtgtgaa agtttgctta acctttcttg   134940
taataagatg aatgcaaatt aaaaccacaa tgtggtagaa tagttcacct atcagattgg   135000
cacagatcaa gaagtttgat aacacggtgt gtttgccaga atgttgggaa acaggttccc   135060
acccaaggct gctggtggta cagactgaac agcatctata caatttggct gtatctgtca   135120
```

```
aaacgacaaa tgtctcatgt tccttgaccc acaatctaat ttccaggaat tactcatgtg   135180
gatgggaaat gacttcttta taagggtgtt cattgcatta ttgttaggaa tagaaactta   135240
tacacatgat tacagtattg tcttgtaatg gcaaaggttt gaaccctatg caactgtaac   135300
acaaacgagg cagctctgtt tatactgacc cagaataata tttgactgta taatgtgagg   135360
tgggaaaaca agcttcagaa cagtgtgtat agtatagtac aaccattttt tttattttta   135420
aaacgtgtgg gtatgtgcac agatacctac tgcaagtgac ctcacaaata tggcaatgcg   135480
aggagccaac ctggcttcct ggggaaggga cgggttgggg agaggactca cgtttcatcg   135540
tgttactttt cggactttcc gaattttgta gcacaagtat gtatcaaata tttaacagtg   135600
taaaaataat tgactttaat ttctaaaggc tcagtagcac ttggtgatga tttgggggta   135660
ggggaggaag agaggacctt cagtgtcctg cactgtcgct gggtgatgac aaggtcttct   135720
cctgagatgg gggagggaga gttaagagat ttattttgga cacacgaggt tggacataat   135780
agaaatctga gagaagatgt tggataggct gttggagagg cttggaatgg agatattaat   135840
ttgggattca tgggcatcta gctgcattta agtccctagg atttgccgaa agtgactgtg   135900
agagatgaga ttggagcacc tgggattgga cccaactact cttaacattt agaagtcagg   135960
gacagaaagg taatctagca gagaaaacgc aatgaaaggg cacagactag cttgctgaag   136020
aaccacggga gtggacagca gagagcattg cagcagggac tggccagcca ggggtaacga   136080
ggatgagtgg tccaggcagg ggacctggtg acatgggagc catgttgatc tagtgcgtgg   136140
tttcctggtg tgaggaagag gggaatgcag cctggagaag gcatgacaga tggggcagga   136200
tccatgagaa tgaactttca ataaatgaag tctttgcatt atgaattcaa agtgctattt   136260
agcagaaaca ttggagaacg agaagaatcc gaaggaaaat ccaggggcaa ataagcatt   136320 atcctccggg agcagaagag tcagtgtccc caggatgcag ccagctttca ggaaaggctg   136380
agactcagaa agcatgggag tagtgttgca atggaaagga cacttgagag aagacactgg   136440
aagtgtttgg gaggtaaagg agtgaaaaag ggctgggtga aaggaaaaca tcagttagga   136500
taaccccatg ggagaaagtg gatagctcta agggcttcta ctgtgggcag aaatatgacg   136560
catggtaggt tgagttgttt gtttcgtttt gttttgagac tgagtcttac tctgtcaccc   136620
aggctggagt gcagtggcac aatctcggct cactgcaacc tctgcctccc aggttcaagc   136680
aattctcctg cctcagcccc tgagtagcta ggactatagg cgtgcaccac cacacccagc   136740
taatctttat tgtatttttt gtagagatgg ggtttcacca tgttggctga gttggtctca   136800
aactcctgac ctcaagcaat ccacctgcct cagcctccca aagtcctggg attgcaggtg   136860
taagccatcg tgcccggccg gtaggttgag ttttaatggt gtctgtgaag atgcaagttc   136920
agctgtagcc tggaagtgtg acctggcatc tgagaggagc actgcagcac cccttttctg   136980
tgctgcttgc attggcatcc atggtgagtg cagcaatagc tgtcatcagt gagcaaagag   137040
gctccagcca ggggccctgt ggtgcctaca gggagaggca gagatctggg tgtccccagg   137100
tttttctgct tgagtcaaag cccctgggag cccaggtatg aaaacctagg ggcttccatc   137160
atgtccggat ggtgggtctc catcattcct cttaatctca tggttttctt gcaaagctga   137220
agaagcccca ttatgggctt ttcctcaaat tgaatgtcat cttgcaacat ctcttcagct   137280
ttgcattttt ggaacatgga tcagaatctt tcctttcctt gactcccttt ctagcagctt   137340
gttagaatgc attcatgtag caactgggaa tgaatgcgac acatttacat ttaacacctc   137400
ccttccattg acttcagctc agacctttcc agagatttct ccattagagg actgttagat   137460
gccactagac gtgtgagacc aaatgatgtt ggcatcatct tggaatagag acggagactg   137520
```

```
gggtctggcc tttcttctgg tcctcagtcc tgcaggctgt cctttctcca ctgcacctcc    137580
tcaaggagca ttcctggtag cctctggaac ctgccctggg tgtgttttgg ttcactctct    137640
atgcttgata ggctttctca aagaacctgc tgcatcgtaa gtgctcaaca cactctttc    137700 aggattgttc ttttatgttt ttagattaca attttatgta attttttct gattaaatac    137760 tttttgtgtg gctacggaaa agttcacata aattaacaca ttaaagacct ttgaaagctc    137820
ctgactggca cagtagacac agccagtaca tattggctat gatcgtttgt gttctgtatc    137880
agattggttt acaggccaca aagatggggg ccctacggat cctctctgtt caagcagtga    137940
agagctggta tctgaggata aagaagctt tgttgtaat gatgtggaaa ttccagaggt    138000
tgtgatggaa tgaatgacct agaatagaga agagcaaagc atgttgggag cagggaggtg    138060
gaaaagggag tataggaaga ggggaagagg ggtcccagtt ggcctccagg tttctggaag    138120
taccaatcct agagtcttct tggtgaaggg agttggccaa ggcaaggaaa cctgagccct    138180
ttgtgaagga gtcagaggag gtttatgact aaaaaatgac aaattatgcc atattacgta    138240
ttctgaacaa atatgtgtaa atacatgatt tagataaatt aggtatttat taaatatttc    138300
aagatttggt tccagaagag tacaatttgt ctcttcacca ttgttagagg gaaaaaaaca    138360
ggtaaagcca atcaaagaaa gatgaaagtt tttagaggaa aaaaaaatct agttttgcag    138420
caaagaggat taatctgtaa agtctcatct tatagatgtg ctactgtagt aatctagaat    138480
ttgtttcttc ttattcttca tttcccaaca gtattaagat gaagtgtgta atctttagaa    138540
ctagagagaa gtctgtttgc atctgtgggg ttaatgcaga gagggaggtg agaggtgatt    138600
cttgccatac ttggtcactt gaataaaact acctattccc atggctttct ctttagggag    138660
tagaaaaccc tcatttcaat gaaatcagtg tttttcataa ttggaagcct accttccaag    138720
agctaatggc atataatgga aatgaattat cccttgctac ctaaacactt gcttcctaaa    138780
ctcatattta actgtgtaag gatatttata ttaatttagg aagttatat ctaagcaggg    138840 atttcccttt aacgaatgaa acaatatgca tactggcaag gtagaaaatg ttttcaattt    138900 gcatttgtt gtttggaggc ctatttaatt cattgcaatc ttatttattc agtgatgtat    138960
attaaacata aatgtattaa aaatctacca ctagaaagta ctaattgtca ttgaatggca    139020
cattttaaaa tgaataattt catgttatgt aaatgctgcc taaaactat aatagaactg    139080 ccatgattaa gacattatgt ctacacagag aaggttaaag taacaatacc ataactactg    139140
tccttttata aataaacaaa taaaacata atatttattc caaggacat tcttgtgtcg    139200 aaagatgaaa cagaaagaaa gtggaagata gtaacagaga aagtggaaaa aaggacgaga    139260
agggatagac atgcaaaact ccagcattcc aaagttaagg gaaagagaat aaccatgttg    139320
tgcctataac cctagaagat tacaaaaatt attctagca aattgacaac ccttctttct    139380
gaaggtagct ttgggcaaaa aggtgctgtt ttgagctttt accctgaatc acctggggtg    139440
cacttgaaaa gaagccattt tgccaatgca ttaaaagtgt ctgagtgaaa gctgccactt    139500
gattgtccta agaggctttt aaccccagcc acataattat ttcataacaa acaatcagga    139560
acatttctct tcctcatcag tttcccagac tacctcatag cacatgcatg atacaatgtg    139620
tgattttgca gccttccatg taacatcgga gtcctaaaga gatggacttg aagaggctca    139680
tggtgatttt aattgcattt tgaaatgcca cacatattct aagagatgtc attctaagag    139740
atgtcatcaa tctcttaaaa catgattttt aatggctgca taccattctt ctaccccatt    139800
gtaccatgat tcatttaacc acctcttaat acttgcttcg ttttggtgtt tctaatttct    139860
```

```
tgcaaataaa aatttaactg cccttgctaa tgattatttg gtaggtgatt cttaccttga   139920
taagtaggtc accatctatc cagttgtgca gctggaaacc tggaaatcat tcttgcaata   139980
gttttcaccc cgaatcccaa tccattgcca aattctgtca attttctatt cttagtatct   140040
ctcaagctta ttcacttctt tccacccctc ataaatattt ttgccgtaat atttctgaat   140100
tccttattgg ttcagcaata tactaggtat ttattatctt ttattttca cacctatcca    140160 ttgttactct tcttccaatt tttctctcaa attttgatg aaattcagtt tatttacctt    140220
aagaactttt atttttact tattggattt ttatattgtg caacatagta cacacataca    140280
aaaagatatt taacatatat gtaagttata aataataata ctttaaaatt ggcatagtca   140340
agcctaaaaa gtaggacatt accaatattt attttgaagt ccactgacta gccttatcac   140400
aatctgaaat tttgtgatta ttgtcctttg gctgtcttca tgattttact ggatatgtat   140460
gtaaacattt tgcattgtac ttaaatttaa gcattataca aatattatca tcctattaat   140520
attcttctgc aacttgctca acagtatggt tttattattg agatgtaact tagataccat   140580
aaaaatgtac aacttaatat tttttagtat aatcacaagg ctgtgaaatt gtcatcacac   140640
tctaagtctg gaatatcttc atcaccccaa aaagaaaccc caagaaactt tgtgcccaca   140700
gcagtcactt ttgagttccc ctcccttcac ccctggcggc cataagtctt ctctctgtcc   140760
ctgttcatcg ttatgttttt gagagaaatg tattacgatt tctgaagtcg tagttcatct   140820
ttttcagttg taataaatat ataactgttt ttcacttctg ccaatagaaa tttaggttat   140880
ttgtagttgt tttaaaatt tctatttgaa catgacttgt ttttttaaaa agtatgtttc    140940
acaattacac acctttaac aattaaagtg cctttaaca attatttatg catacatata    141000
tattcttagg cacactgttt tagacagaag aatagaattg ccagtgttaa ttctgtccac   141060
ctttaatttt aatgtgtaat aaaaatcatt ttcgaaagta agtgtacaaa ttgaaaattc   141120
caccaataag gtgtcattgt cttttacaat tttttcccatt ggattgtagt cattgtttat  141180
agaggccatg tgttaatctt ttataaaaat cgatttgtca aatttattat ttgcttttta   141240
ttttctttat gttttctttt gaatgaacat caatttaaa ttttaactga gtaaaattta    141300
tcaagtttac cttttgagtt ttgtgccttt ttcattttgt tttaattttt ttctctatcg   141360
ccaaattttc aagtacttac tcctgtattt cctttctctc tctctctttt tttagcttta   141420
attcacctgc attatatgtt tgtgcatggt gtctgatagt ggctcaattt cagttttttt   141480
ttaaattgtt tccgaggcgt gtttcaaata tttgacttt tcccactggt ctgaatagtg    141540
cttctcagat acggcaagtc tctaggtttg catgagtcag cctctgtgcc ctctgttctt   141600
ttccccgatg ttcttttgc ttcttcttat gctattacca cactgtctta attactatat    141660
tttattaaca aatctcactt tctggtagac catttcttc acctacttct tcactttcct    141720
tcaggaatgt cttggatatt tgtaactctt ttccttatga tttagcatca gcttgacaag   141780
tttaataaac cttgttagga ctgagataaa attagaaaga ttggacatct ttaaggtact   141840
gagttctcct agccaggaat gtggcacgtt tccctatttc tttagggaat tgtaaaatgt   141900 cttttttataa cgttttataa ttttccccat agagatcttt aaaatatttt gttagattta   141960
ttcctagcac cttatatatt ttgttactct tgtaaaaagt atccttttt ttttttttt     142020 ttttagaaac ggagtctcgc tctgtcgccc aggctggagt gcagtggcac gatcttggct   142080
cactgcaagc tccgcctccc gggttcacgc cattctcctg cctcagcctc ccgagtagct   142140
gggactgcag gcacctgcca ccacgcccgg ctaattttg tatttttagt agtagagacg    142200
gggtttcacc gcgttagcca ggatgttctc gatctcctga cctcgtgatc cgcccgcctc   142260
```

```
ggcctcccaa agtgctggga ttacaggtgt gagccaccgc gcccggccag tatccatttt    142320
taaaaactac attttctctt tgttgcttgg gtagagaaat aaaatcaatt tttaatttat    142380
cttatatctg atcattttgt taaaccctca tattaatttt aatgctttaa agatgtttag    142440
agggaaatat tttataaata cacaaataat accatttcat gtgtcgctta cagattttct    142500
catcttattg aactggctag agccaccaat gtatgctgta aaagcaacct tgttttaatc    142560 cttttttgaaa gggaatgttc cagattctac catgtggtac catgtttgtg ctaagatttt    142620
ggtaggttca atttttttca gtttaaagaa gttctcctct agcccattat gccaatgaat    142680
ttaagctgaa tggatataaa aattaatcaa atattttta gtgcctactg aggtgatctt    142740
acgcctttct agtttgattt ataagtaggg ctaactatat taattgattt ttcaatgtta    142800
aacaaaattt acatttctgg aatagattta acttggtcgt tctttaactt tgcgttcccc    142860
ttaaaaagga ccttgagaga agggctcagc gtctgatagt tccagcatct ggctgtggag    142920
ctgtatggct gagtcatcat ctgttggttt gtttgctgac ttccaacctt tgtgcctaga    142980
tattgaagtc accttctctc cctttgaagg gcagagactt tgtgtgtttg tcctttcact    143040
cagcatggct cttggagttt ctggctgcat gagaaggtcc tgggagactc ttcccttcca    143100
agagcctcca tgttgtcttc tgccttttgg ggctactgaa accgcagcac aaggtgtagg    143160
gaaattacca ggttccccca gagccgtcgt tccttgcacc gcctttccac gatgtgtgtg    143220 ccccctttg ttttgtcccc tgggattict cctacactct tgcgaggtca ttatgaactt    143280
aaaaggatgt ggattttat tttattttat accttagagg tcttttatag cagagatttt    143340
tcagggcatc aagactagac gttttgccca aaagggaaaa ccagaggctt tcaattttttt    143400 tttgaattc                                                            143409

<210> SEQ ID NO 19
<211> LENGTH: 143409
<212> TYPE: DNA
<213> ORGANISM: Homo sapiens
<220> FEATURE:
<221> NAME/KEY: misc_feature
<222> LOCATION: (1)..(143409)
<223> OTHER INFORMATION: Reverse complement of AL162497
<220> FEATURE:
<221> NAME/KEY: variation
<222> LOCATION: (12936)..(12936)
<223> OTHER INFORMATION: Position of polymorphism (a). At this position
      a polymorphic variant of the wild-type would have A instead of C.
<220> FEATURE:
<221> NAME/KEY: variation
<222> LOCATION: (15012)..(15013)
<223> OTHER INFORMATION: Position of polymorphism (b). These bases (AT)
      would be deleted in polymorphic variant (b).
<220> FEATURE:
<221> NAME/KEY: variation
<222> LOCATION: (16359)..(16359)
<223> OTHER INFORMATION: Position of polymorphism (c). A polymorphic
      variant has C instead of wild-type A at this position. SEQ ID NO:
      19 shows the variant base.
<220> FEATURE:
<221> NAME/KEY: variation
<222> LOCATION: (33392)..(33392)
<223> OTHER INFORMATION: Position of polymorphic variant (d). This
      variant has G instead of wild-type A at this position. SEQ ID NO:
      19 depicts the variant residue.
<220> FEATURE:
<221> NAME/KEY: variation
<222> LOCATION: (47315)..(47315)
<223> OTHER INFORMATION: Position of polymorphism (d). Variant (d) has
      G instead of wild-type A. SEQ ID NO: 19 depicts variant residue.
<220> FEATURE:
<221> NAME/KEY: variation
```

<222> LOCATION: (49053)..(49053)
<223> OTHER INFORMATION: Position of polymorphism (f). The wild-type would have C between these two positions. SEQ ID NO: 19 depicts variant having deletion of this C.

<400> SEQUENCE: 19

```
gaattcaaaa aaaaattgaa agcctctggt tttcccttttt gggcaaaacg tctagtcttg      60
atgccctgaa aaatctctgc tataaaagac ctctaaggta taaaataaaa taaaaatcca     120
catccttttta agttcataat gacctcgcaa gagtgtagga gaaatcccag gggacaaaac     180
aaaaggggc acacacatcg tggaaaggcg gtgcaaggaa cgacggctct gggggaacct     240
ggtaatttcc ctacaccttg tgctgcggtt tcagtagccc caaaaggcag aagacaacat     300
ggaggctctt ggaagggaag agtctcccag gaccttctca tgcagccaga aactccaaga     360
gccatgctga gtgaaaggac aaacacacaa agtctctgcc cttcaaaggg agagaaggtg     420
acttcaatat ctaggcacaa aggttggaag tcagcaaaca aaccaacaga tgatgactca     480
gccatacagc tccacagcca gatgctggaa ctatcagacg ctgagccctt ctctcaaggt     540
cctttttaag gggaacgcaa agttaaagaa cgaccaagtt aaatctattc cagaaatgta     600
aattttgttt aacattgaaa aatcaattaa tatagttagc cctacttata aatcaaacta     660
gaaaggcgta agatcacctc agtaggcact aaaaaatatt tgattaattt ttatatccat     720
tcagcttaaa ttcattggca taatgggcta gaggagaact tctttaaact gaaaaaaatt     780
gaacctacca aaatcttagc acaaacatgg taccacatgg tagaatctgg aacattccct     840
ttcaaaaagg attaaaacaa ggttgctttt acagcataca ttggtggctc tagccagttc     900
aataagatga gaaaatctgt aagcgacaca tgaaatggta ttatttgtgt atttataaaa     960
tatttccctc taaacatctt taaagcatta aaattaatat gagggtttaa caaatgatc    1020
agatataaga taaattaaaa attgatttta tttctctacc caagcaacaa agagaaaatg    1080
tagtttttaa aaatggatac tggccgggcg cggtggctca cacctgtaat cccagcactt    1140
tgggaggccg aggcgggcgg atcacgaggt caggagatcg agaacatcct ggctaacgcg    1200
gtgaaacccc gtctctacta ctaaaaatac aaaaattagc cgggcgtggt ggcaggtgcc    1260
tgcagtccca gctactcggg aggctgaggc aggagaatgg cgtgaacccg ggaggcggag    1320
cttgcagtga gccaagatcg tgccactgca ctccagcctg ggcgacagag cgagactccg    1380
tttctaaaaa aaaaaaaaa aaaaaggata cttttttacaa gagtaacaaa atatataagg    1440
tgctaggaat aaatctaaca aaatattta aagatctcta tggggaaaat tataaaacgt    1500
tataaaaga cattttacaa ttccctaaag aaatagggaa acgtgccaca ttcctggcta    1560
ggagaactca gtaccttaaa gatgtccaat cttcctaatt ttatctcagt cctaacaagg    1620
tttattaaac ttgtcaagct gatgctaaat cataaggaaa agagttacaa atatccaaga    1680
cattcctgaa ggaaagtgaa gaagtaggtg aaggaaatgg tctaccagaa agtgagattt    1740
gttaataaaa tatagtaatt aagacagtgt ggtaatagca taagaagaag caaaagaac    1800
atcggggaaa agaacagagg gcacagaggc tgactcatgc aaacctagag acttgccgta    1860
tctgagaagc actattcaga ccagtgggaa aaagtcaaat atttgaaaca cgcctcggaa    1920
acaatttaaa aaaaaactga aattgagcca ctatcagaca ccatgcacaa acatataatg    1980
caggtgaatt aaagctaaaa aaagagagag agagaaagga aatacaggag taagtacttg    2040
aaaatttggc gatagagaaa aaaattaaaa caaaatgaaa aaggcacaaa actcaaaagg    2100
taaacttgat aaatttttact cagttaaaat ttaaaattga tgttcattca aaagaaaaca    2160
```

```
taaagaaaat aaaaagcaaa taataaattt gacaaatcga ttttttataaa agattaacac   2220 atggcctcta taaacaatga ctacaatcca atgggaaaaa ttgtaaaaga caatgacacc   2280
ttattggtgg aatttttcaat ttgtacactt actttcgaaa atgatttttta ttacacatta   2340 aaattaaagg tggacagaat taacactggc aattctattc ttctgtctaa aacagtgtgc   2400
ctaagaatat atatgtatgc ataaataatt gttaaaaggc actttaattg ttaaaaggtg   2460
tgtaattgtg aaacatactt tttaaaaaaa caagtcatgt tcaaatagaa atttttaaaaa   2520 caactacaaa taacctaaat ttctattggc agaagtgaaa aacagttata tatttattac   2580
aactgaaaaa gatgaactac gacttcagaa atcgtaatac atttctctca aaaacataac   2640
gatgaacagg gacagagaga agacttatgg ccgccagggg tgaagggagg ggaactcaaa   2700
agtgactgct gtgggcacaa agtttcttgg ggtttctttt tggggtgatg aagatattcc   2760
agacttagag tgtgatgaca atttcacagc cttgtgatta tactaaaaaa tattaagttg   2820
tacattttta tggtatctaa gttacatctc aataataaaa ccatactgtt gagcaagttg   2880
cagaagaata ttataggat gataatattt gtataatgct taaatttaag tacaatgcaa   2940
aatgtttaca tacatatcca gtaaaatcat gaagacagcc aaaggacaat aatcacaaaa   3000
tttcagattg tgataaggct agtcagtgga cttcaaaata aatattggta atgtcctact   3060
ttttaggctt gactatgcca atttttaaagt attattattt taacttaca tatatgttaa   3120 atatcttttt gtatgtgtgt actatgttgc acaatataaa aatccaataa gtaaaaaata   3180
aaagttctta aggtaaataa actgaatttc atcaaaaatt tgagagaaaa attggaagaa   3240
gagtaacaat ggataggtgt gaaaaataaa agataataaa tacctagtat attgctgaac   3300
caataaggaa ttcagaaaata ttacggcaaa aatatttatg aggggtggaa agaagtgaat   3360
aagcttgaga gatactaaga atagaaaatt gacagaattt ggcaatggat tgggattcgg   3420
ggtgaaaact attgcaagaa tgatttccag gtttccagct gcacaactgg atagatggtg   3480
acctacttat caaggtaaga atcacctacc aaataatcat tagcaagggc agttaaatt   3540 ttatttgcaa gaaattagaa acaccaaaac gaagcaagta ttaagaggtg gttaaatgaa   3600
tcatggtaca atggggtaga agaatggtat gcagccatta aaaatcatgt tttaagagat   3660
tgatgacatc tcttagaatg acatctctta gaatatgtgt ggcatttcaa aatgcaatta   3720
aaatcaccat gagcctcttc aagtccatct ctttaggact ccgatgttac atggaaggct   3780
gcaaaatcac acattgtatc atgcatgtgc tatgaggtag tctgggaaac tgatgaggaa   3840
gagaaatgtt cctgattgtt tgttatgaaa taattatgtg gctgggggtta aaagcctctt   3900 aggacaatca gtggcagct ttcactcaga cacttttaat gcattggcaa aatggcttct   3960
tttcaagtgc accccaggtg attcagggta aaagctcaaa acagcacctt tttgcccaaa   4020
gctaccttca gaaagaaggg ttgtcaattt gctagaaata atttttgtaa tcttctaggg   4080
ttataggcac aacatggtta ttctctttcc cttaactttg gaatgctgga gttttgcatg   4140
tctatccctt ctcgtccttt tttccacttt ctctgttact atcttccact ttctttctgt   4200
ttcatctttc gacacaagaa tgtccttttgg aataaaatatt atgttttttat ttgtttattt   4260 ataaaaggac agtagttatg gtattgttac tttaaccttc tctgtgtaga cataatgtct   4320
taatcatggc agttctatta tagtttttag gcagcattta cataacatga aattattcat   4380
tttaaaatgt gccattcaat gacaattagt actttctagt ggtagatttt taatacattt   4440
atgtttaata tacatcactg aataaataag attgcaatga attaaatagg cctccaaaca   4500
acaaaatgca aattgaaaac attttctacc ttgccagtat gcatattgtt tcattcgtta   4560
```

```
aagggaaatc cctgcttaga tataaacttc ctaaattaat ataaatatcc ttacacagtt   4620
aaatatgagt ttaggaagca agtgtttagg tagcaaggga taattcattt ccattatatg   4680
ccattagctc ttggaaggta ggcttccaat tatgaaaaac actgatttca ttgaaatgag   4740
ggttttctac tccctaaaga gaaagccatg ggaataggta gttttattca agtgaccaag   4800
tatggcaaga atcacctctc acctccctct ctgcattaac cccacagatg caaacagact   4860
tctctctagt tctaaagatt acacacttca tcttaatact gttgggaaat aagaataag    4920 aagaaacaaa ttctagatta ctacagtagc acatctataa gatgagactt tacagattaa   4980
tcctctttgc tgcaaaacta gattttttt tcctctaaaa actttcatct ttctttgatt    5040
ggctttacct gttttttttcc ctctaacaat ggtgaagaga caaattgtac tcttctggaa  5100
ccaaatcttg aaatatttaa taaatacccta atttatctaa atcatgtatt tacacatatt  5160
tgttcagaat acgtaaatg gcataatttg tcattttta gtcataaacc tcctctgact    5220
ccttcacaaa gggctcaggt ttccttgcct tggccaactc ccttcaccaa gaagactcta  5280
ggattggtac ttccagaaac ctggaggcca actgggaccc ctcttcccct cttcctatac  5340
tcccttttcc acctccctgc tcccaacatg ctttgctctt ctctattcta ggtcattcat  5400
tccatcacaa cctctggaat ttccacatca ttacaacaca agcttctttt atcctcagat   5460
accagctctt cactgcttga acagagagga tccgtagggc ccccatcttt gtggcctgta  5520
aaccaatctg atacagaaca caaacgatca tagccaatat gtactggctg tgtctactgt   5580
gccagtcagg agctttcaaa ggtctttaat gtgttaattt atgtgaactt ttccgtagcc   5640
acacaaaaag tatttaatca gaaaaaaatt acataaaatt gtaatctaaa aacataaaag   5700
aacaatcctg aaaagagtgt gttgagcact tacgatgcag caggttcttt gagaaagcct   5760
atcaagcata gagagtgaac caaaacacac ccagggcagg ttccagaggc taccaggaat  5820
gctccttgag gaggtgcagt ggagaaagga cagcctgcag gactgaggac cagaagaaag   5880
gccagacccc agtctccgtc tctattccaa gatgatgcca acatcatttg gtctcacacg   5940
tctagtggca tctaacagtc ctctaatgga gaaatctctg gaaaggtctg agctgaagtc   6000
aatggaaggg aggtgttaaa tgtaaatgtg tcgcattcat tcccagttgc tacatgaatg   6060
cattctaaca agctgctaga aagggagtca aggaaaggaa agattctgat ccatgttcca  6120
aaaatgcaaa gctgaagaga tgttgcaaga tgacattcaa tttgaggaaa agcccataat   6180
ggggcttctt cagcttttgca agaaaaccat gagattaaga ggaatgatgg agacccacca  6240
tccggacatg atggaagccc ctaggttttc atacctgggc tcccaggggc tttgactcaa   6300
gcagaaaaac ctggggacac ccagatctct gcctctccct gtaggcacca cagggccccct  6360 ggctggagcc tctttgctca ctgatgacag ctattgctgc actcaccatg gatgccaatg  6420
caagcagcac agaaaagggg tgctgcagtg ctcctctcag atgccaggtc acacttccag  6480
gctacagctg aacttgcatc ttcacagaca ccattaaaac tcaacctacc ggccgggcac  6540
gatggcttac acctgcaatc ccaggacttt gggaggctga ggcaggtgga ttgcttgagg   6600
tcaggagttt gagaccaact cagccaacat ggtgaaaccc catctctaca aaaaatacaa   6660
taaagattag ctgggtgtgg tggtgcacgc ctatagtcct agctactcag gggctgaggc  6720
aggagaattg cttgaacctg ggaggcagag gttgcagtga gccgagattg tgccactgca  6780
ctccagcctg ggtgacagag taagactcag tctcaaaaca aaacgaaaca aacaactcaa   6840
cctaccatgc gtcatatttc tgcccacagt agaagcccct tagagctatcc actttctccc  6900
```

```
atgggggttat cctaactgat gttttccttt cacccagccc ttttcactc ctttacctcc   6960
caaacacttc cagtgtcttc tctcaagtgt cctttccatt gcaacactac tcccatgctt   7020
tctgagtctc agccttcct gaaagctggc tgcatcctgg ggacactgac tcttctgctc    7080
ccggaggata atgcttattt tgcccctgga ttttccttcg gattcttctc gttctccaat   7140
gtttctgcta aatagcactt tgaattcata atgcaaagac ttcatttatt gaaagttcat   7200
tctcatggat cctgccccat ctgtcatgcc ttctccaggc tgcattcccc tcttcctcac   7260
accaggaaac cacgcactag atcaacatgg ctcccatgtc accaggtccc ctgcctggac   7320
cactcatcct cgttacccct ggctggccag tccctgctgc aatgctctct gctgtccact   7380
cccgtggttc ttcagcaagc tagtctgtgc cctttcattg cgttttctct gctagattac   7440
ctttctgtcc ctgacttcta aatgttaaga gtagttgggt ccaatcccag gtgctccaat   7500
ctcatctctc acagtcactt tcggcaaatc ctagggactt aaatgcagct agatgcccat   7560
gaatcccaaa ttaatatctc cattccaagc ctctccaaca gcctatccaa catcttctct   7620
cagatttcta ttatgtccaa cctcgtgtgt ccaaaataaa tctcttaact ctccctcccc   7680
catctcagga gaagaccttg tcatcaccca gcgacagtgc aggacactga aggtcctctc   7740
ttcctcccct accccaaat catcaccaag tgctactgag cctttagaaa ttaaagtcaa    7800
ttatttttac actgttaaat atttgataca tacttgtgct acaaaattcg gaaagtccga   7860
aaagtaacac gatgaaacgt gagtcctctc cccaacccgt cccttcccca ggaagccagg   7920
ttggctcctc gcattgccat atttgtgagg tcacttgcag taggtatctg tgcacatacc   7980
cacacgtttt aaaaataaaa aaaatggttg tactatacta tacacactgt tctgaagctt   8040
gttttcccac ctcacattat acagtcaaat attattctgg gtcagtataa acagagctgc   8100
ctcgtttgtg ttacagttgc atagggttca aacctttgcc attacaagac aatactgtaa   8160
tcatgtgtat aagtttctat tcctaacaat aatgcaatga acacccttat aaagaagtca   8220
tttcccatcc acatgagtaa ttcctggaaa ttagattgtg ggtcaaggaa catgagacat   8280
ttgtcgtttt gacagataca gccaaattgt atagatgctg ttcagtctgt accaccagca   8340
gccttgggtg ggaacctgtt tcccaacatt ctggcaaaca caccgtgtta tcaaacttct   8400
tgatctgtgc caatctgata ggtgaactat tctaccacat tgtggtttta atttgcattc   8460
atcttattac aagaaaggtt aagcaaactt tcacacattt aagcctttct tgcattaatt   8520
ttcattattg tgaaatttgt attcaggtca ttcaccaatt tttagaatgt ttttagtttc   8580
ttattttta cagcgctctt ttaaagtatt aaataagcat cattagcact tcatctatga    8640
tactggctgc aatttccttc cagcttctac tttaactttg cttttactgt ttttgttttg   8700
tttttactgt attcccccta cagaatccta ttttagaaag tcaagtttat caatatttct   8760
ttacttttct acttggtttt atggtttcat gttttaatat ttaatttttt gcttcacctg   8820
acatttagt gaaaggacac aggcatctaa ttttatgtg tctacaggta tattttctgg     8880
ttctgccaac cccatttact gaataatctc ttatcctcca atgaaataaa ctgccagctt   8940
tataatatgc tttgtccctt gtatctagat ttagttctgt accaaataca actgacctt    9000
tgatttggct atgttcatgt aggttctcca cctcccactg atttgtgagc ttcctaagca   9060
cactgtcagg gtttgagatt ttactccctt tcccttagaa agtaatgtta gcccgtcacc   9120
gttaggtgga tgctggcaga ggatgtaagc ctttccggtc agagactcat ggcacagaaa   9180
gtggcatgac ttgcctctat tcctcttgct tcccgggcag catggggcaa cagggcgggg   9240
cctgttggat gccacgcctg cagtgggctg tgtttcggct gacacaaagg acttgggtaa   9300
```

```
tccaccattt ttgtagcagg aaataagcag gcccgcactt tgttctggaa tgcgacctca   9360
cctcttagtg tggtttgctg caagcacaac ccttaaaaaa ggcttgagta aagcaaagcc   9420
agggtcttgc gtatttcact gacccactaa caggcgtggg agcaggagag acgcacagag   9480
gagggccttt cccagcagac acagctgagt ggttgtggtc ggtttgcatt ttgatgtcca   9540
caggatcagt gtctagtaca aagtaggtgc ttaagaaacg ttgataaatt tgaccgaatc   9600
caacatttca ctgggttaga atgaatttac caccacacag cataactaca tcactacatc   9660
tattgagtat tattctctac tacacagatg ggtcctcaca ctatggaccc aggcagcgtc   9720
aagagtccaa aacggtacct tctaaaggaa gcaacctaaa aataaaagaa atagaattac   9780
tgtttgactc attaaaacta atttctgtga aatgaaattt agaaacttcc tcagctcaga   9840
gataaaagtc actttctcta ctctacacca ttagtaagaa gaaggtaaaa ttgcagcatt   9900
ggacattaaa atcaagcact aagaaagttt ttttaaaaaa gccagatgat ggttataata   9960
tatggcaatt tttatcttca aattatgtgt ggcaatattg taacaaaaga cacaagaaaa  10020
aaatatttga ggaaagaaat agttgaggaa aatagtgcct tattacttag acagaaagct  10080
aatggggcaa agacctatgt tctgggtaat tcttagtata cgtttgaggc ttaacaaata  10140
tctagcacat ttttagtaac aatgtttgcg gatttttata ttttgaattg aaaatgccat  10200
aaatgcacct tcacgataaa gggtgagccc acttttgtat tattctgtaa ctaaaacatg  10260
atgatattta aaacaacaaa gcaaaatgat gatctagata ttaatttcct ttaaagttta  10320
tattgtgaga gacaagggtg ccattttgaa attgtggtgt acttttagtg tgaagaaact  10380
ttaaaactag gtacaagttt atcaaaataa aacaggtaag tatcaagtct caaaaatatg  10440
tatttcattt tctgtgtgct tttagtagca gtgagaatca tgttttttaaa ttctcactttt 10500 tactacctaa aaggaaattt ttgtagtata aaatataatt ttaagatgtt ttcaatatat  10560
aattcctatt ttttttctct tttagcaaga caaccttggg ctgacattcg aaattttttac 10620 taaagaacca gcaagtacta aaatgcaggc tgatgtttac actttcagta gtaattctta  10680
gaatgtgttt atctgaactg aaatctctac ttaacagtca gcgggaaatg gcaataaatg  10740
gcatctgccc taaatttcac aagttgttgc tttatttatt ttcttgtgaa cctcattaat  10800
ccatactccc tcaagtcact ttagtttagt taatatatt tgtgtgacaa aagtgttttg    10860
aacaaggaaa aatggaaaat tcatgtataa atagctaatc attggtctta aacatagcat  10920
atacacggag gctcagagga caggttggta aagattactc aaaaggagaa ttaaaagacc  10980
gctcaattct cagttgtgtc ataatcgtat ctttatggta gctacatatt ataaaatgtt  11040
ttttatttat ccctcatact agtaagcgtc aaattcatga tctttgtgag tatactgaca  11100
aactactctc acaagctatt actattattg atattttata tatcaacttt ttttcatcca  11160
taaaagtacc tcaacgacat gttcagtagc aaataagttt tcagatccct tcactctatt  11220
gaataacagc tctgaacact ttgactaact tgaatatctt ctatttgcaa tgcctaaaga  11280
ttgagaataa agcagttaag aaggaaggtg taatttgtaa atttagaatt gccaaattag  11340
taatgagtat gtaagttcaa ataatttac gcaatcaaaa agatagtgac attcgatgct   11400
tattgccatt tgttatttat gttttttaaaa tacattttg ttatgtgtca ttttcagagt   11460
atgttttctt tcctatctta ctttttccaa tttgctttttc aatctttcaa gatgactttg  11520
gcttatccta aaaagaatgt gagacttaaa ggtcaatgta ggggagaaat acaattaaaa  11580
aacacttggc ttgccagata agcaaatctt gattataact tattttgat taggtaaaca   11640
```

```
ttctaaaata atactgaatt tagattcttg tttttatttt gttggctagt attctaaact    11700
cttaagtggg cagtgatata catttctatt aaactgtata agtaactatg caaattggga    11760
tataaattgc attagaaaat atgaacatat ttgcttgata cttaattcaa ccataaaaaa    11820
taaagtattg cacttattaa tgttctcttc cctcatttgt catctgatat tgctcttagt    11880
cactcactat caaaatttct ttgtttaatc ttacttctat taatttcctt aaagtttcat    11940
gcaaagcaaa tttatgtcag gttgtaagca cctttctctc aaagcaacca ccactgtatt    12000
tgtgacaact catgccagaa ccctgaatct gccttgggaa gaaacattgc cagttggtgg    12060
cagcattcac aagagagggt cacatttcct ctgttatctt taggttgaat ttcaaaacaa    12120
ctctagaaaa cagactcaga gggctagcct tggaaacagc atgcaaacaa ctgcagaaaa    12180
gcggaaggtt tctgactata atacagttct accaaacagc agagcatgtg gcaaaaaagc    12240
caggctggct cccttcctcc tgtttacctc ctgagcagtg tatgaaacag ggtgagcttg    12300
ctcctggaat caataggtga atcaatgaac acaggctggt cttccccact tcataacatc    12360
tgtactctgt acaaggacac tccgggccac cctcgctgag catcctcccg ccctctccca    12420
gaaaatatag ctgtgtcatc ttacagacat ttttaatgtc atctgcttat gatgtgcaga    12480
ttgagaagca gacaattttg ttctgctctg gcatgaaaaa aaaaaaacgt tttaatcggc    12540
agctaggata gcaacatgaa gcaacacaca ggacatcaat ttcatcatgc aaaataccgg    12600
tgtattatat tacaggggcc aagcattcca aggaaaagta atgatctaag aagatgctct    12660
tgcatttttaa aaatatctac tagtgttata cagtcattaa tgtataattt ccatttcaat    12720
aataggaagc cttctgggaa aaaaagcttg tgttgcttct taaatctaga aacacattct    12780
caaaattcaa acagaacaaa atccagaggc atattaataa atattttcaa ctcctaaccg    12840
cagtcacttt ttaattgggc atttatgtat ttcttcaaca taattatatt tataatgaaa    12900
aaatgttgag aatactggat tagctgcatt tgtaactaca acatattttt ctaaacagta    12960
ttaattcaat tgataagact ttaaaaaagt tatagtagtt tgttctatca tatatgcaca    13020
ttaaataatc atttatttta gaaaatcctc cctcataaaa tgaacattta ggaaagagac    13080
tgatccatat ttttaacaag aataataaac acacaagtag aaagccttta taatttccaa    13140
ggggctgatc aattccatta acaaatcctg atactttaaa tgtttgcaat gccatacata    13200
gcaaatgatc caaacagcag ttatattctc tcatgtaagt cattctgttg cccatacaca    13260
gagttagcat gttacaaaac tcttgtgaaa tttcagttga acattagca ataaaatttg    13320
ctggtaaagt gcaagaagtt tccttataaa ccctagatga ggaaaagtct gtccacagtt    13380
cgttcatcag aggaatggaa tttctcaaat gagctactga acaacattat ctaataaaat    13440
gaaatataat gaaatggtgc cactcatttt aaagattaaa tatatccttt gacagaaacc    13500
tgtgaagtta aaaatctttc cctcttaaaa taccttttaa attaaagcta ttctaactag    13560
ttatatagca ttccacttaa tctgcttagt ttttagattg agctcaccta aatacaaaat    13620
actgtcaaac acctacaggg caaagaacta aaaaagaaa gaaatttca caagcaataa    13680
aatgctattc accctttctcc tcccatactt gcctttccta tatgaaacaa agaaaataat    13740
tagtgatgtt cattattggt agtgctacta gtatttgtat tgtgaacctg taacatattt    13800
ttaaatctct acacttttat ataattgatt ctttcttgaa aagtaattat ttcagaagac    13860
ttctaataaa ataatcatta ttgtatatga ttctgttaaa aatagaaaaa acaaacaaac    13920
agaaaaaact ccctgctgaa agatatggcc attttattag ctgtgaaagg aaagaaagct    13980
tccaaggaaa gatcttggac catgagaaaa aatttcaacc aggctgtttg ctggcaagag    14040
```

```
gccatgccag ccccagccag tcctgcgtgc agagcatgtt ggcagatgtt attagctgac   14100
ttttgttgaa aaagtatgga agaacagttg gaaaatcaca aggtgtagaa caagctttaa   14160
ataaataaat agcttatctg gcaatagaaa gggggaaaga aaacaagttc ctcggttgag   14220
gaagaggact gggatacttc taattacaga gtttcttact gttggtttgt ttcatgggct   14280
gactctcaat gagaattgaa attgtatcat ccacatttgt atttggaggt tctaactgca   14340
gaattgcaat taatttccag tttgctgtag gaaatttata ctctctatga cagaatacca   14400
cggacatagg tgataattct ttaaccttct ctcttttgtc cccagtctgg taactgaggc   14460
agtacatggg gaaagtgcta actgccaatc cagagctgct gacaccttaa aaacactggc   14520
ctttaacact aggatggccc caagaaacaa gcaaacagga aaagatgaca cctgctagcg   14580
tgtgacaggc acagcaagta aatgttcaat acggatatga aaatgcaact gcataataaa   14640
agtcaacatg aaaagaaaa agattgcaaa atatactttc tcagaagaaa ccatcacatg   14700
atgtttaaaa gtggtggttc ctttagcatt gtctactgat ggctggcaac atacaggaac   14760
atagaggtgg cccatttaca tcctcataaa agtgggatgt aagtgatcac aaagccaata   14820
aaactacacc acattttctt caagcaccaa gataagaatc ccttcatctt tcctgactag   14880
acatattgct aggcaacatt tgtgaacgta agaaaaggta acaagatcta aaaagaacgc   14940
cgaagcataa tgttcataaa ggtggcgccc ccaacacaca caatcataca cacataccta   15000
tacacacaca atcacacaat ctattatata aacaaacacg cacacatgca cacataggtg   15060
cacagactta aaatggcatt tcttgaggta ttttttttta aggtatgatt taaaaatgga   15120
agatcaactt taaacacacc ttttgaggc acactgggtg atatttgcca caatgattat   15180
tcttcccaaa ttcaggctac tgatcaataa tcctaactgt atacatgcta aaaataaaaa   15240
cgctataatc tttgtactag tcagggctct cttggcacat aaaattagcc aacacaatct   15300
tcaagtcaca tgttacaaaa acatattaaa atatatatca ctctttcaaa aattacactt   15360
attttctctt agattaagat tttattactt ttaagatact tctatgaatt atagaggaca   15420
tccaaaagta aacatccggg acttaaaaac aataaccaat attataagat aaattattgc   15480
tgtaaattat ttcatgaagg cacaattaaa aaaaaataa aataaacagc caaagcctgt   15540
tttgttgagt tttcttcgtt gcgcaggatc gggagcttgc tgggatctga actcaggaag   15600
ccctcacctc accctgactt ggtcattgag gagacgtaat tgcagggtg cttatttgct   15660
ataggctttg aaagtcacaa aagcccagta gatacatgaa ttcgaagcag ttctccaagg   15720
gcatctccaa cttggcagtc accgcccgca ccgcgcacac aggtagtgga cgcccgccca   15780
cctgcccgtc tgctgggcgc agggcgctcc tgggtgggg agggcgctcc tgtggggga   15840
aaagggcgc tcctgcctcg gaggggaaa ggacgcccct gtggaaggaa ggggggctc   15900
ttgaagcggt gtggtgagag gacgcttccg aggaaggaag ggggtgctcc tgcagcggtg   15960
gggggagagg acgcccctgc ggaaggaagg cggcgctcct gcggggctg gagagacgcc   16020
cgcgcggtct cccggctcag ggaccgctgg ctcgcgggtc cgccctctcc ccggcgctat   16080
ggaaaccgca ctttctccgc ctgccgtccc cgatctcttt tcctattac ctcccaaacg   16140
cgatttcaac ttcccgacaa gctgacaagt gaatggcgca gaggacgccc cgtaaagcgc   16200
ccgcgagcgg gtgggacaca ggcgcccct ccgcgccccct ctgtcctcca cggaagggcg   16260
cgcgccgctc tcgatctgga gcgcggtgct cgcgaacccg cggccgcggg ccctggaacc   16320
tccccgcgtt tcgcggctgc ggggggacgg agatgcggcc gggagacggg gacgggaaac   16380
```

```
gggggacggg gatggggcgc gcccaccccg agcgcgggag cggccgccct cgcccaaaat    16440
ggggaccccg cgccccgaga gcacggcccg gctcgccgcc catgcttcca ctgcaaggcc    16500
gcagcccccg ccgccgatcc cgatcccccg ccccgcccag ccgcggcccc gcccggcgcc    16560 ccctcccgg  cggaagctca agcccaatta attgagtccg aggcgggagg aagggccct    16620 gcgcgccgtg gcccgccccg ccctcttcc  gcgcccttt  tcccgccctg ggtggcatct    16680
cctccgccgg catccacaac aagccgctga ttaatgaggc cggggccgcc ccaccccgcc    16740
cggccgggcc ggggccttcg cgggaggggg aggggacggc gggaaacgcg gcccggggag    16800
aaaggggggc gggggcgggg cgcgcggccc gcccccgcga gcgccgcgcc gattggccga    16860
gcgcgccgtc cgtcggggg  cgcggcgcca atgcgaggca gcggggcggg gcggccgcgc    16920
tgtgtgtgcc tgcgtaacgc cgagtcacat gttgtttgc  tcttcttagt tcagtcactc    16980
ggtgcgcgat gtgttactca ctgtgcggcg gggaccgcga cgagcccggg tcgccgttgg    17040
cagcagcagc agcaacacca gcagcagcag cagccccggc ggcggcgcgg accccgagcg    17100
cccgggcgca ccccggcttc cggagcgcg  acgcggcggc agcagccccg gtgcggccgc    17160
gcgcgcctta ggctcggccc cgcggctcgg ggaccccgac tcccggccca gcagcgcgt    17220 cccccggcgc cgcccgagag cccgaggagg cagcggccgc aggcagccgg ggagggggc    17280 ggccaccgcc cgcgccgggc atcctcagga gccccgagagc gcgagggcg cggcgccgcc    17340 gagcggtgct ggcccccgcg ggcctccccg gaccttcccc accgcctggg cccgagggac    17400
gcgtgatcgg gcgggcggcc gggcgcaagg gtgggaggga gccgcccccg cccgcgcccc    17460
ctccgcccct cgccccaacc cctgggcgcc gggcccgggc cgcgcggcct gaagcgcccg    17520
cgatggcgag cccgccgcgg cacgggccgc ccgggccggc gagcggagac ggccccaacc    17580
tcaacaacaa caacaacaac aacaaccaca gcgtgcgcaa gtgcggctac ctgcgcaagc    17640
agaagcatgg ccacaagcgc ttcttcgtgc tgcgcggacc cggcgcgggc ggcgacgagg    17700
cgacggcggg cgggggggtcg cgccgcaac cgccgcggct cgagtactac gagagcgaga    17760
aaaagtggcg gagcaaggca ggcgcgccga acgggtgat  cgctctcgac tgctgcctga    17820
acatcaacaa gcgcgccgac gccaagcaca agtacctgat cgccctctac accaaggacg    17880
agtacttcgc cgtggccgcc gagaacgagc aggagcagga gggctggtac cgcgcgctca    17940
ccgacctggt cagcgagggc cgcgcggccg ccggagacgc gccccccgcc gccgcgcccg    18000
ccgcgtcctg cagcgcctcc ctgcccggcg ccctgggcgg ctctgccggc gccgccgggg    18060
ccgaggacag ctacgggctg gtggctcccg ccacggccgc ctaccgtgag gtgtggcagg    18120
tgaacctgaa gccaagggt  ctgggccaga gcaagaacct gacggggtg  taccgtctgt    18180 gcctgtctgc gcgcaccatc ggcttcgtga agctcaactg cgagcagccg tcggtgacgc    18240
tgcagctcat gaacatccgc cgctgcggcc actcggacag cttcttcttc atcgaggtgg    18300
gccgctcggc cgtcacaggc cccggcgagc tgtggatgca ggcggacgac tcggtggtgg    18360
cgcagaacat ccacgagacc atcctggagg ccatgaaggc gctcaaggag ctcttcgagt    18420 tccgccgcg  cagtaagagc caatcgtcgg ggtcgtcggc cacgcacccc atcagcgtcc    18480
ccggcgcgcg ccgccaccac cacctggtca acctgccccc cagccagacg ggcctggtgc    18540
gccgctcgcg caccgacagc ctggccgcca ccccgccggc ggccaagtgc agctcgtgcc    18600
gggtgcgcac cgccagcgag ggcgacggcg gcgcggcgg  gggagcggcg gccgcgggcg    18660
ccaggccggt gtcggtggct gggagcccc  tgagccccgg gccggtgcgc gcgccctga    18720 gccgctcgca caccctgagc ggcggctgcg gcggccgcgg gagcaaggtg gcgctgctgc    18780
```

```
cggcagggggg cgcgctgcaa cacagccgct ccatgtccat gcccgtggcg cactcgccgc   18840
ccgccgccac cagccccggc tccctgtcgt ccagcagcgg ccacggctcg ggctcctacc   18900
cgccgccgcc cggcccgcac ccgcctctgc cgcatccgct gcaccacggc cccggccagc   18960
ggccctccag cggcagcgcc tccgcctcgg gctcccccag cgaccccggc ttcatgtccc   19020
tggacgagta cggctccagc ccaggcgacc tgccgcgcct tctgcagcca ccgaagcaaca  19080 cgcccgagtc catcgcggag acgcccccgg cccgagacgg cggcggcggc ggtgagttct   19140
acgggtacat gaccatggac aggcccctga gccactgtgg ccgctcctac cgccgggtct   19200
cgggggacgc ggcccaggac ctggaccgag ggctgcgcaa gaggacctac tccctgacca   19260
cgccagcccg gcagcggccg gtgcccagc cctcctctgc ctcgctggat gaatacaccc   19320
tgatgcgggc caccttctcg ggcagcgcgg gccgcctctg cccgtcctgc cccgcgtcct   19380
ctcccaaggt ggcctaccac ccctacccag aggactacgg agacatcgag atcggctccc   19440
acaggagctc cagcagcaac ctgggggcag acgacggcta catgcccatg acgcccggcg   19500
cggccctcgc gggcagtggg agcggcagct gcaggagcga cgactacatg cccatgagcc   19560
ccgccagcgt gtccgccccc aagcagatct gcagcccag gccgccgcc ccgccgccg    19620 ccgccgtgcc ttctgcgggg cctgcggggc cagcacccac ctctgcgcg ggcaggacat    19680 tcccggcgag cggggcggc tacaaggcca gctcgcccgc cgagagctcc cccgaggaca   19740
gtgggtacat gcgcatgtgg tgcggttcca agctgtccat ggagcatgca gatggcaagc   19800
tgctgcccaa cggggactac ctcaacgtgt cccccagcga cgcggtcacc acgggcaccc   19860
cgcccgactt cttctccgca gccctgcacc ccggcgggga ccgctcagg ggcgttcccg   19920 gctgctgcta cagctccttg ccccgctcct acaaggcccc ctacacctgt ggcggggaca   19980
gcgaccagta cgtgctcatg agctcccccg tgggcgcat cctggaggag gagcgtctgg   20040
agcctcaggc cacgccaggg cccagccagg cggccagccg cttcggggcc ggccccacgc   20100 agcccccctca ccctgtagtg ccttcgcccg tgcggcctag cggcggccgc ccggagggct   20160 tctttgggcca gcgcggccgg gcggtgaggc ccacgcgcct gtccctggag gggctgccca   20220
gcctgcccag catgcacgag tacccactgc caccggagcc caagagcccc ggcgagtaca   20280
tcaacatcga ctttggcgag cccggggccc gcctgtcgcc gccgcgcct cccctgctgg   20340 cgtcggcggc ctcgtcctcc tcgctcttgt ccgccagcag cccggcctcg tgctgggct    20400 caggcacccc gggcaccagc agcgacagcc ggcagcggtc tccgctctcc gactacatga   20460
acctcgactt cagctccccc aagtctccta gccgggcgc cccgagcggc caccccgtgg    20520
gctccttgga cggcctcctg tccccgagg cctcctcccc gtatccgccg ttgccccgc    20580 gtccgtccgc gtcccccgtcg tcgtctctgc agccgccgcc accgccgccg ccccgggggg   20640
agctgtaccg cctgcccccc gcctcggccg ttgccaccgc ccaggccccg ggcgccgcct    20700
catcgttgtc ctcggacacc ggggacaatg gtgactacac cgagatggct tttggtgtgg   20760
ccgccacccc gccgcaacct atcgcggccc cccgaagcc agaagctgcc cgcgtggcca    20820
gcccgacgtc gggcgtgaag aggctgagcc tcatggagca ggtgtcggga gtcgaggcct   20880
tcctgcaggc cagccagccc ccggaccccc accgcggcgc caaggtcatc cgcgcagacc   20940 cgcaggggg ccgccgccgc cacagttccg agaccttctc ctccaccacg acggtcaccc    21000
ccgtgtcccc gtccttcgcc cacaacccca agcgccacaa ctcggcctcc gtggaaaatg   21060
tctctctcag gaaaagcagc gagggcggcg tgggtgtcgg ccctgagggg ggcgacgagc   21120
```

```
cgcccacctc cccacgacag ttgcagccgg cgcccccttt ggcaccgcag ggccggccgt    21180
ggaccccggg tcagcccggg ggcttggtcg gttgtcctgg gagcggtgga tcgcccatgc    21240
gcagagagac ctctgccggc ttccagaatg gtctcaacta catcgccatc gacgtgaggg    21300
aggagcccgg gctgccaccc cagccgcagc cgccgccgcc gccgcttcct cagccgggag    21360
acaagagctc ctggggccgg acccgaagcc tcggggtct catcagcgct gtgggcgtcg     21420
gcagcaccgg cggcggtgc gggggcggg gtcccggtgc cctgccccct gccaacacct       21480
acgccagcat tgacttcttg tcccaccact tgaaggaggc caccatcgtg aaaggtgagg    21540
aggccctttg ccttggcgtc tggcgggaag gaggggcggg gcgctgaggg agcctcttgg    21600
gtttcactgc tcccactttt tggggacctt gacccagaag ccgacagcct ggcactggct    21660
ccttgttttg ttttctgcg ggctgccctg ttctcttcct tcagagaact tgccaggaac     21720
attcgtcttg gagttgaatg tgacgttttc cgcgtgggag ggagactgat tttttgaggc    21780
cccacccatt cacccattct gtgcgtccca cagcccctg tcccttaaca cagtggaagt     21840
tctcccagac cggccacact agaggccgcg gggcaccga ctgtcttcat ccggctgcgt      21900
gggtccgtcc ttctggaagg acctcgggtc cggaccgctg ccctcagccg cagcttttcac   21960
cttttccctgt gttcctggag ctgggctccg cctgattctt ggtgagcttg aaggttcaga   22020
cctgaaagtc atttaagaaa tgagcatcca ttttgatggc tgctaatagc gacagttaac    22080
catttccgtt ttacacacaa actgtgggag cttttccatc agaggcattg ttttttctcgg   22140
aaggggtgaa acggtaaggc tgcacacagc ctaatgcagt ggtgttcaac ttgagcatat    22200
gtgggagtta cctggaggct ttgctgaaac atggatctct ggcctgtgtt aaccccgcag    22260
tttccgatgc tgtagctttg gggcgcggcc caggctgtgc atttctagtg agtctccgca    22320
taatgccgat gctgctggcc gggggaccac cctgtgagga ccctgcccca ggtgagactc    22380
acctggggag gattgaaaaa ttacctgttg ggcctcaccc cagacccgtt gaagtgaaac    22440
atgagatggc taggaggcag ggacggacat ttttcagagt tgtccaggtg atttgaatgt    22500
gcagccagga tttacaatca gtgctttgga gaaacaagg gaaagacaaa aaacacaggt     22560
cttctcaaga acaattggat aggagggtgc ctggtattgt tcttcccgtt ctgatcaaat    22620
atccatgagg agagagagct gatgcagaat gcagctggtg gtgcattctg gctgtctaaa    22680
cttttgaatgg tgtttggggt cggggagatg agagggaaag gtgaatgctc aattcgggag  22740
actttattta atttttgtagc tgttttcttt gtagggttcc tagcaggata gaggctttgt   22800
gggaacagtg aaacatatag taaaatttgg atgctggatt agatgtgagc ctaaggtgta   22860
aacagtcttc aagggtcatg agatgaggat caaggtgggc tggagattca cagccttttg  22920
ttcttaaata gaccagttta gtgctatcta aatccagcat ctgttttata gtatacttag   22980
gactgtcggt ccatgggatt taaaattata gctgtggggt gaactccctg ttattctagt   23040
gtaatagaga aaagctattt cctttattaa aaccgtatac tagaagatga agagtcacag  23100
agaattatca ggagtgtggt gcttcagcat ccaattaaat cattggaagt cgccagaatg    23160
tatcctgtga acagtgattc tcagctgaag gtcactttgg ttggagttac ttatacacta   23220
ttgctagtgt gtcagaaagt tgaaggatta gctgccttat aagacacaga ccattataaa   23280
cacagcagca gcagcagcag tataattgag tgggaaaaaa cacacatatt tatggtctgc    23340
acaaatgggt atatgccaga gtgaacatga aagtaaatta catcttaccc gaatctgatt   23400
ctaatcagaa aacagccaag aacataacac cttttcctgc tttcagtgga gctggtggga   23460
caaacctgga ctgggtggag ctggggcccc agcagtgggc tctgccatag caggcgccat   23520
```

```
aagctggaat ttgtgcctcc aggcctggag ggacgcaagg cgtttctgat gaagccgata   23580
cattcagaat tggggtccaa ataggaaata atgccctttt caggctagtg aaaatgttga   23640
actctaagag ataagtttat ttagagactg gattgagctt tgtttaaga tttcccacct   23700 gcgtaaaatt cctttcagcc cataggattc ttgattctga agtccagaca gaagcctgtg   23760
ttctgtagct gctgaacaaa gatgagagat cactgggggct gctgtttgtc cgaagtttgt   23820
gtgggtatca tgatgaaccc tcttctaaga agtaaaagga tcttttaaat caaaatagac   23880
aactgcagtc agtccaccat gcccaacgac atttaaaaaa aaagaaatat ctgccccatt   23940
gggtttctag taaagtaagt tgaacacaga gaacagcaga ataggaaagg ctagtgtcac   24000
cttagtccac gtagcaccaa agttgtggtc cgttgagaca gaaaggaagc atttaggaac   24060
ttgggataaa tacccacttt tatttaactc atacatgcac tagaaatttg tttgggatgc   24120
tcataaatac agagttcaca gtagatcagt gtcctttgag gaaatgattt gtagaaggcc   24180
gacttgcaaa gcatttcttt gaagatgaaa tagagaaagc acttcctggg cggcccctg   24240 ccctgcctgg ctcttagaag tggcctgtgt ttccaccctg agctcttcct gttctgcatg   24300
ggaagacctc gttagtgatg ctgatgcaga ataattttgg ggttatgtgg gtaatgtttg   24360
gtatttgcat aagtgatagc agagaggtaa ggttccagcc atgtctggca cttgtttaca   24420
atagaatcgt gaatgggggt gggctttcag tgcaagagcc agttaaaaag tatatctcag   24480
gtacatctgt ttttattagt ccagagcaaa ctcaaaatta tgcatcttat ttgagggcag   24540
gttaaggtta cttatcatgt gttttttggtg tgtgtgcatg tggaaaactc taaccaattt   24600
gttaggtttc gttgttgttt gggaattgga aagacgctac tgaatttcct gtgctttaaa   24660
actgattttt aaaattaact ttatatgttt ttgtgttagg atggtagatt gatgaatgcc   24720
ataaaatttg ctgttttagt attccttttt agtgatttta gggatttat tctaaaattg   24780 gcgtatatat atgtatgtat gtaagacagattagatca gaattactac tgaaagtatc   24840
catatttaaa ttttgttgaa taaaaggatt atcatttctt aaggggaaag aatgataaga   24900
gatatgtttc caagggaca ataaaatcac gatttatgtt gaaagtttt gccttttgaa   24960 gtcgtaaagc agagaatttt cctaaattca gaaatccagt gaggtgattg acaaaccaca   25020
caagttttct gtttgctgtg gcgggtgcta gtttgcttta gttggctggc tctggccata   25080
ataagacaat agcgtgcact gctgctgccc tattcgcagg agcagacaac taaggtgcta   25140
atgaaaacac acaccggctt tcgtgaatga agtcacatg acttgttctg tttcctttat   25200
tgaaagagaa acctttacaa aaatagtact tcatagaagg aagcatagta tgtggaacac   25260
taaaccagga atcaggaaac caggtttcta gttgctgatc ttaatgagtc attgtgtgtc   25320
tatgggagag ccacttaatc ctgccttctc actttccctg tctgtaaaat ggggtaatt   25380 ataatcctcc cctttctgtg tcacaaggcc gctggaaggt aaatgaggtc ataaacatca   25440
agagtgtttt aagctcttct aaaggaagat gctaataaat ccagttgttg atacttattg   25500
ctttgaaacc atgaatgtat acaggaaaga cacttttgta aatgggtgct cttaaattga   25560
aacaaacagt aacagcatag tctgaaaatg gagccagcac cttaaaaatt gcttaccttt   25620
actgcttatt gctagttccg ctccaggctc ccaagagcca ttgttttccc cctttatgta   25680
acttaagatc tgttcataga tatttatgaa cagattgtaa caaagtggtg ttctaaatta   25740
catagtaaag taacaattag ggaaaacagt atggtaatcc tgaaactatg ttaagactga   25800
acttctgatt acctttttatt actggttttt atattaagag atgttgacaa gatgaaaatg   25860
```

```
tataattaga atatacattt taaaaatcgc ctcttaatgc cgaatgcatt gaaagaaaaa   25920
cagaaccctg aggttgtttg actactcatt gtttagtctg ggggttcatt ctttggggtc   25980
gatttaatga gggtggtcat tcctgcagtt ttgatggtag cactgtgctt atcaaacata   26040
gtaggaaaat gcgtgattct tttgttttc taccacccaa aaaggaatct tagtagagaa    26100
ttgatatttt attttcttta gaagtatgag tatttaaaat gaggctcttt tttctgaaga   26160
gaagaacttg gaaaagtttt agtaacagca tgagtataat gggttttctg ttaaaattcc   26220
cactaatgca ttttctttag aaacgtagtt ctaagagcta attttggtat cagatttggc   26280
aagtagaaag ggttttttgtt tgtttgtttt ggttttttt taggggggagt agcacagaat   26340 caagtgttcc catttcacct tataaactta agggaaaatg taactttatt ctttcatctg   26400
cattgccaag tagaatgagg aaaacactgg gtgaggcaaa gtgctgtgcc cccgccccc    26460 catcctgcat ttggacagct gtaatgcagg tggattctct gtttcatttc tctagtacgg   26520
atgacagcag aatgtatatt tctatacaag atgaacaaaa cgttttaatg ttggcgtttt   26580
aatgaacaaa tgaaaacaaa attttctgaa tgtccaaaag tattggttat aaacacatta   26640
actgtcagat catgattttt gtgaaaagaa tgctgtccaa gttagatag gacactctt     26700 tctatattta gtttgagtgg gttcttcaag actgcagtgg ttattctgac tcatttcagg   26760
tagattattg tacacagagt tcagtgctag acttttctga agaaaactag taaagtcatc   26820
atttggcatg gaggagatga tggggttgat gattgctact gatttcaatt tctttcaaga   26880
tagctacaga gacttacatt aactgggtgc taaaatacaa tgcataggtg aaggttagtg   26940
tagaaagagt tggagtatat gttgtatacc aacattttgc tctgtaggtg caaataatgc   27000
aagatgcttc tgtgtgttat agctttatta cttaagtgaa ttcattacat aagaattctg   27060
aaatagattg gattaaaact tatgggttac atgtttacaa atgataaaat agtcaatttg   27120
gtggttctga ttaattttct attagactag gaaaatacta agtttgtata gagtcacttt   27180
tatgtgtcca aagacactgt aaaacttgaa tgggtaaagg tgaagccttg gaaactctgt   27240
ccagttttct tatgtcatat atgatatcta tatacacaag gttataaaa tattccttgc     27300 ttactgtgtt tttactgaaa tttggaatat ttgatcaaat attttgaccc acgatatatt   27360
ttttaaagat aactgatcac acgcattgca ccctgtaaat gctgggtttt tttcttttt     27420 tttttttgag acggagtctc actctatcac tcagtctgga gtgcagtggt gtgatctcgg   27480
ctcactgcaa cgtccacctc ccgggttcaa gcgattctcc tgcctccgcc tcctgagtag   27540
ctgggactag aggtgcatgc caccatgccc tgctaatttt ttgtattttt agtagagatg   27600
ggatttcacc gtgttagcca ggctggtctc gatctcctga cccgtgatc ttcccgcctc     27660 agcctctcaa agtgctggga ttgcaggcat aagccactgc gcccggccta atgctggatc   27720
ttttaatatt cattttaaag agtatcaggt tttccagcaa caaatatttg gggctggtgt   27780
gtgtgtgtgt gtgtgtgtgt gtgtgtgtgt gtgtgtgtgt gtttccataa tatctcatcc   27840
agtcatgctc caggaggctg gatatgatat ttttctccat aactgaaatt caaggattaa   27900
tgatgtgttc tttgttcatg ttgaaacttt ataacttaag catagtctac tgctacttta   27960
tccctataca gttagtacaa atacttgagt cagttattac ggtgtggtat gaaatttcaa   28020
ttgttttcaa tgcataaaaa cagatattat gatatagttc attatactat gtgatttttgt  28080 tactttacaa tcctattata ctgtgtgatt ttgttacctt aaaatcctta tgtttatgtt   28140
aagaatgatt cattccttgga tgagcttggt ggctcatgcc tgtaatccca gcgctttggg   28200
aggccgaggt gggtggatca tctgaggtca ggagttcaag accagcctgg ccaacatgga   28260
```

```
gaaacccat  ctctactaaa  aatacaaaaa  ttagccagcc  atggtagcat  gcacctgtag   28320
tcccagctac  tcaggaggct  gaggcaggag  aatcacttga  accagggagg  cagaggttgc   28380
agtgagctga  gatcgcgaca  ctgtactcca  gcctgagcaa  caaagagtga  aattcagtct   28440 caaaaaaaa   aaaaaaaaa   agaaagattt  tgcatagtat  taatgcttaa  tctttaatat   28500
ttaagaatat  gatacagtgc  tttctgtatg  cattctatgg  acttaaataa  gtcaatcttt   28560
ggcctccaaa  gtataagtgt  aacagataat  cccacaactt  ggtagacaac  tggcaactga   28620
agattttgaa  agaatcttat  tgaagttgaa  tgcaatgacg  atgtaccatt  attctgatca   28680
atattgacgg  ataactgcct  gccactcttc  tcttggggtt  aaaagagttg  tgtaaaattc   28740
aaagggtgtt  tttcttccct  ttatagtggt  aagacatttt  cctatataca  atatggtata   28800
atattccaaa  aaatcctatg  gcataggcag  aaccaccatg  aaccccattc  tttggaatca   28860
agaacctaca  gtgtggagag  gccagatgac  ttgctccaga  tctctgagcc  aaaaggagaa   28920
ggagtgtcgg  gttcaacctc  ataacatctt  ggtatcccta  gcccagttct  ctaatgtcat   28980
attgtctgct  tgggaagctc  atatgcaata  attacattag  gattttatcc  tagacccttg   29040
cctcaagcaa  catttaagtt  aatattttgc  tggagtgata  gttaatcatc  tcccccttt    29100 tcttccactg  ggtatcaatt  caaggaaaa   tggggaccat  tgaggaggaa  gactggtagg   29160
aaagcgctct  atttattgaa  atcagttttt  acatcctccg  gtttggagag  tttagtattt   29220
gatactattt  tcaaggctgt  gatgttacta  gtgaatttta  agttgacca   tcaagttggt   29280 gatggatctg  ttctggggac  tccagtcatg  cttcctggac  ctctagatgt  gtcaacaaag   29340
tggaaaactt  agattgctct  ggctgtcttt  cattacctct  tggtaaagca  aactgtatat   29400
gatacttggt  aagataccte  cccaccaccg  ccaccatcaa  atacattaaa  actcttgcaa   29460
ctcaggtggt  gacaatacga  aaaaaatata  caagggtgtt  ctgagaagga  agagttgaga   29520
accgttgata  gaatgtaact  tagttattta  aggttgtgaa  aacagaggct  gtgtgaggtc   29580
cggagtctta  gtcaaggtca  ctgattcaat  tagtggtaga  gttgtttgta  gatatcatca   29640
agaaagagta  ggagaatgtg  atacaaacaa  tgacacatct  cagttggttc  tttgtatctt   29700
gatgaataac  tttctcccag  gatacagcct  atgctcttta  gaacaactta  gtatttgtgg   29760
aaatgatatt  agtctttta   ctttggaaca  ttttagtaac  tttcttcatc  catagactaa   29820
aagaaaccct  gaaagccaga  aatagagaat  gcagaattcc  ttaatgaaga  aacgcgttat   29880
aaatcagaga  aatatggctg  ttcatgacta  tgtggacggt  gtctactgag  tggggagaag   29940
atttggcaaa  tatttaaggt  catgtattta  ctttatcaaa  gaaaaggaaa  caaagttatt   30000
gtttcatgaa  gaccccagt   gaaatcgaaa  ggcctagatt  atctagcaga  attgaaggcg   30060
gctctgtgta  acaggttcag  cctgggcggt  gacacagtga  tgagtcagcg  ggtgcattcg   30120
gtcactgctc  tctgtgtctc  taagacaggt  gcttgttcta  taagtgaaat  atcatatatt   30180
ccccattatg  gataagtcca  ttaacatttt  tctaagaaat  gagtcattaa  cctatttaat   30240
gagtttattt  gaaaactaat  caatttagaa  tttgcctaag  gaccaataac  taactaatca   30300
gttgttgcta  ggtggttatc  ttctggggaa  ttgagtattt  tgtcagtgcc  ttttatttt    30360 taacagccct  tgttttttc   tttttttta   attctcagga  aaaaaatcat  ttagctggat   30420
ttttatatga  agataaatag  ttttcataca  aatttaattt  cacagaagct  gccattattc   30480
taatgacgtg  ggtataacct  cactttcaaa  agcagaaaga  aacactttag  caaacacata   30540
aaaattctta  agatattcac  actttaaaaa  atgtaatagg  cggccgggcg  cggtggctca   30600
```

```
cgcctgtaat cccagcactt tgggaggccg aggcgggtgg atcatgaggt caggagatcg   30660
agaccatcct ggctaacaag gtgaaacccc gtctctacta aaatacaaaa aaattagccg   30720
ggtgcggtgg cgggcgcctg tagtcccagc tactcgggag gctgaggcag gagaatggcg   30780
tgaacccggg aagcggagct tgcagtgagc cgagatcgcg ccactgcagt ccgcagtccg   30840
gcctggccga cagagcgaga ctccgtctca aaaaaaaaaa aaaaaaatgt aataggcaaa   30900
tctgtggcct ggaactcttg tgggcagtgc agtgtttgct ttgtgcaagc tgtcaggcct   30960
ctcagcatca agagacagta cctccttcct ggccagcacc cccaacggtg agcgccgtga   31020
cccaccaaac agcaggtgag attggagacc tggctggatg agcaaagcag gaaagcagtt   31080
ttgctatccg ggcgaatgga gttacggacc ttcttccagg ttaagaagaa agccacgttc   31140
ggagcgccct gtgttgcagt gatgggtttg ttgagcaccc accaatttag tcaggaaaac   31200
tgatgcagac gtgtggtctg ggggtcttca tgaatcggcc agaagccttt tccccagcaa   31260
ggtttgggtg cctctgggaa cttttgcctt ctgcagagga cctgggaaga gcgtgcacct   31320
acctgcaccg ctccgtgcta tgaaccaccg aaaataggga ctgaagtcag ggaccatctg   31380
accacgtgaa ttcccgggtc tgcggcagaa gccgcccccg atcccgtcat ctcagtggcc   31440
accctcaccc atgactgccc tgcgctgcct gggcccagcg catgccgggt gagcctctct   31500
gccctccttt ctttgttcgg gacttcccat acccagatgg atggataaat aaggggaatt   31560
gtgaagcagg gagaaaagtt ttggaaatag gccagaattt ctttactaaa tttaaaaacc   31620
atgcacataa tcctttagaa actccacgca ataagcagga ttaagcaagt cgtggattag   31680
agtgtattga gcagagactg tttctgtttg aagaggtcag aaatggaggt actgggaccc   31740
tagtttactg tggacattgc agggcttctg aacttcccag acagcagaaa ttcctggaaa   31800
agtagagtct tgtggtcagt ttcttacccc acaccttttgg tgcattttaa aaaataaat   31860 tactaaagtg ctttgcttca gttttattct ggtatgatag taggtattca cttttttattg   31920 tcttcctgca taaaagcaac ctaaaataac gttttacata cgcaaatgaa acagaaaaca   31980
aatccataag ctacccatac cctcttccag ttctatatat caggtgagtg tgctgagact   32040
tgtacaaata acttatgttg tcaagtagac atctactaaa tgtatagttc aactgaaagt   32100
atatttgagt atgctttagc aaaatgtgtt agttgcaaaa gtaccaaatc tcttttctc   32160 ttttaaagta ttataaatcc aggattgtaa atttatttta attgcagttt cagaaaacta   32220
actttaattt agctggctga gaaagcaaaa gagaaaaaaa ttaaatatta atattgaact   32280
gcatgaaaat actagataca aaggctacac aaaacccttt tagatataaa catccatgaa   32340
tttgcattca ttgatgcaaa gacattgttg agattatttg ttctgacaag ttttttaaat   32400
gagaatttct cctaaaggtt ttgtagcttc tacatgtaag ggcattttgg tgtttgggga   32460
cagatgaaag tttcagtggt ccagtagaaa ggacacacct tggttcagtt tgccgtctta   32520
ctgttatttg cagcttagct tatcagtgtt cctagttcga gatgaaataa tcactgcaat   32580
gaaatgtcca agtttttccca gcagggagca tttaatgaag ttcttagaac aagtctgggt   32640
gatacacatt catctgtgtg agtcttgatc tgtccaggtt cgctgggctg tttagaatca   32700
ctgggtcttc agccatttcc aaaacgcaga acacagttga tattttaagc caatcaatgt   32760
attgagagtt cagcgtgtgt cagcacaaga gtagatgtcc tggagatgc agaagaaatg   32820 tgaagcctgg cctctgttcc ctaggtgcct tcagagtcaa cttggcagca tcccaccggg   32880
caccattttc tgggcagccc ctctgatcct tttcataagt gtccacccc caggcaatct   32940 tggctgagca cagagaatgg gatgtttcac gggatgtctc tgctgcgaca gtggatatcc   33000
```

```
ttgctggaac attcacagta ctggtcccat tcacagctgg gaccactcag atgtttcacc   33060
ccttcacccc tgcgtgaacc tggggtgcat cagatgaggt agtgtttgta agttttcttc   33120
tctgaaaaat agtagctttg attctgctgc tatcccgatt cctagatgtc agcttgccct   33180
gagctcttgg cggccttgcc tccaagctct cctggtactt cattctgtgc tcagtctttg   33240
ttgtaaatgg tagtattcca gaaacttccc cattgtcagg tttcttggct ccttttttgta  33300 ggcagcccca aaggctgcgt taagggtatt gatcacattc tttctatagg catccctagc   33360
ctgttcagga aagcccctc ctttcctgcc agccacagcc cccaccggct caaagggctg    33420
cttgccgctc ttggcctccc tgccctccat ggtggtggcc agtgtaggcg aaagaaggaa   33480
gtcccattgg gttggggagc tccaagtcac ccacccgtga ggctgatggg ggagttagtc   33540
acagatgagt ctcctcccat tctcaccttt tgccaccttt tgcagttttc agaaaaaaag   33600
aaaaatagga actttactta tgggttgctt gagaaaggta gaaagttggg ggcagaaagg   33660
acgatggcaa aaatggtgag atctcccttt aattttttaaa tgtattcaaa ctgttaaatt   33720
tctgcatgtt ttcattacaa agatgacaat tgttgcatat agactatctc aaaaatactt   33780
catccatttg agcaatatga aagaataggc tagagagaaa cagatttggt ttttcaagct   33840
aaaaagaata acagaaagtg ggcgagtctt cagtgagctg tctgcctttg aaacctagga   33900
agtaaactta atttggatgt gcatttagga gatgaagcac tacaggtggt gaaatgctct   33960
agcaatgaag cagggaaggg agaggggga aaggaaattt gagccaagca acctgaaggt    34020
caggggaagc cggtcttaca gatgttaagg gaggaatcca gtaggcaaa ggggatgaac    34080 agcagtgcaa aggctctggg gcagcaggtt gcccggtatg ttccagaaca ggaaggaggc   34140
cagtgtggct ggcatggaga gctaaggctc aaaggagaaa gtgaagagaa agaggtagta   34200
agggaccagg aggaattgag cccggccagc cgtgctactg atgttagccc acatgtcaca   34260
gtgtgtgagg gagatagagt ccttgggaac aataatatgc agagctttta aaactttca    34320 tactgtagcc atcaattcca tcatcatggt ggtggtatcc ctgggtggtg gtggttactt   34380
ggtagagtat acgtcaactc gaatttcttc ctcaaaagta tataaaattt gaaaagacct   34440
agaagtgatc tagtggaatg aagacgctga ggtaccattg aggttgggga aactactggg   34500
acgtgcttac aggataaact gcaaaacaaa agcacaagtt tgtaatcatg gaatgacatg   34560
ccttattctg aaaacttaac gtttgtagcg taccttataa ttcataagac atttaaaaat   34620
ggtattgaat cccaataacc tatgcgtagg gttggatctt gttgttatcc ctgtttttta   34680
atggaaaatc tgaggcctga agatggtagg ccatgtatat gcctgccccg ccgttgagcc   34740
tggctcctgc tgttggagaa actttcccag tctgtagaga gaggatgtgg tcctggcaag   34800
cctggctcct gcctgattct gtatcttctg gtaacacaca gccgtcattt aaaaaaaaaa   34860
agacaaggtc tttccctctg acagactaaa agctgaatcc gcttatttcg aactctgcct   34920
tgaggcggga tgccccgtgc attatggtta actaggacct gctaaccatc ggcttatcaa   34980
acaaatcaat ttcactcttc agctaatttg gaaatgaaaa ttatagaagt tagaaaaaat   35040
gtgcagaaaa agtattattc caatgtatta ttccatttgt ttcatagaga tcctggcttc   35100
acaggaaaga gccaagggca tgggttttgc tgagggcgta agagcttggg gaaggtgagg   35160
gctaggtgtg tacgggtgcc ctgatgtcct cttagcctgc tggtgaggaa agtgcatgtt   35220
taataaatgg gctccagcca actgtgtgca gttatttgta gcctgcataa ttttaaaaat   35280
gtggttgagc atttaggtct atcttcagaa tttaggctcc atttgactta gttttcctga   35340
```

```
aatatgtaga aaactaatgg tgaaagagga cctaattctt gaattatctg cttgaactgt    35400
gttgctagtt attccaagta gaatttgtaa aatggtccat cattctctaa gcaaaatgag    35460
ggaaataaca attattttct agaaatttca tatatattga atattacaaa atcatgtaac    35520
tagaaatgtt taaatggtca cactgggcca ggcacggtgg ctcacgcctg tgatcccagc    35580
actttgggag accaaggctg gtggattaca agatcaggag tttgagacca tcctggccaa    35640
tatgatgaaa ccctatctct actaaaaata gaaaaattag ctaggtgtgg tggcgcatgc    35700
ctgtagtccc agctgcttag gaggctgagg caggagaatc gctggaaccc gtgaagcgga    35760
ggttgcagcg agccgagatt gcaccactgc gctccagcct gggcaacaga gcgagactcc    35820
atctcaaaaa aaaaaaaaaa aaaaaagga aaaatggtcg agctgatttt ccagaatgga    35880
atatcactgc gtgatgctct ctgggaagag aaggcattaa gtctgtaaca cacaggacag    35940
aactactgtc tattctgtac gcatctgctt gatcctcagt tttgtcacct tggttactaa    36000
caaggtggtt agaaagttac atctctcttg aatccattct taaaggcctt caaggactca    36060
ggcacagcct tgggaaacca ggaaatgtga ctgtgtcaat caccacacag tccaacttcc    36120
ttttcgtgta ggaaatgttt tctttatcat taattgatca gttctcccct ttccaaactt    36180
ctggcaattt gggaaatgga atctttatgt tgctgggtat tttctccttc cacacctcct    36240
tctccttgct ggacaggagg ggagggcaga agacgtgttt gtggccacat tcccggtgtg    36300
gcccgcctgg acaggagcca gggtgcacac tgacctgcac agcctctggc ctctgtccct    36360
gggcctgaga ggcaggagca aggggcctgt cctcactctg aatccaactg ctggtgactc    36420
agggcaccct gctggaccct ccaggagaag ttggggccca cgtttctagg ctgcccactc    36480
atccaaacct ccctccatgt ccctgaccaa agcatttcgc agatctgggt cctctggtgt    36540
gtgaggctcc tcccagccca tgagcattgg aaaatgtcta caagatcttt gccattttag    36600
gttctaccga ggctaaagaa tgtatgtttc ctctgcttag acttaagttt ttgagtaact    36660
ttatagacac tttggcattt tggctgaaag gcatgtgca gtaactgaat atgacttgtg    36720
cactgtttca gtgccagtgg gtcacatgca ggggagtcag agccaaggtg gatgaggctg    36780
ggatatctac atgcttggtg gggagttgga gtcagggtgg atgaggctgg gatatctaca    36840
tgcttggtgg ggagtcggag ccagggtgga tgaggctggg atatctacat gtttggtggg    36900
gagttggagt cagggtggat gaggctggga tatctacatg cttggtgggg agtcggagcc    36960
agggtggatg aggctgggat atctacatgc ttggtgggga gttggagcca aggtggatga    37020
ggctgggata tctacatgct tggtggggag tcggagtcag ggtggatgag gctggatat    37080 ctacatgctt ggtggggagt cggagccagg gtggatgagg ctgggatatc tacatgcttg    37140
gtggggagtc ggagtcaggg tggttgaggc tgggatatct acatgcttgg tggggagtcg    37200
gagtcagggt ggttgaggct gggatatcta catgcttggt ggggagttgg agtcagggtg    37260
gatgaggctg ggatatctac atgcttgtg gggagtcgga gccagggtgg atgaggctgg    37320
gatatctaca tgtttggtgg ggagttggag tcagggtgga tgaggctggg atatctacat    37380
gcttggtggg gagtcggagt cagggtggtt gaggctggga tatctacatg cttggtgggg    37440
agtcggagcc aaggtggatg aggctgggat atctacatgc ttggtgggga gttggagtca    37500
gggtggatga ggctgggata tctacatgct tggtggggag tcggagccag ggtggatgag    37560
gctgggatat ctacatgctt ggtggggagt cggagccagg gtggatgagg ctgggatatc    37620
tacatgcttg gtggggagga ggagccaagg tggatgaggc tggatatct acatgcttgg    37680 tggggagttg gagccaaggt ggatgaggct gggatatcta catgcttggt ggggagttgg    37740
```

```
agtcagggtg gatgaggctg ggatatctac atgcttggtg gggagtcgga gtcagggtgg   37800
ttgaggctgg gatatctaca tgcttggtgg ggaggaggag ccaaagtgga tgaggctggg   37860
atatctacat gcttggtggg gagttggagc caaggtggag gaggctggga tatctacatg   37920
cttggtgggg agttggagtc agggtggatg aggctgggat atctacatgc ttggtgggga   37980
gttggatcca aggtggatga ggctgggata tctacatgct tggtggggag ttggagtcag   38040
ggtggttgag gctgggatat ctacatgctt ggtggggagt tggagtcagg gtggatgagg   38100
ctgggatatc tacatgcttg gtggggagtt ggagtcaggg tggttgaggc tgggatatct   38160
acatgcttgt tggggaagag gagccaaaga tgtggatttc ctctgtctcc acatccttgg   38220
gcaaggactg gtgatcagct gctgctgtct tattttattt gcttctccag taaatgaact   38280
ttatatagtt ggtagcttgg cgttttccat tttgcattac tgaaatttca ataaatagtg   38340
ctttagttag atgtaaatct ctgtcatttg tggcagagga acttaaatgt cggcctgcat   38400
tttagggcac cttttgtat agagcagaga gaagggaagt gctgtccccc agtggcctgg   38460
accaggcgga gcccagcctg ttgatgatgc attgtgtgtg cttggcatgt gtgacgtggc   38520
aagggattca tgttctctgt gggcagctgc ctgagtagta gacatgtgag gccccttccc   38580
gggcattttg tcctgtcctc aggacatgaa gaaagcagct aggcaaaggc actctttgca   38640
gctttaaatg gcctagagtt accccagaa aaacaattct acttctgttc cacttctgtc   38700
caattaaaac aagtttgttc attttatttt aggagcaatt tgccattgtt tttgtgcatt   38760
cggcagttgt ttatttgctg cttgcagttg tggttgttcg tggtatcatt cacgaataca   38820
attttgaacg aggaagagct gtgatgacaa atgcactaag agacaccact gtggctctcc   38880
acaaattagc cagaacataa gggtgggagg agcctgtctt tccctggcag cacagggctg   38940
cctggtctta agaagtctgt agttgagaac acagcatgtg gttacatgta tacattattt   39000
gaaggtgcac aaagcaaagg gaagccaacc acaaaatgcc agttgtgcta gtagcatgtg   39060
cttctttatg aatgaaagaa catacgcatt tttggtatta attatttata tattttatac   39120
atgaaatctc atttgacagg ttccctgtga ctccactggg gaattcaggg tgggagaggt   39180
agtgccccca tcttcataag agggagcaga cttagagaca tagctgtaga gattacacag   39240
ctggtaagaa gtggttccta gatgctagcc ctggggaccc ggctctggtg tggcgacagc   39300
gcctttcaca cctgtatcct gagagtcgtg ggaatggcat gtagtttaaa gtacagagat   39360
gggggcatgg agtcattcct aggctcccag ggaagagcag gatgttttg atatggccga   39420 ttaggaagaa tgggcacttt gatctctgca aagagagcct gcgcttcagt gactaagtag   39480
gatttgaccc ttcaaccttg actctagtag atggctcagt taaaggctac gtggtgattc   39540
ttaggaggct tttaaattag atagatggat ttgtccctgg agagacaaag ctgaaatcct   39600
atatcacata gatgttatag accgaggagg ggggatttac ctacagttat ttaagctttt   39660
aaagtagaaa aaaggtccag ttgaaatgat atataacaac aggctatctg gagatggata   39720
tattgtgaat aaataattat tctacattct cttaatttgg cagcaaaaat ataattaggt   39780
tttataattt ctgatataaa caatataaac attgttatgg tgtacataaa attttttag   39840 attagtaaga aaaccatacg tataaacatg tgttaagtct gaggaaagaa ttacgtcgtt   39900
cattggctat ttgcgatttt aatgcacctt atatcacttg gcccaaatac tcttagggca   39960
gaagcataat gcttacattc acattctcaa atgacccaag aaagagaaaa gatttggacc   40020
cttaatgagt tgtagatctc atatataaac ctttacttct gttaaaggaa gaatgctagt   40080
```

```
gtaggatgta tttagcaatg attagattta ttgagcactt ttgtgttatg catgaaaaat    40140
caaatagaat agcggtagct aagagaaatt cattccaaaa gtgtgctggc ttcataaatg    40200
attttgtgat gtgtgtcctc tttttcagta gggtctgtaa caggatagtg tggtttttag    40260
tagatagtat tgcatttcta aagtacgtaa gcttgcagat aattttcaaa gggatatcaa    40320
ttagtttccc agtataacac acagatggaa atatatggtg ttttctgac aaatttgcct     40380 gttttcttc gcattgtctt ccttagtaaa ggttgccatg ttcatgtgct ccttgaagga     40440
ttaacaaaca ttctgtgaaa ggtcaggtag taaagagttt aggttcattg ccatgcagtc    40500
tctgtcacag ctgctccact ctgcttatgg tgtgaaagca gccatatgta aatgcgtgag    40560
cacggctgtg cccaaataaa actttatttg cagagacagg caagccagat ctggccttac    40620
tttactgacc tctgcttgga acgtcactct ccaagtgggc tggaaagggt tttcttttct    40680
tctgggtctc acgcagtcct aaagcttcgt tctgttttag aaaactttgt tctcttttag    40740
aaaactttat tgagcatttc tgcctgtgag aaatggcatg aaccacatgg ggttttcgct    40800
tcaatttaat acctataagc tttactaagg acctgaccag caggctgctg ctgctgggg     40860 acagggaggt gagaaggcag ggcctgggca tcagctggca aggaagacca accatggagc    40920
acaccctcat cgactcacag gcttcactga atcttgtgac atgctagcat gctgtttaat    40980
gtccttcgag gagagtttta taagagcta gtggttcact gtggaagttg acactctggg     41040
gccccaggtg acagttgcag gtgtctctgc tcctgccctg tcccacccat ctcattgtca    41100
ccaaagggga gcagagagga aagtgttctg ggagaagttg aggaccctgt tcttccacag    41160 actgcaggg aggcttcagc aagttgttcg tgcttcctgg tctgggtttt aactaaaaag     41220
ggtctaacat ttcataattt aaaagaaagg gtccacccgc aattcttgga acttttgta    41280 tctcaggtgt ttgtgcagaa gaatcatcga tactgtttct cctatggcat tggcggctgc    41340
tgcaggggca gtgggcaatt cttgccatag acgaatagct cacttcatgc acatggcagg    41400 gttttaaca ataacactca gaaaagaacc gtgtacattc tgtgttacac aatctgctgt     41460
agccgtgcac tgtaaaattt atacaggctc ctgtatagga aagttgaatg tgtagaggga    41520
attggaagtg cagtaggtaa aagtttagga ggcctgattt tcctagtttt ggatgattaa    41580
gaccaggtct tatgtgcagg attaaacagg agttaaaggg ggagatacct tttactaaat    41640
ccagcctgtg agacaactag attgtctcat cctatttgt attgtgtcat taacatcaag     41700
ttgcaacttg atattcggaa ttttttttac taacaagcat tcaaaatgaa atgattttaa    41760
ttgtcagtgg aagtgatgag ctcatagaaa agaatgtttt cagtctttct caaggagggc    41820
agcaggaaag caagttattg cccctgtttg tcatggggaa cttattcttc catattttcc    41880
ttttaagtta gttttttttc caatttaaaa gaaaagttca agtaaccgtt tttcctagaa    41940
tctctggctt ttgttatcat acccaacctt accttttttt tttttcatg ttcttagagt     42000 gtcttgcttt agtaaagtct ggagatacta aattatcggg tttattttc tcagaattgc     42060 tcctgcaact gaaagtcaa ttttcccttg taattctgtg tttaacataa aaggctgaaa     42120
ctgggcactg agatgtacct gtacgatatg tttgagctca tggaaggttt ccttgctttc    42180
ggaatcacat ttgctactag aaatacaaat tttaatttta agaagtgtat cgtttcattt    42240
tgtcaagtac atcagtattt gtaacactcc taattcagct atggctgaaa atgtgaaagc    42300
atctttacct actccatgaa tttggcctct gggtggtcca gtgttgctca ccaaaggcct    42360
gtgaggcccc atgtcccaca gccgtgccat ggggccctac gtggtggccg taagcccctc    42420
tgcagagagg accggggcct ccctgggcag agctgccacg acccaggtgt atatcctgga    42480
```

```
ttttgaacat cgaaatgtaa cattggaggc aaacatgtcc aaacccaaat tgtcaggaga    42540
aattatgaag aaaaaggatt ggtgagtcag actgtgtgcc gaaaatgctg cctgatttta    42600
ttggctggag caaattgacc ttatttccaa catgttctag gcttgatgcc cacttcagtt    42660
ttctgtaatg tgattgcagt catggtgccc agctccgtgt gacatgtcat tgttgggaca    42720
ttgttccata tattacaagg aagctttcct ccttgtctta atcacaatgt tttctagtga    42780
tttgttttct ttcctccttt ctctctttcg ggggagtcaa gttgagcagt ttgaaggtgg    42840
agcttttact gacagctctc tccttcattt gcattctgat tgctcttgta agtggaggag    42900
aaaaggggag gaattattgc ccatctgcag ggcattatgg tgagtggcac aggggactgt    42960
atcccacgta tgaatgtcat ctgtcacaag cgacagcaga aaggagatgc ggagtggata    43020
cactgcacga catgtcacat ggaacaactc tcatctctgc taaaagtgtt tttgtttgtt    43080
ggttttattt gctcaaataa ctctacgtgg atacgtctgt ggatggattt cctcacaaag    43140
caacgtctaa gggacagagt agtacagtgt gtaatgagcg atgtgacaaa ttcaatgagt    43200
atcagtaagt ttacattttt tatatagatt acctgtagca gcagaactgg tgtgtggtgt    43260
tctgtcattg tgttcatgag caacacgtga gtcttattgt tttcttttg gttttgccat    43320 tacagctgat gaattcagaa aatctcttcc ttcttagtga atattcaggg tagaacagcc    43380
ataaaattaa taattctttg cttctactaa aatgaacaca gataatacaa caaataaatt    43440
tttgctggaa tctcatcttc aggaagcctg aagtttgatc atatttaaag gttgaggatg    43500
tcagatgatt agtgttagaa aattgttggt gtgttttttt cccctggtca ggatgaacca    43560
ggctgatttt cagggtgagg gataacttca gttactttga aagtaaatga atataaaggc    43620
aaaagtttac tctcattcct aggtttgaat ctctggagtg ttttccagct tcttcttcc    43680 tggggtaggg gagtgtcact gatgagtggg tggctgtcag gtgggtggta ggtatcgtgt    43740
tgccgtggtg gtttcaacca ggggcaccag ctccttggtgt ttggtgtctg aaagctgtgt    43800
gtgaactaca gagagccctc ctgagcccctt gcacgtgtta atcatttagc cctatgcctg    43860 gggccttttaa tagtatgtgt ggcaaagatt ctaccaccag ctcaattgga aaaggtatt    43920 tgagacatca gttcaggcag atggcttctg tcttagacct tctttctcta acaaatgaat    43980
aaaaatgata cttagggttt caaaacagat ccctttttc caccataaat tcttagtact    44040
gatgcttctt aggtctctgt tgtatcccaa tccctctgct gcggctggca ggtcctagtc    44100
atctgggtcc aatctgaggt gtgctccagc cttttcctcg ctgccctttt gcacctccgc    44160
aaaggattgt ttctgctggt taattctgtt taaatcaccg cgagcgcttc caagcatccc    44220
aaagggtcac ctggaatcag cctcagcctc ctggggtggg gggatgtcta agcaagcagg    44280
tctgtgagag gcagggcact ggggagcaaa accacaggcc tgtgcccgct gagcacaccc    44340
agaccacagt tctcgcttta ccgtgaaagg aggcggccgt tgaaagcggt tgtattaacc    44400
taacaggaga caggctaggt gagacacatg cacgttgtgc ttgctctggt gcacgtgtgt    44460
gcatgtagat gtgtgtgaaa cgctgcacag ctgacacccc catgcctggc tctgagcggg    44520
tggtcatcct gtttctggtc tccctcacct cagctctctt gtgtcctttg agtgtgccat    44580
taacaggttc atcttcctgt aataacccctt cctcctcccc ttctccttcc ctttcccctt    44640
cctccctcct tcttttttttt tctttccttc ccctccttct tccccttcct cttcctcttc    44700
cgcttgccct tccttttccc ctttccttct tttttttttt tttttgtca gccatcttcc    44760 cccaagttat cagtgaggcc ttgcaccaga gtagaattaa aaaagaaaa ttgttgaaag    44820
```

```
gtcattgcat gaataaatgc atggatgaat tacttccttg ccatttatca gctcttttct   44880
tgcataatgc taatgcttag aaattaacgt tttgataact gtattctact tccaaaaaat   44940
aaaattacat gttcaactta attggagctc gcaaagatgt aatgataaga gttgaatatt   45000
acagcgatac agcatcctaa aaaaaacaat gaaaatgtca gtggcctcat gaaatcacaa   45060
atgaaaatgg aaagtaattt ttttcagcaa taatttaccc gccatttata tgacaaagtg   45120
cttaagtttg agaaactgaa gaacttacta gtttagctgt tttcaaaata acagacttag   45180
agttaacatg agataattca gccacattta gctaattgtt agtgtcaaaa taaaataagc   45240
aattgattag aaattcttct gtcaatggat ttgcagagtc tcagttacct gcttgtggtg   45300
gccatgggat tcttcccaaa tcagggtctc agggacaaaa tgcaagctca ttttagggtg   45360
aattacaagt ctcaaggtgt gttttagcaa atgcctgttt tttttttaggg gatacaaaca   45420 attagattct cactgaagtc tcctgggatt gaaaatcaca acaataatga atcagataac   45480
tcaaagacag atctttcctt aggaagaaat taattctgtt aaggttcatt ggcagaacat   45540
tgtttactta ttaaatttat aatggacata aagcttttta aaaataacaa gataggccgg   45600
ccgcagtggc ccacgcctgt aatcccagca ctttgggagg cctaagtggg tggatcacct   45660
gaggtcagga gttcaagact agcctggcca gcatggtgaa accccgtctc tactaaaaat   45720
acaaaaatta gccaggcatg gtggcacgta cctgtaatcc cagctacttg ggaggctgag   45780
acacgagaat tgctcaaacc tgggaggtga aggttgcagt gaaccaagat catgccactg   45840
cactccagcc tgggtgacag aataagactc catcttaaaa aagactaata ataataataa   45900
ataaaataga taaaacagcc tcagaatgtc gcgttgtagg gaattttaaa atgtccactt   45960
tgtatattga caagtatttt ttctgtaaag cttttggggt ttttgggggg ctatagcatg   46020
tagtgcctcg agttcataag gagatgtggt tttgagggac tcactctcag cttcagggca   46080
cactggaagt ttctgtcttg ttgagttcag tcctctaaac ttaagatgga gagaaaagaa   46140
tttggttcac aaaaaagtaa gtcagggagt atgataagag gctaggatca gaattctaaa   46200 ggatttttaga agagtgtcca gaaatgcagt tggtataaat gcatctgcaa aggaaggaaa   46260
tgtacctgtt tgagagcaaa gcggtgctca ccctcatgtt gctgagtgat gaaaatgaac   46320
agtatgtcat tttggttaaa aagccaagaa gcttagaaag aagaaaacag cacgctgtga   46380
aaggtcaaaa tcttccaatt tgttctgtcc cttgaagaag gaatatatca gtaaaaata    46440 ggcctaaaac actggaaatt gagaaaggtt aaagaatttt gatccttcat cctggaaggg   46500
aggaagcaat tagatctggc cacgtgtcct cagtccctgt cccctctgag cacagcgaaa   46560
gggtaaatta cttaaactgg aacatatgaa agtttgagtg gataaaaata acccttttcct  46620 aatgttgagg gttatgcaac aacacatgag gccgtgcagg aaccttccat tgctgggcac   46680
gttcaaaaag aggtagatga tccggttgga agttttctga gggcagaagt gtggagttat   46740
tagttactcc actttcataa cataatgcac atttgtagaa taaacatagt ttacagagca   46800
ttgtaatgtg tgtcatagtt tttcatctct gcagccctgg gaggaaggca agtggattct   46860
gtgtatccca cacaacacag gaagcatcaa ggcctaagga gttacagggg tcattccatc   46920
acacagacac gcagtgcaac ctaggaactg gcccttcttt ttctatcttg ttcgacagaa   46980
tgattcacaa aaacacatgc gaatattttt cttaaattga aaatacgaac ctaactgtct   47040
agacaactca ccatgaacct aacagctctg cttccaggaa aactcagagt tttcccactg   47100
aactcacctc tggaaaacag aatgaataca tgtttctttc tcaaaggtca tcagtttatg   47160
aaaatgaccc aggtcctagc tgtgggttag aggggcccctt tctggaactc cagagattgc   47220
```

```
tctgttctcc tgagggtctc tgctaacttc cctcctttct ttttcagagt gaagatctgt   47280
ctggctttat caccaggatg tcacatgtca gagagtatca ttaaaagaag acgctcagca   47340
ctgtttcagc ccgaagctgc ttgcagtttt cttttggatc tgagcaatga ctgtgtttgg   47400
aaacatctgt ggactctgtt agatgaggca ccaacaaggc aaggtcacct gcctctttcc   47460
cttgttcccg gatggggcat tcatcattgt gctgtttgcg ttttgttttg ttttgtttta   47520
acaaaattag ctgaagaagt tattctcaag aaaattggat gttttcattg gccttcttaa   47580
attgtggcca gtgtctttta atttcttctt cttttccttt tggcaaagca gatataaccc   47640
tcagcatgct aggagagtgc acccgtacct atggaagtgg taaaatctgg tatttactgg   47700
cttacactca aaacgaccac agtcctacct cagttcaagg taaagccgga tttccgtggc   47760
gggggtccca caggacctcc tgtagtagcc cctgcgctgt gtgtctggag cgcggtcctc   47820
ggccttattg aaatggtcca agtagacagc tgcttgttgg attccagtgc aggtacctgc   47880
gatgtttacg tccacaccga gcccagtgtg ggactgacat ttctcaatgg aagtgaaatt   47940
tgggattgga ctttgaagac ggattactaa ataataatta ttatatgtaa ctgaagcaac   48000
ctacttttga aaatcaactg tattgggtag tgggaggtgg gagggaaggg ctttgggaag   48060
gggatgaata tctcttttta cctttaacag acttgtttaa tcttctcgat gtagatgttt   48120
atgtaggtac ttcacattgc aaacgccttt tattctattt acaagctcag atgtctctgc   48180
tctcctgaat cttgggcatg cctttctgta accaaaaatc cctgtaggcg tgctagcaat   48240
tccagggtgg tccgggtttg gcagatttga tttttaaaaa acgtattatc tttaataaaa   48300
tgttattatg tcaaccagtg aggctgccct gaacaaaaaa aacaaaaaga aaaaaaaaa   48360 aggaaagaaa gaaactgata aaagaggca  ttccagcccc tatgttattg atggaaaaag   48420
aaaaagaaga aaagcaatct cgcagtacat gttacttgtc gaaaaaattc cggacaagac   48480
tacccttgtt ttatgttttc agtattctga aaataccagt gtgtggcagt tctcgcagat   48540
gttacctaaa actgctgaac ttgaccggca gaatgttctg ccgttttctg ctccctcgac   48600
acttgattgg agggctgtcg acctctcctc ccgtgggggc ttccccagtg cctatcttct   48660
ctgatagtca tggagaggtt acactaattc attggagatg taagttgttg gttttgtttt   48720
gttttgtttt tagaaaaata tatataaata tataatagat atctatcgct atagaataat   48780
gcattaataa aatgaggctt ttttagagga agaccaaaaa attcaatgtc ttaaaaatat   48840
atttaatggc aatgcaaaag tcttcctgct tccgtgctga actttagaac agaggattgt   48900
attgcaagac aaagttgaat gtaaagtgat ctccctgaac attttttaagg ttttactttt   48960 ctgaaattat acatcacagc agtgcatagg ccatataatg ttagctggaa ggtcaatttc   49020
agtgtatgat atactttatt aagatgtata aaaatcctga agttttttatt tagttttggg   49080 aataggcatc aatgggtggt atttgctttg taactccccc caggtacgat agggactgaa   49140
tatggaccct gctgaaagca gtgtattgac gcatatttaa ctcgccctct atccgtagag   49200
tagtcatgac actatacaga tggttcgtgt tcatactgca gcttaaaaca agcaaaatac   49260
acagatgata atatgctaaa ttttcctcta tcctgtacat ttcacaaaaa ggcatatgca   49320
atatttacat ttttaattta gtttacagaa tggaaccaaa atgtataaat gttatgtttg   49380
ctaaaacttc acaatgtata ttgggtcttt gtacattttg cctgacttac cttaaatttta   49440 aaatatttttt tgctatataa actttaacag ttattaaaca gtgttttctt tttgggtacg   49500
tattgtttct ggatatcaag atgttaaata tatttcttgc tattgtgata tgacaagaga   49560
```

```
cttaacttat cttgctctgt cttccactgt acacgctgta tatagggtc aatgtgatgc    49620 tgctggagac gagaataaac tggactagaa tagtgcattg tatttagtct gtattgatca    49680
tggatgccct ccttaatagc catatgcaat aaaataaagt acattattta tgaaatgaat    49740
acagtcctga agatttttc tgtacgaatt ctctgtttaa cataaagcca atctactttt    49800
agagtttggg agtaagtgag gaaatactag gctcctaaaa atacttggat acccctttta    49860
attttaaaac ttttattctg gaagccaaaa aatacctgcc agataacaac atttatgaaa    49920
agtaaatgtg ttatataaca aaacagaaca ttcgatgtac tctacaaaac agagtcctta    49980
tgacgtgctg gatgccattc taaatacata acaaatatta acttcttgat agctcatgac    50040
aatcttagga ggtaagaatt gtcatcctca ttctacagag gaggagcccg aggtacaaaa    50100
atgctaagag acttgtgtga gagcacacag tccatgagtg gtaaaaccag gaccgctccc    50160
cagctctgca gtccagaatc tgcttatgca cctctgctta gtgctccctt cctgatgtgc    50220
acacagaaga tacaccaacg tgtacatcaa gaatgctccc tccatgacat gcacacagaa    50280
gatgtaccaa tgcatacatt aagaatgctt cctccggccg ggcgtggtgg ctcacacctg    50340
taatcccagc actttgggag gctgaggcag gcagatcacc tgaggtcagg agttcgagac    50400
aagcctgacc aacatggaga accccgtctc tactaaaaa tacaaaatta gccaggcgtg    50460
gtggcgcatg cctgtaatcc cagctactcg ggaggctgag gcaggagaat ggcttgaacc    50520
cgggaggcag aggttgccgt gagccaagat aatgccattg cactccagcc tgggcaacaa    50580
gagcgaaact ccgtctcaaa aaaaaaaaa aaaagaaga gaatgctgc ctccatgaca    50640 caaacacaga agaagacata ccgatgcata catcaagaat acaagaaga aaatcatcag    50700 atccaggaaa atgcaattca ggaagcagaa aatagaaaat tgatgctgtg aattttatc    50760 caggagagtt ttacctcctt gcttgaaaca tttgtccgtg catccacttt gccctaaaat    50820
gatagtcatg taataatgtg tgtgttatct tttgaacaaa taaaatcagt gcaatttgga    50880
aggtgatttt taaattacgg ttgttaagtc agcaagatgg actcacactg tggtgtggaa    50940
acctgtgatg ggatagccac aggctgcatc ccctgtttgt gcctggatgg tttgttctgg    51000
gggagcctgt tagtcacaca gagtaagagg cctgatctgc aagtcttgat ataccctgaaa    51060 tctgataacc atttcaacaa tgaaagggca aatgatgcag tcattccaca ggcctcatct    51120
aaggcaggaa cggacaagtg atttatctga aagagccatt gtggagaaag tacagcaaaa    51180
tggagttgtt tcaaaggtcc acagattctg gaaataccac tcaaaaccaa tgcagggcct    51240
tttccagaat gttaagtgtt atatgacaag atgagaagac tgcaggctgc ataatttttg    51300
gaagaatttg gttctaaccc actgatggcc tcgacaggca gcttgcaaga ggcaccttag    51360
ctcatggtac tgtcatgata tttgagtccc atccttgagc tgatctgcag ctcgtccttc    51420
ctcaaacctt ccttaagcat tgcttcacag attagatggg ttgctcatta gtgcatatca    51480
ctgtgagttg accaggggta atagcatttg agtgaagcta gcattacttg acatagcaac    51540
ttttggatgg caccagttga aggacagagg ggacgattcc tccactgaga atgtgcagtg    51600
tctcttccct gtcattgccc cagtagtatt tctctgaatt ctataaccaa gtgaaatctg    51660
atgtttatgg gtcttgcttt ggcaatgata cacagatgat agacctagca tgctgcagtt    51720
gatagcttga aaacattaag catcccttca ggagctcctt ttagattttg accctcacag    51780
ctgtgtcttt cctcttgtct cttcagcctt gtttccctct gcagatccca atgaccctaa    51840
atagcaattt ggtggtttct tgtcctctta tcattagtgc ctccttcatt tcacactggt    51900
cccgctttcc tacctgagcg gtcagatgac tcacagcctt tccgctgcat ctggagactc    51960
```

```
tgtcctattt taggcacttg gttcctctga caggagctct gtctgagttt gtgcctctga    52020
acttttcttt ttctgcattt caaaatcctc tcctttcacc ttggaactca aaaagttcta    52080
aatttttacg aaaattactt atacccagg aaacctaccc cagctcttt ccagcctgtc     52140 tgggtgtgtc aaatacatat caggaactgt acaacgtgct cctgtctctc cagatctttc    52200
tggttatgac acttaattct cagatgacat tgacagaaaa catactgatt gatagatttt    52260
tctagaaaag atgcataaaa caataaagga gctgtattaa ttagcatgca tttagctgca    52320
agtaattgaa acctcaattc aatggctctt agctgatctg agctgctata acaaaatgcc    52380
atagactggg tagcttatag gcaatagtat tttttttccc tcacaattct ggaggctgag    52440
aagtctaaga acaagctgct ataatgtggt gtctggtgaa ggcctgctgc ctgcttcata    52500
gatggtactg tctcagtgcc ctcccgtgac agaagggttg acctagctct ctgggtccc    52560 tttcataagg gcactaatcc tattcatgag agctctgccc tcatgactga atcacttcct    52620
aaagaccccc acctcctaat accagcactt tggggattca aattttaata taggagtggt    52680
gggaggacac agacattcag actgtagcaa gctcagagca gtagttctca aacttcagga    52740
cttcttagaa ttatctggag gggcttgtta aaaacagatt gctggactcc actcctagac    52800
tcttctcagc aagtctgggg tagggcccca aaatctgcat ttctaaaaat ttccagatga    52860
tgctgatact ggtctgggac cacacagtga aaatcactaa attgcaaagg gatgtgttaa    52920
ctcacacaac aggaagccca gggctggtta attaggcagc taagtggcgt gcacagaagc    52980
cctggatctc ttcatctttc tactcagcca tcctcccgat ctttgctttc atttcagacg    53040
cttggccccc tgtgtttcta agatggttgc ggcagctcca ggcagcatgt catctcataa    53100
caatgtccag caaagcagtg tctcttcctg gggtgtcttt ttggaatgat gcaaatgacc    53160
ccagagccac cccaccacca gctgcctctg cctcacttcc attgtctggg attgggtccc    53220
aagctcctgg ttccattgat tatgaggaag gagatggctg atttacacta aaagagatgc    53280
accctccagg gctgggaggt gtccacatcc catgaagaga cagttgaaca aaagctgggc    53340
attggaaacc aggaaaaagg agtactgtca cttcagtagc aactaacagt gtctgctata    53400
acagcagaaa atgaaagggc catccttttc aaatgcaatt atatctctaa tgtatgatct    53460
ccatctacag cgattttgaa aggggggatt taaaatagg taaaagtaga acaaaattat     53520
gaatctagca tggtcaaaaa gaggatggcg tcattgcttc actataggct tcacgtatct    53580
ttgcttttgt tattaaattt tgtgcaacat gggaagctgt tttataaaag atcaagtat     53640 aaaggattgg aaaattggac atttgaaggt acatcaaaga gctaggacta tttagactgg    53700
aaaagaggaa actacgtggt gattgattag cattgataac attagggct atagataaaa     53760 taaagattag tcagctgacc tcctcaaaag atgataaaac cagagaaagg ggtagaatac    53820
aattagaaaa atgtgtccga tttccataaa aaataaattg ataataacga gggttattaa    53880
atatcaactt tgaaataatt gttgatttca ttgcctggag gccttaaaaa ataggacttt    53940
gcagctgtct ttcttcgtag tgatgggaga ggggacatag accacataat ctcgaccagc    54000
cccttccccc aggggctcag catcgcacag ctgaggaggc agccaccccc tttgttgctc    54060
atgtcaacag ctcccctgga cttgcacagg gcatggcctg aagcctgaga tcctggcttc    54120
tctgaggata agagaactac tgagcatgga tttaatcagc aaaaagaatc accatagttt    54180
tttctgccta gttagtctg taaagtgttt accaaagtag tatttaggaa tctgaaggaa     54240
agatctgaaa tttgaaggaa ggatcagagt atgaggtcca tcctgaatag tccagattca    54300
```

```
taagattata agatcataag atcatgctga tagagcagct ctaaatcatg ttgcttaaag    54360
aggtttttaa atacaggaca gccaaagtga caaagtgatc tttatcaaat agccgggccc    54420
tcttgctggc acctgtagtc ccagctactt aggaggctaa gttggagggg tcacttgagc    54480
ccaagagttg ggggccaaac tgcacaatat agctagatcc tgtctcaaaa aagaaaaaaa    54540
aaataaatgc atgtataatt caaattctcc ttcctcccca ctcacccatt atcttttagg    54600
aaaagtcaaa gttcctgaac gtggtaggcc tgagacataa ggcactatat gaactggctt    54660
ctgcctaatt ccccagacac atcttcaagg ccctgtccct cccgctccac ccctccctgt    54720
gtctgcacct aagccttcct agagcacata aagtgcacct agctcaagta aggaggagaa    54780
cataaaatga aaagacaaag aattgctgaa cctaaaaaca aatgtttatc taccaagagt    54840
tactatttcc taaaagatcc cttgaggaaa ggtatgcaac aagttagaag cattttttaaa   54900 aataccattt aaatgctata cagcattgct tcacttcttc ctttgaaatc tgaggacatt    54960
catcatctca tttccattca cctctccttt ctccttttc cccaccttaa catttgtcag     55020
ttacattatt ttctgcattt tcaaggtaaa aaaatacatt ttttctgtaa tgtaattcct    55080
atgagtttaa aatacttatc cttcatttac attgatccat ttcatgccac ccgttctttg    55140
aacatgctta ttttttaacc atctattaat tgcttggatt ttgttactga aaacaaacaa    55200
ctcaaaactt cttccagac actttttaat atgctctgtt ccctgagctc tctcatattt     55260
gagaggtaat ttgcctgttg tctttataga tgagcaacaa attggctatg tagatcactc    55320
ttaggtccca tacgccttc caaagaagtt tgtgacattt ctccagcctt cttatttatt     55380
gaatcaggag atttttgatga gtggttttca agttcaaatt actctgggga aattcacctt   55440
gcacaaaggt gccctaaata tacaacccta tctacctaac cagactcacc ttctgccttc    55500 taccaccca tgaacccagc gttggtcaca gttgcactga tcctatcacc aaattttaat    55560
ccttttatga ctcggctttg cataaaaatt tcatttgccc tagagtgttg aaacctcttt    55620
cttcatctag agacttgtac tgactcttca agacaactct accatgtgtc aggagaagga   55680
aaactggaaa tatccagtga atgcttccaa tgactataat gcaacctgat ttcaactcac    55740
ctaaacagag ctagtgaccc acttctccag attctcaaac cactctgctt acccttctgt    55800
tacggcacct tccaagtttc actgtattat ctgtttatct gtgtttctcc cacgaggggg    55860
ctccttgatg gaaaggatca cattgcagac atggtagcta gcaaaactgt gttactgtaa    55920
ccgctgagca actctgttca gacatttatc tacctctcat tccatattca cacacctctg    55980
agaactaagt gctattaaga aaactgaagc tcagaaaggt taaacacctt gctcagggtc    56040
acaactaata agcagtgagt cagaattcaa agcatttatt ccaattccag ctctttccta    56100
ctgtgtttta gtgaacctaa cacaatacac gacacatagt agtaggtact caacaaatat    56160
ttgttgaata tttgaatgaa tgcatttgtc ttgtatacat ctagaacact cgcaggctaa    56220
gagactaggt tgccttgaat gattgtattc tatatttgca caatttcttc aacaattacg    56280
ctgttttatt ggcttatgaa aggcataaca ttgctcagag aagtaaagtg cattcgttga    56340
attataataa gtgactaaaa ttgaatccca atggttctct gatatatgta taggaaacct    56400
ttaactatat atagcagaaa agccaaaaca acaatggctg gaacatatat aatgtttat     56460 tctctcagat gaaactagac agatgtgggc attccaaggc tggcacgggg tttccatcac    56520
ttcccaggac ccaccttccc accgtcattc agctttagca ttttcagtgc acacctttct    56580
gtcttcaagg tgcctcatag tccaacgtgg ctcctgaagc tccagccatc acactggctt    56640
tatccacaag aaaggtgaaa ggggaaagta taaaaatggg tgcctctgct gggcgagtca    56700
```

```
gctactttat aagtgagtct tccacttaag tcttgtacgc tgcatatttg aaacacctca   56760
ctgagaacat ttcctttctc catgattgat ttctgcgact aatttctatt gcattctcct   56820
cctcatccga tatgcttctg gatactggag atcgagtgga gaggaagcct gagtgcctgg   56880
acttataagg ccttcttctg gtgatcagca agtaaaacaa atatgaaaca caagatgaag   56940
ataagaaccg ggaggaatag cccaggcgtg ggggagagaa ggctggtttc caggggatgg   57000
tcagaggcgg cctctcggag aaggcaacac ttgatcagag ttcccaaagg gcctactgtg   57060
gggacctgaa ggaagagcag cgcagcaggt gcaaaggccc cggggtggag gcatacttga   57120
catggtggag accaggaagg agggccacga ctcggtccct catctctcat tccactttt    57180 aacagttctc tatttagaac tcccatgttt caatgagaac ctattataga aacagtctat   57240
caaagtcttg ccatttaagg gtgatcatta agagctttgc tttacttctt cacacagaga   57300
aggggtggga gaggaggaag gacagtgtga agcagacaga cagaaactcc cctttggctt   57360
tgaaggtgta ttctttgggg gtgccgacat attccacaag acaaggcagg gcacagggag   57420
gctgggcgtt cacgtagaca gtgtgtcttc cagcagaagg tgtgcgtgac gcccgcctgc   57480
acaggaacgg gtgcaagcac tcaataccctg gtttctatcg gggcactgcc tgggctctgc   57540
tgtttcaaca atgcacttgg cttcttccat gacccagagt tgctgcagaa accactgctg   57600
agagtacgat tgattctctg tatgccgacg tgtccaagga cagttagtag gagcggaggt   57660
ttcagggcat caaggagtac tgtccttgca cacgggcaag gtactgataa gctgttgtct   57720
gaagcccgag agccggtgca ccctgccgtg accaggcgca gctctgtgct gcaggataac   57780
gcgagctatc tcatcactgt ctcatcactc aaaaggcttc tgatgaaggc cgtggctgaa   57840
tgggttcggt ctcatgctaa caaaatcttg atgcggatgc accctccatc ccatgtttaa   57900
gatctttaat tttatgggta cgagtaataa aaaataatca ggctgtgtat tttctgtatc   57960
cactgatata aatgttggca tcagcattat tataatctta attaccatca ttggttacac   58020
gtgctaaaaa tgttcacgcc gtctaaaaga aaataaaaac aagcggcggc aggaccctg   58080 ctctcacaca gtaaagggca ataaacattt atcgacatgc tgaggagagg agattgtcat   58140
atcctattaa aataaccaaa gataaggttt taaagaattc aacctgtcgg gctgtctttt   58200
catacgaagg ccagagactt cccggaaacc gcgatgtccg cagtggcgtg gtaggatctg   58260
gttggtaact gtgcaccgcg gggtatgtga gcgcaggcgc tcccggagca gcgacacaga   58320
cctgttcatt tgaaaggcat tagaggagaa actcctgcgg tcagccttgc caacctcctt   58380
tgtccccgtg gatgtgtctg gacacccttc atcaccctcc ctcggggac gggaagcctc    58440 agttaagagc gaggcccagt gccctccctc caggaaaccc cataaccttc acttccaggg   58500
taagggcctt cgtctacaca agctccaccc gtcagcccca gcagcctttg agctagagct   58560
ggcggagggc accgcctggc tctgcttctc ctccaccgcc ctgcccttca gagagccagg   58620
ccagggagtg gaggcatgag gggcgaaccc taggggcgtt tgcctgggat tctgctgttg   58680
gcctccctgc tgggtgtggc tgaggcccga tgcccactgc tgcatggcgc cacggcagcc   58740
cttgccccgc cacccccatcc acagccctaa ggaggcttcc tcagccgctc tgtggagctt   58800
tcgaggatcc gcttgaagat gtcagcacac tcctccctgg ccggcagcca atagtttgtt   58860
tattgctctc aaagcacact cacactcttt cctcccgtcc agtccatttt ctgaaaacac   58920
tgagctcttg gctcacggtc aatgccttct gcttttatct gctcggcctg aaacagtgac   58980
gtccagccaa gaggccagag ctagggctcc tccgatgctc ctccgatgct caacggtgg    59040
```

```
tggccctgct cctcgatgag gccggttccc gcaaggccga tgcttaggca tttcagagag   59100
atgcactctc cctcttctta tcgctttccc cttctgcttt attaaaatta ggtgactttt   59160
caagactcca tgcaaaaggt ggcatgcata gctctggcca tgcaatagaa actaaagtaa   59220
ggttcccgtg tataatccaa tcacacagct gccccgcctt ggtctcacac caggtctgca   59280
agatggcagc ccctttggtt tgccctccag ccttctctta agtcctggag ccgctctggt   59340
aattgagcct tccttctggc atcctctgga aggctaattg aatacagcag gaggcagtca   59400
cagagctttt tagcatttct acttcctttc atttgcacac ttttccaata ggaagcaaag   59460
ctactcaatt caggagagaa ctcccctctc ttcctactta acctttctcc tgcatacaca   59520
atcgggctac tcaaaggtat gctgtttcct ttccgctaaa agtttcctcc taattacctc   59580
gaggcatcca ggtgtggctg aaaatatgct caaccccggg tgtaaatatc tgcacctaag   59640
ggcagtgagt agcagagcaa acagcttgt gcagggcgca gtgtgcttaa acaacctgc    59700 agctatttat cgggtgactc agacaggatg caggggccag atggttagca tcttgcaaag   59760
gctgacgggc actttcattt gattgtttaa gaataagttc acaccggaaa ggggatttca   59820
cacgtcctct tccattctgg attttcagtg tttcattaag ctactttata aactattatc   59880
ttggagaaga aacaaaaaaa cttttaatta tgtttccttt gcattggcgg tcaggcagac   59940
agatgaaatt tttaattatt gaactgctcc aaggtgtgcc tgtaagtata tctaaaatat   60000
gtcttgaaat agttattgta cctttttcta gaaaatgata acttctatgt tttctttgta   60060
aaataaaaac ccacttgtga ctggtataca aggaagaagc tgacctgaag ctgtctaaat   60120
aataaaggca aaactagtag accccccaaaa acgatagagc tcactcttct ctgtctctgg   60180
cacgtggaga aggcatgaaa ctatcaaagg ccccaggaat tgaacttggg aaaacttggt   60240
tcaagtcggg tggggcagtg ggcaaagggt tgatgttgtt gaatgtcatg gacttcataa   60300
tcagtaggca taaggatatg atcgcttaga tgtttagcgt ggcagtgaaa tagtaaaagt   60360
gcataaaggt agtctttaaa gagtgagcga agcaccatgc cgggtaggta ttgaagccat   60420
gtcagttact aagctgaaca tcaacaattt gctttggtgc tttggcacat acctaaaatt   60480
gtcaagtgag tcctttattg aaaggtaagg atgcttgttg tctagtttct ttggatgttt   60540
ttatttggaa aaccttgggt gaagtgtcat taaataatat atgatactgc ttttccttct   60600
ttccttcctc ttcccttct ccttcctctc tctcttcctt tcctctttct ttcttgacag    60660
ggtctcactc tttcactcag gctggcatgc attaggtgct atcagagctc accacagttt   60720
cgaaatgcca gactcaaggg attctctcac ctcagcctcc tgagttgctg ggactacagg   60780
catgcaccgc acctggctaa tgtttaaaaa tgttttggcc gggcgtggtg gctcatgcct   60840
gtaatcccag cactttggga ggccgaggcg ggtggatcat gaagtcagga gtttgagacc   60900
agactggcca acatggtgaa accccgtctc tactaaaaat acaaaaatta gctgggcgtg   60960
gtgtcacacg cttataatcc cagctacttg ggaagctgag gcagaagaat cgcttgaacc   61020
tgagagatgg aggttgcagt gagctgagat catgccactg cattccagcc tgggcaacag   61080
agtgagactc catctcaaaa aaaaaaatat tttgtagaga tggggtttct tttgttgccc   61140
aggctggtct tgaactcctg gcctcaagcg atcctgccca ccatggcctc ttaaagtgct   61200
cggattacag acgtgagcca ctgtgcctaa taatgctttt caaatgtcaa catgcacaca   61260
aatctctctg gcgatctcgt taaaatgcag agtctgattc aggaggttgg gtggagattg   61320
agagcctcat ttctaaccag ctcctgggtg atgctgatgt tgggctgggg cacgcatttc   61380
ggacagtgag gggtgggtga tgtgaagcag acagtagaca ggaaatgcat gttgagaaga   61440
```

```
ggagctaaat cctgaaagtc agtggccctc accttattcg ttcttcctca aactctgcct    61500
tacccagggg gcacagtaat acgccttaca agtcctgagg tggaacagga ggatggactc    61560
acagacatgg caggaaggga gctgggaacc agaactgtct gggctctgag gctggagtgc    61620
tgagggcctc cgccctgact aggggtgtct ggtggaggat ccagcacaga cccactggct    61680
ggaaggatcc ctgtaaaatc cctgaaagag aggaggagcc tcaccccaaa tgaatgcctc    61740
ttctctaggc ctctctgcag ccacccatgc atgccagagg tccatgcaag atttgccttc    61800
tggagcttgg ggagaagtaa ccagaagtca tgtaaacatc atggtcttga ttctttccct    61860
tcctgctgat cctgtctcac tccagtgtgg ccctcaatga ctttccttct ccttttctgc    61920
aaatgtacct gacggcttgc cagacagaat ttccatgctt ggttagaaag gacgatgcag    61980
ctgagatgtg agatatttat tgcctctcga ctggagtttg tgtgacaccg cacctttcat    62040
ccgcacgttt gtctcccatc tcataaaggt cagagttctc atctgtgcac cgctctcttg    62100
cttgacaccc cttccccagg tgccctcatc ccccatgac ttcagctccc tcatctacat    62160
cctcaacttt gacttccacc ctcacatcca ctgctgcctg cgcggcaact cccagggctg    62220
tgccatggat gccccatgcc tagcttctca aacagaaggt ctcaccctgc catggcctgc    62280
tcctcctgct gaatctaagc cccactcagc cattgcagcc aaacatactc tgcctcttcc    62340
gaacaagacc tgggctggca tctcacaaga tcgcatggcc tgagtccatc tgcatgccga    62400
tggcactcaa atccactctg catctccaca tgcctagcct gcacatgcct caaaaccaac    62460
atgatcaaag cgtggtcttt cctgaacaga cccacccagc ccaccctaa ggtgccctcc    62520 caccagcctt ctctgcaccg ataaacggca ccaccagccg tccacacact caggccaacc    62580
agccgagcac tcgccaggac tcctccatct cacagcccac attccatcct tcagcaactc    62640
tgtcgccttg acctcagagc atatcccggt ctcagtccaa cctcctctca tcccttcccc    62700
tgatagaaaa gtcgccatcc tttcttgctt gggctacaca gcagcctcct aagtggcctc    62760
cccctggcat ccttcccctc attccactcc attctcccta ctacagtgca gcgtcagcca    62820
gttcagatcc ctcccatgtc ttccagcaca cttgaagcag aatctgccct cccttccagg    62880
gtgcacaaag gcctactgtg tgtcacgtcc attcgtgcca atattgcaca tccattcacc    62940
tttaaatgtt gttgggctga gggtacgact gggaaaggag aaaataaaga tctaattttg    63000
attaggcgat tcatgttcac acaatcattt gaactgaaaa tgcccatctg aatgcccaca    63060
cagacgtcat ctatatgaat tggtataatc agcacatgag aataaaagtc cttgcctgca    63120
cttcctcttt tcctttata acagcagtgc tcgcacattc aattccggca cggtcacctc    63180
tgactcgctc gtcactgccg cttgccatca caggtgtttc ctggtcagtc actgtccact    63240
ggctgcatcc catggtgcaa gctcattctg gaaccttgtc tttgagctgc ttcctctcgt    63300
tctatcttct gcagatacca ctcctctgtg gtctggggat tttctctgcc aagaacatca    63360
tgcagtttgg gggtgcagtt cccatttgtc tcttgacaaa gggaaacaca agtggattga    63420
aagcaaaaac ataagggctc ttttccccgaa gccattcctg aatcctgaaa ctgaaagagg    63480
ggatccagag gaagtgtgga attagttatc atggaaaaat ccagggtgga aataaattag    63540
gctaatgata aaataattga acaacattct tgggtctgac ttcttaagcc acagtgttag    63600
aagttggcat agaatctgat cccttatgtt acaggatcat ctatttcatg ccgtataata    63660
tagtacagta ggcataatcc ttttggggat agacttggat taaataaaaa ttatgaaact    63720
taatgtcact gtgtcttcaa tcattttctt ttcctttctt tattattatt ttgagacaga    63780
```

```
gtctcactct gtggcccagg ctggagtgca gtggcacaat ctcggctcac tgcaacctct   63840
gcctcctggg ttcaagcgat tctcctgcct cagcctcccc agtagctggg attacaggcg   63900
tgtgccacca cacgctacta attttcgtat ttttagtaga gacggggttt tcactatgtt   63960
ggccaggctg atctcaaact cctgaccttt tgatctgccc gcctcagcct cccaaagtgc   64020
tgggattgca ggcatgaacc accatgccca gcccgatcat ttttcttttt aatcacttac   64080
aaaacattaa ttttcaaaag gagaaaagaa ggtgggtag actaggatcc aggagaaaag   64140
tgtgttcacc tgtgtgggac tcagcaaaca tttgacctct cggggcctca ctttccttct   64200
acctgaatca tctcacaggt gactgaaata gattaatgca gcaaatatct atactgatca   64260
cctaccttct atcagtgccc ctatgcccca aggcatgggt ccttcataca attcttttaa   64320
aataaattat tacaaattga tatcaaatta ttatttggag acagggtctt gctctgttgc   64380
ccatgctgga gtgcagtggc atgatcatac cttattgcag ccttgacctc ctgggctcaa   64440
gcgatccttc cacctcagcc tcccaggtag ctgggactac aggcacatgg caccacgcct   64500
ggctaatttt ttggattttt ttttttagtag agatgaggtc ttgctatgtt gctcatgctg   64560
gtctcaagat cctgggttca agcaatctgc tctcacaaag tgctgagatt acaggtttga   64620
gccaccatgc ccagccaatt agataaaatt attataaaat aaattaattt tataataaat   64680
gacaaccatt caaaataaac cctgaagatc ctttacccaa ttcactaagt tacattgtat   64740
atgacagatt atagtatcaa acggcaagtc tcagggccat acactaagcc ttatcgggaa   64800
ctgaaagtga tccatctcca agattttgaa cacagaagtt cccctgcttg gccacagcgc   64860
ccctcttccc ttgtcctttt ccccttcctg gagcatcctg gggtagactg actgtcaaaa   64920
cagcccacgc gttccgctgt cttgccctgc cctgcatcca gctgcggtg atgtcacttt   64980
gtggctcttc tcatctggaa gtagagggta tttctctgca ctcctgagtc tggccagcct   65040
tgcaactcac tgtggccaat ggaatgtgga ggaagtggca ggtgcccgtc ccaaacctat   65100
cctcagaagc tgtctgctgg gaaacaagcc caggcaaatc tgcgagatga agagagacca   65160
cacggagccg gcaccagtcc atccggttgt ctcagacacg taggaagccc agcaggatga   65220
gccgtcgcca gcccccatc ccgactcaca gactatgag caaaggtcaa ggtgtgctgg   65280
tgtccgccat gaggttgtgt ggttgttcag tcccgtgtcc aggtgatgga cacctcctgt   65340
ccctccccctc ttcctcattc tcccagccca tctccgttgc acagtctcac gtaccttct   65400
gtccacactg atcctgaggc agctgtgtga gcataaactg aggcaagaga ccagcccaga   65460
aaggctgaca gatttcaaat ctcagacccc aggtgacctt gtggtaaggg acattcctca   65520
ccctgggtgg caggtgacac tacaagtcaa gtcggtaatt ctaatctcaa cttaggtccc   65580
attgatgttt tgttattcct gtctctttaa atgcacacctc aggtgactca atacatggac   65640
tttttcactc cctccccttc ggcccactta cctgctacta ggcctgctcc acacaagtga   65700
tctcatatcc aggaggtggg gtgccccaag caggagtccc cctcctctcc ctcctctctt   65760
ctttaagctg tccctgctcc tcctcacaca ccccagcttc ctgcattttg cttcatgctc   65820
agagctagcc agctgttcag caagcactcg atcagaggct gttctacgac aagggcatcg   65880
ttcctgcctt gagtcactct caagctaatc agcgtgggtg gctggtggaa acatgcctg   65940
tgagaaagca aatgagtgga tggcatcatt gggacctcat ataaagaaca aagactcatg   66000
gagacactag aaaatggaac cgccccaggg aagctctata gagagaaaat ccagctacac   66060
cttgaagga aaaagacctt tgtccagata gagaaaggaa aaaatagaac atccatctac   66120
ttcttgcctc gccacttatg ccgtgctcct ttgcaatatg gactctgcca ccctcagccg   66180
```

```
ttgacagggc tgtgttgaca accttctcga tgccaccgtt gcaagagctc ccaaccccct    66240
gcagcagcag ctcactctgt tgactccttc ctgcctaata aaggtcatag gcaccattcc    66300
ttagtgctag ttgtcacaag accttgcacc aaacacctta cgtcttattt cacccttgca    66360
acaactccca tttacaatgc agagaagcgc tgacagggcg ctcagataga tgtcccaggt    66420
tacaagacca cactagcaga atcatggctt caccctgagt ccggctaatt ccacatctat    66480
gcgcagccac cctgcccctc gccttccctg cagggcgagt ggctgaacat tttctttggc    66540
tagtgcaatg gccacccctt ctttctccct ctgctctcta aatgtccttg accctcaact    66600
tcccaacaat gacttcccat ccctcacttc cttcctgtgt gatctccttc tctggagatc    66660
ccttactgcc tttctctctt tgcagccacc tctcaaatcc cagaagccag gatgttacat    66720
gtgcaatttc cctgcaaggt gccttaattt ggttttccta atggcatctt aaattcaaca    66780
tgtccagaat ggatcagtgt cttccctgaa aaccaattcc atctcttgac cattttctct    66840
aagtcactgg ggctaaaatt tagagggcca cttatttctg acagctccct ccccacatcc    66900
ttgggccctc cccacatcca atcaactcct gtctgaaatg tgacttgtaa ccgcccctcc    66960
cttgccattc ccactgatag cactttactt attacttgtt acttcttgct gggccacaga    67020
aacggctgga ctcaccttcc tgtctctggt ttatgtgcca ttcagagaaa ctctgagaca    67080
tcacctgacg aatcattgtg atgctcagct tgcaggatcc cacttctcta ctcagggacc    67140
cccagtactt ccccgttctt actgaataaa gtccaaattc tacacttcag tgttctagcc    67200
ccttatcacg tgggcggtga aacctttggc tgcatctcgg acagctcatg gcaggtccc     67260 ctctgctgtc acacccagag ttaggaaggc ctcaaattca ctccctgcac acttgcttcc    67320
ctgtctcctg gcaaactgct ttctctttgt tcttaactct gcctgggaaa atcttcccca    67380
tccttgaagg cctttctcca ctgttacccc tgcatgaaga cctcactgac cccccaaaaa    67440
gtgtttgacc cagaacactt tggcttttgc ttataatatt tacctctgac ttggggcacg    67500
tgtttcattc tctatttgag tgtatgctct ttgagggtag gaatgagtga ctgtctggcc    67560
taccctgaat cttgactctc atgaatcaag ttttataaat tgactcaaaa taataagtta    67620
gagttacaag aataaggtgg taacggtggt tttataattc agaaataatc cttttaaaaa    67680
tgtaaaaaat actctaaaaa agtcagctgt agaggtttgc tcgtggttgc caaggagcaa    67740
agactttcag agagcttaac tccagtgggt ttgagcctct ttctgattaa agcatcagtg    67800
ccaatagcat tggatccctc caagaatgtg gtgtttggga ctttaccatc atttgtttgt    67860
ggaattgtgt gtaggtctga aaattcaggc ctgtggggaa ctaactttga attttgataa    67920
atgactttcg tggtcagttc gggtcaccca gctacactct gttgtgtata ttttggcaca    67980
tctgctcttg aaagatatga ttatatgtaa ctccaacaaa tatatcaaaa gtgtgtttta    68040 attttttttgc cttttagatt taatgaacca gttcctaaga gaaccctaca tgtttcttta    68100
gaagacctaa ccaattgata ctgcattatg acaaaccctc taccagaatt tcctcattca    68160
ttcaaaatta tgtttaaacc cataatgtcc acattctttt ttttttttaac atgaggagac    68220 atcataagaa atgaaacaac agtttgagtc agggcaacag agtccaagtt tccttccaag    68280
aggccaagtt gttttagcag aaaaggacat tggcgccaaa acccacacta ggtccaccgg    68340
cagcaaacac agaatggtgc cctcactcta ggaagctggc tgttccatat ttttatacta    68400
gatttaaggt tcaaaatttc atgttggtgt tcataaatgc aaacacacaa gccagcaaag    68460
aaaaaggaga gttatttagt ttatatttttc ttctcccatc cttctctctct ctctttctat    68520
```

```
gcaaatgttt caatcacata ggtttgacca aatagctgcg tcttacacca ttctcctcta    68580
tgtaaagatg taaagcaact ctgcactttt tttttttttt ttttaagac aaagtctcac     68640 tctgtggctc aggttggagt gcagtggcac aatttcggct cactgaaacc tctgcgtctt    68700
gggttcaagc gattctcctg cctcagcctc ccgagtagct gggattacag gtgtgtgcca    68760
ccacacctaa ttttttgtatt tttattagtc aggggttca ccatgttggc caggctggtc    68820
ttgaactcct gacctcaggt gacctgctg cctcagcctc ccaaagtgct gggattacag     68880
gcctgagcca ccccgaccgg ccatgcactt ggttttgaga gcagcacagt ggcggtctgt    68940
tctccctgcc cgcctgctcc agggagagga gttgcttgct cccttacagc cctcacctcc    69000
catgggaccc tgcaggtgct gagggctcag gcgcagctgc tgccagtcgt cacagccatc    69060
tcatccattc cagagttgta aataggctga tgattccgtt ttttgttccc agagctgtat    69120
atccagtggc ctcctggagt cacctactgg gatggctgat gatctccaaa agtgtcaaca    69180
ctgtcccaaa ctgagcaccc cgccccacag cagagccctg cccagcgcc tcctgttctg     69240 gctctatggc aattccctct tcccagcggc cgcagcaaga gtcgggtccc ctgcgccctg    69300
gcccagcccc tgccgcccct gcctggcctg gatgttggca atggtggttt cccagtgccc    69360 tgccccccacc cttccccctta ccccttttcag cccgttcctt actaagaagc caccgcaatg    69420
ttggtgagaa agtgggtcag atgtgccaca gccttaggcc gcttcaaagt ctaaccacgt    69480
cctgaaaacc ttctggtttg gttcccagct cctgctccga tctcgcctct atttgaaaac    69540
caccatcccc acatcggcca cctctcagtc accccatcct ctggctcacc cccgagaccg    69600
ctgccaattg gggggacccg tccatagcac ggatggcgct gcttccggca cctgcgccgc    69660
ccgagggtct cctggccatg gcctgggggt gccacgcagc cgtggccacc gcatcctccc    69720
tcagtgctcc ccacggctct caatgcgctc cccaagtgct gaccacgcgc gcccccacgg    69780
ctccccgaca gctccgccac gccctcccca cggctctcca cgctctcccc aagtccccaa    69840
cggctccccc aagcgctgcc cacgctcccc cacgactccc ccactccctc tccacgtgct    69900 cccccacgtgc tcagaggagc ctggacaggt ggatccgggt tgccccgggg actcattcag    69960
gggtgagcac accttgtact tttccctcgt tgtttccctc cttcccctcc tggaaatgcc    70020
tcctgcggaa accactcaaa cccttgtctc aggaccatgg cagggtctc ctttcttaca     70080 gggctggctg cttcctcagt caaggcttct ttggctattt acttatctaa aatgaaaact    70140
ccagccatat tctcagtatt tcatagcctc cttttccatg ttgttctcat tctttaaagt    70200
actacctatt tcacctactt gtagtgttct ctgtatccct ctcctaccag aatgtgacat    70260
ggacggtaat gtcagccttc ttcactcctg gttaagcaga cttgagaaaa gggcctggca    70320
tacagtaggc attcagtaaa tgctttgtga ctctgtcgag aggtgacagc atgctggcag    70380
ccctcacagg ccttgctcgc tctcggtgcc tcctcggcct cggcgcccat tctggccgcg    70440
cttgaggagc gcttcagccc gccgctgcac tgtgggagcc ccctcctggg atggctgagg    70500
caggagccgg ctccctcagc ctgcggggag gtgtggaggg agaggcacgg gcgggaacca    70560
gggctgggag cggcgcttgc gggccagcta gagttccggg tggcgtggg cttggcggc     70620 cccgcactcg gagcggccgg gcagtgaggg gcttagcacc cgagccagca gctgcggagg    70680
gtgcgccagg tccccagca gtgccggccc accggcgctg cgctcgattt tcgccgggc     70740 cttagctgcc tccccgcagg gcagggctcg ggacctgcag cccgccatgc ctgagcctgc    70800
ccccgcaccc ccgccgtggg ctcctggcgg cccgagcctc ccctatgagc gccgcccct    70860 gctccacggc gcccagtccc aacaaccgcc caagggctga ggagtgcggg cgcacagcgt    70920
```

```
gggactggca gacagctcca cctgcagccc ccgggcggga tccactgagt gaagccagct    70980
gggctcttga gtctggtggg gacttggaga atctttatgt ctagctaagg gattgtaaat    71040
acaccaatca gcactctgta tctagctcaa ggtttgtaaa tgcaccaatc agcactctgt    71100
gtctagctga tctggtgggg acttggagaa catttatgtc tagctaaggg attgtgaata    71160
caccaatcag cactctgtat ctagctcaag gtttgtaaat gcaccaatca gcaccctgtg    71220
tctagctaat ctggtgggga cttggagaac ctttgtgtct agctcaggat tgtaaacgca    71280
ccaatcagca ccctgtcaaa acagaccaat cagctctctg taaaacagac caatcagctc    71340
tctgtaaaat gggccaatca gcaggatgtg ggtggagcca gataagggaa gaaaagcagg    71400
ctctccgagc tagcggtggc aatctgttag ggtttgtgtc tgtcgtgtgg aagctttgtt    71460
cattcgtctt ttgcaataaa tcttgctact gctcagtctt gggtccaca ctgctttat    71520
gagctgtagc agtcaccacg aaggtctgca gctgcactcc tgaggctagc gagaccacga    71580
acccaccggg aggagcgaac gactccagac gcgctgactt aagagctgta acagcttacc    71640
gctaaggtct gcagcttcac tcctgagcca gagagaccag gaacccacct agaaggaaca    71700
aactccggac atgccgcctt taagagctgt aacactcacc gccagggtcc gcagctgcat    71760
tcttgaagtc agtgagacca agaacccacc aattccagac acactgtcat caaaaagtgg    71820
gatatctttt taaacagaga taacattgca gaatcttgga gttggaaata gacctcagct    71880
ggggtttagt cctgttttct cctcagagca gaagtcctgg gatgccgttc tggactgatt    71940
gtcagttttt tctcctgtcc ttgagctatt ctaatgccag acatctgtgg ctttacacag    72000
ccaggctttc agttagagaa cttggttagc tcaggtcaac aaatgctgct ctgagaacac    72060
tgactcccat gtggggagac tctgcacctg gagctccggg agagccggct caggcctctt    72120
cctgctatcc agggaactgc agtggcgttg gagggccttg ctggggctgg ggctggggag    72180
aagggattcc aaccctactg ataattcgtt tggaaacacc gggctgtgga tttcagaagt    72240
tcttgggcag cctgattacc actggcagtg agccggggac gaagccgaag ctatgagtga    72300
cagacggaaa gaactggggg ctttggtgaa ccagagaaca cttagctcct ccagccctga    72360
agcaggcgtc accgcagggc ttatggtcct aagagccact tagtttcctt attcattaaa    72420
ctagtttaat ttgggttttc tgcatcctgg aggacaccaa gtcggtgtgc ggagggaccc    72480
tgtagacacg tgtgcaaaga ataagccgac gatcatggaa tttctgatga cgccactgac    72540
acgtgggatg gaggcctcct tcccagggca cccctacact catgacaatg aatcctggct    72600
cttattcacc cctttggatt tcacaagcaa gtagtaagta gaaaaatagt ttcattttat    72660
tttcagtaca tcaactgaat gtgctaatac ttgtatccac ttccacatgt aagaactctg    72720
ttacataaat ttgagaataa tctgctcttt gctatttga ctttattttc actgcagatt    72780
accaattgtc cctacaattt gcgttttata gttacatca tcgtacactt gattttatag    72840
ggaacaaaag gttctcaata attacaaaga aatgtgttga tttaacatac tccaagaatc    72900
tcatgaacac agtccaaata ataattcaaa attgaaggtg gtatattggg ctaaagtgtc    72960
cagcaactaa ggaactaacg atgacttaac ttttattgtc ttgggtcaca gacacataaa    73020
attgactaga aaattaatcc tggtatatct tttgtatctt caacatcact atgaatattc    73080
tacttttaa gtgacatgga acattcaaa ttgagacatg gagtctgaga gtgacacggg    73140
ctgctggagt ccacaccctg ttgaccaaat ccacaccttt ggtggccagc tccgttttgg    73200
ttttcaaact ttaagctcca ttgtatcccc aaaatatatg aatgaaaaca aatcaattta    73260
```

```
tttattttca ttttagttat ttatttgaga cagggtcttg ctctgtcgcc caggctggag   73320
tgggttgttg tgatctcgcc tcattgcaac ttccatctcc tgggtttaag cgattctcct   73380
gcctcagcct cctgagtagc tgagattaca ggcacggacc accttgcccg gctaattttt   73440
gtactttagt agagagaggg ttttgcaatg ttggccaggc ttgtctggaa ctcctgacct   73500
caagtaatcc tcctgcctca gcctcctaaa gtgctgggat tacaggcgtg agccaccaca   73560
cccggcccaa gtcaacgtat ttataatatg tgaattgttt gcacacctat ttcaagcact   73620
ggaaaagaaa aaaagaaaa gaaacaggtc catgaatgag gtaagcagag ttggacccaa   73680
atacttcaat gccttctcaa caatttcttc taaatggctt cccgaaatta gctctgcacg   73740
acctatcttt cttgggggt ggggaagcga ttacttttta aaagccacat taaagtgtgt   73800
gttctatatc acgatggcag ttaagggagg ggaggcgtct acagctgacc tggggaagtt   73860
ttaatcattg aactatgcac aagtggggcc ggggcgggaa gcggcaggaa aatgaggcac   73920
cttctgcaga acctagccag cctgcaggcg ttcctgatct gaggaaaaca ctttaattaa   73980
tatgtaaaac agcagtgggg agaaaagcaa ggttaatttc caaccacat cactaccagc   74040
ggtatttggg ttatgaaacc ttgggaaact tctaggagat cctgtttgaa ggcacagagg   74100
tgcttttgtg tgtgagtagc ttctgagatg ctcaaaagct cttttatctg cccctgcag   74160
tggtattgct ctttctgtgt ttaaaaacac tgcctttgac tggcaggctt ttgttttaa   74220
tttgcagtgc atcctccatt tttgtttgga acttgcctga aagcagcgtt taggggagag   74280
agagctgttt gatttccttt gttgcggctt tcttagctgc tggctacctt tggaatgtgt   74340
gacacaggcg tctctcctgg ttaggaaaat gttctgtact tgcctggggt gagactgtag   74400
ctcatttcct gggttgagat ctaaaatcct gagcagagtt aagtgtatca aatagtggct   74460
gtgccaagga tcagtgtctg gtggagacag cggattttcc aaggtcatgg aagtgaagaa   74520
acagctgaca agtctttccc tagcttgagc agaaacagct ccattcagtg cgtgaacaat   74580
taactcaatt agagaatgtg cagctttcta aagacgcgtc cactgtgagt gcgtgtgcct   74640
gcgtttcctg cctccctctc ctcacagaca cctcaaaagc aacatatctg aaaagtcctc   74700
ttagctaccc tgtctaggag aagtcagagg cttgaggacg atactgtgtt cctcccaccg   74760
cttggtatcc caccaacacc cgctcctggc cattagacac tcaagcatct ttcaagtagg   74820
gagatgactt tttgggggt catagactcc tttgagaatt aaagtttacc ccaggaggaa   74880
aataatatct gcacatacca agatcagcac acactttcag gggttttccc ataccctactt  74940
taagcccaat taggatttct gtactaaaat caatccctct gtcccatttc ctctgccaca   75000
gccgtatgtg cagccccacg cgttacttac atctagcctg gagggttaac tttgacttcc   75060
cagcttctgg cacaatttcc ttctccatcg caggccggag tggtctccac attccccaag   75120
ggctcaccca tgacctttag aagaaagtcc aagcactagc ttggcactca agtctaagg   75180
aattcttcat cccgtgctcc aggcacatga aatgcctgtg ttttcgtgag caaacgtttc   75240
tcctgtggcc ttccagtttc tcccagtaca tcctgtggac tatcgtggag gatttgcatt   75300
gcagtgtgtg cctctcaggt ccatgttgga gtgcccgcg tccgcctccc tctgcgcggt   75360
ccactcagct gggtggcgtc actggtgact gggcttctgc ctccttcctt tcactgggag   75420
actcctcagt cagagtctgg gtcttcatct ctaaaccccc cggggcagca gcagtccctg   75480
attttgacat aggagattag gactgcagct tgtagggagg tggtgatcca cggaggggct   75540
tcttctgaag ctgactttg tagcaagcac agtgttccaa cttacattaa atacacgtgg   75600
ggtggcttga tatgacgatg gagaagatcc cacattgcac aaggtgggag ctaaagcccc   75660
```

```
agtcctcgcc ctgcagctgt agtacacagc ttcacagtta cgtgcactgc cacatgtatg   75720
taataatctg gtatgtaaca ggtgcttgtt gaatatttgt tggatgaata gatgagtgac   75780
cctagaaaaa cacaatgcag acctatgggt agaagaagaa aagaacctgg agtttcctgg   75840
aagttagggg ttccagccca cctctgtcca cagccatgtg atctcacaca cacacacaca   75900
cacacacaca cctacacctg cacccatgag cctccccact ttgtcaggga tcatgattca   75960
caggttatgc tgcatctcct aacttttcca tttctttgca ctcactttt cactccattt   76020 ataggcacac agcaaccccg tctcctgcaa tgacccctgc tccaggcctc acataaacca   76080
cctgctatct gtactcggca gccctggtcc gaaggcaaac acagtcctgg ttgccccacc   76140
tgacgcaatt gctcctagca tttcttattc actctccagc tttcgcttgg ctctaccctc   76200
tgctgaaaca gctaaccctc ttgcctggca gagtcaagga aattttgag tccagggcct   76260 tcaaccttgt gtcttcagga gcctctgcaa agctgggtgc catgtaggtg ggctctctcc   76320
ttccactccc tgtcgtcttc attctctagc cctccgtatc acccttctgg gcaattcttt   76380
ctcagctcac ttagcgaatg taaggaagtg tttcattttc agtctttcaa atctttttc   76440 aaatacttcg tattcaatca tttcctcttc ttggatagag ttttgtgttt taagtacagt   76500
gttatccaat ggctagatcc gcacctctag ccagctcacc actctgtggc ccagactctc   76560
tttgccaact gtttaactct cgtgtataaa tgacaggcag ctgcatatgt ccatatgtcc   76620
agctgtctgt tctgcagtgg gtcacttatg ggatcagatt gtacatctgc ctgtttcact   76680
tcaaattgcc tcttctttgc aagcatccag gggtgtcttg cctcacatac aaacaaacac   76740
agaacaaaac taaaaacctc aaaggaattt ctgtgttgaa gaggttttaa tggtaaaata   76800
attaagttta cttgcgatta aaaataatt gtaaattttt attaaaaaac cctcaaaact   76860
atcttgctgt attttctttt tattataatc aaagtttagg caagaagagg ggtatctatt   76920
ggctcatgaa gtttaacagt tccctggatt gacctagaac agtgcttttc aaaataagca   76980
tcaggcccat ctagagagct tggaaagaga tctcactgag tcagctccat cttccagagt   77040
ttgtaatgca gtgagtctgg gagctgaggt tgagaattcg catttccagc aaggccatga   77100
ggctgctgct gctgctttgg gggccccact ttgagaactc atagcgtcag gcaccacagg   77160
acccagatgg tcaatgatat ccggagaatc aagtctcgct ttccccagtg acacagaaag   77220
ttcctggcac tcccaggcta acatcctctc tggagttggt aatttccaaa agagatcttt   77280
ccaacttcca taaaaacttc aaaaatatga ctctggtgct acatgagcta cctgcttacc   77340
cctgggccaa tcactgatgt tccctgtggg gtaacctgat tctctggcct gggtcacatg   77400
actcgccttg tggtgggcag gctcccttcg tgactgacag ctttcctgcc cgccccacat   77460
tcagaatcct atctaaagca aggaatgtag ggcaaacaga gtgttttaa agtatatttc   77520 aatctctata tctatctacc tgcctacctg tctgcctacc cacctattga tctaggccag   77580
ttacgtaatc tctctgaacc tcatgtttta tttatccaga taagtgattc cataatactt   77640
acctttcagg ccattgtgtg gattagaaat atcacctgct tcaaacagcc agcatattgc   77700
ctgcatcaac tatgtagaat aaatgatagc tagatatgaa gaggaaattg cttcatcctt   77760
gaccctgtct cccccagtaa aggtggttca ttaggtgtct ggcgccagat agggtggggc   77820
cagattgagg atgctcaccc tatcactttt ccccactcat ctctaactcc ttgaccagtg   77880
actatgacct ctccatgcac tcatgtgtat atggagtttt tccattggaa aatgaggcat   77940
atattacaga aacacccatc acatatctgt atcccttgg tgagaggtgc aggggcacgt   78000
```

```
ggagtactcc ttcctgctgc taagttcatt tttgtgtggc tttcaccgtt tgttccctgt    78060
tgaagccttc tccaagcttc gggtgttcac aagtctccaa gggctctgtg agattagaac    78120
ttccttcctc tttcagctga taattacagc tctgtggttc tcccttgtag gtctttcctt    78180
gagctccaaa acagagtttt cctgcagtgg agcttctatt cggataatta gggcactcag    78240
ttgtattgga ggagggttga attaactacc tctgtctcct gtgctacttg gttctgggct    78300
tctacacatc acagctacct ggaggataat catcatgata taactatta tttactgagc     78360
tgatgatgcc ctaggcaaga ttcttttttcc attgcattct cccaaagcct agaaggtagc   78420
tattcaattt tacagatgag gaaactaagg ctgtgtgagc taaatgcctc cgctaaaatc    78480
acacagcagt acaaagcgtg gcagggtggg gaggcccgca gagttgcgac cccagcccag    78540
cctgtgaatg cagactttct gtgtgaactg cgctgttctt gcagctctct ttggacctgg    78600
attgaagttt tcccatgaag aactggggaa cattgaattg ttgatgttgt tgttgttgtt    78660
gctctgaatt ggattacata taaattctct tttccttcaa tattcagtga gattttggca    78720
gtcaatggag actcattgcc taatggttgc catgggtgat tttctcaaat cactgctccg    78780
ggcccagggc catcagagca attcaccatg ctgaagagac gcctttgtta gtccaaaggc    78840
aacctcaggt aatcaactgc ttgacccacc tctgatttta agcaccaaat taattttaga    78900
cgttgcatag agaaaggtcg atcctcctgt tttctctggg agtggcaagt gagcagctca    78960
gctggagcgc ggcagggttc tgcctgtgtc cctgtcctca ccccatctct gctttcacca    79020
agcaagagct gcatttgggg ttggccgggg ctttctcacc tctggagatt cctggtccaa    79080
tgtcattggc aagcacgtga cctgagagaa cctgaagatt aaaacactgg ccttcgaatt    79140
ctgagaagtc ctgtcatcat ctatcaggga acttagcaat accacttctt ttcatagcag    79200
atatatttat gtgcttgact tacatttttaa tggtttataa aagctaaaag caatcgcagt    79260
ttgggggggcc ctacgtggac ttccctgcaa ttctgtgatt gtcccttaat gaagtcaaca   79320
aacacaatgg gcagatgaat gaatgctccc aacctaatta aatctaacat ttgagaataa    79380
aataatacta aatatgtaat ctcatttcca tttggaacca actagagctt ctttgaaatt    79440
tggggctatt tggaaagcat tatagatcac aaatagatgg aaccataatg gaaacacatt    79500
accgctcaag aagattgaaa atagccctcc cgtaaaccta gtgttgtatc tctgtacttg    79560
tgaaggaaaa gactctactt tgacctgagt gggctctgtt gaataatatt gaaaatgcac    79620
agctgaatga ggctgcatta gactgtccca gcgggagaac aaatcagaag ttatgttgtt    79680
gatgcaaacc gttttgtctg gccacctttc taacgtgctt gttttttcatt ttcctctttt   79740
tctgtctttt ttgggaggct ggggggtggg gtattaccta gggagagggg aagccaatca    79800
ccatttgact gtgtgttgaa tttaaggacg cctagaggtg aaaagaggaa accttatgat    79860
tgaattttgc ctactaatga aagttcatat aaatcaaggc tcacatagct cttatatgaa    79920
taaaatatta tacctggagg caggaggatg tgatctattt tactatcttc attaatctgc    79980
aaatttgctg ttcaaggctg tggccacata tcactgtgga gaaagacat tcccttctgc     80040
actgctgttt tctcaggtcc agaacatgct ctttctttag tatgacacat gtctttttttc   80100
tgataatcac ctggcttcac ttttttgtaag gtttacaaaa ttcattaggc atattcaggt   80160
tcagaggttg gtgaagtgct tgaaccatat ctttaggtga ttactatccc gcatgctgca    80220
ttttgtaatg atgatgcttt actcagttat agtcaggtca aacaagtgac aatgataaag    80280
accattgtgg acgcagcaca gtcactgact ggacctacaa acacactggc agggctgtgt    80340
ttgccttaca atctgggctt tataattaaa ggaaacatca gtgcttaagc ccagaccttt    80400
```

-continued

```
ggtggggcag ttatcatgaa ctctggaaga ttcgatccat taaatatttt ggtttgttcc   80460
aatcaagcag tgttcatgac ctactttgac aggtatttgg gatgtgcagt caggtgattt   80520
ttcttttaaa ctatcttatc aaccaagcag attcttccat gtggccatct gctcagtttt   80580
gcagccctca gctgttcttg gagctagaaa aaaattctcc tgtggaaaaa tcaatgtact   80640
tctctcaagg agatggagat ttaatatgtt acaggaatag atgcagtaga aattgataac   80700
ccttgttata tctccatttg attgagagat cttagggtaa ataaaatatg gctcaattta   80760
cagtcagatt acttaggttg ttattttaat aactaattca gtaattttag aaagtaggag   80820
agtaaactta tagcattttt acactaaaat agatttcaga catccttcat gtaggtaatg   80880
tcttgttgag actattttcc tggtgttttt gaaactgtgg ttctgtttgt agtttcgtaa   80940
gagctttgaa tttggctcca tttggggttc agcaaattag tgtagtttgt tctggttttt   81000
atttgaggtt ctgctcggga tgagtcccag gaatggatgc catgtttgtg aacagggccc   81060
actttcatct gagcatgtca ataacaggaa aagccagatg ggcagcaagc ctccaccagc   81120
acccccacca catctgcact catacccacc cctccgtgtt ggctccagag gtgagagctg   81180
ttttctttgt tcaccatttt agggtgagcc cagtgaaagg caggcagggt gtccatcggt   81240
ggatacatat ggagatcaag atgcctgact tccattccct acccccagcac acctgctggc   81300
gggatccagg cacacagctc tcagcactgt gtttgcccctt gaaccagtga ggggtctcag   81360
tcgctgactg gaggggggcgg atcacgatcc agcaaggcct ctgagtgcca gacagtgtgc   81420
taagccctct gtacagttag gagatccctg tggaaggtga tatcaccccc atttttatgt   81480
tcaaggaaaa gcagtcccag aaaggactcg ggtttgagtc ccgcggcagt aagtgctgga   81540
ggtaattcga gcgcgttttg gcttcctggc tgttctgtgc tctgtcctgt agcctccata   81600
aatacaggta gttggtgacc taaagattgt aatctttagc attttttacaa gccaaacatc   81660
tgtgaaaacc acagtagtat cattataaaa atcccatgta agtataaata gtatagtaaa   81720
attaaataac agcaactcct cttatttgaa tatagcagta ttttttaggcc aagggttgtt   81780
ttggtcaaac atgatcccta tatctggaaa acctggtatt tttgggacat agtttccctt   81840
attcttgctg caagaatgac ttttttctgga ttaaaaaata gactatggga ctactacctt   81900
gttttttctgt ttacagaagt aggctgactt acgatgtgg gggaattatt catttacgat   81960
tatttcatga agccattcat cttcaggtct tccttccaat aaggaagacc tgaagttcaa   82020
ttagtggctc ccttacaatc tgagcataac atgaaattta cataaatctc tacttctctt   82080
ttgctttgga ttaatgaaat caaacaggca actagaatat gctgccagtg cagaatatga   82140
ataaaataaa taaagtatt acccccagctg tgattgttaa ttttagtgta tagtgagact   82200
cctacagtgt ggtttgttat agatttttttt tctttttggt tcctttttt ttttaattga   82260
ggaattatgt tttctgtttt tatctctttt tttatgtgtg ttttgtggtt tatactcctg   82320
gatttttccta ttagttttac ccctcctaaa attctagctc atcgtactta gctatgtttc   82380
aatatatgat tacagtgacc ctttaagtga acagaatgat ccctttgaac cgtggaatag   82440
gtgaacgacc ttttggaata cacacagact ctggtgcaat gtagccagaa aaaccaaaca   82500
aattgacagc cagatgaaaa gcgattggtt caattgaggt cacctgcca aatcagggct   82560
gccagctggg aaattcttac gcattttcct aagtggctgt tacataaaat attgagcctg   82620
cgtgtatctg ttaagtcatc atggctctga tatttaaaga gccttgttct tttattttt   82680
ccttcctgga atggggaatc aagagaccag ggtttacata ttgaaaacaa gaaaccaaat   82740
```

-continued

```
caaacagtgg cttattcttt aaagtaaaca gagcaaaggc tatcagtggc agatgtaacc   82800
aagagctggc tctatgcaga caaagaggag attatgaaaa caaaaatctc ttccactgaa   82860
ataattatgt ttaattactg atccaggaac tgcatttaac gttttcatt tgcacaaatc   82920 ttaagggtaa atgaggctga caaatactaa tcaggagaca ggggagatta tttcatggtt   82980
ttgggtggga tgagcatcta aaagcctatc cttctctctg ttttgccgg cctagaccct   83040 acgtctccct caaagatctg ctgagaccag aactttgagc cccactcttc ggggagtgcc   83100
agcccattct ttccaacctt cttcttctg catttctgaa aaccacaaaa ttgagttatc   83160
actgcggcaa caccttgtca cttggctgag ctctttctct ttagctgata acttgggga   83220 acaaagcctg gttccatcca gggttcatat ttgaaaacta ataacaaaa catagaatac   83280 ttgaatgaac tctattctgt cttgtatatt gtccctggca taccatctgc actgaaagct   83340
gctcagaggc agggatactt catgtctctt ttttcccagc tcccagcagg atattgagtc   83400
aatcgtgaat gatggatgga tgggtggatg gatgaatgga cggatggatc tgggatcgtg   83460
tccaagtgat tgcactgtgg ttcttaaagt ttattcagat atttggaaca agatcataga   83520
ctatctccta cagatagtaa aaaattcaat cctttagcca actggtggaa ggagatcaag   83580
gctatccatc tgtaagattg ctccagagtc atgcctgatg ccatttcaca gagaatgtca   83640
accctgctct tgcttactg tgcgtttccc gtggcagggc tgatctctga aactgtgaa   83700 gtagttgttg attgttgttg tttggttgtt agagtctgac ccttgttgga gtcattccgt   83760
gttctaaaaa gtctccactc ttttagagaa aatcacagtg ggcaagggtt acaatggcag   83820
cagaatgttt cctgatgaga tcaatgcacc cttcaaaatc ccatgactga cccttcacca   83880
aaggtcctaa acagaatacc accaaggagt taaggactgt ccagtaacgc aggtattgcc   83940
aattcacttc tttaccctaa aaaacaattc ttgctttgag actccatcag cagtccctgt   84000
aaatattaca caaagcacta attttcttct tctacaaaag cagtaatttc tgtctccttt   84060
actctttttt tatgaagttc tatggagaac tgttaaatat ttaattcctg ctgtgtatga   84120
gagatcagct ctgatttcta agtacaaaac taaacttcag caagctataa gaatagtctg   84180
tagtcctggt gattgacact gtgataatat atctctaaat ggtgactgtg tgaacacagt   84240
attacagtct taagaaatag atttggtaca aataattatt actagcttgt gtggtatatg   84300
ttgcatgtat gtgatacatg gtgtcacgtg gtgtatgtac atagaccata tatgatgtgt   84360
ttatataggc gtatatatgt gtatacacac acccttttca gccttttgg atatggtctc   84420 gatttctttg caaacatat ttattttttc atcccaagaa aatatttgtc ttgcagaagt   84480
gcactggaaa acttaggtt gttgattcaa ataattatc cttgaaaaaa gcatgatttg   84540
tgttcagtct cacagcacca tttgattgct tcccatgccc tacagaacta tatttataaa   84600
aggattttgt ccttttgccc tttccataac tcaccatcaa ctgtgaatca agtttcagta   84660
acaatggagg ctgttttcct gaatcaacag gcaagcttta ttgctttttc tttttcaggg   84720
cttctttact tgctcatttt ccagagttct gctgttctag actctcattt atattaatca   84780
gtcagagtcc ctcatctgct tactgaattt gctgttgcct ggaagaattt ccaagtactc   84840
ttttgcaagg aaaacaacat attttgtagt aggaagtaga agttgcccac gggccactta   84900
caatccaact ttcaatcagc agcttgaatt agatatttgg agttagattt ttttgtgtgt   84960
cttgtttatt ttataaaagg acattcttat ttctcatttt tgagtttaag ttggctaata   85020
aatgtataat gtgactttcc taagaagtca caatattact taatatatat tactatatta   85080
tatagtattt atatattata tagtattata tatattataa taagtataat aaatatttac   85140
```

```
ttattatgta tttattagcc agtaaggact tctaaatggc tttctaaata aagcagattt   85200
tcttttcttg tagtaaaagc aaataaaata agaccaaaaa tatttcagag tattatcaaa   85260
tatccaccac acctatactc cctcagaagc ttctgtttct ccctccctgc tatcaattta   85320
gttacaatgt aacctcatta aaaataggtt cctttcctct ggggcacctc gtaggatggc   85380
ttcctccagg aagttcccaa aatatgggga tggatagccg gggtcatctt ctgccagctt   85440
tggtctctac atgcttatac ccacttcagc caggtcccac ttcctctagg actttccgtg   85500
gcttgatgcc taggctggct gggtcatcgt gaaggggcca aaacacagaa ttgcaggtag   85560
gaaaaaccct aaggtttatg tgtgggtatt acctgaaggc tttgaggcag gtgcctcttc   85620
tagatgatct cagtgagtct ccactccaac tctggcacag cccactgtgg caggtcttaa   85680
gcttcagaga ggtttaggag ttggcctagt cgcagacagc aggtgggcaa gatgggcatg   85740
actgcaggtg agcacgagcc tgcctctctg cagctttctt cctggtccca atccttctgg   85800
aacagaggtt cttgccctgt cctcctatcg ctgtggtctt agacctgcag gctctcgaga   85860
aggctccttt tatacatctg ctgtttacct cccgcagatg cttggagctc cattggtcac   85920
ttgccccatc cctgctggag gtaaatcctt aaggctcctc atatcctgcc caccattcac   85980
tcactcattc actcattcac tcttgtagcc tcttacccac ttcaagtcat ttattacatt   86040
cactcactca ctcactcatt cattcttgta gcctcttacc cacttcaagt catttattac   86100
attcactcac tcactcactc attcattctt gtagcctctt acccacttca agtcatttat   86160
tacattcact cactcactca ctcattcatt cttgtagcct cttacccact tcaagtcatt   86220
tattacattc actcactcac tcactcattc attcttgtag cctcttaccc acttcaagtc   86280
atttattacg ttcactcact cactcattca ttcttgtagc ctcttcttac ccacttcaag   86340
tcatttatta cgttcgaggc actaggaaag aatttcccat tcaaagaca tgcagttttc   86400
tggagtggat gacctctgct ctaaacatga tactaataat agttgttatt attacctata   86460
tcaacagcag tatggattga attgtgtctc ctccaaattt atgtgatgaa atttgaaact   86520
cccagcatca cataatatga ttatatttgg gggacagggt cttagagag gtaatcaagg   86580
tcactatggt tgctgtcctt agcgaaaggg gaaagttgca catagacaca agcatagagt   86640
aaagacgatg tggagagact cagggagaag ataggcgtct acagccaggg agaggcctgg   86700
agcagagcct ccctcacaga tgtcagaaga agccagccct gccaccacct ggatcttgga   86760
cttctggccc acagaaccgt gagataatca atttctattg tttaagccac caagtctggg   86820
gtactttgtt gtgacagcca tggtaatgta atacaaatag gaataatata tatatggaaa   86880
tgtaggcctt cgctacgtgc aaggtatggt gaaaattgct tttagtgcag aatcttactt   86940
aaatctcacc caaaccttca tattaccagc actactaaga tttaaagatt aagaaactta   87000
tccaagacca gacagctagt agatgagaaa cccagggttc aaacccacac ctgtgactct   87060
ggagccatca cctttaacca tcactttgtc ttatttttccc ccaggctgaa aaagtccttc   87120
ctactcactg gatgtgagtc ctgcgtgtcc cattgtaaac tgtccctctg cctcaaatgt   87180
caacagcaac attgaaacaa cagtattttt tttttcaaat cagtataata ttcagaggac   87240
attaaattaa gtaggcattc tcatattctt ggtctccaca tagcagaaaa atctgttaga   87300
atgaagaagg taatctcatt agtgaggtat tacgttgacc tgaggagcaa atgctgttgt   87360
tgtttctggc aacagaggat tttgtccctg aacaaaagtt agcctggcac tgtgaagtag   87420
gcttttatat gaacaggtca ctccttgcaa cagcaacaag tgttgcttca gaatgagcct   87480
```

```
ggctcctgcc atgtgggtca gggctgacag cagggatttc acatgtgaca gatgactaag    87540
ggtttatgtg gacatggaag atttgaggct cctttctgcc cccatcctct cactgaggca    87600
attgaagatc tttttctcct agcagaccta gaaattgttt gccagtgggg gcagaatgag    87660
ggagggcatt tgaaactcag ttgctacaag ttagcgtgta cgtttagatg aactcatgtt    87720
aacaatatac ttttccagtg gatccattcc agattaaact gtggtctttg agtttctcaa    87780
cttccttttt cttattgttt gatatttatt gcttttaaa aagatttgct aatcttacac      87840
gcaaaacttt cagacaaaga cttcagggaa taatctttca tacaaagatt tcaggcaata    87900
aatttctagt gtttatacag ctagcgaata gaacttcttc ctaaaattgt ttgaagccca    87960
aaatctaatg gcaagagatt ggctctcatt tttggtagcc ttgattgaag ccgattgatt    88020
gaattgctgt tcctgtcaat cttgtgacat tcttacacta atgaggtaaa ataaatgctg    88080
agtcctgagg tcacaccagt cctcgctgca catgtccttc acctgacttg atattttgaa    88140
atttttatcc ataatgagaa gttgagatct atcgccctt tttgtgtgtg tgaaaatatg      88200
gctggtttta ctcattggtc tgtccttgta acaattaca ctttctcaac aattgagatt      88260
ccaaactgtg agccgaccct tgcttccaca gagagaggag atggtagaga ggcaggaagc    88320
catggagtcc tgtgggataa cggcccccag aggacaaggc gacgttaaat gatggcatgc    88380
atggtaccca tccaataagt tctattctag ttttccccat cgatgggctt gactatgacc    88440
agggaatcat acagctttgg aacagaaaag aatcatctag ttgtggtcaa atgtcacact    88500
ttttgggaga aaaacctaga ggtgagggag acacagtgac ttgttcaagg tcacataact    88560
agtaaatgtc aacgctggga tgataaaccg agtcttttgg gcatgagttc agtatttttc    88620
aacagaattc acatactgct atttcacaaa ttagacccag tttactaatt gttgccttat    88680
gctagatctt gagaggcaac agctgtgttt gtccttatcc tttgacaccc agagcctagc    88740
acggtacctg gggcacaaga gaaactcaaa tgtgtttgcc aaattaaagc actaaggaat    88800
aagcacattt cctcttaatg atcactttca aaataaatct actattcatt taggaatact    88860
aatagctttg acccttcact tgctcacgat tatggttgcc taaggttaaa ataaggtaa      88920
ggtaatgaat gtaaattcat ctctgtctgg ctctttgtta ttggtgatag tgaaaagttt    88980
catggcaaaa aagatacaa atcaatgaaa aaaatggagt ggggagatac cttctgtctg      89040
tgctgcgtgt gttccccatg atcataaatg gagaagtgga ggcaatatta acgaaatgtg    89100
cacttacaaa gcctgtgctc agcaactttt gataatattt aagtccatta gggcctaccc    89160
atacagtcat agatccgaag aggtcgatta aactttgaag agcttgttta gctttgttgc    89220
ctccaggaag tccgtaggaa aaagtatcag aaaagcataa aacaaaaaa agttaaaaaa        89280
aaattatttc ttctatgtgg tgtggttcca agaaaggact ataacaggct tctgccctaa    89340
attgatcagt gtaagctgac atttgaagat aaagcataaa tactctaaga ctgtaacata    89400
ctatacccag agtagtaaga acaattaaaa ataggctcct ggggaaaaaa aagattccta    89460
aaactgaaga gaaattctct ttttctatta tataagctat ataccaatgt ccctcaactt    89520
atgatacagt tacatctggt atggtttggg tctgtctctc tgccaaaatc ttattgcaat    89580
ccccactgtt ggaagagggg cctggtggga ggctattgga tcatgggggt ggatcttccc    89640
cttgctgttc ttgtgacagt gagttctggt tgttgaaaag tgtgtggcac ctcccgcttc    89700
actctcttcc tcctgctcca gccatgtgcc tgcttcccct tcgcccgcac atgattgaaa    89760
gtttcctgag gcctcctgag ccgtgcttcc tggagagcct gtggaactgt gagtcaatta    89820
aacctctttt gtttataaat tatccagtct caggtatttc tttatagcag tatgagaatg    89880
```

-continued

| | |
|---|---|
| gactaataca cattcctata aacccattgt aaactaaaaa tgtaagtcga aaatgcattg | 89940 |
| aatacaccta ccaaacgtca tagcttagcc tagcctaccg taaacgtgtt cggaatactt | 90000 |
| aacattagcc tacagttggg caaaaccacc tcacacaaag cctgttttat aataatgagt | 90060 |
| tgaatatctc atataattga ctgaacagcc tcttgaaaat gaaacacgga atggttattt | 90120 |
| cagctctgga aatacagttt ccactggatg tgtgttgctt ttgtgccatt gttaagtcaa | 90180 |
| aaaatcctaa ggcagggcac atctgggttt tttttttttt tttttttttt gagaaggagc | 90240 |
| ttcacaccat cgcccaggct ggagtgcagt ggcgccatct cagctcactg caacctccgc | 90300 |
| ttcccgggtt caagagattc tcctgcctca gcctcctgag tagctgggac tacaggtgcc | 90360 |
| cgccaccatg cccgactaat tttttgtatgt gttagctaga gattgtagct gtgtgagtgt | 90420 |
| ggtttatttc atacggaaca gaaatgtttc ttttagtaga cagggtttt caccatgttg | 90480 |
| gccaggctgg tctcgaactc ccgaccttgt gatctgccct tctcggcctc ccaaagtatt | 90540 |
| gagattacag gcgtgagcca ccgtgcctgg cccatctggg gttttttgta gtgtatctta | 90600 |
| gttgcaatct agaagaatct gatgagtttt cactgtgtag gcttattaag acttgctata | 90660 |
| tttttactgt gtccttttacc ttcttaaaat gcatttataa tttaaaaagt ctgatctcat | 90720 |
| gtatataaac aatcctcaga aataatttga atatgttcta agtaaagtta ataattttca | 90780 |
| attatacaaa ggccaatagt gggtttattt tgtttgtatt ccatgcagac ttaagttgct | 90840 |
| tgcaagataa tctgggaaat tgtaggcttt ttggtggtgt tatagaatcc agaatttggg | 90900 |
| agtctccact gtagaccaaa tgctctggag tacgtgaaat ttgtctatca gcaaatcaac | 90960 |
| agactagtta acctttctcc aggcagtgtc tcccctccag ccctcaggca ttttgcctaa | 91020 |
| atcccatttc tttttctctg ccggctgtct gctaatccct cggaaagtgt tagctgataa | 91080 |
| cttaaggtgt gaccactctc aggagtattg catttcaaaa gaggcctcca agatagaaaa | 91140 |
| tacttcactt aaaggagcta gacaaggaag gaaggttgtt attttttaac ctgcttgtaa | 91200 |
| gttgagttcc aggccattta actcagtctt tagcgagatc ctctgtgagc ttccccactg | 91260 |
| catgaatttc cctccaattc tgagagccag tgactctgga cggcacttcc tcacttgaaa | 91320 |
| gcatcacatc acaatcattt cggcctaaaa cttattactc atctgtgtta gctagagatt | 91380 |
| gtagctgcgt aaatgtggct tatttcatcc agaacagaaa cattaaaacg attcgactcc | 91440 |
| tgcaggacat cttaatagtg tgtgaaagga agaattcata tttccagaac tctgtacctg | 91500 |
| ttacagctca ggcggtctat gctttcataa acatagtgac atattttatg cattgatctt | 91560 |
| aaaaccctat tacaaattct attccatatt ttcttagaca tttggacaca cttaaagctg | 91620 |
| aagcaaccat gtgtcagggt tcgctcatta aggttttctg ctcaaatctg tatgaacaat | 91680 |
| gtatagatga catataccta tatatgtaaa tatgtatata gattatgcca gtatcttcca | 91740 |
| tttattctca tataattaga gttataacaa caatgattta tatgttcaaa agcaaacatt | 91800 |
| tattgagttt attctgtggt cagcggatac tagacattag atgtgcagat agaaatgtat | 91860 |
| atagttcagg gcccggtgca gtggctcatg cctgtaagcc cagcacttcg ggaggccgag | 91920 |
| gcaggcagat cacgatgtca ggagatcaag accatcctgg acaacgtggt gaaacccagt | 91980 |
| ctctactgaa aatacaaaaa ttagctggtg tggtggcgct cgcctgtaat cccagctact | 92040 |
| tgggaggctg aggcaggaga atcgcttgaa cccgggaggc agaagttgca gagagccaag | 92100 |
| attgcgccac tgcactccag cctgggcgac agaatgagac ttcatctcca aaaagaaaa | 92160 |
| aaaaaaaata acagagcttt aggttatgag gggttttgtc tcctcatccc atttcagttt | 92220 |

```
ttctgaaaaa gtgaagacac ttaactatgc tcacaatttc aggaaatatg ctcagttttc   92280
agtttcttca gctcttacag ttacaactat ctaatcttta tttgggttgg tcaaagactg   92340
cagccaacaa tctgagaata tgcttcctaa agtggctttg tcttgtatat ttaattgagg   92400 aagtatatt ttatattcac acatgcacat gtgacttcta tcttcagata tcaatggtca    92460
aacttaggaa gtgcagcaga ggtgaaggag tagtcagctt tcttcccact tgctcttgca   92520
aattggttgt gatctgtacc catgggtaaa catctatttt ggcacacata caaaaataaa   92580
atcagaatct agagttggta aaatttgatg aatgattcct agtaatttag ttttcactta   92640
caactctaga aattttttaa atcttttctg cataacaata ttgttttta agttttgggt    92700 ataaaaaaat gacattctcc ctgaaacaag caggcagctc tccattcagc agaaagttat   92760
gcaataagat ataagggatt gcagagacgt tctccatcct cctctctctc tctcccttct   92820
aaggggaaaa cctcctaagt taccttgggc aggtgcctac atttggtact cctggacagc   92880
tcagccatct gccaagaaac aattctatat agatgcctga cctgctcagt tcagaaggag   92940
ttttcttctg actgctgcta ataagccga ctgaatgata catttatttg ttaatggata    93000
ctcttttttg gctctcaatt taaaaacatt ttttaatggg caattgaaaa atatacagat   93060
gaagaggcca tggtctaatg agaagccatg gagtcatcac ccagcttcag cagctataaa   93120
ctcaggatca gtcttgtttc acctagagct acagtagaga aacaaagtgt ttggaaaact   93180
ggagaatcaa caatcttggt gagcagtgtg tgtgtgtgtg tgtgtgtgtg tgtgtgtgtg   93240
tgtgagagag agaaatctgt aggtttgggg ctttattgtt tttcctaata tgtaatatag   93300
cttgtgcatc catataatat tattattgga agtatggctc caaaaaattt taggcctata   93360
ttttaatttt aaacttaatg actaaatgtg tatattttca agatatcaga tatccacatg   93420
taaacaaaaa atacggtcaa cttctggaa gttcatatct ctagatagct atctctgtgt    93480
ggataaaaca tctagtttat gtttaacaat gaatgaagaa tgggctctgg tcatagctga   93540
acagggaacc tggggtttgg ccacttcagg gtgacctcag gcaagtcatt aaatcagtta   93600
cttgggttta tactttcctg tttctttcat ttatttatta aacatatatt gagtggatta   93660
ctttctacca ggcactgcag agaacaaaac aaataaatcg cctttctaga tataaagtgg   93720
ctccagtcca gaggggatga gagtagaggc tggatattct gtccctaacc ttttggcac    93780 cagggactgg tttcatggaa gacaactgtt ccacagacca ctgggggtgg ggagatggtt   93840
ttgggatgat tcaagtgcgt gctttatttt tattattatt atatcgtaat atataatgac   93900
ataattatac aagtcaccgt aatgtagaat cagtgggagc cctgagcttg ttttcctgca   93960
actagacagt cccatctggg gatgatggga gacagtgaca gatcatcagg cattagattc   94020
tcataaggag tgcacaacct agatccctcg catgcacagg tcacaatagt gtttgtgctc   94080
caatgttcct gaatctaatg caagtgctga tctgacagga ggcggagctt aggtggtaat   94140 gctcccgtg gcttgtggct catcttctgc ggtgcagcca gttcctaaca ggccatggac    94200
ctggtaccag tccatgccct ggagctcgcg gacccctgct ctaaagctac ttccggcgct   94260
ggtagtatgt ttttaattat ttcttttatg ttaattttat tttccaaata attccctatt   94320
ctccaataat tacaggataa aacctttagt ctaatatttg agatttacca cactgttgtt   94380
caaatctgcc ttcccaactt acaattctac ttctcccctg ctaaaattat tctctctagt   94440
tacaatgagt tgtggacagg aagtttgctt cattcatctt tgtatccaca atacctaaca   94500
taatatctga cccagtgtag atgctcaata aatgattaat gagtagtaga taaatggaag   94560
cctcagtcta tctcctttct tgtcttataa tattatacct tgagtatgtg gaaaaaagta   94620
```

-continued

```
ctgaaaatct tgattctttt caaggtgccc agggtatgat ttatctagag gatcttgaat    94680
taatagctag atttcatttc caatttatga aacagatttc agggtctttc aggaactaat    94740
aattttttgaa aattacttac tcagcttcca aaggttttat cagtcatgat aaaggtatac   94800
tatgatactt gctgattaca tacaatttca agtatttaga tgtttggaaa tacgtggatg    94860
ttattagtac tatgtacata aaatttgttt ttgaatgtcc ttacaatctt gatagttctt    94920
tagaagaaaa tttaaaatga ttttactaac tctgcttcat ctaacataaa atcctgaaaa    94980
cctcaaatga tagtactcct tgtgcctaga gctgctggaa agcacctctg aagcactgtc    95040
atggagtttg tgttttcga accttataat gaacagcgaa gtgggaagtt tccaggctta     95100
ggtgttcttt cacgaggagg aagttgggtt taacacccgt cttagtagtg ctgtacagag    95160
agcaataaac aagccataat gtggtttatt tgggttaacc tattagccat gtaacctaaa    95220
agcttgaacc acatggaaaa tagacatgat gaggtgagaa gcaaatatga caaccaagaa    95280
aagacaggga ttgtgacagc cgcagtgatg gacggcgggc cttgaaacac agtgaggtgg    95340
cccgaagctg gccccgctgg gcctcaggct cccggcccag cctcttgggg cttttgtttc    95400
ctcttccatg aagcagagga ttgtgccgat tgctctgcgc cttcatatgt gtgaagctcc    95460
catgtcagtg cctggcacat ggctggtggg atatgttttc ttttattact gtacaaatga    95520
atttgataac aggctggtta ctcagagcca gctttgtgac accttacttg tctgtatatt    95580
ttgctctttg ttcagttcat tcattcatcc atagataaac attttaaata actattcaat    95640
tgcatatcat gaatatttat tatctgctct gtaacagcag tgtgtgaggt gctacatctt    95700
ttatgtaaga tctggagagt gactctcccc acctgggctc cgtaggttat gggagggtca    95760
ggcacagcac tcccaccaag ctatctgctg gggcatgagc tggggtaacc tcgaggagag    95820
gcccctgctc taaagtacac acctaccatg tggctgtcat tctgctcaca gtcgcccctc    95880
cctgctggcc tgggagtttg ctgctcacct gctgtgacag tcaccaagct ggccatgctc    95940
cctgggaaac agggaaggga ggagacactc ccatcctgtc ctcactgcct ccagcctaga    96000
gaagggctct gaagacgacg gggctctgag gatgtgatcc cacgtgtcct cgtcctgagc    96060
agatgttcta ttcgtgtcca actgcagcct cccttcccat gacacacaga cgtacacaga    96120
tatcctgaaa tcagcattgc ctttgtatcc aacatggag atccttgcct gcaataatgt     96180
ctcgcttttt tcttcaatca ctggaacctg acttttcttc tgaaccacgc tatgtgtcca    96240
tgaacttctc aagaggttct ccaccttcct ctgcaacggc tcagctccac tcccaggcct    96300
ctcttgagaa tttccgcacc agctgcagcg tgccccctc ctctctgtga atttctcctg     96360
tgacaagatg cctatcgctt tgcttttgcat caggttgcat catatgatgt cagaaaagct   96420
gaaagaaaac aaagtgctgt ccctggggag tggggcactc acaacacaga aaggagcctt    96480
ggggagggc cgcgcttggg tttcacctgc agaacaccca cttctggctt caagtaacca    96540
ttctttagtc ccacattcta tattgccatt tgttttcat gagcattaaa aacgcattct     96600
tagttcttag gtgttttctg ggactcagag ttcattctgc tgtttcattc aaggttcagt    96660
acacttcttg attttatgtc cattgtattc caaggataga tgattaaaat atcatcaaca    96720
atctagggca ctttgtgaaa accttcaccc cagaactctt atccactgat gactctcctg    96780
gtctgctaaa aactcactta ttgtgaaaga ctttcctggg atcaaatgtt ttgaaataaa    96840
aatttatatg taaagaaaca ttgttttgtt taaaacagag gtaacagtat gacttgaatt    96900
ttattcgttt cttaatcatg attttttttt ctaatgatga cctttgatta aattgtataa    96960
```

```
aaggaccttg aaattgaatt gacacatctt ctccggtgag accttggtcc agctgctaag    97020
gtaggatttc tgacagtgcc ggctgtccag tggaactggc tgacaccttt tctcagagga    97080
caaggcacag ctgtgaggtt cttggagga actgtgcgcc tgccccattg ccagtgtggg     97140
gcccggtcca caggaaggcg cccctaatgt gctcagcgtg tgtgaagatc agaagcacac    97200
agatgcaaac atgggttagt aagtcacaca ccgtaactga ctcgaactca cagctctaaa    97260
acaagagtaa agaagatgaa attcatccag ttttgtcacc acctgtgcat ttccaccaga    97320
gaggaaacca ggcagttgtg aaatcgaagg ggctgggctg cccactcctg gcccacaggc    97380 cccctaccc tgagggaggt cctcaaggca aggacagga agcggtgggg ttgggagctc      97440
tgtctgatgc tctgttctcc caaaataatg tagactttc cactggattt gaggacgtgt     97500
tctcaagtgc atttcaggct tgggacaact ggaggcagtg ttggtggaca gctaaggagg    97560
gtgcaggaga atcactcagt ggaggaccct cattttgctt gctttggctc tgagcatgtc    97620
tgggagaatt tttttttttt ttttgagat ggagtctcac tctgtcaccc aggctggagt     97680
gcagtggcac gatctcagct cactgtaacc tccaactccc gggttcaact gattctcctg    97740
cctcctgagt agctgggatt acaggcgtgc gccaccacac ctagctaatt tttggatttt    97800
tagtagagac ggggtttcac catgttggct aggacggtcg caatctcatg acctcgtgac    97860
ccgcccgcct cagcctcccc aagtgctggg attacaggtg taagccaccg tgccaggcct    97920
tctgggagaa ttaaattcca cagttgaggg tggggccgct tggaagaagg tggggtaacg    97980
caggaaggga gccgggattc ggtccttggg cagagctggc acctggggct cacaacccttt   98040 gcctccttca gcctgtggat catgagtgcg tcagctgaaa ggggcatgaa accaacccta    98100
gcaggcatca gattttgtaa tcttatgtgc tctgtgccag agctgccgca acagtatccg    98160
ctgccggccc ctcccatttt tcctctcctt ccctttagag cagggagaca tggccacgcc    98220
tgacaaacgc aagccttccc tgccctgcca aagcccactg tctggcatct ccttatgcct    98280
cttgttctct ctccgttctg cagccctgtg ggctttcttc agttgtttaa acacagatgc    98340
tcctgtggcc tctggctatt tgcagacacc attcatttg cccggaaaga aaattaactt     98400
cctcttccac caggtgcttc ctatggttct tcaaaactca cctcgagcat tactccttca    98460
ggaatctttt ttttcagtt tcaaagtagg caaatattct cttggtgat gtcaccgtgc      98520 catgtacttc tcgagttgtt acgaaatagg gcaaacagtt ttgagataca ctgatgtaat    98580
tttatgcttt gcatttcccg gtatatgggc ttctcctacg caacctgggc agcctcctgc    98640
cctacaggga ggagggtgac ctgccaggat gcagacagcg ggtttactca tacgggggaag   98700 gatgggcagg ttctgcatgc taatgaagct atctgagttc acagaaacac acgaggcccg    98760
aaggccaagc tttgtagaga aagaaaaata tttcccagtt tgggaagctc ccttttggc     98820 atattcaaag ctaggcaaag tgtaattgat catagagttt tgtgtctgga aggtgtggtg    98880
gaacagaaag agaagaggga tggcctgtcg ggtgccacac catgggggcag ggaaggcaaa   98940 gcagagtgta aagcagcaca gtgccaggtc ctgtccacgc caagtgtggg gccttctcct    99000
caaggttgat gggcaggatg tggggtgagg gtgggagtgc atggcaaaaa tccagaaaga    99060
tggagggtcg cctgtcaagg gcagaggggc agtgcacaaa tacggccttg taggatgccc    99120
ctgctccggc acttcagggt ggtcttctca cagtgctagt gactgcacag ctcaaatagg    99180
tagagtgagg atctgagctt gctgtccttg tcactgtggc atggaaagca tcaagacatt    99240
cccacaggta catggagggc atggaaggag gctgagaaca ttccgagggt catctctgtg    99300
gcaaagggtg cctgtacctg gaacccaaca gaagtcactg acaacctcag ggggtccatg    99360
```

```
gggccagtga gagtaagacc cagtgggcac gaggaatggc tggtggttcc caggaaaaca    99420
gcctgaagcg aaacagaaca gctgttcagt caccacaagg tgtagttgtg aatggcaggg    99480
aagcattagg aggggtcttc aaagtggctg ggattgacgg tttggcaacc tggaagcgtt    99540
atggaaagct tggagcccga agagagagag agcacatgtt ggtgggtagc atgttcatag    99600
tgaccggctc tgtgttcaga tatacattag caacttggat ctaccacatg caaagtagat    99660
aacaataggt atgttttaaa aactctgtga ttctcaattt gctcattggt agaaagtcat    99720
ttagttgtga aaatttaata aagtaagtaa agcagagaga acagtgccct tggatagaaa    99780
gcacacagat ttgcattgtt gtcctgctgt tagtatttt agaaggtaag cttcaagatg      99840
gcaactcata tgtatctttt tcaccaaagg gttttcagtg gctagtacaa ttccatgatg    99900
taatagagac tttacaaaat attcctggag caaatgtata aatgaacgat ttgaagccttt   99960 aagttagatc agggtgattt atttttttaaa atgtcatata cctgtgttaa tagcagtgaa  100020
tgatgccaaa agtaatatgt gtgtgtgttt cagaactctt atcaagaaga tcactcatga  100080
taatatacag taaatataaa tgggtcaaac ttcctttaca aaagatattg tcatattaaa  100140
ttttatatac acatacatgt gtacgaagca aaatgacata gaaatagat gagtaaattc    100200 ttaaatgtaa gacaaaaaat aaaatgaacc ccaaagtgca atattaatat catcaaagt   100260 ggaacttgag agaaaataag gaatgagcga gggctacttt atattaattt tctaaagtat  100320
aatttattat gagaatgtag tagccagaga tgtttaaaaa ccaaataaca gcatcaaaag  100380
acataaaagt tgttataaat gcaataagaa actggcaaag cacagtctta acaggctact  100440
taacaatatc tctactttt atgttatgta cataaacttt acagagaact gaataattaa   100500
tatgttttat ttactcagta tttctttaaa gaaaatgtct tcaaatgtgc atcgtatagt  100560
taaacattga ttatagcttc tgtgtcaaaa aaaagctcaa tacaaagcat tcccataagc  100620 catatttga caataaacaa tagaatttaa gtaataaaaa gtttaacacc aaatctaaaa   100680
ccatgtggaa actaaaaata ctccctgaat aatccatgag ctgttaactc aaagaaaatg  100740
atagagaaaa ttaaaactga ataaagagat tgtttagaag atgccataat atatggaatg  100800
taacccacat tgtgctagga gaaaactttg taagttttca aggtttttat aagaaagttg  100860
caaatgaaat atccatgtta ctgcagaagc aaaaaataat ttaaaagcc ccaacaaaag   100920 catgagtaag aaaacgaaga tatagtagaa attaatgact tagaacctga aaaactataa  100980
caaatatagt aattcaaacc tttattcttt gatattaaat actactgatg acaaatcttt  101040
ggaaggctaa gagaaaagca gagaacatac aaatattcag cattagaatt caggacactg  101100
gggagaggca tagtggtgag agcagtccct tagccgaggc acactgggtt gacttcaccg  101160
gtactcagct gtgtgatcca ggaacgctgt ccagccttct tgtctcatgc cttggattcc  101220
cacggctcat agtgctgtta aaaaaattac attgagttac catttgtgat atggtttggc  101280
tgtgtcccca cccaaatctc atcttgaatt cccacatgtt gtgggaggga cccagtggga  101340
ggtaattgaa tcatggggc aggtcttttcc catgctgttc tcgtgatagt gagtaagtct   101400
cacaagatct gatggtttta taagaggag ttctcctgca ccagatcgat ctctctgcct   101460
gctgccatcc gaggtgtgac ttgctcctct ttatcttccg ccatgattgt gaggcctccc  101520
cagccgtgtg gaactgtaag tccattaaat ctctttcttc cgtaaattgc ccagtctcca  101580
gtatgtcttt atcagcagtg tgaaaactga ctaatacaat ttgtcgagta cttttataac  101640
agggtttcaa aaagaaaata tgtatgtgtt tcttatgtaa aacaagcaat atggaaagga  101700
```

```
ggttgcagtc cacagccatg agataatcca ttttgatatc tagctgaaat gaatgaattt   101760
ctaggaaaat atattaccaa atatgactta agaagagaca gaaaacttaa tttgtcagtg   101820
ctacaggaga tactgaagaa agtttgaata gagctatact tctgatggta gaaaggcata   101880
tattttgcat tcacgcattc atttaacaaa tattgattaa ttacctacta tgtgcctgat   101940
gctgctttta ttccactaaa agtacgataa ttttttttaat ttcaaaagaa atttatactc   102000
tgttaaaaaa tgagagtatc aagtggtgaa gattaaaagc aaacatcttc acctcctcta   102060
ctccccaatc tcagctgtct gctacgtatt ctagatattt ttaaattcct ctctctctac   102120
ctacctacct acctattatc tatctatctg cctatttgtc tagttgtgcc tgtgtatgtg   102180
tatttaagct cagtaggatc ctattatcca tttgttttgc aacttgtttt tcatgtgatg   102240
gatgtccctc cacgtcagca catggtatta taattatgca tattttattc tctttgaaac   102300
aaggtgaata aataaacctg tagcaaggga aacgctatct gtcaccaaaa ctcccactac   102360
tcgaagcgtg acctaaggcc aagatctgcg ggaccttttt cacaaccttt gtgcgtcttc   102420
ttagcttctg atggcagcca ctggttccta cacagcatgt tgtcccttc tgtgttgtgg    102480
gagcttttag agttttttctt ttattttggg gtctataagt tttatcaggg gacctgtggg   102540
tggacacaca gccctcagtg gatcactgta taaggaactt cagctccaga aaagaggctt   102600
caatcatttc tcctagtatt tcttctaat attttgttc tctatttgta aaagtctcta    102660
ttagtttgac cctcctgaat atatcttgca agacttttag gttttattc attcgtctgt    102720
ttatttttcc ttttagatct gggaggtttc tttggctcga ccctctagct gcctggtctc   102780
catggtggaa cagcccctct tctggacagc cagcttggca gttccattta attttcattt   102840
tgtcagttaa attttattta ccatacctct tcctttttcg taagtgctgt tatcttctta   102900
ttccctgttc cttaccctcc ctacctcctc ctcctcctaa ttgtagctaa ttctaatttt   102960
atgggtgcaa tttcctctct aatctctcag tatcaagttg gatttttatt attattatta   103020
cttctatttc ctctcaggtg agctgttttta tttgttcaca ttatcctcca ccctggtatt   103080
tgcctcctgt attgggtggc acttgatttg gttctttttt atgaatgaag atggggttga   103140
ttgcttgtgg gtttcctttg cagccaggca catctgtttc ctgctcagcc tcctccctgc   103200
ctggctaact acaggcctgt gtctgtggat gaggctccaa cagcaggaag aactatccag   103260
cagcctgggg acctcctcct gcccacgccc tcctgggcc agctgccaag ccaggagggt    103320
ttttctttcc tgagagccga taactacagc acagagactt cctcgctttc ttggttcaag   103380
tctctatcat tgtttcagta attttttttac agtggccta ggccagagca acttcttaac    103440
agttctgtgt ataagtagtt agagccaaac gacataatta tgcatgccct aacaacttag   103500
taactgtttg aaaaaccaat acatatacct ttaaagaaaa aacaaacaaa aacaaaacaa   103560
aacaaaaaac aacccatctt ttcttttgct ctgaaattcc catcacttag cagcgctgca   103620
cgcgcctgct ggggacagca cagcctcacc taccttggca tgagattgga gagccctgct   103680
gcgttttctg ttccctgctg gtttttcatac ggggcctgct ttttatcaga gcacctgctg   103740
aacatccagc cagggcctcg tggaaagtaa agtagcgctc ttgagccttg gatcggtggc   103800
tttgctagag cagacgtttc atggaggggc tgatggatgt ccaagaggtt gtgtttctct   103860
caaaaatgaa gaaactccac agcgcccctg tgggtttgcc ggggcgaaga tctgctgtgc   103920
ttcttttagg ccctgtaagt tcaccgacaa attaattttc tttaaaaact agtctttggg   103980
cttttgtcttt gggagaaaca atttctccga ccgtcatttt tcgactctat tttgggggat   104040
tggtggtagg agctgtagtg agccgttcca gctctcgccc taatgtttga ctcatggcaa   104100
```

```
ggtctttgcc tccttgactt tgctctcaga gcttttcta ggcttgcttg ggaagaagct   104160
ttcaacattt ctattccatg gctatttca ttttctctt ttccagtaat gttatgtttt   104220
catttatatg tattattttt ctcaaaagta acttgaggaa tagaaaaatt ggagccaagc   104280
cagctcctcc atcagccatt tgaatttgct tgagcttcta tattgggctg gacatcagtt   104340
ttaattctta aaattttatt tgaattagaa tggtgaactt tgaatcatac tgactctttg   104400
tggattccac attttatgtt gtcagttatt atccagctct acttgaattc taaatcacaa   104460
aacaaaacta ttcaaaccat catggtttct gcacttttaa tgtaagtatt tgaggttcaa   104520
agttagctaa tcatacaata tattccagag ttagtgagaa tggacactga aaaattactc   104580
ttttctggga taaggatgac taagaaccac agggaacaga gttcctctaa aatgagttgt   104640
tttcaaacgg aaataaaaaa accacaaaac attgcagaat tgctcatttt atcagatggc   104700
tgaaacttac atttgtaaaa atgcagtttg attgattatg atggctaagc cagggtttgt   104760
tgaccttgaa gaataaaagc ttggcacata cttattggaa agtgtgagcg acatgaaaaa   104820
gatataacga gaaatctttt aaattttgc aataggactc aagaaataaa agatgtcata   104880
tcaacacaag gtaaggcttt gcctagcagc cacttggtgt ggaatattta caaattgttg   104940
acagttgtat actttaatac gtatgtgcct ttccaaaata tgaaggtatc agaattttag   105000
atgaggtaga atattttca tacttcttct tttagtatgt cacagaaaca agttatttga   105060
tattatctct tttatatgta tagtacatcc atggatagca accacagtag gaagtaaaat   105120
taccagcaaa actcttgcca gggattgtaa ttagttatta aaaaataatg tctccctacc   105180
ccatattctc ctcctgagtg tattttgggt ttttcttcca ctgccaaagc cttaaagcaa   105240
atgtctagac aaacctccta cactctgata atttcaaacc tgctgatttc gagtgataga   105300
cctacatctt gatgtcattc tatgaatggc aaggcctgaa tttccaaagg ctctctggac   105360
atctgggcag tcatcagaac tcaccgtgcc ctaatctgat gggccttcct tccctgctgc   105420 ctttctcct gtatttcaca tttgagctgc tgataactgc agctgtccca gctgccgggt   105480
aggaacgtca gcctctcccg cgggacgtca atccctagca cggacctgtc tgacccttcc   105540
cctataccac gtcctcttgc ttctccctct gaaatatctc ccaaatcctt ctctctgcct   105600
tcttttccta ctcctcac tcacatgact gcctcgggcc ccattttcct tcacttggat   105660
ctttttgtga tggtctcttt acaaagacac tgttgctgga accccttttcc agaagctgag   105720 gtagaatcat accgctcctc tagaacctca gacactctca gtgcatttaa agacataccc   105780
aaattctggc aacatgacac aagtctgcac cctgtcctgc ctcatcttcc acttatttat   105840
gagctgtgtg tcactgagct ttccaaaata tacctttgt tttcacagcc cattcttctc   105900
ttatcctgaa atgaacttct cttctatgcc tctgacacct actcacgtat gaatgtcctg   105960
ctaacacacc acttccgcca ggacccaagt ttgctcatga accctcttgc ccattccagt   106020
ggctacttca gaactcgcca gatctttctc tcgttcccat gttattgatc tgccgtcttt   106080
gtttgctttt cacactcctt ctcttatcca agaaagattt tcacagcatc acactcattt   106140
aaatgtctat agctttagtt ctagactagt ttatcttctt gctatatttt tagagacaaa   106200
tttccatcca aatttactat gcaaaataaa attcttaagg aatctctaaa tcagaaagca   106260
attttggcat gtttgcattg tgtattttt ttattaactg agatttactc agaaagaatc   106320
aaatgagcca aaaatttgga gctgaaatgc ttgacattta accctctgg aaagaataat   106380 gttggtctta caatgaatta attgtacatt tttgaaacgt gtaagatttt taaaaagtta   106440
```

```
tatgttctag ttgttaagcc attagaaagt ttgggtaagt ggcccctttt gtaggaaatc  106500
ctgtgtgcct cacagtctct ccatagcctg gtgagtagca agtgagaaat attttgcaat  106560
agaaaacaga aaagtcaagg ctgaggaaaa atagaatttc caccacaaat atctgataaa  106620
tttatctagg agccaaattt ggggagctat atgggtagtt caaaatctgt ttgtattctc  106680
ctactggaca gaaagaggaa agtaaatgga ttaatcaggt agattggcat ctactgatgt  106740
aagcaacagg tagataaatg ggatgaatcc agtcatcctg gttcttactt ttctgtgttg  106800
ggatagaaga tggttttctc tcataagtgg atgtaaggga aactggtggg gataatgtgt  106860
tgattgaaat ttaaattttc ttatggaaga cttgttgaag aattcaattg ttttattcca  106920
acaatctggc agtttggatg cctgccatag ccttaccgtg cattagctgt gttacctcaa  106980
acaaccagc tagtcttcct tggcctcagt ttccttagct attgaatgag ggtttggact  107040
gggcgatcac atagatctct tttggtggcc aaatcctgtg gctttgtgat tctgtgtaca  107100
gcccagttgc ttattctgtg cagttagacg atagcatcca gactcatgca ctaggggtgg  107160
aaaccgttga ctccttttctt ctttcttcct ttagtttctg aagcactcct ctgtgactac  107220
acattatcag tttcttcttt ctctctatat gttttttttct ttttttccag ataatgcagt  107280
tccccttgac tctaatccca aactgctttt ttcctccctg accctacata cagttcatcc  107340
aagacaactt catctgtaca catgcattca actaccatac tgttactatt agcttggggc  107400
tctttccgga gcttcagact cctgtcttcc accccatgg acatctttgc ttcaatgccc  107460
tgtgagtgtc tctaactcac tatgtacaga gctgaattca ttatctgttg cccttaattg  107520
atctttcttg ccatggaata ctaattgact tccttctctt ccatgtaacc acctccaatc  107580
catcttcaat ctgtcaacag aatgatccta ctaaaaccca gatctaatca tgtctgtctc  107640
atgaggaaaa attttagtt tccctattgc ctccagaatg catttgaaac ctctttctag  107700
ctctgtacag ccctgccacc tgcttcttga gtctttatgc actactgcat gggcccttca  107760
gccattcagt aaaattgact ttttctcttt tagtgcatag gtctatcaat tttgactcat  107820
atatagattt gcgtgatcac taccacaatc aggttacaaa caattccctc acccccaaaa  107880
ctccttgggg ctatccctttt ataggctcac cctcctgaat tctgacgcca gcacccacta  107940
ttctgtcctg catcactgcc gatgtatctt tccaatgctg tcataccagt gcaatcatac  108000
ggccctcacc tattgaggtc agcttcatta gctcaccgta atgcctgtaa aatccatcta  108060
agttgttgat tcatgtttgt cccttgctgg gttgtattcc attgtgtgga ggagccacag  108120
ctgattattc actcactttt ggaggggcat tttagctgtt tccagtttgg acaattatg  108180
aacagagctg caacaaacat tcatgtacag gttttttgtgt gaagacatat tttcatttat  108240
ctgggataaa tacccaggag cagaattgtt gagtcatgtg gtaagggcat gtttaccttg  108300
ataagagcct gtgaaaccat ttttgagagt ggatgcttgt atttttttaaa caagattcat  108360
agttgactct gaggcccagc caggtttggg agccagagcc ggaataatca cttacatgtt  108420
ggtcgttcgc acacactaca ggttgcttaa caggactctg tgcctgcatg tttgtgtcat  108480
ctctgcaacc tcaaagccta gtgaagattt catcttaact tgattgctat gtgtttgcat  108540
agttgaataa ctaagagaga gtgctcacag cgtggctgct cccactaagg tgtagtcaga  108600
acatgtgata tacagtacag atgatttttcc acacttctct cctgcacgta acaaaattac  108660
ttttagtaat gatcatgtaa gactcagtag tagtaatgac tttctttaat attatttatt  108720
aaatatttta ttaatatt tatatttata taatatatat ttatatttat ataatatata  108780
tttatattta tataatatat atttatataa tatatattta tatttatata atatatattt  108840
```

```
atataatata tatttatatt tatataaat atattatata atatataata tatattatat   108900
aatatatatt tatatttata taatatatat tatataaat atatttatat tatataaat   108960 atattatata atatatattt atatttatat aatatatatt atataatata tatttatatt   109020
tatattatat atatttatat aatatatatt tatatttata taatatatat ttatatttat   109080
atatttatat ttatttatat ttatatatat tatatattaa atatatgtta tatataacta   109140
tatattatat attaaatata tgttatatat aacatatata ttaaatatat attatataac   109200
tatatattat gtattaaata tatatattat ataactatat attatgtatt aaatatatat   109260
attatatatt gtatattaaa tatatattat acataactta tatatgatat atatatatta   109320
tatattatat atgaaatata tattatatat aactatatat tatatatatt atatgaaata   109380
tatattatat ataactatat attatatata actattatat ataatatata ttatatatta   109440
aatatatatt atatattata tattatatat aaatttatat ttatatatat tatatatttta   109500 tatttcttt aatattaaaa tgagtagaaa tcagttaaaa ttatacattt ctattttaa    109560 aaaaatttt cagattcagt aaaatgtttt atgaactgac atttgcattt actaaacaaa    109620
aatattacat tgtgcagttt gtcccctgtt gcactgtttt agattttaag cacaaacttc   109680
caaatggtcc cctctgatga ctgaattaaa ataagtcaag ttgtgttcct ttattttgac   109740
aggcactgtc ctgtcacgtt taatttagaa tctaaggttt aagtgcgaga atatgtatta   109800 tccccgggt tggagaagca cctggaacca gtgttaatag tttactccat ccagctcctt   109860
ccgttcacat gaaggcgggg ggctgggtgc ctgtgtgcca gggtcagctg aataacttgg   109920
agttttctgg aataacttc ctgtagagta tgatgtttat taagtgataa agatacaaat   109980
gaattgattg aagcttgcat aggtgtataa gtttcgccag actgctgtca caaatgacca   110040
caaactgtgt ggcttaaaat aacagacatg tattcctcat ggttctcgag gctggaggtc   110100
tgcagggctg gttcctttgg aggctgggag aaggaatcgg ccccctgcct ctctccagct   110160
tctggtggtg gctggggcca tcggggtact gcttggctct cagacacatt gcctgatctc   110220
tgctccatgt tcacatcttc cacattctct tgtgttgtct tggttttctt ccctcttct    110280 tatcaggaca ctagtcactt tggatgaagg acccaccata cttcagtatg gtttcatctt   110340
aacttgattg cttctgcaaa gaccccccac ttccagataa agtcaccttc acaggtacca   110400
ggggttagga cttgaacata gcttttggg cgatgcattt caacccatca cacacgcgca   110460
cacacgtgca cgcacacaca cacacccaaa tatatgtaat gaaaactcaa cagtcacaag   110520
agcaattatt tagaactttc atcaacaaat gattgtgtgt gtgtgtgtgt gtgtgtgtgt   110580
gtgtgtgtgt gtaggactgt ttcatcacta actgtgtttg gaatgactct cttgttggga   110640
taaaagcagg ccagttttgc ttggcttact tatcgtgtat gaattatctt ttaacagaaa   110700
ttttctgtac cccaggcaag accattccct tcatcccagc ccaggtagct gctgtcccca   110760
aacaccctca gtgggcatga ggtggtcctc ataattcctg gtgatgtcca tttcttcttc   110820
catgttttca aacagcggta tggcactttg aggtgaaata tggctctatt taatgtcact   110880 ggttcttga agctctgagt tttctgggac cacaagtttt acttgaaggt aagcaattta   110940
aagtatttta atataaacat aactacagta taaagtgtga tgcgtatatt acatatatct   111000
ttagaactaa acatgagatg aaaaaatatg aacatggttg cagggccctg aaatttcttt   111060
cctctgttac tgtggtaaac aaagcaaagt aaactaagac agtggaaagg gttcatttca   111120
aacctgtaag atatgtccta tctctaagtc tgacttgatc atttgtttgc tctgatgcat   111180
```

```
aaatggcaat ggaaataata ccaccttctt cttatcccag taaacaagtt tgtgagcaaa  111240
taatttaata tggggaaaga gcttctgagt tctcagagga tcgccatttt ctcagagcta  111300
ggagatgact tagtgcgggg ggtgagccat cttttcggcc agttcgtgaa tgtcttgggc  111360
tttgtgtggc agaccttctc cgatcaaaca actctgccgc tgcagcttga aaacaaccac  111420
agacaacaca cacacaaatc cagcgtggct gtgttccgac gcaatttgac aaaaacaggc  111480
actggccaga cttggcccat ggactgcagt ttgccagcct ctgaacttag aggaaaaaaa  111540
ttggaagaat ggagtgaacc ttgagcacag ggaggagcag gcactgaagc tgtctgtgtg  111600
ctcttttcct gtcttgatgg agaacaagac atttgtatgc tttcacaaaa caagacaag  111660
tgtaactgtg agttcaaaga ttacatcatt gatttcagta gtgttgatac tttaagcatt  111720
tgctatgttt cctctgagct attgggacat tacactgaga tgcagtcggt ggtatgggga  111780
ggtgctcagg ggttctcctc tctgccctca ctgcttggtg cttacagaca gctactgaag  111840
cagtgccttt catgctgggg agcctgacta tttgcaggtt gttaaatcaa tttaatgggt  111900
cgtggtctgc atttgaaaga atagaactgg ctcaacttcc ttgggctaga atggaaaatc  111960
acaaggtaca tcctttatag tattttgtga attttgttg tacacttgaa catatataaa  112020
catatatggg atgcatacat aataaagaac tattagggga aaatcaagct gttttttgta  112080
aagttaaaac tttggaaaga gtatagtcga gtcacaaact tttctctgtt aagttatacc  112140
tagatgtgat gattgtgaaa aattggcaaa caaaaactct agaaaagtt tgcattcaga  112200
ttgtttccca atggcttcct aagttactga aagacatctc aactagaatt taggaataga  112260
cactttcagt gttatgtatg ccaaataata ataataataa taagtgccga actctaatcg  112320
actgatccat ttctgttgcc caggctggag tgcagtggca tgatcttggc tcactgcaac  112380
ctccacctcc tgggttcaag caattctcct gcctcagctt cccaagtggc tgggattaca  112440
ggtatgcacc accacacccg gctaattttt gtattttag tagagatggg gtctcaccat  112500
gttggcaagg ctggtcttga actcctgacc tcaggtgatc cacccatctt ggcctcccta  112560
agtgctgaga ttacaggcgt gagccaccat gcccggccct gatccatttt taagaaaagc  112620
ctttatcctt aaagcaaata ttggtgcatg agtatgtaat gtatgaacac gtgatgttta  112680
tgatttccaa cttgcagtca ccttttcttt gaactgttct aatattttgt tcagtcctca  112740
tttgtatctg ctgaacctcc ccttgagggg attgtcaggt accctccttt cgcctgtgag  112800
ctgagggaaa ggtgagaatg actttagggg aagagaaggg tgaaaagtac caatttccaa  112860
ctcttcctcg caatcttgaa atgtttgatt ttgatctcat ctttgcactt tcccctccct  112920
gccgtaaaga gagacacaca gttctgtgct gggctaaaag catgtttgaa aagtaaagaa  112980
attggaatat aagatatata tcagtccaca ctggactgat gtggccaggc aaggcaactg  113040
acctcttcta acgttttcct tcttccagca gagcacgtct ctgtcctctt aagaggccac  113100
atgtcaggtg tgtggctctc tctgactctg tcctaatggc agtgccttcg tattttttgt  113160
ttgtttgttt ttgttttgag atggagtctc actctgtcac ccaggttgga gtgcagtgtc  113220
acgatctcgg ctcactgcaa gctccgtctc ccgggttcat gccattcttc tgcctcagac  113280
tcctgagtag ctgggactac agacatgtgc caccacgccc ggctaatttt ttgtattttt  113340
agtagagacg gggtttcaca ttttagccag ggatggtctc gatctcccga cctcctggct  113400
ggtgatccac ccgcctcagc ctcccaaagt gctgggatta caggcgtgag ccaccatgcc  113460
cggccggcag tgcctctgtt tttatggcat gagggcagcc ccggtgaact gggggttcttc  113520
gtggaggagt gtgcccgtgc gtgacggaag catgcgcctc ctctgacctg gatgcaggct  113580
```

-continued

```
gggatgccat cggcactggg gctaccacat ggtgctaacg ggctcagaag aagccagcac   113640
agggtgattt aaacagtggc cagtgatcca gggtcgccag tgctgaagga aggaaaaatc   113700
aatgttgaat aatatacttc acagccctaa agtagactca tatgtaatgt tgagacaact   113760
aacaatttgt aaagaggaca gtactaagca gaagagacga cagaaatacc ctgctttggt   113820
ttcgtttgat gaattttctt gaggagggat ttctagggca gttcaaaaag aaaacagaaa   113880
gcaggtgaca ctcaggtgaa atattcagca tccatctcct ttgtgtctaa gccctggtga   113940
gtctgtgtgc aatcagctaa gggccttagc ccatggaccc caggctgcag gcagcccttg   114000
ctcactgaga ctggggacca caccagctga tggcctccac tgggttacat gcccacaggc   114060
agctgctgag tctcaggata gcgggaagaa aggtcctgcc acaagaagac atcaattaac   114120
aaaaaataga taccataatg taaagcaatt acgtggcctg cctttggaa acttctgggg    114180 agaggaggga ggaagtctaa acatgaattg caaatgctgt acatgaaaac agtatgcaga   114240
tatatttagc tctatcaatt agttgaagtc acaacatcca gggatgtttt cactaatgca   114300
tttcattagt aaatatctat tactattggg tatttattgt taaatatatg catgcgaaaa   114360
gacagactaa ggaacactca agtcctcacc tctcagcttt gctgtatctt agcattttgc   114420
cacattcgcc tcagatagtt tttaaagaat taaaacatta gatgctatgg aagcccattc   114480
tacctcttac tgtgacttct aagatatttt caatgattta agaaaaattt tgaaaagcaa   114540
tgaagtcaaa cagttaaaga cactgctgcg tggaggtttt ccctctgatg gtgagatgca   114600
gacgctgcac tcagaggaac atgagctggg aaatggggag tctgaagaga agagctgagt   114660
tgcaaacaaa tgtccttttt gcttccagcc ttagctttgg ttttatgatg gataagatgt   114720
atttgcatat tatgtcctct gtccaatagc atattccaga caggggtttc tgggggcatg   114780
attaggaaat aaaatatatt gctgtacagt tgactatggc aagcaaagac tgcagacctc   114840
aatcacttaa cttaatataa atgttggagt tatcacagtt ggacaaggat tatggtgatg   114900
ttctctacat ttctatgaaa aagtcactat ctggtagtgg ccaccgagct tttattaatt   114960
ttgttattgc acaggagaag gaagtcattt cgaggcaagt gtttgcgccc tgatattagt   115020
aaaacttcag agggctcagc catcccctcc cactgccata ttttttaggag aaacagcagc   115080 tgaggcctgg agagaggtga tgtgagattt gtagtgagag atggaaagca tcctggagtt   115140
attccaaaaa gtgatcaggt agaacctcta tgcccacgac atagtgtaaa tcctttgtaa   115200
aaccaacacc caaagcattt ggggttttgc ggtgctagtt tcaccacgca gtggcttgat   115260
tttgaacact gcccttttgca gacctagcac catggaaacc caggcctttg cggaggacaa   115320
cgcggcctgc gtgctcccat cctggctact gttcaccaag tgtgggtgac cctgggaggc   115380
tgcccttgct tgtttacttg ttttttcctgg ctgttgattt caaagaaatc tcggtcaaat   115440
gagaaacccg ccaacaattt tgaggaaata cagggatgag ctttggcagg aattaggtac   115500
gttctcaaag caggccttct gcccgaagtc acagtgaatt ccaacacca caggagctca    115560 tctttctttg tccctggtgc agggaaagta aataagagca caattagtgg aaaccataaa   115620
gagaatgctt tgaaacttgc atctgagatc aagccaacag gagtttctgg tagaggtgat   115680
attggaattt tgaaaagaca gaaatgttca atccaaagga ctttgacttt tgcttatct    115740 cataaaagaa gtcatttgga ggctatttaa atgtgtaaaa ggtacaaagg ctttgtggac   115800
caattagttc taggagggtt aaagagcaaa ccctgcccag agccggtgca cctgctggtc   115860
cctcttcctg cttcctggaa tgctcttgtc ccagatagct gtgtgctttg ccctgaattt   115920
```

```
ttctttcggt ttcccgttta aatgtcactt tatctgcaag gccatcccett accactctaa  115980
gaagaatttt tctttctgtc cccttgatcc tgccagtttt caataacact agcatctgac  116040
attttatttt attaaatgca tattgcattg tttatctcct gtttatccct tccagaatgt  116100
aaattctctg tgaccaggca cctgtttttt ttttttgttc ttgcttttg agtcagagtc   116160
ttgccctggt tgtccaggct ggagtgtagt ggtgccatca cggctcactg cagactccgc  116220
ctcttgggct taagtggtcc tcccacctca gccttccgag tagttgggtt ggcaggtggg  116280
caccacaatg cctggttaat ttattattat tattttttg agacggagtt tcactgtcgt   116340
tgcccaggct ggagtgcaat ggtgcagtct ggctcattg cacctcccag gtttaagcga   116400
ttttcctgcc tcagcctcct gagtagctgg gattacaggt gcatgccacc atacccggct  116460
gattttgta ttttagtag agacagggtt tcaccacata ggccaggctg gtctctaagt    116520
tctgacctca ggtgatcagc ccgcctcggc ttcccaaagt gctgggatta caggcgtgag  116580
ccactgtgcc cagctccaat ttctaaattt tttgttgggt ctcactgtgc tgctcaggtt  116640
gatcttgaac tcctgggctt aagtgatcct tccacctgag ccccacaaaa tgctgaaatt  116700
acaggtgtga gttactatgt ccagcatcct tggtatgtgc ttaataacca ggactgaacc  116760
aatgtttgga gtagaattag tttgcttaa ttattcactg aatgaatgat tacataaatg    116820
actaaataga agttaaat gctaaattc tagactccag agtttagagt gaattagtgt      116880
ttgtttttg tttgtgttgt atttaagcaa cttatttata cctcttcaaa agggtatctt    116940
tggtgtctta taaatgtac atagaataat ataaaaatag atcctgaaat cagagcaaag    117000
agaaaaataa gagtggcttc attcttgtag cagaaaatct gtattctaaa aatacatttc   117060
taatatagtc taagacagag catgggaagt gaaaaacatc acaggacgat ggttctccaa   117120
cttgattcct gtggaaaacg tgtactctgg aggctgaacc tggggtttta ctattaaagt   117180
gagataatga tcgtttccag gtgcacatac aaggttgaga aaagggatag gcttttttca   117240
atttaaaaag ttccccaata acttttctt aaatctttgg aaattctact gcttctctgc    117300
tggaaagcac ttaaattgat aagaaaaaca gtgaacaagt accaaactct caaccgagta   117360
ccttggaaat agctacctga gttagcctga cagctggatt ttcatggaca gctgtgctca   117420
tagttgtgaa tttgtattgc gtgatttaa tgttgccata cttttaatcg ctaaaataac    117480
cctagttcaa aaaacagagg taaacattga tattttatca tgtttcgtaa cttctgatg    117540
tttcattccc taagtaattt taagaaccct tgtttagaca tctggcttta tgggacaatc   117600
aaaaatatga tttgagttct ttatttcagg acaatttatg cacataaatg tgctacagaa   117660
ataaggagg agtaggtttt acttaagccg acttttgtttt ctcctgtggg atgaagagca   117720
gctcttttcca ttgatctgat tgtcccaaat aatgtttcag tgcttcagtt cattttgacc  117780
acgtggtcac accccaaaat gtcagccaca acattacact gtacacacaa aagtccagat   117840
ttaccgctgt acctttggtc caacaacatt tatatttagc ctccaataaa ggctcaactt   117900
gctccaagag attttaatg aagagcacca taacattccg gttgcaatta tgcagtgaat    117960
ggcaaattcc agaagcataa gtaaatcaat ggagaaagca caatgatccc ttctacacta   118020
gcatctggat ttttaaaaat ccacatagcc tcttccttcc tttctccctc cctcccactc   118080
ctccttccac cctctccect gctgggcatg tgaggcttgc tccaagcttg attctgagtg   118140
gagttttcgc atttctaacc tgcacagagg ccgggtccag ccttaggtgg ctgtcccatg   118200
gtggacttgg ggctgccata cccagttcat tttctcaacc cttcacttca tttttcgcccg  118260
ttgacacagg cttagtgggc tccggatttt attttttta attccaaacg gttgcctaac    118320
```

```
tttcccttt cgcctaaaca cgatagagct gtctttcttc gctggagctg cttgcacggg 118380
cacggtggca tttgctgcta tttcagctct ttccacgcag caaatctgct ttccccagcc 118440
ccgaagtaaa catcacccttt tccctagttg acctgcctct gctgaaaaca cacccacccc 118500
ttcctgctcc aattacaaac ttagacttga ctgtgggcca agttgctttt cccacaggag 118560
caatgtctct gcctcacact tggttttttcc aagggaggcg gtgactgagg ccagcacaga 118620
caatgctcca gcctttgtat ttgctgggcc acagagagcc acgtaacatt tattcagatc 118680
cagtgaaacc taatgcgagg aagccaaggg gaaggtggtt tctcctgcgt gccattttca 118740
aaagtgtgcg agctgtctgt ccaactacac atctcttttt aatcatgtct gctgaggtct 118800
gacctagatg tgtcccatcc ctcacttcct cttggggtgc ctaagagggt taccatttgg 118860
ggcgatgaca ggtgtgtcct ggaatgggcc ctgttacaca ggtggattga cctgatcctg 118920
ggtgtgtgag caaagcccag tgctagcaga ttagttatgt cataaaacat taggaaatat 118980
tttatacagt ggagataagt cggagaactg caggctgctg ggttaggcca aatcgttctg 119040
gaagcagggt caaatgatct tatatactgt gtttgcctga cttggtggag ttgaaactaa 119100
tgactcttct tcgctttgtg gagcaaaact tccaaactgc attatatttt tggctctgac 119160
cttgcacctg ccaccccaca gccccaggca tcattagaca ccagcacaag tcattttctg 119220
aagacgtgaa ctcctgttgt ggtttatttg ctttcatgac ccaaagacct gtcaggcttt 119280
gagttttctc tggtagcgag tgttccctct ctgcacctca gcttgtagag ctcttccatg 119340
ggaagtcaca gagtttatac ccagggatgt ggctgcattg atgctgctgg caggggctgg 119400
ggggagggt gtcctgtttc agcttctaga aagctgcctt tcccattgcc tacaacggtc 119460
attgcatact ttcaccatttt tcattttccc ccaactccta ccttatccct tccccaccct 119520
ccacactgaa cacccaactg tgattttgac tttttaaagg aaacagatac atcaggacaa 119580
acccctcaa ctttcaggtt acttttctac caactcattt ctacctgttc acatacctgt 119640
tttaagctca tatcagagaa gttattcctt ttgcttttca agaaggcact caatactgct 119700
ttttttccta tcaatgtatc aacgaatctg tcatcttccc tctgtttctt accctttgc 119760
cactgtctta aaaagtcaag aaaaaacctt ctctaaacct tcaatgttaa atttctcctt 119820
aatccttcat ctcctcctcc tcctcctctc tgtatttctg tttatcactc attttctaca 119880
ctcaaaactt tattaccgtc atcacgatgg tacttgccat tttatattca tctaacacat 119940
ttattgagca tttttttttta aatgtcaaaa atggggttgg atcttggggg atagaaaaga 120000
aaaagctaca gttgtgaagc atccatcatt ctcagcaatt atcttgttta tttatacaat 120060
tgcctatttg cgagcatcga agtcacagag cctgtgcttt cactgctgta tgttgggagt 120120
gctggctgtg ggatagggc tcataaaaag cttttgaagg aatgaccgaa gccatcacca 120180
ggagtttacc gtagaggaga catgagcacc tgatcacagc tcaactgtgc ttgtgatggg 120240
gtgtggggaa tgtcttcaga actgcagtgg agaaagcact ctgactttgc ctacgggtgg 120300
tgggaggttt tcctggagct acatctgaaa ggatgaaaag gagtaagtcc agtgaaggag 120360
gaccgaggga atgggaacat tctaggcaga gaaagggagc agaaagctca tgagtgaggg 120420
gctgagaaca aacttgatgc attcaggac tatttagctg aaccaagctc ggggaggaca 120480
agatggccag gtgtggactg gagggaggga ggtaaaaaag gtgagcatgg gctttgtacc 120540
tcgtgagtat gggagcatgg ggaaggagg cacgtgttgg cattggtgga gcccctcatg 120600
agtatgggag catgaggaaa ggagactcag gttggtattg tgaagacac tcttgatttc 120660
```

```
agtgcagaac tcattaaaat agtgcaagat taaagcaggg tgacctttct aggaagccaa   120720
gggagggcta atgatggtgg gagcactgtg atggtgggag cattgacagt gatggtgcaa   120780
ttggagggaa gatgacaggt tcaagcaacg ttgggctaaa aacagactga ccttggagag   120840
atgaagggct cactctgtgg ggaaggcgag acgtggagga cacacgcctc tgctgtattt   120900
tggaatgagt tttactgtca aaacaattga acctatgtta tttatcactg ttttttcttt   120960
tctttttttc tttcacaaaa ccagttgctg tgctctagtg ggtcaggtga gccagctcct   121020
aggtaaggag agttgtgtgg ggctcctccc tcaagccgcc tgcgcacttc attccagcct   121080
ctgcacaagc tgtggattg tgtttcccgg tccaggtctg ctgtcctttc ctgtcaccag    121140
catctcccag agtctggcag ggggtttgtg gatcgacagg tccacctgtc tgtgcttgtg   121200
tttttatcct tttctgtgct ttcctactta ctctaggaag gaattggaag tgtttgagcc   121260
aggcactgtc agatactgtt ttagttctga agtaccctct gcttgaaata cgttggggg    121320 gagcttgtaa cttgtagaag aaaaggagga ggcactaaag tgaaccgctt ggtgttcaga   121380
acttcgcagg ctctgtgctt atgtgtatgt gtgtgtacac accagcactg gctatgtgca   121440
aagaatgcag tgtttgggga aaagcataga atttggaatc ataaacctga ggtttgtcag   121500
ctatgtaatc gcagtgtttg gccactctaa acttcatttc catcagctgg aaaataagat   121560
gaataaatca tcagtcccgg acatctatga ggaagacatg aaataactat gcatggtaa    121620 gtgtttagtt cagtgggtga tgacaatgat tatgacatac gattatggaa aaagcccctt   121680
tccttccaaa atccccaaaa tgaacaaata catacgttgt tatggtataa atctggtttt   121740
catgttatac aaggagttat tagaacaatt tggaaattct ttccaaatta aagctctttc   121800
tgtatgttga tctaattta aaaatttct gtttttatgt ataaaaagca atcagggcca     121860
ggtacggtgg ctcacacctg taatctcagc actttgggag gccgaggtgg gtggatcacc   121920
tgaggtcagt agttcaagac cagcctggct aacgtggtga aacgctgtct ctactaaaaa   121980
tataaaatta gctgggggtg gtggtgcatg cttatgatcc cagctactag ggaggctgag   122040
ccaggagaat tgcttgaacc cgggaggcgg aggttgcagt gaatcaaggc tgtgccattg   122100
cactccagcc ccggtgacaa gagtcaaaac tctgtctccc gcctccccc caaaaaaac     122160 gcaatcagcc atgattataa aaaggaaaa atgtgttact gaaatttact taaaatgttg    122220
acaaaaagat gacaaaataa tactctggaa tacaagccta gtataaatgt ttttatttgt   122280
tgcatttaca atttaaagca gaaacttgtt taagttttg catcgcacat agccaaaagg    122340
aggatgtggg cgaagtggcc aatgtcattg tttaggcct gtgcctggaa tgtggcgctc     122400
ccactggtcc tgctcacagc tctgccatgc cccctgacct tggtgtgctg tttcacaaga   122460
gcatgccctg gtgcaggatg agggacaggt ggctggagag gatgggcagt caacacagtc   122520
catccttgtg tttggaaaca catgttcact tgtgtgcaat gttgggattc gtggagaagc   122580
tggctggaaa gttggtaaag tatccagaag acaaggtttt gccccagcta ctcatcatct   122640
gaacagccag gtagattcta ctttgcagac tgagcctaag ccttgaactc tatcgggaaa   122700
taaacagaga tggtgaactg cgatggaacc caagtgcagt tagttacagc aaacacatct   122760
catgtgaata cataactccg ttgtgaatac ataactctgt tttccaccct taatacccat   122820
cacatctaac cccaatacat ccaggaagta tgtagggtct ccacgacaca gaccatcatt   122880
gatgtccttg tctgatgagg gcagggggaag agctgataaa acacctggag acaattctgc   122940
ttggagaagg tagcttggag acccttgcct tgcttctgag catgacaacc agcaccactg   123000
ctctgggccc taatggcaca tgcccccatt gctgaacctt ggctctatgg ttcataggtt   123060
```

```
acaattagca ctattgtgta attctgtgtt ttctagttaa ctgcacaccg tcttggctct  123120
tcaccatgta cgatattcct tatttagtcc ctggaccttc tcatctggac ccgttattac  123180
ctcttcccct ttcgtgtccc atctctgctt cctaagccaa tcaaagctcc ccatatgggc  123240
tgaggcttca gcttctccac aaggttccct cccagaaagt accttatctc cataaactga  123300
agtgctattc catcctcaaa tccagtccca gatgccctcc actcaggagt cagctctttt  123360
tttttttttt ttttttttgg tagaatttgc ctatatctct cttatggtat tgatcatttt  123420
atagctggtg gggttggtat ttgtggatgt gttttggcat tccttctgga ctgtaaactg  123480
ccaagaacat gaccatgtct tggttttta aaatacttt caacatttat cacactgttt  123540
ttcccattat aggtgcttag gaactttatt gtagggatgg caaggtcgac tcctttgttc  123600
ttgcctcagt ctgagtgttt atgccataaa acaatgtct gtgcaacaat ggcaacaaca  123660
acaagaagtt acacacagtt ttatttcctt tttagtctc tacctaaaaa gtttgcactg  123720
aaaattggac catagaatgc ctaaaattca ttcattcaac aaatacatat tgattatgca  123780
cctactatgt tccaggtaca ttaacgtatg cctcccccgc cccttcaaaa aaatccctg  123840
ccttattaaa cttatattct ggaagaagaa gacagataat aaactataga cataataagt  123900
acataatgca gtatggtaga atatcataaa tattgtacac acaggaaaac aaagatatgg  123960
gtgatgcgct aagggcaatc ttaagcaggg tggtcaggct gaacctgatt gagacaatgt  124020
gacaattcag atacagagag aggtgagcaa agtttgcatt taatatgata attgttcaga  124080
ggcataaatg gaaagaatt tctatttgga atgtaatttg taaataaggc ttgtgggttt  124140
tcaacattag ctactttttt ctttagcctt tataagtctg ctagaaataa tgaaatcaat  124200
tgaataatga ggtagagttt ttattataaa ggggagattt atgaacccac aataaatggc  124260
tttgaatctt agttttcaat caaggaccag agtacctaat atttaatctg tctgtctgtc  124320
tatctatcta tctatctatc atctatctat ctatctgagt ggattctctt tagtcttctt  124380
tctcatctct aatctacctg gatgttgttt tgctatttta gtttcctaga atagcatttc  124440
ctctttgact ttttccttta actctgcttt ttgtctttgt ggtgactaat tgatgtgtta  124500
aaaaaataat atttataata tttgtattgc atttcatcac agctctgtag ttaaaaagta  124560
taaaaattgt tttcaaaata aataggttta ataatacata aagccaaggc tcgagatgac  124620
tatttttcat tacaaaaata gtcatttaga taattgactt tcatttaga taattatttt  124680
catttagata attgtagatt cacctgcagt tgcaagaaat aatacagaga gacttgaggt  124740
acccacttgc ccccatggtg atattttgca aaaacatggt ggaactatta cagccaggat  124800
atgggcgttg acacagtcca ctgattttat tcagattcc tcagtagtgc cagtagtgtg  124860
tgtgtgtgtg tgtgtgtgta tgcatgtgta tttgcgagtg tgtgcctgca tgtgtataca  124920
tgtgtgcaca tgcatgtgtg tacacgtgcc tgtgtgcaca cgtgtgtgca tgtgtatgtg  124980
tgtgtctctg tgtgtgttaa gttctatcca cttctctcct gtgtaagttt ttatattcac  125040
taccagagtc aagacactga acaattccat agcctcttcc ctctcacccc acttccccca  125100
tccctaactt ctgggtaccg taatctgtct tccatttcta aaactttgtc atttcagaaa  125160
cgttacaaaa aaagaatcat atgtcatctt tgagaattag attttccac tcagcataat  125220
tttctgaaga ttcattcaac gtgttgtatt agtacttggt tcctttgcgt ttctgaacgg  125280
cagtcctcag tagggaggta ccatggttta tttcaccaat cagctgttaa ggatgcctgg  125340
gctgattcca ccattgggcc attgggtgat gatgaataaa gctgctccgt acattcctat  125400
```

```
acagctttcc atgtgataca taacatttgc tttcataatt actcttgatt aagattcaga   125460
atttgaatgt tgaccttgaa ttttaacata atttctctgt ccttatgtaa aattggcttt   125520
agtaaaattg gttgccaatt tgtgttcaga tgtatatgga taaggaaact ttccaaagca   125580
aatatataaa atgtttgaca gaagtacaga agtattaatt acattttaaa ttttttataga  125640
gaacctcaat gaatgaaatt ggggatttta tagcattagg taggaaatta tataacaatg   125700
gaatttgttt ttaaatagaa acattgtcat aactgttctt aaattaaggg gttgaattgt   125760
gtcccccaaa atgctgaagt cctaactctc catgctcact caccagtgtg acctcgctta   125820
gaagttgagt ctttgcagat ggttaaggtg aggccattag agtgcctcta gtagaatatt   125880
actgatgttt ttatagaacg ggaaaatttg gacacagaga cacctgtaga agaagatgat   125940
gtgaagacac acagagagag gacagccacc tacaagccaa gggaggccaa ggccagaaga   126000
cactgggaga gcacggggaa cagattttcc cttggaagga tccggtgact ttttttttt    126060
tttttttgaga caaggtcttg ctctgtcacc caagctggag tgcagtggtg caatcatgtc   126120
tcgctgcagc ctccggctcc caggctcaag ggatccttcc acctcagcct cctgagtagt   126180
ggggaccaca agtgttcccc aacattcctg gctaattttt gtattttttg tagagacacg   126240
gtctctctat gttgcccagg ttggtcttga actcctaagc tcaagccatc tgtttgcctt   126300
ggcctcccaa agtgctggag ttacaggtgt gagccatgct gtctggcaga tccaacacct   126360
gaatctcaga cttctagcct ctagaactgt gagacaatac atttctgtca tttaagcctc   126420
tagtttgtgg tactttatta tagaagggtc aggaaacaaa tatgatatat tattctgcat   126480
gtatagaaac tttaaatttc tgactagtct atcaaagcaa cacttttttac tttatctgtt   126540
ctcaagactt aaaaaataac cttgcatgta tggaatttgg attggagttt ctccttccca   126600
tctctttagg aatctttctc agtagcaccc ctgctgtgtt tctctgttgt tttacctata   126660
tatttagaca gatcccaaat tatgaggaaa agacaaaaca ataaaaaagc aaaagaaaa    126720
caaaagacta acttttgatt tttgccatcc cccaatttac agccaatccc ttatcccttc   126780
ctgcccattg atggttggaa tttttttttt ttttttttga gattgagcct tgttctgttg   126840
ccagggctgg agtacagtgg cgcgatctcg gctcacttca acctctgcct tctgggctca   126900
agcgattctc ctgcctcagc ctcctgagta gctgggatta cagccatgtg ccaccacacc   126960
cagctaattt tctgtgtgtg ttttttagtag aaacggggtt tcgccatgtt ggccagtctg   127020
gtcttgaact cctgacttca aatgatctgc ccgcctcagc ctcccaaagt gttgggatta   127080
caggcgtgag ccaccatgcc tagcttttgg atttcttaat aaataatctg tcccaacatg   127140
aggcagagga agctgaggtc taccagatgt ccgttttcct tcctaggtgc agaattctca   127200
gtgcttagct gagtgcgtca tcatctggga taaaggctgc atctcctagt cttgcttaca   127260
cttatttgtg gtcttctgat taaatcatgg ccagtgagat gggtgtggga gtaagcgtgc   127320
ccgtaaaaag ctatgagaac taggtactgt aatttgggaa ccatagatct atccactgta   127380
gtttgggaac cataggccta tcctctgcag tttgggaagc ttggatttat ctactttctt   127440
atcatctact cacccccatct ccttgaatga ctgacgttgc ttgctgagtg tcactaggaa   127500
ccacattact gcccagtctg atggctttct taatctatta gcctctgcag tttctgcaga   127560
gtctgaccca gtgaaactc tccatttccg gaaagctcca tcctgaggct cttttgcttc     127620
atctctcttg cttccactgg ttctttttct ccttcccaac ccctaaatgt tgttctctca   127680
ggcttttccc ttaaccctct tttctcatct agtctttcct caatctaagc caattgcatc   127740
cattctaaga tgtcaacttt cattctaggc aaacgacttc cacatcccca gtttaatccc   127800
```

```
tctgactgct gaaccctagt ccatgttttc aactgcacgg tatccatctc cacctgaacc   127860
cccacccttg cctttgacat aaactattca aagcatttga actcaacctt gctttcaaat   127920
gagctcccct tttacctgtt tcttgcagaa gccttgagcc cttgctgccc aattctcggc   127980
ctgagagtta ccccagtgcc tccccccaac cctcccattc ccttctctct gtttcaccct   128040
cattccaacc ccatctgcct ttgggttccc ttgattcaca gatgggttgt acctctaact   128100
cctggctatt cttttctacc tccagttttt tgtttctcca atccatccct gccagatcag   128160
attttctgaa atgcagttct aatctgattc tccctagcaa aaccttactt caagcccagc   128220
cttttcaccc tattgtgtga gcttctctct tcagttctgg caggatctat aatgtgcacc   128280
accaacggga ggtgtgcggc ctgagtcttc tcggctcagc acgtttgctt gtttgtcctt   128340
cctccagccc aaaattacca caaaagttgt tttttatcca acaaacacct tcagagccac   128400
ttattatatg ccaggcactc ttctaagcaa tttgtaaata tgaattttt ttaatcctca    128460 taacagccta ataccagaag ttctattgtt attcccattt tacagagaac actgaggtaa   128520
agagaagttg aataacttgg cccaggtccc cagtgttctg taagtggcag agctggggtt   128580
ggagcacgaa cccatactgt taccagtgaa agcagtgtac caaaattta agtagagatc    128640 actgttctgt aactcattaa gttttttttaa aaaatagta attatccctt aaaaccatta   128700
caaaaacaga gaatgaagaa ttaaaaaaaa atagatttgt tgtaaatccc cagaaagaaa   128760
attaagcagg tctccatcaa agactcataa tagaggaact caaaattttg gtcttctaaa   128820
agaagacatg gactttggtt actattattg tttaggtttt tctccagtgg tgatgaagta   128880
aaaggagact ttgaccttt catagacctt ataagttggg ctctggcatt tactgtttaa    128940
tgctctaaag gttcaatata caaatgtag aataaaaaaa tcatcttgcc ctgggttgcc    129000
atctctgaca gctgtgcttt gattattgtg gcagtgctaa gaggttcatg tggaggtggg   129060
agtgctagga caagacagcc tgagttaaat ttcaatcctc acacttacca gatctgtgta   129120
caggtgtcat cacctgtcaa atagaggtga taccagtggc taccttactg aggaatggga   129180
gagttccact gaggtaatat gagtaaaaca gctcttaaca ggcataagca cttaaaaacg   129240
gtaattatca tcatggcgtg atgtatttgc ccatgttcac actgcttgaa agatactacc   129300
tgagactggg taatttataa agaaagaagg cttaattgac tcacagttct gcatgactgg   129360
ggaggcctca ggaaacttac aatcacggtg gaagatgaag aggaagcaag gcaagtctta   129420
catggcggca ggagagagag agcgtgcagg gaaaactgcc acttttaaac catgagaact   129480
cactatcatg agaacagcat gtgggaaacc tcctctgtga tccaatcacc tcccaccagg   129540
tatgtccccc ccttgacaca gggggattac aattagagat gagatttagg tggggacaca   129600
gagccaaacc acatcacatg ctattcaata ataatagaat tgctctgcaa aataaaaaaa   129660
atgaagctaa caaatttttgc ttataacttt gcaggagtat tggaagtttt tattcctact   129720
gccaacaaag actatttatc tggtatactc atagtgcctt taaaaaatta cacagcactg   129780
ccctgtttat ttttagttttt gtaatagaat tcatggattg gttgttcata gtctttacta   129840
tggcatcatg agccttaagg aaagaacaag gagatttctg agagtcccag cgggttatac   129900
tgtgaatttt actcatgtta ttcttacact gggaacagca aggaacttga cttgactttt   129960
accctggcag acaatcttga aacagttttt caaataaaag atgttatttt taacaggaaa   130020
caactgatac taaagatctg actcagactt tactctcctt caaatgatgt ttgaagttca   130080
gcttgtctgc agctgttcat tatgtgccta ctatgtgcag gcctggaggt aaacaagact   130140
```

```
cagccttcat tatcaggggc tcatactcca gtggagaagc cagattcatc aacagatgat    130200
ttccaagaag tgtggggagc acacatggtc ccagaaactg ggaatccagg agatactcat    130260
tgcactgtcc tttaggctga aattcaagtt ggagcttcct ccttgagtcc cttgtcagtt    130320
tctgcttcta tgtagctgac tgtccatctg agaggacgca tccctatct gaggtcatca    130380 aaagacctgt ggcagccagg attcaagccc aagtgtcctg tctcctagct ctatgcttgg    130440
gcacaccaag catagagctt gggtagagat gttgggacaa aaaccaagtc aaataaacaa    130500 aaacccagt tcttacattt aaggatccgt agagcctaca acatagtttt gtgtctcaaa    130560
tttaagccac aaagttctgt taaccgtcat tcatctagca tatagttgtt aaatttctcg    130620
tatgtggcag gcattttttt ccaggtccta gaatttagaa gagggaacga tgaattaatc    130680
agagattgct gagatagaga caaaccaacc aaccaaccaa acaaccagcc agccagcaag    130740
caattagccc tcgctgtgca catccttcag tgattatggt cagcagaatg tggaaggaat    130800
tcatttgttt atttcttttg agggatgaga gagttgagga ttagcctctc caggaattgg    130860
catcaagaat caacagggca aagctgaagg ataagccaca attaggcagg atgcagaggt    130920
gagactgaag ggagagaggt cagaacccag agaggaatgt atgcatggat cattaaggac    130980
tggaactggc aaacatcttt gtagataata atgggaaact aggtataaac aagggaaaac    131040 taggaaaacta tacaggttct aatagagagt ccgttgtcgc cctgggaagt gtgcttttt    131100 tctttgactt aaccaccgta gagcggctca caaggagcac agatccactg aaatgcctga    131160
cgattgggag agacgaaatc tctgttgtct gtttatattc ttatttttatt aggtctgttt    131220 catgtcttca agatccacga gtgtaggaca cgatgccatt tccctgtat gtcttcggtt    131280 tctaagcaat taagaaatat aatttctttc tcaacattta ctgatgtgga aatttgggga    131340
tctgagccag ggggcttgcc atcatccggt cattggaaaa gtgcataagg gaacacaaag    131400
ctagagtacc taggttggga aatctgcttg cctgcaaatc cagctcaagt tggccaggaa    131460
accctgccct atagatggca aaatgtaaat cccctgagac tagttaaaga caaacacatt    131520
tcattgagtt ggggttttgt tacaaaatag gtaaacgtgc atggtttcca ggccaacgtt    131580
attcagacta ctaaggtctt gaccaagttg gcagttcttt ctagaggcct tagttccact    131640
ggaattagca ggttcattaa aactaaaact caaagaggga catgtcagct agccaggaaa    131700
ctgagttgac taggtcctct tgaaggtttc attgtaacat tgggtaccca tccaagtcct    131760
agtggccttt gtctcagatt gctgcataaa agtggctcaa catgaaggcc aatgtgaaga    131820
catattggat aagggaattc attctgtttt ctttctgcca ccgcccctca tttattttat    131880
caccataaag atgtaattca catatcatga taccaacttt taaaaggagt gtagttcagt    131940
agttgttcgt gtattcacag agttggcaac catcttcacc atctaatttc agaatgttct    132000
atcatcccaa agagaagccc catagccatg acaccccatt tctcttgact cctagtccct    132060
tacaactact agtccacttc ctgtcatgat tgacttgggt actctggata tttcatataa    132120
atggaatcat acgttatatg ttgtgtctgg cttctttcac ttaacgtaat gtttaaaggt    132180
tcatgcacgt tgtagtgtgt gctagcactt catttcttt ttatgactaa ataatattcc    132240
attaaagaga tatataccac attttgtttc ctcattttct aacttttcag taagaattta    132300
aaaaaacaca ccaatacaat atgctgtctt ttaacatgct agccctaaca tggtaatgcc    132360
tggaatattg tccacgaatt tctctggtgt ttctttggtg acttgtttac ttcctcagtg    132420
atgttgcact gttgtgttct gaccctgtct gagtcctgtc tgttctctgg cttgagagtg    132480
gctttgactg agctttggga taggactgct gttggtctgc agttatcacg ttcagacttt    132540
```

```
atctgagatg cggactttgg gccagataaa tgcaggattt tctgaactca ctggtgagga  132600
aaagcatttg ctaccgctgg ttcttcgaca gcatataact ttccctaagt caggagtgcg  132660
tgtgtgtggt tgctgggtgt gggtgaagat aatcaatttt atgcttctga taacctttca  132720
agatttgcag caaaagaact tggtggccct gaagactctt tttcctcttc ccattcctgg  132780
gtctaacagt tacagtcatg gctgttctga agctgagcac ttggtggtgt ccatgacttt  132840
aataacatgt gctgggagcg gtggctcacg cctgtaatct cagcactttg ggaggccgag  132900
gtaggcggat cacttgaggc caggagttcg agaccagtct ggccaacatg gtgaaacccc  132960
gtctctacta aaaatacaaa aattagccgg gcttggtggt gggcacctgt agtcccacct  133020
actaggaggc tgagggaggt gaatcgcttg aacccaggag gcggatgttg cagtgagcaa  133080
gatcttggca ttgcactcca gcctgggtga cagagcgaga ctccgtcaaa aaaaaaacaa  133140
caaaaacaaa caaacaaaaa acaaaaaaaa ccctaaacag tgctggggac aggcaccaca  133200
acttaacagg gcatctgccc tgtgaagcca cagaggtagg tggtgggtgt cttgaggtgg  133260
ggggagaaag gcaagattgc tgctgggcaa agtggagaca gtgaggttca agccaccatg  133320
cgtcccagca ggtgtggagg tcacaccact cagcaggtgg aggatgcacc gtcacccact  133380
gtgaggcagg gaccttcctg tgggttcaca gaggagccct ccagcaatgg agtaacactg  133440
cagctggctg ctctgctcag ggtcgcagcc cagggtagag tggaagacag aggagcaggc  133500
tggtgaggac aggctgctga aggcttccac tttagtcttc acatctaact cggggcggct  133560
tcatagcagg gagatagtca gcaagaactt ccaaatcatt tcaaagtct atcaggaaca   133620
tttctggctc agaatctcac gctccctcct ttccagagct acgttccttt gtattttcta  133680
tagaagcaga cgtaggatct aagcatatgt ctctgagggt gcctggacta agaaatccag  133740
gagattcagt gaagaattgt gttatgtttt tttttttttt tttttttttt tttttttttt  133800
ttttttttg tcgtatgctt ggcagagagc aggtaattgg gcccatcatt atttagggct   133860
aaaaatttgt tgatttgaga tttttttggga ttggctaaaa cctacttcag aacaacatgg  133920
gaaggaaaag aaaagctatc tttgtttcag gaatgccggg cttcagcttc cctggtgagt  133980
aaatgaagaa actgcctgcg actgcttggc ctcagactgc cttgcgaagg ctccttctgg  134040
cacaatttgg gctttgaact tctcccttaa tttctgaatc tgtgttgtga taattggctt  134100
tggaaaggtt acgagaggtt gactctggcc tgacacggag gctctagcca atgccagaga  134160
ggtaggcttg gtgccagagc tcacctcaga cccacatctc cagggagtga caggaacaga  134220
aaatcagcca agctactgtg acccagtcgt tcagcaaatg tcggagcgtt gcaatgcctg  134280
cccccaccct accccagagc aaggctgggc acctgaacac tgtgtgggt actctgcgtc   134340
tgtgctctgg gaagggggc tgtgaaattc acctggagat ctgttttaag acctgcgctt   134400
tcgaaatgct ctcaaactct tttatcaaga cagtacagct tggacaaatg tccacaatag  134460
agaagcagtg acatcccttg gacctccggg aacagcagcc ctgtctgtct ctgaacgggc  134520
cttcctccct caggctcctc tcaccccctcg ggctgccct caggggagga tggcctcacc   134580
cagtgaaggt taactgggcc ctttgtttgc aaatggcagg acaggagctg gtgctagctg  134640
atcatgaggc ttttacagc atcaaagtgc tgcagtttac taagaaatca ggaaagcata   134700
ttccaaaaca gggttgtctt ctaggaagga acagagagga ctctgccttt ctactttcag  134760
gcatccagcc ctgtatgctc caccaggta tctgtgagga gaggcagcgt gagcaggccc   134820
agtggaagca gggatggaga aggaggggtc tcccataact cactgcagat gctgagtata  134880
```

```
attaaaatgt gaattacatg tgtctaacat ggtaaagagg ctcaggtaac tgagcgaggt    134940
tttctccttg aaggtagaaa tgtctgtgta aggaggtcat tccaccttt gggctacctt    135000
taaatgagtg ttttttgaagt ggtattcttt aaaaaaaatt tttttaaatg caatctgtcc   135060
ttgttctctt taaagcaaat atctacagag atgtttatca cattatcata cctctggttg    135120
gaaacaatat ttttgacttg atggatttta tattttcact attagaagct actcctttat    135180
tcccaagtat aaaattctag cttcaaagta aatgcttggc caatcaacac caaataaggc    135240
aggaaaaaaa aaaaaaaaac gcagaaaact cacaaagcct cagattataa ggggcctagt    135300
caggtttcag aaactctagt ccaaacaggc attcctaacc tagcccaggc agctcttacc    135360
tcaggcactt agcaacgcgc aggccttttg aatttgctta aaactattaa gaagtaatta    135420
agtagttaga gggtcttttt cagccctgag gtccaggagg tgggctaaat gaagaaaac    135480
aagcgcaatc gctcagcctt gtcttccttc tagctgacct tgcacgctaa taaattcatc    135540
ctgtattttt ctgctactgc caatttatgg cctacaggaa actaatcttg tacaataact    135600
accttcctgt acttagttcc taaatagagc caaatggatt tggtggcgga agagctcccc    135660
agcacttcct gtgaggcagt tgctgagccc agcaagatct gatagaggct tgatgcgctt    135720
atcgactctg acgatataat tatgttcttg ttttggctgc cctgcactta agcacagaaa    135780
ataaaaaagc aatcctctgt acaacgccta ccacaatgat ttaaacttca aactggaggg    135840
taagatgtgt atttgaaaca agccacgtag gcacagttat ggtgaattta gggagtgaaa    135900
cacacaggtg atcaatattt cactggagtc tttgatataa aatatatatc tgctctgtga    135960
tttcaaaata ttcacaaagg agtaaatttt ttaatgagct aatgaaagaa ctgtgttttc    136020
atttcaaacg ggaagagagg gagaaagaga gagagaatag aaatatagag ccatttcttc    136080
agtaatagtt tacaaccagt ttgccacagg cttggattaa agtaaggaaa ggctgtcaaa    136140
acgcagggta acctgtgtga tatcttttca gaccctcaaa tagctcaaat actacgctgg    136200
gaaaactcag agtttgtcct ttaaagaacc tgaaagtgtt taatctttga taagtgcagg    136260
ctcctcaggc tttgccgctt ccccacaccg gatttgcctg ccactcaccc ataccgatct    136320
gatgacttca tgtggacacg gatcggtccc gtatgacagc gtcttcttcc tgtgctcatt    136380
tattctagaa ctatagcaaa gctgctaatg caaagggaag ccttctacaa aaaggatgaa    136440
gaaatcaccc tgaccaagag accgaagcaa agatgaaagg aaggcataaa taatcgcagc    136500
tcgggtccga tgagacttat tgctgggggct ttcagaccta gagaggtagc aggggcgggg   136560
tgggggtgcc tgtacgcggg ggcggggtgt cccacccagt tgacctggat tagagcccat    136620
ggggctgcat tccgggcttc cgtgtttccc aaagttatgt ggtggcgggg ggcctggctg    136680
ttaaggatct ggggatgtgg ttacctatgg cctctgaggg tgcaccagc tgtccagcac     136740
tgtgaaatca acaatggta gtgggccaga aagatggctt agcttcctcc tgagtatgag     136800
caagtttccg taactgtgaa tcatccttcc ccaaccataa agtgggcat attaatacct     136860
gtcttgtaag aatcctgtga agatcaggga taacaaatgc aacttaataa agtaacctg    136920
ttatgtgttg gctggtgatg ccataaaatgt attttgtaaa atctttataa tggtgactaa    136980
ccaatatatt attattaata gcaataggag tattgtctga ttcaaagggc gcatttagat    137040
tgtggtaatt ctgtgtgtgg ctggatggga gactggaggg ggctggaggt tttaggatga    137100
gtgggacagg gattattaga agtggctaat aaagagatca aagaagtaac tttgttccta    137160
attttttaaaa tcatcattct acctcactct cctaaaagtg atgaggatca taatatttat    137220
gccttacgtt tatacaggac tttatacttg aatatccctt ttacatctct ggtccgtttt    137280
```

```
agaaatttga gcctaaacat gggaagcaga aaaaaagtca atgtggaaaa gcactgtgcc 137340
catcccagtt tggccagaat gatttcagat tgttatcaag aaagggaata gcggcagcat 137400
ggtttggttt tcctctctca agaggactgg acacagggaa ggaacaggaa aaaacctcct 137460
gagcaaagca aggttccaga acagactagt tcaaagccta cacatggtta gtgctccgtg 137520
gaggtgccag ctcacggttg gtgcaccgtg gaggtgccag ctcatgctta gtgcaccgtg 137580
gaggtgccag ctcacggtta gtgcaccgtg gaggtgccag ctcacgctta gtgcaccgtg 137640
gaggtgccag ctcacgctta gtgcaccgtg gaggtgctga ctcatggttc gcgcacagca 137700
gaggctctgc gttttgggat tcgtctgttc taattgtagc ctttcactta ctgccctaag 137760
actggcatgg aaactatgtc tttgagtgat gaaagggcat ccggtgtgtg aagctcctt 137820
gcagagtttc tccatattgt ctccttgata gaatgtagct tactgctggc ttgctttgca 137880
catggcagtc actcggtgca tgctggtgga ataattgaat ggaagctcca gggccatcac 137940
ctgcacacag tcccccggag gccctttctt ctctcatatc tcagcttccc actgctcagc 138000
ttgatgtcag ggagacatcc ttggtctcca ggaggtgaga gggaacagaa cactaacacc 138060
ccagtgaaac acagattgac ttattgttta gcagcaacca ggcaggcatg ggctccctcc 138120
ccgctgccag catccacacg cacctcctcc gtagccatgg taatatttcc cacatgccac 138180
aagtccgtga catggtccta atgaatagaa tgctttatgt ttagcccaa acgtggtcat 138240
tatccatata tttgaaagaa aaggctcaaa caaaaacaag gacgcctgat gcgaagctcc 138300
cagcctgtgg gttctttgcc atgggcctat tggatgggag gtttgggctg caagacaagc 138360
tgtgacttta cctccttgaa tgtgctgatt ctaaagagtc gatttcaatc taaggaagga 138420
cattgggggg attggaaaaa gtgaagagat tgtacagaag ctcacagcta gcaggtgatg 138480
gaggctgagc ccaggagtgc ttttccact ctcccaggct gcttaaaaaa taaattgtat 138540
ttgaatgtgc tcacattaat tttgctacca gtttactgtc gtcaaaatag tgtcaatgaa 138600
tgcaagttct taaaagacct gcaagtccca cctgggaggt ggggcagcac aggacatgag 138660
gagttggtgg tgaatgagaa tttgagaatg ttcaattcat ccctcattag ccatgtgatc 138720
tcaggcagcc cgctgatcat ttctgtgtct caggttccta ctctgtgagg gagagagaga 138780
gaataattgc accccctttg aatgtaagca tctcccttag gagatgaata cacacgtgtg 138840
agtgacagta gccaagtttt ttttttttta tactttaagt tttagggtac atgtgcacaa 138900
cgtgcaggtt agttacatat gtatacatgt gccatgttgg tgtgctgcac ccattaagtc 138960
gtcatttaac attaggtata tctctaaatg ctaccctccc ccctacccccc accccacaac 139020
aggccccagt gtgtgatgtt ccccttcctg tgtccatgtg ttctcattgt tcagttccca 139080
cctatgagtg agaacatgcg gtgtttggtt ttttgtcctt gtgatagttt gctgagaatg 139140
atggtttcca gcttcatcca tgtccctaca aaggacatga actcatcatt ttttatggct 139200
gcatagtatt ccatggtgta tatgtgccac attttcttaa tccagtctat cattgttgga 139260
catttggggtt ggttccaagt ctttgctatt gtgaatagtg ctgcagtaaa catacgtgtg 139320
catgtgtctt tatagcagta tgatttataa tcctttgggt atatacccag taatgggatg 139380
gctgggtcaa atggtatttc tagttctaga tccctgagga atcgccacac tgacttccac 139440
aatggttgaa ctagtttgca gtcccaccaa cagtgtaaaa gtgttcctgt ttctccacat 139500
cctctccagc acctgttgtt tcctgacttt ttaatgatca ccattctaac tggtgtgaga 139560
tggtatctca ttgtggtttt gatttgcatt tctctgatgg ccagtgatga tgagcatttt 139620
```

```
ttcatgtgtt ttttggctgc ataaatgtct tctttttgaga agtgtctgtt catatccttc 139680
acccacttgt tgatggggtt gtttgttttt ttcttgtaaa tttgttggag ttcctttctg 139740
agctttcagt ttctcatggc ccatatgaga tagtaacggt actcacttcc ccagactatt 139800
gcgatgatgg cacgcgatgg ggtgagtggg aggtttatca cacagaataa atgataccct 139860
tggttatttt tagtgctgcc cttatcctgg gtcctaagat tctctgatct cttcctattg 139920
ggtgttcgtt tgactagatt ccaagaacaa aaattacttg acccacactg gtagggctag 139980
gcaatctttc cagccctcct gggttggcag ctgatggata tcatctgttg gtctcactgt 140040
cctttactga ggacactggc aaacttaggg gggttttcat catgatgcca tgcactgaca 140100
tcgtgaggca tacctgtctc attacagcag agactcatgt gacctgggaa ccactgcagg 140160
tcaaaactac agcgcatgaa agccaggagt ttaccaaatg ggtgcagagg ctgcccaggt 140220
gtttgggaat ttattttcat tggaaatttt tatcatttct tcacacataa ggatattagt 140280
tataagaagt ctgaattttt ttttttcctaa caagtacaaa ctacttacaa aatagttgca 140340
aggacaacag aaataatttt tttttttgctg gacctttttga gagtaagttg cctgcatgat 140400
atcttgtcat ccctgaatac gaatacttta gtgtgtattt tgtaccaaca caaatatgct 140460
cctacacaac cacagtagag ttaacagaat cagataatca acgttgatat attcctaatg 140520
cctaattctc agaccctgtt catatttgcc cccagacatc cttaaaaaca aaaggaacca 140580
tctcagagct acatgctgca tttggctgtt gtgttttatt aggctccatt cacctggaaa 140640
agttcctcag tctttctgtg actttcgtgg ccttgacact ctaatggctc taggccagtt 140700
acattgcagg atttccccca gcacggggct gcctgatgct tcctcatgag cagattcagg 140760
tttagcgtcc ttggcaggag aacccaggag cgaccctggg accgcctcac tccgtgctct 140820
caggtcggca ggactgcaat tgcccggtt actgacgatg ttcacactgg tgacctgatg 140880
gaggtggtgt ctgtggtttc ttcactcctt tcttcctttg taattaatta gtattacatg 140940
gaggactagc ttaaaactgt gtaaatactc tgctcttcat tcaacgttta atttattcat 141000
ttatgttgta tttatgtcag tatggatgtg tagttttcta tcttatttat tggattataa 141060
cctggaatta tcattactta tcttactgtt caccttttgct gggggtttgga agctgttccc 141120
actggcccgt gtgttgtcat tctctgagca ggtcctcaag atgttctga gtcattgtgg 141180
accctgcctg ctctggatca tgggtcagct ggttctccaa aaagagctga atcccaagag 141240
gagaatgggc tttagatacc atgatctggg tgtacctcag tgcacagagc tggacagcat 141300
atgcatatag acacacacac acacacacac acacacacac acacacagat gtttatgtct 141360
atgtttgtct ctagctctgt ctatatggaa agccatgagt tggtgctaat atcttcagtt 141420
cactcaagca cctcagagtc caccccactt tcttcctttg tatatttgtg actctccattc 141480
acaccctgtg ccaccctgc cattttctat cagcattgcc acctccccct gcacagtccg 141540
attccaaaatt ctgtatgatc tctgaggcca ggcactggcc tgcatcccag ccagcatcc 141600
tccctgccca gtaatgctgt gccattcctg tctggaccat ccgcccacat gaaagcccct 141660
tttcctcct tcctacaccg aagccctcct tgccctgccc agaggcacac tttgctccag 141720
ctgcttcccc cttaaacccc attcattttt ctgggtgcct gccacccttc cattcagtcc 141780
cttccctgc ttggacactc tctctaccct actcaggctg aaagtcccat ggtcctactc 141840
ctgcaggagc ccggtcctca ttgcactggg gctctgacac catgacccag ccatgtggac 141900
cgccaccgtc ccctaccaat gcccagctcg ggctcttgca aacctccccc aatcccatcc 141960
ttgctcacta tgttcctctg tggtcccttc catcggtgcg gatatccccc ttgtttggat 142020
```

```
acacacagtg gctttaggat cagattgttc agaaagtgga agacctgaaa aaatgtttta  142080
tagttagagc taacttctag aacacactgt cactagaaat tcatcagtga gccctagaga  142140
gtagcaggca ggaagatgag ccatgtccct caaatctgca tgtcactcag caaggtctct  142200
ggctgtggaa ccaggcatgg gagccaccct gtcccagctc ctgatagaga ctcagtggca  142260
gtgacccagc cagtaacctc catcaaagta ttctgcattt agatagactc taccacaccg  142320
agctattgcg ggaagcccca tggcttcttt cttactgttc ctcttcaccc actgggtggc  142380
tggtgatgat cccccgaggc aggggaaggc agtagtgtca gctcttactc cagggtggtc  142440
agggccctta gtgtcctcat ttcgtgcctg aaatctctag aggtgttcat cttgcatgtg  142500
ggctacgttg tgtcctccaa cttgcatctc cccagaaccc tgctttattt tctatctcca  142560
tttgaatttt tcttttaga ttccacatat gagtgagatc atgcaatatt tttcttactg  142620
tgtctggttt attccactta gcataatgtc ctctagcctc atcgatgttg tggcatatgg  142680
gatgatctca ttctttatga ggtccaaata acattctgtt gtacatatgt gacattattt  142740
attttagttt attattttat ttttccataa ggtattgggg aacaggtgat atttggttac  142800
atgagtaggt tcttttgtgg tgatttgtga gattttggcg cacccatcac ctgagcagta  142860
tacactgcac catatttgta gtcctttatc cctcatcctc ctcccagcct tcccctaag   142920 tcctcaaagt ccgttgtgtc attcttatgc ctttgcatcc tcatagctta gcttccgtat  142980
gtcagtggga acacacgatg tttggttttc tgttcctgag ttacttcact tagaataata  143040
atctccaatc tcatcgagga atttcttcat ccatttgtct gtcaatggac acttaggtgg  143100
tttccatacc ttggctactg taaataatgc tgcagtgcac atgggagtgc caatattttt  143160
ataaggtagc catttcctct ctgttggata tacccaga agagggttgc tgggtcttat    143220
ggtagttcta tttttcattt atttaaggaa gctccatttt gttttccaga atggctcttc  143280
caatctacat tcctaccaac agtgtacaag aattctcttt tctccacact ctgcaaacat  143340
ttatcacttg tctctggtaa tagccatcct aaagggtgta ggtgatatcg cacagtggtt  143400
ttgatttgc                                                          143409
```

METHOD OF JUDGING RISK FOR ONSET OF DRUG-INDUCED GRANULOCYTOPENIA

TECHNICAL FIELD

The present invention relates to a method for assessing the risk of drug-induced granulocytopenia by use, as an index, of a polymorphism of the human insulin receptor substrate-2 gene; to a method of detecting the genetic polymorphism employed as an index for the aforementioned risk assessment; to oligonucleotides employed for these methods; and to a kit for the assessment and/or the detection.

BACKGROUND ART

The mainstay of modern medicine is drug therapy, which employs drugs for treating or preventing various diseases. Almost all drugs employed in drug therapy (e.g., low-molecular-weight compounds) intrinsically are foreign substances to the human body, and thus administration of such drugs provides therapeutic efficacy, but may cause a variety of side effects. Such side effects often compel the drug therapy to be abandoned. Also, some drugs have encountered a situation where research and development have to be suspended due to severe side effects, although the drugs have been proved to be useful for patients with a certain disease. Moreover, the use of some other drugs is strictly regulated in order to detect the sign of their side effects by mandatory examinations.

According to the statistics published in the United States, the cases of drug-induced side effects account for two millions or more a year, and more than 100 thousand due to such side effects (JAMA, 279, 1200 (1998)). In Japan, 26,545 cases of drug-induced side effects (including redundantly reported cases) were reported, and 1,239 deaths due to such side effects only in one year of 2000 (Ministry of Health, Labor and Welfare, Jun. 6, 2003, House of Representatives, Responsive Pleading No. 55).

Among side effects due to drug administration, granulocytopenia is a fatal side effect. Particularly, a decrease in granulocytes tends to lead to an infection, and onset of agranulocytosis involves a very high risk for a serious infectious disease such as pneumonia or sepsis. Examples of drugs that are generally known to induce granulocytopenia include analgesic-antipyretic drugs (aminopyrine), antibiotics (Chloromycetin), antithyroid drugs (Mercazole), anticonvulsant drugs, antidiabetic drugs, and diuretic drugs. Occurrence of side effects caused by such a drug is less likely to be related to its dose, and is considered to be related to the predisposition of a patient (e.g., allergic predisposition or idiosyncrasy). Therefore, occurrence of such side effects is almost impossible to predict. In order to avoid occurrence of such side effects, doctors must handle respective cases very carefully, through detailed interviews with individual patients regarding, for example, drug administration records in other departments, and analysis of blood test results, etc. Notably, if and when a patient has onset a side effect of granulocytopenia, doctors must take immediate measures, including hospitalization.

Other drugs that are known to induce granulocytopenia include dibenzodiazepine (clozapine), which is an antipsychotic drug. This drug is expected to have high efficacy, but clinical trials of the drug have been suspended in Japan.

Other drugs that induce granulocytopenia include vesnarinone, which has inhibitory activities on PDE3 and K channel. This drug is an effective inotropic drug that is less likely to cause arrhythmia and other cardiac events (e.g., onset of heart failure and hospitalization). However, administration of this drug may cause side effects; i.e., leukopenia, granulocytopenia, and subsequent agranulocytosis. Therefore, the use of this drug is strictly limited.

Single nucleotide polymorphisms (SNPs) are the most frequently used genetic markers in human genetic analysis. SNPs have already been shown to be useful markers for an association study between genetic background and common diseases or drug response (see Non-Patent Documents 1, 2, and 3). As has been known, analysis of haplotype, constructed of multiple SNPs, is useful for analysis of the susceptibility of polygenic diseases (see Non-Patent Documents 4 and 5). In practice, some diseases such as Alzheimer's disease and hypertension have already been intensively analyzed by such an analysis method (Jeunemaitre, X., et al., Am. J. Hum. Genet., 60, 1448-1460 (1997); Martin, E. R., Am. J. Hum. Genet., 67, 383-394 (2000)).

In recent years, advances in genome analysis have led to development of toxicogenomics, which studies relationship between genes and toxicities such as the effect of a drug on cytochrome P450 (CYP) (i.e., a drug-metabolizing enzyme) Particularly, association studies of individual genetic background and sensitivity/response has been proposed as a powerful tool to elucidate the cause of adverse effects. So-called tailor-made therapy is expected to be realized through these approaches Non-Patent Document 1: Brookes, A. J., "The essence of SNPs," Gene, USA, (1999), 234, 177-186

Non-Patent Document 2: Cargill, M, et al., "Characterization of single-nucleotide polymorphisms in coding regions of human genes," Nature Genet., USA, (1999), 22, 231-238

Non-Patent Document 3: Evans, W. E., & Relling, M. V., "Pharmacogenomics: translating functional genomics into rational therapeutics," Science, USA, (1999), 286, 487-491

Non-Patent Document 4: Stephens, J. C., et al., "Dating the origin of the CCR5-Delta32 AIDS-resistance allele by the coalescence of haplotypes,"Am. J. Hum. Genet., USA, (1998), 62, 1507-1515

Non-Patent Document 5: Tishkoff, S. A., et al., "The accuracy of statistical methods for estimation of haplotype frequencies: an example from the CD4 locus," Am. J. Hum. Genet., USA, (2000), 67,

DISCLOSURE OF THE INVENTION

Problems to be Solved by the Invention

A primary object of the present invention is to provide means for assessing the risk of drug-induced granulocytopenia by use, as an index, of polymorphisms of the human insulin receptor substrate-2 gene, or means for detecting the genetic polymorphisms employed as an index for the risk assessment means.

Means for Solving the Problems

In order to solve the aforementioned problems, firstly, the present inventors have selected, as genes for polymorphism analysis, 115 candidate genes, including cytokine-related genes, MHC region genes, G-CSF-related genes, TNF-α-related genes, NFκ-related genes, cAMP-related genes, and K-channel-related genes, searched for SNPs in these candidate genes from the database of Japanese Single Nucleotide Polymorphisms, and picked up 188 candidate SNPs for analysis.

Subsequently, the present inventors have determined the frequency of these SNPs in the genomic DNA of samples from the following two groups: a group of subjects with granulocytopenia induced by administration of a specific drug, and a group of subjects without granulocytopenia who have received the same drug. As a result, the present inventors have confirmed that SNPs with the most statistically significant difference between the aforementioned two groups are present on the insulin receptor substrate-2 gene (J-SNPID: IMS-JST040476) (hereinafter, the gene will be referred to as "the IRS-2 gene").

Furthermore, the present inventors have conducted extensive studies on the relationship between polymorphisms in the human IRS-2 gene and drug-induced granulocytopenia, and as a result have confirmed that six SNPs of the human IRS-2 gene are intimately related to granulocytopenia induced by administration of the drug.

The present inventors have found that analysis of these specified SNPs enables assessment (predictive diagnosis) of the risk of side effects induced by drugs for various human diseases; particularly, the risk of onset of drug-induced granulocytopenia. The present invention has been accomplished on the basis of this finding.

The present invention provides a method for determining the presence of the risk of drug-induced granulocytopenia, a method of detecting a genetic polymorphism markers employed as an index for the aforementioned risk determination, and oligonucleotides and kit employed for these methods, which are summarized below in (1) through (19).

(1) A method for assessing the risk of drug-induced granulocytopenia, the method comprising detecting polymorphisms of the human IRS-2 gene of a subject, and determining the presence of the risk of drug-induced granulocytopenia of the subject by use of the genetic polymorphisms as an index.

(2) A method of detecting polymorphisms of the human IRS-2 gene of a subject for determining the presence of the risk of drug-induced granulocytopenia, in which the genetic polymorphism is employed as an index.

(3) An examination method for the risk of drug-induced granulocytopenia, comprising detecting a polymorphism of the human IRS-2 gene of a subject, and carrying out an examination using the genetic polymorphisms as an index for the risk.

(4) A method as described in any of (1) through (3) above, wherein the presence of the risk of drug-induced granulocytopenia is determined by use, as an index, of at least one genetic polymorphism selected from the group consisting of human IRS-2 gene polymorphisms described below in (a) through (f): (a) a polymorphism that is C (wild type) to A conversion at position 4,587 upstream of the translation initiation codon; (b) a polymorphism that is AT deletion (wild type) at position 2,510 upstream of the translation initiation codon; (c) a polymorphism that is A (wild type) to C conversion at position 1,164 upstream of the translation initiation codon; (d) a polymorphism that is A (wild type) to G conversion at position 15,870 downstream from the translation initiation codon; (e) a polymorphism that is A (wild type) to G conversion at position 29,793 downstream from the translation initiation codon; and (f) a polymorphism that it C deletion (wild type) at position 31,532 downstream from the translation initiation codon.

(5) A method as described in any of (1) through (4) above, wherein the genetic polymorphisms is detected through at least one technique selected from the group consisting of direct nucleotide sequencing, allele-specific oligonucleotide (ASO)-dot blot analysis, single nucleotide primer extension assay, PCR-single strand conformation polymorphism (SSCP) analysis, PCR-restriction enzyme fragment length polymorphism (RFLP) analysis, Invader assay, quantitative real-time PCR assay, and genetic polymorphism assay employing a mass spectrometer (mass array).

(6) A method as described in (5) above, wherein the genetic polymorphisms is detected through direct nucleotide sequencing.

(7) A method as described in (5) above, wherein the genetic polymorphisms are detected through PCR-restriction enzyme fragment length polymorphism (RFLP) analysis.

(8) A method as described in (7) above, wherein the PCR-restriction enzyme fragment length polymorphism (RFLP) analysis is performed by use of the restriction enzyme Afa I for detecting A to G conversion at position 29,793 downstream from the translation initiation codon of the human IRS-2 gene.

(9) An oligonucleotide which can be hybridized with the human IRS-2 gene and is employed as a primer or probe for genetic polymorphism detection, the oligonucleotide being selected from the group consisting of oligonucleotides described below in (a) through (f):

(a) an oligonucleotide having a sequence including a genetic polymorphism that is C to A conversion at position 4,587 upstream of the translation initiation codon of the human IRS-2 gene;

(b) an oligonucleotide having a sequence including a genetic polymorphism that is AT deletion at position 2,510 upstream of the translation initiation codon of the human IRS-2 gene;

(c) an oligonucleotide having a sequence including a genetic polymorphism that is A to C conversion at position 1,164 upstream of the translation initiation codon of the human IRS-2 gene;

(d) an oligonucleotide having a sequence including a genetic polymorphism that is A to G conversion at position 15,870 downstream from the translation initiation codon of the human IRS-2 gene;

(e) an oligonucleotide having a sequence including a genetic polymorphism site that is A to G conversion at position 29,793 downstream from the translation initiation codon of the human IRS-2 gene; and (f) an oligonucleotide having a sequence including a genetic polymorphism that is C deletion at position 31,532 downstream from the translation initiation codon of the human IRS-2 gene.

(10) An oligonucleotide, which can be hybridized with the human IRS-2 gene is employed as a primer for genetic polymorphism detection, the oligonucleotide being selected from the group consisting of oligonucleotides described below in (a) through (d) and (f)

(a) an oligonucleotide having the sequence of SEQ ID NO: 3;

(b) an oligonucleotide having the sequence of SEQ ID NO: 6;

(c) an oligonucleotide having the sequence of SEQ ID NO: 9;

(d) an oligonucleotide having the sequence of SEQ ID NO: 12; and (f) an oligonucleotide having the sequence of SEQ ID NO: 17.

(11) A kit for assessing the risk of drug-induced granulocytopenia, the kit comprising an oligonucleotide as described in (9) above serving as a primer or probe for detecting a polymorphism of the human IRS-2 gene.

(12) A kit as described in (11) above, which comprises oligonucleotides as described in (10) above.

(13) A kit as described in (11) above, which comprises the oligonucleotide as described in (e) of (9) above and the restriction enzyme Afa I, the kit being employed for detecting A to G conversion at position 29,793 downstream from the translation initiation codon of the human IRS-2 gene.

(14) A method as described in (1) above, which assesses the risk of drug-induced granulocytopenia attributed to vesnarinone administration by use of oligonucleotides as described in (9) or (10) above.

(15) A method as described in (1) above, which assesses the risk of drug-induced granulocytopenia attributed to vesnarinone administration by use of the oligonucleotides as described in (e) of (9) above and the restriction enzyme Afa I.

(16) A kit for detecting a polymorphism of the human IRS-2 gene employed for determining the presence of the risk of drug-induced granulocytopenia, the kit comprising oligonucleotides as described in (9) above as primers or probes for detecting the IRS-2 gene polymorphisms.

(17) A kit as described in (16) above, which comprises oligonucleotides as described in (10) above.

(18) A kit as described in (16) above, which comprises the oligonucleotides as described in (e) of (9) above and the restriction enzyme Afa I, the kit being employed for detecting A to G conversion at position 29,793 downstream from the translation initiation codon of the human IRS-2 gene.

(19) A method as described in (2) above, which detects a genetic polymorphism employed for assessing the risk of drug-induced granulocytopenia attributed to vesnarinone administration by use of oligonucleotides as described in (9) or (10) above.

(20) A method as described in (2) above, which detects a genetic polymorphism employed for assessing the risk of drug-induced granulocytopenia attributed to vesnarinone administration by use of the oligonucleotides as described in (e) of (9) above and the restriction enzyme Afa I.

(21) A method as described in (3) above, in which the examination is carried out concerning the risk of drug-induced granulocytopenia attributed to vesnarinone administration, by use of oligonucleotides as described in (9) or (10) above.

(22) A method as described in (3) above, in which the examination is carried out concerning the risk of drug-induced granulocytopenia attributed to vesnarinone administration, by use of oligonucleotides as described in (e) of (9) above and the restriction enzyme Afa I.

EFFECTS OF THE INVENTION

According to the present invention, there are provided methods for assessing the risk of drug-induced granulocytopenia in a human; a method of detecting a genetic polymorphism employed as an index for the aforementioned assessment; kits for these methods; primers and probes for polymorphism detection, which are employed in these methods; and a gene relating to a risk factor for drug-induced granulocytopenia in a human. These are useful for examining or assessing the risk of human drug-induced granulocytopenia, particularly useful for examining or assessing the risk of human drug-induced granulocytopenia before administration of a drug which has already been reported to induce granulocytopenia (including agranulocytosis).

BRIEF DESCRIPTION OF THE DRAWING

FIG. 1 A schematic representation showing the structure of the human IRS-2 gene and the positions of polymorphisms of the gene.

BEST MODE FOR CARRYING OUT THE INVENTION

As used herein, abbreviations of amino acids, peptides, nucleotide sequences, nucleic acids, etc. are according to IUPAC-IUB nomenclature [IUPAC-IUB communication on Biological Nomenclature, Eur. J. Biochem., 138: 9 (1984)], "Guideline for preparation of a specification, etc. including nucleotide sequences or amino acid sequences" (edited by Japan Patent Office), and commonly employed symbols used in the field.

As used herein, the genomic sequence of the human IRS-2 gene is included in the sequence reported by Mohammadi, M. at Sanger Center (GenBank accession No: AL162497, version 20) (SEQ ID NO: 18), which has a full length of 143,409 bp.

The IRS-2 gene, whose structure is estimated by the genomic sequence on the basis of the sequence data of IRS-2 mRNA sequence obtained from GenBank (accession number XM 007095) and the sequence data of the aforementioned AL162497, is a 32,730 bp composed of two exons and one intron. The IRS-2 gene corresponds to 93,673 to 126,402 bp in the sequence of AL162497. FIG. 1 schematically shows the structure of the IRS-2 gene. In FIG. 1, "Ex. 1" and "Ex. 2" correspond to the aforementioned two exons. Abbreviations with arrows correspond to the below-described alterations (SNPs). Notably, the SNPs are synonymous; i.e., the SNPs do not cause amino acid substitutions, and therefore the protein sequence does not be changed. The position numbers of SNPs as described in the specification or the FIGURE correspond to the position numbers counting from A of ATG that is used as a codon for Met at N-terminus of protein when mRNA is translated into protein (translation initiation codon).

C-4587A: C to A conversion at position 4,587 upstream of the translation initiation codon of the human IRS-2 gene;

AT-2510del: AT deletion at position 2,510 upstream of the translation initiation codon of the human IRS-2 gene;

A-1164C: A to C conversion at position 1,164 upstream of the translation initiation codon of the human IRS-2 gene;

A15870G: A to G conversion at position 15,870 downstream from the translation initiation codon of the human IRS-2 gene;

A29793G: A to G conversion at position 29,793 downstream from the translation initiation codon of the human IRS-2 gene; and C31532del: C deletion at position 31,532 (in Ex. 2) from the translation initiation codon of the human IRS-2 gene.

As used herein, the term "gene" encompasses double-stranded DNA, as well as single-stranded DNA (sense strand or antisense strand) constituting the double-stranded DNA. Unless otherwise specified, the gene (DNA) employed in the present invention encompasses double-stranded DNA including human genomic DNA, single-stranded DNA including cDNA (sense strand), single-stranded DNA having a sequence complementary to the sense strand, and fragments thereof. The aforementioned gene (DNA) may include regulatory regions, coding regions, exons, and introns. The term "polynucleotide" encompasses RNA and DNA. The term "DNA" encompasses cDNA, genomic DNA, and synthetic DNA. The term "polypeptide" encompasses its fragments, homologues, derivatives, and mutants. The term "mutant" refers to a naturally occurring allele mutant, a non-naturally occurring mutant, a mutant obtained through alteration (deletion, substitution, addition, or insertion), and a polynucleotide sequence which does substantially not change the function of the polypeptide encoded by the polynucleotide sequence. Alteration of an amino acid sequence, which may naturally occur through, for example, mutation or post-translational modification, can be artificially performed by introducing mutations into the gene.

As used herein, the term "SNP (single nucleotide polymorphism)" refers to alteration of a single nucleotide in a gene or gene cluster, and "SNPs" refers to plural form of SNP. The term "haplotype" refers to the type of the aforementioned single strand marker constructed of multiple polymorphic sites of a continuous gene region or gene cluster.

The present invention has been accomplished on the basis of the finding that a polymorphism(s) including alteration at a specific site of the human IRS-2 gene (the entirety of the IRS-2 gene including the promoter region involved in transcriptional regulation), particularly, SNP or SNPs are intimately correlated with human drug-induced granulocytopenia, and the risk of drug-induced granulocytopenia can be assessed (pre-diagnosed) by detecting the SNPs as a genetic polymorphism marker at the specific site. The assessment method of the present invention involves detection of a polymorphism(s) (i.e., SNP or SNPs) of the human IRS-2 gene of a sample (derived from a subject).

The SNPs detected and analyzed by the method of the present invention (i.e., genetic alterations serving as an index for assessing the risk of drug-induced granulocytopenia) include the aforementioned six polymorphisms; i.e., C-4587A, AT-2510del, A-1164C, A15870G, A29793G, and C31532del. The positions of the SNPs on the IRS-2 gene are as shown in FIG. 1. Notably, the position numbers of the SNPs correspond to the position numbers counting from A of ATG that is used as a codon for Met at N-terminus of protein when mRNA is translated into protein (translation initiation codon).

The present invention enables detection of polymorphisms (SNPs and haplotype) of the human IRS-2 gene, which provides data or means useful for elucidation and understanding of the mechanism of drug-induced granulocytopenia in human, and for diagnosis and prevention of the disease. According to the present invention, when a subject having the risk of drug-induced granulocytopenia is determined, and administration of a drug to the subject is avoided, drug-induced granulocytopenia can be prevented. Moreover, when other assays are performed frequently in addition to the present invention to monitor side effects upon administration of a drug, effective measures can be taken against such side effects.

The method of the present invention will next be described in detail.

In the method of the present invention, polymorphisms of the human IRS-2 gene of a subject are detected, and the presence of the risk of drug-induced granulocytopenia is determined by use of the genetic polymorphisms as an index.

Detection of the polymorphisms of the human IRS-2 gene is performed through, for example, the following procedure: the genomic sequence of the human IRS-2 gene of a subject, or its complementary strand is prepared, and, if desired, the genomic sequence or the sequence of its complementary strand is determined, followed by detection of the gene polymorphisms.

Preparation of Human IRS-2 Gene Including SNPs

The human IRS-2 gene derived from a subject is prepared as a sample for DNA analysis. Specific examples of the gene having polymorphisms (SNPs) are as described above. The IRS-2 gene encompasses the above-exemplified complementary strand of the DNA sequence of the human IRS-2 gene.

The human IRS-2 gene, which has genetic polymorphisms, or its complementary strand can be readily prepared through a generally employed genetic engineering technique on the basis of specific sequence data of the human IRS-2 gene as disclosed herein [see, for example, Molecular Cloning 2nd Ed, Cold Spring Harbor Lab. Press (1989); or *Zoku Seikagaku Jikken Koza "Idenshi Kenkyuho* I, II, III" edited by The Japanese Biochemical Society (1986)].

Specifically, cDNA or genomic DNA is extracted, through a common method, from a subject (e.g., a patient with human drug-induced granulocytopenia who has SNPs of the human IRS-2 gene), and a target clone is selected through a common method employing, for example, an appropriate antibody, restriction enzyme, or probe which may include a specific polymorphism of the human IRS-2 gene [see, for example, Proc. Natl. Acad. Sci., U.S.A., 78, 6613 (1981); or Science, 222, 778 (1983)], to thereby prepare a target genomic sequence of the IRS-2 gene.

Examples of the source of the aforementioned cDNA or genomic DNA include various cells and tissues having the IRS-2 gene including SNPs, and cultured cells derived therefrom. Other examples of the source include body fluids such as blood (e.g., serum or plasma), saliva, lymph, airway mucus, urine, and semen. The aforementioned source material (serving as a sample) is preferably DNA or genomic DNA derived from a human subject before administration of a drug (in particular, a drug which has previously been reported to induce granulocytopenia). Isolation of RNA from such a source material, isolation and purification of mRNA, preparation of cDNA, cloning thereof, etc. can be carried out through a common method. In the present invention, various commercially available cDNA libraries (e.g., cDNA libraries available from Clontech Lab. Inc.) may be employed.

No particular limitation is imposed on the method for screening a target gene from cDNA libraries, and the gene screening can be performed through a common method. Specifically, there is a prepared probe including a polymorphic site which can selectively bind to the DNA sequence of target sequence around SNPs, and plaque hybridization, colony hybridization, etc. These methods are performed singly or in combination by use of the thus-prepared probe.

The primers employed for screening may be a forward primer or reverse primer designed on the basis of target nucleotide sequence data of the human IRS-2 gene. Such primers can be synthesized through a common method by use of, for example, an automated synthesis apparatus. The probe for screening is generally a labeled probe. However, the screening probe may be an unlabeled probe, so long as it can specifically bind to a directly or indirectly labeled reagent. The labeling reagent and labeling technique such a probe or ligand have already been well known in the field. Examples of the labeling reagent include radioactive labeling reagents, biotin, fluorescent dyes, chemiluminescent reagents, enzymes (e.g., luciferase), and antibodies, which can be incorporated through a known labeling technique such as nick translation, random priming, or kinase treatment.

The thus-extracted genomic DNA or mRNA including the human IRS-2 gene can be amplified through a gene amplification method. This gene amplification enables easier and accurate detection through the detection method of the present invention. Examples of the gene amplification method include PCR (Saiki, R. K., Bugawan, T. L., et al., Nature, 324, 163-166 (1986)), NASBA (Comptom, J., Nature, 650, 91-92 (1991)), TMA (Kacian, D. L., and Fultz, T. J., U.S. Pat. No. 5,399,491 (1995)), and SDA (Walker, G. T., Little, M. C., et al., Proc. Natl. Acad. Sci., U.S.A., 89, 392-396 (1992)).

Gene fragments amplified by means of, for example, PCR may be isolated and purified through a common technique such as gel electrophoresis. Alternatively, purification of such gene fragments may be performed by use of a column. The gene fragment purification can be confirmed through, for example, mass spectrometry. In accordance with properties of the thus-amplified gene fragments, the gene fragments are applied for detection of the human IRS-2 gene (SNPs) employed in the present invention.

Detection of Human IRS-2 Gene Polymorphism

In the method of the present invention, subsequently, the presence of a polymorphism(s) of the aforementioned sample is detected. Specifically, this detection can be performed through, for example, any of the below-described methods (1) through (8).

(1) Direct Nucleotide Sequencing

Detection of the IRS-2 gene polymorphism(s) can be performed through a direct nucleotide sequencing method, which has conventionally been employed for sequencing of such a gene; for example, the dideoxy method (Sanger, et al., Proc. Natl. Acad. Sci., U.S.A., 74, 5463-5467 (1977)) or the Maxam-Gilbert method [Methods in Enzymology, 65, 499 (1980)]. The genetic polymorphism detection may be performed through a combination of such a direct nucleotide sequencing method and a DNA amplification method (e.g., PCR). Particularly, a combination of such a direct nucleotide sequencing method and PCR or a similar DNA amplification method is preferred, since this combination needs only a small amount of a DNA sample, and enables simple and easy detection with high sensitivity and accuracy.

Basically, this preferred method can be performed through, for example, the following procedure: a PCR-amplified gene fragment or a purified product thereof is cloned into a plasmid, followed by direct nucleotide sequencing through the dideoxy method, the Maxam-Gilbert method, or a similar method. For the sake of convenience, the preferred method can be performed through nucleotide sequencing by use of, for example, a commercially available sequencing kit. Thus, the presence of polymorphisms at the aforementioned specific sites of the human IRS-2 gene can be detected.

In the aforementioned method and the below-described methods, no particular limitation is imposed on the PCR-amplified DNA fragment (i.e., sample), so long as the DNA fragment includes at least one of the aforementioned specific sites at which polymorphisms is expected to occur. The DNA fragment generally has a length of about 50 to several thousands of bp, preferably 50 to several hundreds of bp.

(2) Allele-Specific Oligonucleotide Dot Blot Method

Alternatively, detection of the IRS-2 gene polymorphism(s) can be performed through the allele-specific oligonucleotide (ASO)-dot blot method (Conner, B. J., et al., Proc. Natl. Acad. Sci., U.S.A., 80, 278-282 (1983)). This method can be performed through, for example, dot blot analysis in which a PCR-amplified gene fragment by use of a forward primer and reverse primer designed so as to sandwich a target is hybridized with an allele-specific oligonucleotide probe containing SNP site. Thus, the presence of SNP in the gene fragment can be determined.

(3) Single Nucleotide Primer Extension Assay

Detection of the IRS-2 gene polymorphism(s) can also be performed through a single nucleotide extension assay, such as the SNaPshot assay, pyrosequencing, or the point mutation detection assay disclosed in Japanese Patent Application Laid-Open (kokai) No. 2000-279197. In such an assay, a probe designed so as to correspond to a nucleotide immediately (or several nucleotides) before a target polymorphism (SNP) (i.e., a probe designed such that the 3'-end thereof corresponds to one (or several) nucleotide upstream of the polymorphism) is annealed to a DNA sample. Each of the aforementioned assays can be performed by use of a commercially available SNPs detection kit and the software attached to the kit.

For example, the SNaPshot assay can be performed by use of ABI PRISM SNaPshot ddNTP Primer Extension Kit (PE Applied Biosystems). Detection of SNPs can be performed through detection and analysis of fluorescent fragments generated after reaction by use of ABI PRISM 310/377/3100/3700 DNA Analyzer (PE Applied Biosystems) and GeneScan software.

Pyrosequencing can be performed through, for example, the following procedure. Specifically, genomic DNA is isolated from, for example, a blood sample through a common method; several tens to several hundreds of nucleotides (including a polymorphism) are PCR-amplified by use of a biotin-labeled primer; single-stranded DNA is purified by use of magnet beads; and the thus-purified DNA is employed as a sample. A primer designed to have a complementary sequence corresponding to several nucleotides upstream of a target polymorphism is annealed to the sample, and then each dNTP is added to the mixture none after another according to the sequence in the vicinity of the polymorphism input in software. Pyrophosphoric acid (PPi) released from nucleotide extension of DNA polymerase is converted to ATP by ATP sulfurylase, and luciferase generates detectable light using this ATP, which can be detected with a chemiluminescence detector, a CCD camera, etc. Thus, genotyping can be performed through analysis of the peak of luminescence obtained through addition of the dNTPs. This method enables genotyping in about 15 minutes for 96 samples.

The aforementioned method can use a generally employed reagent and apparatus. Examples include reagents such as commercially available SNP Reagent Kits (Pyrosequencing AB) which contain, as components, a mixture of the following four enzymes: DNA polymerase, ATP-sulfurylase, luciferase, and apyrase, a substrate solution containing luciferin and APS (adenosine 5'-phosphosulfate), and dNTPs containing DATP (deoxyadenosine 5'-triphosphate), dCTP, dGTP, and dTTP; PSQ96 system for automatic DNA sequence analysis (Pyrosequencing AB); and SNP software employed for the analysis (Pyrosequencing AB).

Alternatively, pyrosequencing can be performed through, for example, the method described in U.S. Pat. No. 6,159,693. Specifically, an isolated genomic DNA is amplified; the thus-amplified PCR product is purified; and the resultant product is reacted with pyrophosphoric acid by use of READIT™ System (Promega Corporation), followed by analysis of the resultant data.

(4) PCR-Single Strand Conformation Polymorphism (SSCP) Analysis

The detection method of the present invention can employ the PCR-SSCP method (Orita, M., Iwahara, H., et al., Proc. Natl. Acad. Sci., U.S.A., 86, 2776-2770 (1989)), in which an amplified PCR product (single-stranded DNA) is subjected to non-denatured polyacrylamide gel electrophoresis, and the presence of single nucleotide polymorphims is determined on the basis of the mobility difference.

(5) PCR-Restriction Enzyme Fragment Length Polymorphism (RFLP) Analysis

In the present invention, in the case where, for example, a nucleotide sequence including a polymorhims, which are targeted for detection of SNPs or haplotype of the human IRS-2 gene, contains a restriction enzyme recognition site, the detection can be performed through restriction enzyme fragment length polymorphism analysis (RFLP analysis: Botstein, D. R., et al., Am. J. Hum. Gen., 32, 314-331 (1980)).

Specifically, for example, there is employed a restriction enzyme which can recognize nucleotides around the polymorphism, in order to detect whether the nucleotide at position 29,793 is A (wild type) or G (mutant type), the position being counted from the translation initiation codon present in Ex. 2 of the human IRS-2 gene. The enzyme employed in the RFLP analysis may be any known restriction enzyme, so long as the enzyme can recognize nucleotides around the target polymorphisms. Specific examples of the restriction enzyme include Afa I.

The RFLP analysis is more preferably done as PCR-RFLP analysis; i.e., analysis performed on a large amount of sample DNA which has been amplified and prepared in advance through PCR or a modification thereof. Thus, the presence of polymorphism can be detected on the basis of the presence of a specific cleavage site.

More specifically, detection of SNP of the human IRS-2 gene by the PCR-RFLP analysis is performed through, for example, the following procedure. Firstly, the genomic DNA of the human IRS-2 gene is extracted from a human biological sample, and a DNA fragment of the region including a polymorphism of the gene is amplified, thereby preparing a large amount of a DNA sample. The forward primer and/or reverse primer to be employed may be a primer whose sequence is not completely identical to the genomic sequence, as long as is a primer containing a sequence for introducing a restriction enzyme recognition site. Subsequently, the above-amplified DNA sample is digested by use of a specific restriction enzyme (i.e., an enzyme which can digest either a wild type or a mutant type), and DNA cleavage patterns (e.g., the presence of cleavage, or the base length of cleaved fragments) are confirmed through a common method such as gel electrophoresis.

In the case of the polymorphism (A29793G) of the human IRS-2 gene specified by the present invention, which is associated with human drug-induced granulocytopenia, a specific recognition site (GTAC) of the restriction enzyme Afa I is generated by the SNP in the region including positions 29,793 to 29,796 of the nucleotide sequence of the human IRS-2 gene. Therefore, this polymorphism can be detected through the RFLP analysis.

(6) Invader Assay

Detection of SNPs of the IRS-2 gene can also be performed through the Invader assay. The Invader assay can be performed with reference to the following publications:

Lyamichev, V., et al., Nat. Bioltechnol., 17(3) 292-296 (1999); and

International Patent Publication WO 9823774 (Japanese Kohyo Patent Publication No. 2001-526526).

The Invader assay enables analysis of SNPs of genomic DNA without amplification of target DNA. For example, the Invader assay is performed as follows.

In order to detect the presence of target SNPs of the human IRS-2 gene, firstly, genomic DNA is isolated. To perform this assay, two oligonucleotides were prepared by use of, for example, an automated DNA synthesis apparatus. One oligonucleotide, the allele-specific probe, contains the complementary base of the SNP nucleotide to be analyzed, and extends to the upstream of the SNP. Additional non-complementary nucleotides, which are composed of 15 to 50 nucleotides (5' flap), were added to this probe on its 5' site. The second oligonucleotide having 15 to several tens of nucleotides, the Invader oligonucleotide probe, has a complementary sequence to the downstream of the SNP and the end of the probe is a non-matching base overlapping the SNP nucleotide to be analyzed. The two oligonucleotides and an enzyme (i.e., Cleavase for the Invader assay employed in the present invention) are added to the target genomic DNA, which is extracted from described above. This enzyme recognizes the specific structure composed of the two oligonucleotides and the target genomic DNA. This reaction mixture is reacted under the appropriate conditions.

When the genomic DNA of a sample has a target SNP, a first reaction proceeds; the enzyme cleaves the 5' flap. On the other hand, when the genomic DNA of a sample does not have a target SNP, the enzyme does not cleave it.

The 5' flap released from the allele-specific probe which has been cleaved by the enzyme is complementarily bound to a fluorescence resonance energy transfer (FRET) probe serving as a target, and the 3'-end of the 5' flap is invaded in the FRET probe. In a manner similar to that described above, enzymatic reaction (second reaction) occurs, and a fluorescent dye is released.

The FRET probe employed in this second reaction is formed such that it doesn't depend on a target to be detected, and contains the following two essential elements:

(1) a 3' region which is complementary to a product cleaved through the first reaction; and (2) a self-complementary region which forms a duplex for mimicking a single-stranded probe, which is hybridized with a target, and which contains a reporter fluorescent dye and a quencher fluorescent dye.

When the reporter fluorescent dye and the quencher fluorescent dye are bound to the same probe, the fluorescence intensity of the reporter fluorescent dye is quenched through fluorescence resonance energy transfer. Whereas when the reporter fluorescent dye and the quencher fluorescent dye are not bound to the same probe, the fluorescence intensity of the reporter fluorescent dye is not quenched. When the 5' flap released from the cleaved first probe is hybridized with the FRET probe, the resultant product acts as an invader oligonucleotide in the second reaction, and an invasion complex that is recognized by the enzyme is produced. Thus, cleavage of the FRET probe by the aforementioned enzyme separates the two fluorescent dyes, thereby yielding a detectable fluorescent signal. The signal can be read by use of, for example, a standard fluorescence microtiter plate reader, whereby the presence of target SNPs can be detected. A combination of the first and second reactions can amplify the signal by a factor of $1 \times 10^6$. Employment of two FRET probes having different fluorescent dyes also enables detection of the presence of SNP.

(7) Quantitative Real-Time PCR Assay

Detection of polymorphisms of the human IRS-2 gene can also be readily performed by quantitative real-time PCR assay (TaqMan assay).

This assay can be performed through, for example, the following procedure. Specifically, firstly, to confirm the presence of a polymorphism, a DNA fragment is prepared as a forward primer or reverse primer formed of, for example, 15 to 39 nucleotides. In this case, the forward primer or reverse primer is prepared so as not to contain the polymorphims. Subsequently, there is prepared a probe which has both a reporter fluorescent dye and a quencher fluorescent dye, and the probe contains, for example, a 15 to 50 bp oligonucleotide which correspond to a partial sequence of amplified fragment. The nucleotide sequence of the probe has to be selected such that a region with which both of the forward and reverse primer do not hybridize. The probe is designed so as to have a sequence complementary to an allele-specific sequence for detecting the presence of a target single nucleotide polymorphism. By use of the probe, a target DNA fragment of the IRS-2 gene of a sample to be detected is amplified through PCR, and fluorescence from the resultant reaction mixture is real-time measured. Thus, the presence of polymorphism can be detected. Employment of two probes having different fluorescent dyes also enables detection of both alleles.

The reporter fluorescent dye employed in the aforementioned Invader assay or TaqMan assay is preferably a fluorescein fluorescent dye such as FAM (6-carboxy-fluorescein), whereas the quencher fluorescent dye is preferably a rhodamine fluorescent dye such as TAMRA (6-carboxy-tetramethyl-rhodamine). These fluorescent dyes are known, and are contained in commercially available real-time PCR detection kits. In the present invention, such a commercially available fluorescent dye can be employed. No particular limitation is imposed on the binding position of the reporter fluorescent dye or the quencher fluorescent dye, but generally, the reporter fluorescent dye is bound to one end (preferably the 5'-end) of the oligonucleotide constituting the probe, and the quencher fluorescent dye is bound to the other end. The method for binding a fluorescent dye to an oligonucleotide is known, and is described in, for example, Noble, et al., (1984), Nuc. Acids Res., 12: 3387-3403 or Iyer, et al., (1990), J. Am. Chem. Soc., 112: 1253-1254.

The TaqMan assay per se is known, and apparatuses and kits for the TaqMan assay are commercially available. In the present invention, such a commercially available apparatus or kit can be employed. For example, the TaqMan assay can be performed according to the method described in Japanese Patent No. 2,825,976, or according to the ABI PRISM 7700 sequencing system user manual (PE Applied Biosystems).

(8) Genetic Polymorphism Assay Employing a Mass Spectrometer (Mass Array)

The mass array assay detects the difference in molecular weight between polymorphisms. Specifically, a region including a polymorphism to be detected is amplified through PCR, and then an extension primer is hybridized with a sequence immediately before the position of SNP, followed by extension reaction by use of a reaction mixture containing a ddNTP/dNTP mixture (e.g., a reaction mixture containing ddATP, dCTP, dGTP, and dTTP), thereby yielding a fragment having a length depending on the type of SNP. The resultant fragment is purified, and then subjected to analysis by use of, for example, a MALDI-TOF mass spectrometer, whereby the relationship between the molecular weight and the genetic polymorphism can be analyzed (Pusch, W., Wurmbach, J H., Thiele, H., Kostrzewa, M., MALDI-TOF mass spectrometry-based SNP genotyping, Pharmacogenomics, 3 (4): 537-48 (2002)). This assay can be readily performed by use of, for example, Sequenom Mass ARRAY high throughput SNP analysis system (http://www.sequenom.com/Files/applications/hme_assay.html).

(9) Other Detection Methods

Detection of SNPs of the human IRS-2 gene can also be performed through, for example, any of the below-described various methods, which have conventionally been known as DNA sequencing methods or mutation detection methods.

(a) PCR-SSO method employing sequence-specific oligonucleotide

A method in which a probe for a mutation is immobilized on a carrier; a sample (gene amplified product) is hybridized with the probe; and a difference in hybridization efficiency is determined on the basis of the presence of mismatch.

(b) PCR-SSP method for point mutation detection

A method by use of a sequence-specific primer for gene amplification which is designed such that a nucleotide corresponding to point mutation becomes the 3'-end nucleotide, which method utilizes that a significant difference in PCR amplification efficiency occurs depending on the complementarity of the 3'-end nucleotide of the primer.

(c) PCR-DGGE (denaturing gradient gel electrophoresis)

When DNA fragment including a mutation is hybridized with a normal DNA fragment, and then the thus-hybridized product is electrophoresed on a polyacrylamide gel with gradually increasing denaturant (e.g., urea or formamide) concentrations, the product is converted into single-stranded DNA fragments at a position of lower denaturant concentration, as compared with the case of non-mismatched homogenous double-stranded DNA fragments. The single-stranded DNA fragments migrate at a rate higher than the migration rate of the double-stranded DNA fragments, and therefore single nucleotide mutation can be detected through comparison of the mobilities of the DNA fragments.

(d) PCR-DGGE/GC clamp method (Shefield, V. C., et al., Proc. Natl. Acad. Sci., U.S.A., 86, 232-236 (1989))

This method is a modification of the aforementioned PCR-DGGE, in which a region having a high GC content is added to a target DNA fragment for detection of a mutation. This method compensates for the disadvantage of the PCR-DGGE in detection of substitution, deletion, addition, or insertion of multiple nucleotides. This method requires a step of adding a GC clamp to a target DNA fragment for mutation detection.

(e) RNase protection assay (Finkelstein, J., et al., Genomics, 7, 167-172 (1990))

(f) In situ RT-PCR (Nucl. Acids Res., 21, 3159-3166 (1993))

(g) In situ hybridization (h) Southern blotting (Sambrook, J., et al., Molecular Cloning a Laboratory Manual., Cold Spring Harbor Laboratory Press: NY. (1989))

(i) Dot hybridization assay (see, for example, Southern, E. M., J. Mol. Biol., 98: 503-517 (1975))

(j) Fluorescence in situ hybridization (FISH: Takahashi, E., et al., Hum. Genet., 86, 1416 (1990))

(k) Comparative genomic hybridization (CGH: Kallioneimi, A., et al., Science, 258, 818-821 (1992)), (Spectral karyotyping: SKY: Rowley, J. D., et al., Blood, 93, 2038-2042 (1999))

(l) Method employing yeast artificial chromosome (YAC) vector clone as a probe (Lengauer, C., et al., Cancer Res., 52, 2590-2596 (1992)).

Thus, polymorphisms (SNPs) or haplotype of the human IRS-2 gene can be detected.

According to the present invention, when a test sample is confirmed to have a polymorphism(s) of the human IRS-2 gene through detection procedures described above, the sample is judged as a subject with a high risk of drug-induced granulocytopenia.

Thus, before administration of a drug, it is determined whether the subject has a high risk of drug-induced granulocytopenia. Therefore, granulocytopenia, attributed to drug administration or other causes, will be prevented by this test.

Particularly, detection of SNPs of the human IRS-2 gene according to the present invention is effective in detecting the presence of a risk factor for drug-induced granulocytopenia in a human. That is, screening of the SNPs enables detection of a risk factor for human drug-induced granulocytopenia.

Thus, the present invention provides a method of detecting a polymorphism(s) of the human IRS-2 gene of a subject who may develop drug-induced granulocytopenia. That is, the genetic polymorphism(s) of the human IRS-2 gene can be used as an index to detect a subject who develops drug-induced granulocytopenia.

Oligonucleotide

The present invention also provides an oligonucleotide serving as a primer or probe for genetic polymorphism detection, which is used in the assessment (detection) method of the present invention employing PCR. No particular limitation is imposed on the oligonucleotide, so long as it can specifically amplify a specific region including polymorphisms (SNPS) of the human IRS-2 gene. The oligonucleotide can be appropriately constructed on the basis of sequence data of the human IRS-2 gene and synthesized through common methods.

More specifically, the oligonucleotide can be synthesized through a generally employed chemical synthesis method such as the phosphoroamidite method or the phosphotriester method, or can be synthesized by use of a commercially available automated oligonucleotide synthesis apparatus such as Pharmacia LKB Gene Assembler Plus (product of Pharmacia). A double-stranded fragment can be obtained by annealing of a chemically synthesized single-stranded oligonucleotide and its complementary strand under appropriate conditions, or synthesized by using an appropriate primer and DNA polymerase.

Preferred examples of the aforementioned oligonucleotide serving as a probe or primer include partial oligonucleotides corresponding to a DNA fragment designed so as to contain a polymorphism of the human IRS-2 gene. These oligonucleotides have at least a sequence of 10 bases (generally about 10 to 35 a sequence of bases). The oligonucleotide serving as a primer pair may be oligonucleotides having two sequences which are designed and synthesized so as to sandwich SNP of the human IRS-2 gene (genomic sequence). The oligonucleotide serving as a probe may be its positive clone per se.

Preferred examples of the aforementioned oligonucleotide serving as a probe or primer include partial sequences corresponding to a DNA fragment designed so as to contain at least one of the following polymorphisms: C to A conversion at position 4,587 upstream of the translation initiation codon of the human IRS-2 gene (C-4587A); AT deletion at position 2,510 upstream of the translation initiation codon of the human IRS-2 gene (AT-2510del); A to C conversion at position 1,164 upstream of the translation initiation codon of the human IRS-2 gene (A-1164C); A to G conversion at position 15,870 from the translation initiation codon of the human IRS-2 gene (A15870G); A to G conversion at position 29,793 downstream from the translation initiation codon of the human IRS-2 gene (A29793G); and C deletion at position 31,532 downstream from the translation initiation codon of the human IRS-2 gene (C31532del). These primer or probe has at least a sequence of 10 bases (preferably at least a sequence of 15 bases).

Specific examples of the oligonucleotide include forward primers and reverse primers of SEQ ID NOs: 1, 2, 4, 5, 7, 8, 10, 11 and 13 to 16, and oligonucleotide primers for direct sequencing of SEQ ID NOs: 3, 6, 9, 12, and 17, which are described below in Examples.

No particular limitation is imposed on the gene-specific probe employed in the present invention, so long as it can detect any of the aforementioned C-4587A, AT-2510del, A-1164C, A15870G, A29793G, and C31532del.

Kit for Assessment

The assessment (detection) method of the present invention can be more easily performed by use of a reagent kit for detecting SNPs of the human IRS-2 gene of a sample. The present invention also provides a kit for such assessment.

A kit of the present invention includes, as an essential component, at least a DNA fragment which hybridizes with a partial or entire—nucleotide sequences or its complementary sequences—including six SNPs of the human IRS-2 gene, or which hybridizes with a sequence containing an ologonucleotide with one base or several bases before a polymorphic site. Another kit of the present invention includes, as an essential component, a restriction enzyme (e.g., Afa I) that specifically recognizes a sequence formed of several nucleotides (including the aforementioned polymorphic site).

Other components of the kit of the present invention are, for example, a labeling reagent, and reagents required for PCR (e.g., Taq DNA polymerase, deoxynucleotide triphosphate, or a primer for DNA amplification). Examples of the labeling reagent include chemical modification substances such as a radioactive isotope, a light-emitting substance, and a fluorescent substance. The DNA fragment per se may be conjugated in advance with such a labeling reagent. The kit of the present invention may further include, for example,— appropriate reaction diluents, standard antibodies, buffers, detergents, or reaction stopping solutions, to perform measurement conveniently.

Use of the aforementioned assessment method of the present invention enables provision of an examination method for the risk of human drug-induced granulocytopenia by use, as an index, of a detected genetic polymorphism which may cause drug-induced granulocytopenia in a human, particularly, an examination method for the risk of granulocytopenia attributed to administration of a drug (e.g., vesnarinone) which has already been reported to induce granulocytopenia (including agranulocytosis), before administration of the drug, as well as a diagnosis reagent and diagnosis kit employed for such an examination method.

The present invention will next be described in more detail by way of Examples, which should not be construed as limiting the invention thereto.

EXAMPLE 1

Example 1

(a) Screening of Genetic Polymorphism in Relation to Granulocytopenia Attributed to Drug Administration In order to find genetic polymorphisms in relation to granulocytopenia attributed to drug administration, there were employed subjects who had received vesnarinone (3,4-dihydro-6-[4-(3,4-dimethoxybenzoyl)-1-piperazinyl]-2(1H) - quinoline).

In Japan, vesnarinone, which is a commercially available drug applicable to chronic heart failure (mild to moderate heart failure), has been reported to induce side effects including leukopenia, granulocytopenia, and agranulocytosis, and therefore, administration of this drug requires observation of such side effects and frequent examinations of granulocytes.

Among subjects who had received vesnarinone, had orally agreed to cooperate with investigation of the cause for vesnarinone-induced granulocytopenia between May 1991 and October 1996, and had accepted to provide a blood sample, there were employed 84 subjects (male/female ratio=1.21:1) who had again agreed in writing to cooperate with genetic analysis according to ethical guidelines between July 2001 and December 2001. Genomic DNA was extracted from a blood sample (or a cell sample derived therefrom) of each of the subjects who had again agreed described above. through a common method, and was employed for the below-described tests.

(b) Classification Criteria of the Subjects

On the basis of the below-described criteria, the subjects were classified into the following two groups: a group of subjects with granulocytopenia, and a group of subjects without granulocytopenia.

Among the subjects, subjects having leukocytes or neutrophils which were decreased to half or less following vesnarinone administration, and having the number of leukocytes of 2,000/mm$^3$ or less, or the number of neutrophils of 1,000/mm$^3$ or less were classified as "subjects with granulocytopenia". On the other hand, subjects who did not decrease the number of neutrophils after vesnarinone administration for 90 days or more were classified as "subjects with granulocytopenia".

Each of these groups was further classified into two groups according to sex, to thereby become four subgroups; i.e., a group of 13 male with granulocytopenia (group A), a group of 17 female with granulocytopenia (group B), a group of 33 male without granulocytopenia (group C), and a group of 21 female without granulocytopenia (group D).

(c) Gene and Polymorphism (SNP) to be Analyzed

115 Candidate genes were selected from among, for example, cytokine-related genes, MHC region genes, G-CSF-related genes, TNF-α-related genes, NF-κ-related genes, cAMP-related genes, and potassium channel-related genes.

Polymorphisms (SNPs) of these candidate genes were searched from the database of Japanese Single Nucleotide Polymorphisms (JSNP: http://snp.ims.u-tokyo.ac.jp/index_ja.html), and 188 candidate SNPs were selected.

(d) Analysis Method

The SNPs were analyzed by the Invader assay. The Invader assay was performed with reference to the following publications (1) and (2):

(1) Lyamichev, V., et al., Nat. Biotechnol., 17: 292-296 (1999); and (2) International Patent Publication WO 9823774 (98/6/4).

In order to amplify genomic DNA regions including each of the candidate SNPs by PCR, a set of primers for amplifying these regions was designed on the basis of genomic DNA sequence data around the SNPs searched from JSNP, and each of the primers was synthesized.

An Invader assay reagent for determining genotypes of the candidate SNPs was prepared by a common method on the basis of genomic DNA sequence data around the SNPs searched from JSNP.

Each PCR was performed by use of genomic DNA (1 ng) as a template. A reaction mixture (15 μL) contained dNTPs (0.25 mM), the PCR buffer attached to TaKaRa Ex Taq (Takara) ($\frac{1}{10}$ of the total amount for reaction), a set of a forward and a reverse primer (130 nM each), and TaKaRa Ex Taq (Takara) (0.5 U). Each sample was amplified in DNA Engine PTC-0200 (MJ Research). The PCR was performed for 94° C. for 2 minutes; then 50 cycles of 94° C. for 30 seconds, 56° C. (or 58° C. or 60° C.) for 30 seconds, and 72° C. for 90 seconds.

Invader assay reaction was carried out mixing the Invader assay reagent with the PCR product that was diluted with a range of 10 to 1,000-fold. A reaction mixture (15 μL) contained 5.5×Invader buffer (2.75 μL), 10× Bioplex FRET Probe Mix (0.75 μL), Cleavase VIII enzyme (200 ng/μL) (1 μL), PPI Mix (3 μL), and the diluted PCR product described above (7.5 μL). The reaction was performed at 62° C. for 60 to 120 minutes.

(e) Genotype Determination Method

Genotype of each subject was determined based on the intensities of two different fluorescent materials detected as a result of the Invader assay reaction. Thus, the genotypes of the 188 SNPs located in the 115 genes of each subject were determined by the Invader assay.

(f) Statistical Analysis Method

The allele frequencies in the group of subjects with granulocytopenia were compared to that of subjects without granulocytopenia by the contingency χ square test. The odds ratio was estimated through the Brown method (Brown, C. C., Am. J. Epidemiol., 113: 474-480 (1981)). The 95% confidence interval of odds ratio was calculated through the Woolf method.

(g) Results

The results of analysis of the 188 SNPs in the 115 genes through the aforementioned method revealed that polymorphism with the most statistically significant association was located in the insulin receptor substrate 2 (IRS-2) gene (JSNP ID: IMS-JST040476). In these subjects, this SNP was in Hardy-Weinberg equilibrium.

The result suggests that the SNP in the human IRS-2 gene is intimately related to the granulocytopenia attributed to vesnarinone administration, and that the human IRS-2 gene is likely to play an important role in the pathogenesis of granulocytopenia.

The Human IRS-2 protein (translation product of the human IRS-2 gene) belongs to the insulin receptor substrate protein family (IRSs: IRS-1, IRS-2, IRS-3, and IRS-4). IRSs are activated by insulin receptor tyrosine kinase that phosphorylates tyrosine residues of IRSs. As has been known, Phosphorylated-IRSs are related to the insulin action that is to promote glucose uptake by accelerating translocation of glucose transporter 4 (GLUT-4) from cytoplasm to cell membrane via PI-3 kinase activated by phosphorylated-IRSs. In order to conduct further studies on the relation between the human IRS-2 gene and vesnarinone-induced granulocytopenia, another polymorphisms of the human IRS-2 gene were analyzed.

Example 2

Association Analysis of the Human IRS-2 Gene and Drug-Induced Granulocytopenia By use of the subjects described in Example 1, polymorphisms of the human IRS-2 gene were analyzed as follows.

(a) Discovery of Polymorphisms in the Human IRS-2 Gene

In order to screen the entirety of the IRS-2 gene including a promoter region involved in its transcriptional regulation, the genomic sequence including the IRS-2 gene was obtained from GenBank (accession number AL162497, full length: 143,409 bp) by inquiring the human IRS-2 mRNA sequence, which is registered in GenBank (accession number XM_007095). The structure of the human IRS-2 gene was estimated through detailed comparison between the human IRS-2 mRNA sequence and the genomic sequence including the IRS-2 gene. Notably, a complementary strand of the above-obtained genomic sequence was employed for the comparison such that the above-compared sequences were in the same direction (from 5' to 3').

It is inferred from the result that the human IRS-2 gene has a full length of 32,730 bp including two exons and one intron.

On the basis of the above sequence data, primers were designed and synthesized.

For discovery of polumorphism, there were employed genomic samples from 12 subjects with granulocytopenia and 12 subjects without granulocytopenia among the subjects described in Example 1.

Each PCR was performed by use of genomic DNA (5 ng). A reaction mixture (10 μL) was prepared to contain dNTPs (1.25 mM), magnesium chloride (3.9 mM), ammonium sulfate (16.6 mM), Tris-HCl (67 mM, pH 8.8), β-mercaptoethanol (10 mM), a set of a forward primer and a reverse primer (1.25 mM), and TaKaRa Ex Taq (Takara) (0.5 U). If desired, DMSO (dimethyl sulfoxide) was added to the reaction mixture such that the final concentration was 10%.

Each sample was amplified by use of DNA Engine PTC-0200 (MJ Research) or GeneAmp PCR System 9700 (PE Applied Biosystems). The PCR was performed at 95° C. for 2 minutes; then 37 cycles of 94° C. for 30 seconds, 56° C. (or 58° C.) for 30 seconds, and 72° C. for 3 minutes with final extension at 72° C. for 7 minutes.

Each of the PCR product was employed to react with BigDye™ Terminator RR mix (PE Applied Biosystems).

On the basis of nucleotide sequence data obtained by ABI Prism 3700 DNA Analyzer (PE Applied Biosystems), genetic polymorphisms were detected and their positions on the human IRS-2 gene were confirmed by use of SEQUENCHER 3.1 (product of Gene Codes)

(b) Sample Amplification and Genotype Determination Method

In order to determine the genotype distribution, all polymorphisms identified by the discovery above were analyzed in the all subjects described in Example 1 by amplifying the regions containing the polymorphisms with primer sets and sequencing the PCR products under the condition described above.

(c) Statistical Analysis

In addition to the statistical methods employed in Example 1, a pair-wise linkage disequilibrium coefficient (D'=D/Dmax or D/Dmin) was calculated by use of the method by Thompson, et al. (Thompson, E. A., et al., Am. J. Hum. Genet. 42: 113-124 (1988))

(d) Results

The analysis results revealed that, in the subject groups, all the polymorphisms analyzed in the present Example are in Hardy-Weinberg equilibrium.

The analysis results also revealed that six polymorphisms were intimately associated with granulocytopenia induced by vesnarinone administration. Tables 1 through 6 show the results of statistical analysis on the six polymorphisms respectively.

TABLE 1

| Polymorphism The number of genotype | subjects with agranulocytosis N (%) | subjects without agranulocytosis N (%) | $x^2$ (df = 1) | P | OR (95% CI) |
|---|---|---|---|---|---|
| C-4587A | | | | | |
| CC | 7 (25.0) | 29 (59.2) | 8.36 | 0.0038 | 4.35 |
| CA + AA | 21 (75.0) | 20 (40.8) | | | (1.56-12.16) |
| Total | 28 | 49 | | | |

TABLE 2

| Polymorphism The number of genotype | subjects with agranulocytosis N (%) | subjects without agranulocytosis N (%) | $x^2$ (df = 1) | P | OR (95% CI) |
|---|---|---|---|---|---|
| AT-2510del | | | | | |
| AT | 7 (24.1) | 28 (57.1) | 8.02 | 0.0046 | 4.19 |
| ATdel + del | 22 (75.9) | 21 (42.9) | | | (1.51-11.64) |
| Total | 29 | 49 | | | |

TABLE 3

| Polymorphism The number of genotype | subjects with agranulocytosis N (%) | subjects without agranulocytosis N (%) | $x^2$ (df = 1) | P | OR (95% Cl) |
|---|---|---|---|---|---|
| A-1164C | | | | | |
| AA | 8 (26.7) | 29 (59.2) | 7.90 | 0.0049 | 3.99 |
| AC + CC | 22 (73.3) | 20 (40.8) | | | (1.48-10.73) |
| Total | 30 | 49 | | | |

TABLE 4

| Polymorphism The number of genotype | subjects with agranulocytosis N (%) | subjects without agranulocytosis N (%) | $x^2$ (df = 1) | P | OR (95% Cl) |
|---|---|---|---|---|---|
| A15870G | | | | | |
| AA | 10 (37.0) | 36 (73.5) | 9.67 | 0.0019 | 4.71 |
| AG + GG | 17 (63.0) | 13 (26.5) | | | (1.72-12.88) |
| Total | 27 | 49 | | | |

TABLE 5

| Polymorphism The number of genotype | subjects with agranulocytosis N (%) | subjects without agranulocytosis N (%) | $x^2$ (df = 1) | P | OR (95% Cl) |
|---|---|---|---|---|---|
| A29793G | | | | | |
| AA | 11 (36.7) | 39 (73.6) | 10.90 | 0.00096 | 4.81 |
| AG + GG | 19 (63.3) | 14 (26.4) | | | (1.84-12.56) |
| Total | 30 | 53 | | | |

TABLE 6

| Polymorphism The number of genotype | subjects with agranulocytosis N (%) | subjects without agranulocytosis N (%) | $x^2$ (df = 1) | P | (95% Cl) |
|---|---|---|---|---|---|
| C31532del | | | | | |
| CC | 9 (33.3) | 34 (70.8) | 9.93 | 0.0016 | 4.86 |
| Cdel = del | 18 (66.7) | 14 (29.2) | | | (1.76-13.39) |
| Total | 27 | 48 | | | |

In the Tables, a polymorphism with the symbol "del" corresponds to a deletion polymorphism, and the position number of each "polymorphism" correspond to the position number counting from A (position number: +1) of ATG (translation initiation codon) of the IRS-2 gene. A polymorphism shown by the position number with the symbol "-" is located 5' upstream of A of ATG (translation initiation codon) of the IRS-2 gene.

As shown in Tables 1 through 6, a subject having at least one of these six polymorphisms has showed association with the granulocytopenia by vesnarinone administration. In other words, these results suggest that one of these polymorphisms, "C-4587A", which is a polymorphism obtained through C to A conversion at position 4,587 upstream of the translation initiation codon of the human IRS-2 gene; "AT-2510del", which is a polymorphism obtained through AT deletion at position 2,510 upstream of the translation initiation codon of the coding region; "A-1164C", which is a polymorphism obtained through A to C conversion at position 1,164 upstream of the translation initiation codon of the coding region; "A15870G", which is a polymorphism obtained through A to G conversion at position 15, 870 downstream from the translation initiation codon of the coding region; "A29793G", which is a polymorphism obtained through A to G conversion at position 29, 793 downstream from the translation initiation codon of the coding region; and "C31532del", which is a polymorphism obtained through C deletion at position 31,532 downstream from the translation initiation codon of the coding region, is associated with granulocytopenia by vesnarinone administration. FIG. 1 shows the positions of these six polymorphisms in the human IRS-2 gene. In FIG. 1, "+1" corresponds to A of ATG (translation initiation codon).

Table 7 shows the results of analysis of linkage disequilibrium between these polymorphisms.

TABLE 7

| | D' | | | | |
|---|---|---|---|---|---|
| SNP | C-4587A | AT-2510del | A-1164C | A15870G | A29793G |
| AT-2510-del | 1.000 | — | — | — | — |
| A-1164C | 1.000 | 1.000 | — | — | — |
| A15870G | 1.000 | 1.000 | 1.000 | — | — |
| A29793G | 0.956 | 0.956 | 0.957 | 1.000 | — |
| C31532-del | 0.952 | 0.953 | 0.953 | 1.000 | 1.000 |

As is clear from Table 7, all the polymorphisms, which are intimately associated with granulocytopenia by vesnarinone administration, are in almost complete linkage disequilibrium. Specifically, when the allele at position 4587 upstream of the translation initiation codon of the human IRS-2 gene is A (mutant type), each of the polymorphisms at the other five polymorphic sites has the genotype which shows association with granulocytopenia by vesnarinone administration.

The results strongly suggest that these six polymorphisms of the human IRS-2 gene play an important role in the granulocytopenia by vesnarinone administration.

Recently, it has been reported that when HL-60 cells (myeloblasts) are differentiated into granulocytes by DMSO stimulation, the amount of IRS-2 protein is increased (Schacher, D. H., et al., J. Immunol., 164: 113-120 (2000)). This report suggests that IRS-2 is closely associated with granulocytic differentiation. Among the human IRS-2 gene polymorphisms analyzed or identified by the present inventors, three polymorphisms (C-4587A, AT-2510del, and A-1164C) are located in the promoter region, which regulates the transcription of the human IRS-2 gene. Therefore, it may be supported that the transcriptional levels of IRS-2 gene are reduced by these polymorphisms located in the promoter region, whereby a differentiation into granulocytes is also reduced.

Example 3

This Example is related to other methods for detecting the six polymorphisms of the human IRS-2 gene of the present invention. In this Example, these polymorphisms were detected through the below-described methods (a) and (b).

(a) Direct Sequencing

DNA fragments were amplified by use of forward primers (SEQ ID NOs: 1, 4, 7, 10, 13, and 15) and reverse primers (SEQ ID NOs: 2, 5, 8, 11, 14, and 16) described in Table 8, such that these amplified PCR products included the six polymorphisms according to the present invention. This operation was performed by DNA Engine PTC-0200 (MJ Research) or GeneAmp PCR System 9700 (PE Applied Biosystems) Each PCR was performed for 95° C. for 2 minutes; then 37 cycles of 94° C. for 30 seconds, the annealing temperature shown in Table 8 for 30 seconds, extension reaction at 72° C. for the time shown in Table 8 with final extension at 72° C. for 10 minutes. For each of the DNA fragments, as described in Table 8, the annealing temperature and the extension reaction time are 58° C. to 60° C. and 0.5 minutes to 3 minutes, respectively.

TABLE 8

| | Forward primer | Nucleotide position number in AL162497 | Reverse primer | Nucleotide position number in AL162497 | Annealing temperature (° C.) | Extension time (min) | DMSO |
|---|---|---|---|---|---|---|---|
| C-4587A | SEQ ID NO: 1 | 131420-131399 | SEQ ID NO: 2 | 130318-130339 | 60 | 3 | − |
| AT-2510del | SEQ ID NO: 4 | 128930-128911 | SEQ ID NO: 5 | 127491-127510 | 60 | 3 | − |
| A-1164C | SEQ ID NO: 7 | 127837-127818 | SEQ ID NO: 8 | 126460-126479 | 60 | 3 | + |
| A15870G | SEQ ID NO: 10 | 110260-110240 | SEQ ID NO: 11 | 109859-109879 | 60 | 3 | − |
| A29793G | SEQ ID NO: 13 | 96209-96190 | SEQ ID NO: 14 | 96070-96091 | 58 | 0.5 | − |
| C31532del | SEQ ID NO: 15 | 94616-94595 | SEQ ID NO: 16 | 93139-93159 | 60 | 3 | − |

The component of a reaction mixture is as described in Example 2-(a). Notably, DMSO was added to the reaction mixture for detecting "A-1164C" such that the final concentration was 10% (see the column "DMSO" of Table 8).

G at position 23 of the reverse primer (SEQ ID NO: 14) employed for detection of "A29793G" described in Table 8 was a replaced base to create the polymorphic site that is recognized by the restriction enzyme Afa I.

The polymorphisms other than "A29793G" were detected by direct sequencing [the dideoxy method (Sanger, et al., Proc. Natl. Acad. Sci., U.S.A., 74, 5463-5467 (1977) or the Maxam-Gilbert method (Methods in Enzymology, 65, 499 (1980). Table 9 shows primers to determine genotype of each polymorphism (SEQ ID NOs: 3, 6, 9, 12, and 17).

TABLE 9

| | Primer for sequencing | Nucleotide position number in AL162497 |
|---|---|---|
| C-4587A | SEQ ID NO: 3 | 130343-130363 |
| AT-2510del | SEQ ID NO: 6 | 128581-128562 |
| A-1164C | SEQ ID NO: 9 | 126912-126929 |
| A15870G | SEQ ID NO: 12 | 110249-110231 |
| C31532del | SEQ ID NO: 17 | 94556-94537 |

(b) PCR-RFLP (Restriction Enzyme Fragment Length Polymorphism) Analysis

"PCR-RFLP (restriction enzyme fragment length polymorphism) analysis was performed to detect "A29793G". Specifically, a reaction mixture (20 μL) contained the PCR product (10 μL), 2 units of restriction enzyme Afa I (10 units/mL, Takara), and 10× Buffer T attached to the restriction enzyme (2 μL). BSA was added to the reaction mixture such that the final concentration was 0.01%, and the resultant mixture was incubated at 37° C. for 16 hours. Digested DNA fragments were separated by use of 4% agarose gel and visualized by ethidium bromide staining and ultraviolet transillumination.

When DNA extracted from a subject sample is applied to any of the detection methods for the six polymorphisms of the human IRS-2 gene described above in the Examples before administration of a drug which may induce granulocytopenia, there can be determined the possibility of an drug-induced granulocytopenia (including agranulocytosis); i.e., the risk of drug-induced granulocytopenia. Thus, according to the present invention, the risk of granulocytopenia attributed to vesnarinone administration can be examined or assessed by of the analysis of DNA from a subject.

INDUSTRIAL APPLICABILITY

The present invention is useful for examining or assessing the risk of human drug-induced granulocytopenia, particularly useful for examining or assessing the risk of human drug-induced granulocytopenia before administration of a drug that has already been reported to induce granulocytopenia (including agranulocytosis).

The invention claimed is:

1. A method for assessing the risk of vesnarinone-induced granulocytopenia comprising:
    detecting in a subject in need thereof at least one polynucleotide polymorphism of the human insulin receptor substrate 2 gene in the polynucleotide sequence described by GenBank Accession No. AL162497 (version 20) (SEQ ID NO: 18), and
    assessing the risk of vesnarinone-induced granulocytopenia by detecting the
    presence of at least one polymorphism correlating with the risk of vesnarinone-induced granulocytopenia; wherein said at least one polymorphism comprises a polymorphism A29793G that is a T to C conversion at position 96,095 of SEQ ID NO: 18.

2. The method of claim 1, wherein the genetic polymorphism is detected through at least one technique selected from the group consisting of allele-specific oligonucleotide (ASO)-dot blot analysis, single nucleotide primer extension assay, PCR-single strand conformation polymorphism (SSCP) analysis, Invader assay, quantitative real-time PCR assay, and genetic polymorphism assay employing a mass spectrometer (mass array).

3. The method of claim 1, wherein the genetic polymorphism is detected through direct nucleotide sequencing.

4. The method of claim 1, wherein the genetic polymorphism is detected through PCR-restriction enzyme fragment length polymorphism (RFLP) analysis.

5. The method of claim 4, wherein the PCR-restriction enzyme fragment length polymorphism (RFLP) analysis is performed by use of the restriction enzyme Afa I for detecting T to C conversion at position 96,095 of SEQ ID NO: 18.

6. The method of claim 1, wherein said polymorphism is identified by a method employing a probe or primer selected from the group consisting of:
    (a) an oligonucleotide having a sequence including a genetic polymorphism that is G to T conversion at position 130,474 of SEQ ID NO: 18;
    (b) an oligonucleotide having a sequence including a genetic polymorphism that is an TA deletion at positions 128,398-128,399 of SEQ ID NO: 18;
    (c) an oligonucleotide having a sequence including a gene polymorphism that is T to G conversion at position 127,051 of SEQ ID NO: 18;

(d) an oligonucleotide having a sequence including a gene polymorphism that is T to C conversion at position of 110,018 of SEQ ID NO: 18;

(e) an oligonucleotide having a sequence including a gene polymorphism that is T to C conversion at position 96,095 of SEQ ID NO: 18; and (f) an oligonucleotide having a sequence including a genetic polymorphism that is G deletion between positions 94,356-94,357 of SEQ ID NO: 18.

7. The method of claim 1, wherein said polymorphism is identified by a method employing a probe or primer selected from the group consisting of:

(a) an oligonucleotide having the sequence of SEQ ID NO: 3;

(b) an oligonucleotide having the sequence of SEQ ID NO: 6;

(c) an oligonucleotide having the sequence of SEQ ID NO: 9;

(d) an oligonucleotide having the sequence of SEQ ID NO: 12; and (f) an oligonucleotide having the sequence of SEQ ID NO: 17.

8. The method of claim 7, comprising assessing the risk of vesnarinone-induced granulocytopenia before vesnarinone administration.

9. The method of claim 1, wherein said polymorphism is identified by a method employing a probe or primer having a sequence including a gene polymorphism that is T to C conversion at position 96,095 of SEQ ID NO: 18 and employing the restriction enzyme Afa I.

10. The method of claim 9, comprising assessing the risk of vesnarinone-induced granulocytopenia before vesnarinone administration.

11. The method of claim 7, further comprising obtaining a cDNA or genomic DNA sample from said subject.

* * * * *